(12) United States Patent
Robinson et al.

(10) Patent No.: US 11,834,493 B2
(45) Date of Patent: Dec. 5, 2023

(54) ANTIBODY COCKTAIL AGAINST SARS-COV-2 SPIKE PROTEIN

(71) Applicant: Immunome, Inc., Exton, PA (US)

(72) Inventors: Matthew K. Robinson, Blue Bell, PA (US); Pavel Nikitin, Exton, PA (US); Michael John Morin, Salisbury, MA (US); Jillian Dimuzio, Exton, PA (US); Ray Howanski, Exton, PA (US); John P. Dowling, Willow Grove, PA (US)

(73) Assignee: IMMUNOME, INC., Exton, PA (US)

( * ) Notice: Subject to any disclaimer, the term of this patent is extended or adjusted under 35 U.S.C. 154(b) by 0 days.

(21) Appl. No.: 17/568,576

(22) Filed: Jan. 4, 2022

(65) Prior Publication Data
US 2022/0235118 A1 Jul. 28, 2022

Related U.S. Application Data

(60) Provisional application No. 63/284,963, filed on Dec. 1, 2021, provisional application No. 63/270,665, filed on Oct. 22, 2021, provisional application No. 63/236,479, filed on Aug. 24, 2021, provisional application No. 63/220,881, filed on Jul. 12, 2021, provisional application No. 63/178,848, filed on Apr. 23, 2021, provisional application No. 63/150,070, filed on Feb. 16, 2021, provisional application No. 63/134,159, filed on Jan. 5, 2021.

(51) Int. Cl.
*C07K 16/10* (2006.01)
*A61P 31/14* (2006.01)
*A61K 39/00* (2006.01)

(52) U.S. Cl.
CPC .............. *C07K 16/10* (2013.01); *A61P 31/14* (2018.01); *A61K 2039/507* (2013.01); *C07K 2317/34* (2013.01); *C07K 2317/565* (2013.01); *C07K 2317/92* (2013.01)

(58) Field of Classification Search
CPC .............. C07K 16/10; C07K 2317/565; C07K 2317/76; A61P 31/14; A61K 2039/507
See application file for complete search history.

(56) References Cited

U.S. PATENT DOCUMENTS

| | | |
|---|---|---|
| 7,491,530 B2 | 2/2009 | Dessain et al. |
| 7,566,772 B2 | 7/2009 | Green et al. |
| 8,980,268 B2 | 3/2015 | Lowy et al. |
| 8,999,707 B2 | 4/2015 | Dessain et al. |
| 10,787,501 B1 * | 9/2020 | Babb ............... C07K 16/10 |
| 2018/0371085 A1 | 12/2018 | Brentjens et al. |
| 2019/0351049 A1 | 11/2019 | Kyratsous et al. |

FOREIGN PATENT DOCUMENTS

| | | | |
|---|---|---|---|
| CN | 111925444 A | 11/2020 | |
| CN | 111995677 * | 11/2020 | ............. C07K 16/10 |
| WO | 2019222575 A1 | 11/2019 | |

OTHER PUBLICATIONS

Machine translation of CN111995677, published /2020 << retrieved from Patenscope on Jan. 9, 2022 >> (Year: 2020).*
Almagro JC, Fransson J. Humanization of antibodies. Front Biosci. Jan. 1, 2008;13:1619-33. (Year: 2008).*
Kussie et al. A single engineered amino acid substitution changes antibody fine specificity.J Immunol.Jan. 1, 1994;152(1):146-52. (Year: 1994).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Anonymous (Aug. 20, 2020). "Progress Report a Pandemic," Nature 584:326, 1 page.
Baum A. et.al. (Aug. 21, 2020). "Antibody Cocktail To SARS-CoV-2 Spike Protein Prevents Rapid Mutational Escape Seen With Individual Antibodies," Science 369(6506):1014-1018.
Berlin, D.A. et al. Dec. 17, 2020). "Severe Covid-19," N Engl J Med. 383(25):2453-2460.
Bonsignori, M. et al. (Nov. 2012). "Antibody-Dependent Cellular Cytotoxicity-Mediating Antibodies From an HIV-1 Vaccine Efficacy Trial Target Multiple Epitopes and Preferentially Use the VH1 Gene Family," J. Virol. 86(21):11521-11532.
Braun, J. et al. (Nov. 12, 2020, e-pub. Jul. 29, 2020). "SARS-CoV-2-Reactive T Cells In Healthy Donors and Patients With COVID-19," Nature. 587:270-274, and supplemental material, 20 pages.
Callaway, B.E. (Sep. 10, 2020). The Coronavirus Is Mutating Does It Matter? Nature. 585:174-177.
Cao, Y. et al. (Jul. 9, 2020). "Potent Neutralizing Antibodies Against SARS-CoV-2 Identified By High-Throughput Single Cell Sequencing of Convalescent Patients' B Cells," Cell 182:73-84.
Chakraborty, I. et al. (2020, e-pub. Apr. 22, 2020). "COVID-19 Outbreak: Migration, Effects On Society, Global Environment and Prevention," Sci. Total Environ. 728:138882, 7 pages.
clinicaltrials.gov No. NCT04425629 (Jun. 16, 2020). "Safety, Tolerability, and Efficacy of Anti-Spike (S) SARS-CoV-2 Monoclonal Antibodies for the Treatment of Ambulatory Adult and Pediatric Patients With COVID-19," 15 pages.
clinicaltrials.gov No. NCT04427501 (Jun. 17, 2020). "A Study of LY3819253 (LY-CoV555) and LY3832479 (LY-CoV016) in Participants With Mild to Moderate COVID-19 Illness (BLAZE-1)," 13 pages.
clinicaltrials.gov No. NCT04452318 (Jul. 13, 2020). "COVID-19 Study Assessing the Efficacy and Safety of Anti-Spike SARS CoV-2 Monoclonal Antibodies for Prevention of SARS CoV-2 Infection Asymptomatic in Healthy Adults and Adolescents Who Are Household Contacts to an Individual With a Positive SARS-COV-2 RT-PCR Assay," 19 pages.

(Continued)

*Primary Examiner* — Aurora M Fontainhas
*Assistant Examiner* — Jennifer A Benavides
(74) *Attorney, Agent, or Firm* — MORRISON & FOERSTER LLP

(57) ABSTRACT

Provided herein are antibodies that are useful for treating SARS-CoV-2 infections in a subject. Also provided herein are compositions comprising one or more antibodies, methods of treatment comprising administering one or more antibodies, and kits comprising one or more antibodies.

35 Claims, 54 Drawing Sheets

Specification includes a Sequence Listing.

(56) References Cited

OTHER PUBLICATIONS clinicaltrials.gov No. NCT04545060 (Aug. 27, 2020). "VIR-7831 for the Early Treatment of COVID-19 in Outpatients (COMET-ICE)," 7 pages.
Degorce, F., et al. (2009). "HTRF: A Technology Tailored For Drug Discovery—A Review of Theoretical Aspects and Recent Applications," Curr Chem Genomics 3: 22-32.
Dougan, M. et al. (Jul. 14, 2021). "Bamlanivimab plus Etesevimab in Mild or Moderate Covid-19," N Engl J Med. 385(15):1382-1392.
FDA (Apr. 2020). "Guidance for Industry: FDA's Recommendations for Investigational COVID-19 Convalescent Plasma," U.S. Dept. of Health and Human Services, 12 pages.
Fehr, A.R. et al. (2015). "Chapter 1: Coronaviruses: An overview of Their Replication and Pathogenesis," In Coronaviruses: Methods and Protocols, (Springer New York), pp. 1-23.
Ferretti, A.P. et al. (Nov. 17, 2020). "Unbiased Screens Show CD8+ T Cells of COVID-19 Patients Recognize Shared Epitopes in SARS-CoV-2 that Largely Reside outside the Spike Protein," Immunity 53:1095-1107.
Greaney, A.J. et al. (Mar. 10, 2021). "Comprehensive Mapping of Mutations In The SARSCoV-2 Receptor-Binding Domain That Affect Recognition By Polyclonal Human Plasma Antibodies," Cell Host & Microbe 29:463-476.
Grifoni A. et al. (Jun. 25, 2020). "Targets of T Cell Responses to SARS-CoV-2 Coronavirus in Humans with COVID-19 Disease and Unexposed Individuals," Cell 181:1489-1501.
Gupta, A. et al. (Oct. 27, 2021). "Early Treatment for Covid-19 with SARS-Cov-2 Neutralizing Antibody Sotrovimab," N Engl J med 385:1941-1950.
Hansen, J. et. al. (Aug. 21, 2020). "Studies In Humanized Mice and Convalescent Humans Yield a SARS-CoV-2 Antibody Cocktail," Science 369(6506):1010-1014.
Hastie, K.M. et al. (Oct. 22, 2021). "Defining-Variant-Resistant Epitopes Targeted by SAR.S-CoV-2 Antibodies: A Global Consortium Study," Science. 374:472-478.
Jacobsen, H.J. et al. (2015). "Pan-HER, An Antibody Mixture Simultaneously Targeting EGFR, HER2, and HER3, Effectively Overcomes Tumor Heterogeneity and Plasticity," Clin. Cancer Res. 21(18):4110-4122.
Korber, B. et al. (Aug. 20, 2020). "Tracking Changes in SARS-CoV-2 Spike: Evidence that D614G Increases Infectivity of the COVI D-19 Virus," Cell 182(4):812-827 e1.9, 42 pages.
Lan, J. et al. (May 14, 2020, e-pub. Mar. 30, 2020). "Structure of the SARS-CoV-2 Spike Receptor-Binding Domain Bound To The ACE2 Receptor," Nature 581(7807):215-220.

Levites, Y. et al. (Apr. 22, 2015). "A Human Monoclonal IgG That Binds AP Assemblies and Diverse Amyloids Exhibits Anti-Amyloid Activities In Vitro and In Vivo," J Neurosci. 35(16):6265-6276.
Li, Q. et al. (Sep. 3, 2020). "The Impact of Mutations in SARS-CoV-2 Spike on Viral Infectivity and Antigenicity," Cell. 182:1284-1294.
Morens, D.M. et al. (Sep. 3, 2020). "Emerging Pandemic Diseases: How We Got to COVID-19," Cell, pp. 1077-1092.
Nikitin, P.A. et al. (2019). "C1s Inhibition By BIV V009 (Sutimlimab) Prevents Complement-Enhanced Activation of Autoimmune Human B Cells In Vitro," J. Immunol. 202:1200-1209.
North, B. et al. (Feb. 18, 2011, e-pub. Oct. 28, 2010). "A New Clustering of Antibody CDR Loop Conformations," J. Mol. Biol 406:228-256, 50 pages.
Puligedda, R.D. et al. (2019). "Capture and Display Of Antibodies Secreted By Hybridoma Cells Enables Fluorescent On-Cell Screening," MAbs 11(3):546-558.
Puligedda, R.D. et al. (Aug. 2014, e-pub. May 10, 2014). "Human Monoclonal Antibodies That Neutralize Vaccine and Wild-Type Poliovirus Strains," Antiviral Res. 108:36-43.
Puligedda, R.D. et al. (Feb. 28, 2020). "Human IgA Monoclonal Antibodies That Neutralize Poliovirus, Produced by Hybridomas and Recombinant Expression," Antibodies 9(5):1-17.
Robbiani, D.F. et al. (May 13, 2020). "Convergent Antibody Responses to SARS-CoV-2 Infection in Convalescent Individuals," BioRxiv, 51 pages.
Shi, J. et al. (Jun. 26, 2014). "TNT003, An Inhibitor Of The Serine Protease Cis, Prevents Complement Activation Induced By Cold Agglutinins," Blood 123(26):4015-4022.
Stamper, C.T. et al. (2020). Distinct B Cell Subsets Give Rise To Antigen-Specific Antibody Responses Against SARS-CoV-2, Research Square, 35 pages.
Sun. D. et al. (2021). "Potent Neutralizing Nanobodies Resist Convergent Circulating Variants of SARS-CoV-2 By Targeting Diverse and Conserved Epitopes," Nat. Comm. 12(4676):1-14.
Tursi, S.A. et al. (2020). "*Salmonella typhimurium* Biofilm Disruption By a Human Antibody That Binds a Pan-Amyloid Epitope On Curli," Nat. Commun. 11(1007):1-13.
Von Holle, T.A. et al. (Jun. 25, 2019). "Influenza and Antibody-Dependent Cellular Cytotoxicity," Front. Iininunol. 10(1457):1-8.
Zhou, P. et al. (Mar. 12, 2020, e-pub. Feb. 3, 2020). "A Pneumonia Outbreak Associated With A New Coronavirus Of Probable Bat Origin," Nature 579:270-273.
International Search Report and Written Opinion, dated Jun. 15, 2022, for PCT Application No. PCT/US2022/070026, filed Jan. 4, 2022, 17 pages.

* cited by examiner

|  | EC50 (nM) | | | | |
| --- | --- | --- | --- | --- | --- |
|  | REF | U.K. | S. African | Californian | Brazilian |
| IMM20184/IMM20190/IMM20253 | ND | 0.7 | 23 | ND | 31 |
| IMM20184/IMM20253 | 37 | 25 | 66 | 15 | 12 |

FIG. 6C

|  | Washington | U.K. | S.African | Brazil | California | Germany |
|---|---|---|---|---|---|---|
| Overall HSA Score | 2.1 | 15 | -8.4 | 1.8 | 7.5 | 1.6 |
| Peak HSA Score | 24.5 | 61.1 | 19.8 | 34.0 | 36.0 | 14.2 |

FIG. 7C

|  | EC50 (nM) | | |
| --- | --- | --- | --- |
|  | REF | UK | S. African |
| IMM20184/20190/20253 | 1.1 | 3.1 | 7.4 |
| IMM20184/20253 | 7.9 | 10.2 | 7.4 |

*FIG. 11D*

Ab1: IMM20253
Ab2: IMM21084
Synergy Score: 12.48

Ab1: IMM20253
Ab3: REGN987
Synergy Score: 9.52

Ab1: IMM20253
Ab4: REGN933
Synergy Score: 5.63

ANTIBODY COCKTAIL AGAINST SARS-COV-2 SPIKE PROTEIN

CROSS-REFERENCE TO RELATED APPLICATIONS

This application claims the priority benefit of U.S. Provisional Application No. 63/134,159 filed Jan. 5, 2021, U.S. Provisional Application No. 63/150,070 filed Feb. 16, 2021, U.S. Provisional Application No. 63/178,848 filed Apr. 23, 2021, U.S. Provisional Application No. 63/220,881 filed Jul. 12, 2021, U.S. Provisional Application No. 63/236,479 filed Aug. 24, 2021, U.S. Provisional Application No. 63/270,665 filed Oct. 22, 2021, and U.S. Provisional Application No. 63/284,963 filed Dec. 1, 2021, the disclosure of each of which is incorporated herein by reference in its entirety.

SEQUENCE LISTING

The content of the following submission on ASCII text file is incorporated herein by reference in its entirety: a computer readable form (CRF) of the Sequence Listing (file name: 224192000100SEQLIST.TXT, date recorded: Dec. 30, 2021, size: 98,788 bytes).

FIELD OF THE INVENTION

The present invention relates to antibodies used for treatment of SARS-CoV-2 infections.

BACKGROUND

Since its emergence in Wuhan, China in late 2019 [Zhou et al. 2020], the prolonged spread of the severe acute respiratory syndrome coronavirus 2 (SARS-CoV-2) virus has resulted in one of the most devastating global health challenges of the last century [Nature Editorial 2020, Morens & Fauci 2020, Chakraborty & Maity 2020]. With greater than 289 million confirmed cases and over 5.43 million deaths world-wide, the virus continues to pose an extraordinary challenge to the scientific community, consequently becoming an unprecedented socio-economic disaster and burdening healthcare systems around the world. Infection with SARS-CoV-2 results in a myriad of pathologies [Berlin et al. 2020] collectively referred to as COVID-19 [3]. While a majority of individuals who become infected with the virus are capable of generating a productive anti-viral response, for many their anti-viral humoral response will not be sufficient to shield them from a potentially deadly infection. Therefore, as the global community braces for the next Spike in infection and mortality rates, the urgency to develop effective therapeutics recapitulating the productive anti-viral response to combat the swelling health crisis has never been greater.

By the end of October 2020, a mere 11 months after the virus was first identified, the Clinicaltrials.gov database listed more than 3500 distinct clinical trial activities directed at patients infected with SARS-CoV-2. There is significant diversity among these efforts, from the assessment of existing drugs to the use of convalescent plasma from recovered patients, to the use of specific vaccines and antibodies directed at the viral S protein. It is not yet apparent that there will be a single approach that will prove to be uniformly effective at preventing viral infections or accelerating viral clearance in all groups of COVID-19 patients.

SARS-CoV-2 genomic RNA contains a large viral replicase gene, genes encoding non-structural proteins at its 5' end, and a region encoding four major structural and multiple accessory proteins at the 3' end. Structural proteins include Spike or Surface glycoprotein (S), Membrane protein (M), Envelope protein (E) and Nucleocapsid protein (N) [Fehr & Perlman 2015]. The membrane surface glycoprotein S consists of two subunits, 51 and S2, that mediate viral binding to the host receptor ACE2 and fusion with the host cell membrane, respectively. The 51 subunit contains the receptor binding domain (RBD) that directly interacts with ACE2 and is a target of multiple neutralizing antibodies currently in clinical trials [Lan et al. 2020, Robbiani et al. 2020]. The vast majority of the ongoing efforts are all targeting the S protein. Both passive (therapeutic antibodies) and active (vaccine) approaches directed at S protein are expected to promote virus neutralization, that is, inhibition of viral entry into healthy cells. Unfortunately, mutations in S protein have arisen, including ones the Center for Disease Control (CDC) has identified in a series of viral variants for which there is evidence of an increase in transmissibility, increased levels of hospitalization and/or deaths, significant reduction in neutralization by antibodies generated during previous infections or vaccinations, reduced effectiveness of treatments or vaccines, or diagnostic detection failures. These virus variants are considered Variants of Concern include Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2. Additionally, the CDC has identified Variants of Interests, which are defined as having specific genetic markers that are predicted to affect transmission, diagnostics, therapeutics, or immune escape. Data also demonstrates these variants of interest were the cause of an increased proportion of cases or outbreak, but they are of limited prevalence in the US or other countries.

Studies are described herein that elucidate the memory B cell antibody response in convalescent patients, using an approach that enables the generation of large, stable hybridoma libraries from primary human B cells. This approach was previously used to identify a panel of monoclonal antibodies from convalescent patients infected with natural polio virus (PV), oral PV-vaccinated and inactivated PV-boosted healthy subjects [Puligedda et al. 2014, Puligedda et al. 2017, Puligedda et al. 2020], and, most recently, an anti-amyloid antibody with the anti-biofilm activity [Tursi et al. 2020] from a hybridoma library generated with memory B cells from an Alzheimer's Disease patient [Levites et al. 2015].

Hybridoma libraries were generated from the memory B cells of convalescent COVID-19 blood donors who were eligible to donate convalescent plasma based upon their high titer of IgG antibodies against the SARS-CoV-2 virus. Monoclonal antibodies derived from those libraries were selected on the basis of their selective binding to one of multiple SARS-CoV-2 proteins used as targets in both cell-based and soluble protein-based screens. Characterization of these antibodies revealed broad responses to diverse viral antigens. Fewer than half of the antibodies were directed at S protein, while the remainder were directed at other viral proteins including N and ORF-encoded proteins. Even though the antibodies were directed at highly diverse SARS-CoV-2 antigens, they were generally characterized as having variable levels of somatic hypermutation (SHM) and a diversity of VH and VL gene usage. Functional properties of anti-Spike antibodies were successfully confirmed against reference strains (e.g., USA/WA_CDC-WA1/2020), as well as multiple variants including the CDC variants of concern, in series of tests ranging from in vitro neutralization of both pseudovirus and live virus isolates to in vivo neutralization activity in a hamster model of COVID-19. Three anti-Spike antibodies were identified that when mixed together in a cocktail exhibited combinatorial effects against those variants. These studies indicate that an unbiased interrogation of COVID-19 patient B cell repertoires is an effective approach to identifying specific antiviral antibodies and antibody mixtures with the desired binding and functional properties. Antibodies identified and characterized in this manner could be recombinantly produced to yield therapeutic or prophylactic products to address the COVID-19 pandemic. The rapidity with which antibodies from convalescent patients can be identified and characterized suggests that this platform could be a useful component of a rapid response to future pandemics.

SUMMARY OF THE INVENTION

Provided herein is composition comprising at least first and second recombinant antibodies that specifically bind to distinct epitopes of a Spike protein of SARS-CoV-2, wherein the first antibody binds to an epitope in an ACE2 receptor binding site of the Spike protein and the second antibody binds to an epitope outside of the ACE2 receptor binding site of the Spike protein.

Also provided herein composition comprising at least first and second antibodies that specifically bind to distinct epitopes of a Spike protein of SARS-CoV-2, wherein the first antibody neutralizes SARS-CoV-2 via an ACE2 independent mechanism and the second antibody neutralizes SARS-CoV-2 via an ACE2 dependent mechanism, wherein the first and second antibodies are recombinant antibodies.

In some embodiments, the composition further comprises a third antibody that specifically binds to the Spike protein of SARS-CoV-2 at an epitope distinct from the first and second antibodies. In some embodiments, the third antibody binds to an epitope outside of the ACE2 receptor binding site of the Spike protein. In some embodiments, the third recombinant antibody neutralizes SARS-CoV-2 via an ACE2 dependent mechanism.

Also provided herein is an antibody or antigen-binding fragment thereof that binds a SARS-CoV-2 Spike protein comprising
- a HCDR1, HCDR2, and HCDR3 of a heavy chain variable region (HCVR) comprising the amino acid sequence set forth in SEQ ID NO: 1, and a LCDR1, LCDR2, and LCDR3 of a light chain variable region (LCVR) comprising the amino acid sequence is set forth in SEQ ID NO: 2;
- a HCDR1, HCDR2, and HCDR3 of a heavy chain variable region comprising the amino acid sequence set forth in SEQ ID NO: 3, and a LCDR1, LCDR2, and LCDR3 of a LCVR comprising the amino acid sequence is set forth in SEQ ID NO: 4;
- a HCDR1, HCDR2, and HCDR3 of a HCVR comprising the amino acid sequence set forth in SEQ ID NO: 5, and a LCDR1, LCDR2, and LCDR3 of a LCVR comprising the amino acid sequence is set forth in SEQ ID NO: 6;
- a HCDR1, HCDR2, and HCDR3 of a HCVR comprising the amino acid sequence set forth in SEQ ID NO: 7, and a LCDR1, LCDR2, and LCDR3 of a LCVR comprising the amino acid sequence is set forth in SEQ ID NO: 8;
- a HCDR1, HCDR2, and HCDR3 of a heavy chain variable region comprising the amino acid sequence set forth in SEQ ID NO: 9, and a LCDR1, LCDR2, and LCDR3 of a light chain variable region (LCVR) comprising the amino acid sequence is set forth in SEQ ID NO: 10;
- a HCDR1, HCDR2, and HCDR3 of a HCVR comprising the amino acid sequence set forth in SEQ ID NO: 11, and a LCDR1, LCDR2, and LCDR3 of a LCVR comprising the amino acid sequence is set forth in SEQ ID NO: 12;
- a HCDR1, HCDR2, and HCDR3 of a HCVR comprising the amino acid sequence set forth in SEQ ID NO: 13, a LCDR1, LCDR2, and LCDR3 of a LCVR comprising the amino acid sequence is set forth in SEQ ID NO: 14;
- a HCDR1, HCDR2, and HCDR3 of a HCVR comprising the amino acid sequence set forth in SEQ ID NO: 15, and a LCDR1, LCDR2, and LCDR3 of a LCVR comprising the amino acid sequence is set forth in SEQ ID NO: 16
- a HCDR1, HCDR2, and HCDR3 of a HCVR comprising the amino acid sequence set forth in SEQ ID NO: SEQ ID NO: 17, and a LCDR1, LCDR2, and LCDR3 of a LCVR comprising the amino acid sequence is set forth in SEQ ID NO: 18
- a HCDR1, HCDR2, and HCDR3 of a HCVR comprising the amino acid sequence set forth in SEQ ID NO: 19, and a LCDR1, LCDR2, and LCDR3 of a LCVR comprising the amino acid sequence is set forth in SEQ ID NO: 20;
- a HCDR1, HCDR2, and HCDR3 of a HCVR comprising the amino acid sequence set forth in SEQ ID NO: 21, and a LCDR1, LCDR2, and LCDR3 of a LCVR comprising the amino acid sequence is set forth in SEQ ID NO: 22;
- a HCDR1, HCDR2, and HCDR3 of a HCVR comprising the amino acid sequence set forth in SEQ ID NO: 23, and a LCDR1, LCDR2, and LCDR3 of a LCVR comprising the amino acid sequence is set forth in SEQ ID NO: 24; or
- a HCDR1, HCDR2, and HCDR3 of a HCVR comprising the amino acid sequence set forth in SEQ ID NO: 25 and a LCDR1, LCDR2, and LCDR3 of a LCVR comprising the amino acid sequence is set forth in SEQ ID NO: 26.

In some embodiments, the antibody comprises
- a HCVR comprising the amino acid sequence set forth in SEQ ID NO: 1, and a LCVR comprising the amino acid sequence is set forth in SEQ ID NO: 2;
- a HCVR comprising the amino acid sequence set forth in SEQ ID NO: 3, and a LCVR comprising the amino acid sequence is set forth in SEQ ID NO: 4;
- a HCVR comprising the amino acid sequence set forth in SEQ ID NO: 5, and a LCVR comprising the amino acid sequence is set forth in SEQ ID NO: 6;
- a HCVR comprising the amino acid sequence set forth in SEQ ID NO: 7, and a LCVR comprising the amino acid sequence is set forth in SEQ ID NO: 8;
- a HCVR comprising the amino acid sequence set forth in SEQ ID NO: 9, and a LCVR comprising the amino acid sequence is set forth in SEQ ID NO: 10;
- a HCVR comprising the amino acid sequence set forth in SEQ ID NO: 11, and a LCVR comprising the amino acid sequence is set forth in SEQ ID NO: 12;
- a HCVR comprising the amino acid sequence set forth in SEQ ID NO: 13, a LCVR comprising the amino acid sequence is set forth in SEQ ID NO: 14;

a HCVR comprising the amino acid sequence set forth in SEQ ID NO: 15, and a LCVR comprising the amino acid sequence is set forth in SEQ ID NO: 16;

a HCVR comprising the amino acid sequence set forth in SEQ ID NO: SEQ ID NO: 17, and a LCVR comprising the amino acid sequence is set forth in SEQ ID NO: 18;

a HCVR comprising the amino acid sequence set forth in SEQ ID NO: 19, and a LCVR comprising the amino acid sequence is set forth in SEQ ID NO: 20;

a HCVR comprising the amino acid sequence set forth in SEQ ID NO: 21, and a LCVR comprising the amino acid sequence is set forth in SEQ ID NO: 22;

a HCVR comprising the amino acid sequence set forth in SEQ ID NO: 23, and a LCVR comprising the amino acid sequence is set forth in SEQ ID NO: 24; or a HCVR comprising the amino acid sequence set forth in SEQ ID NO: 25 and a LCVR comprising the amino acid sequence is set forth in SEQ ID NO: 26.

In some embodiments, provided herein is an antibody or antigen-binding fragment thereof that binds a SARS-CoV-2 Spike protein comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60;

a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72; or a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, the antibody is an Fc IgG1, IgG2, IgG3, IgG4, IgM, IgD, IgA1, IgA2 or IgE isotype. The antibody or antigen-binding fragment thereof of claim 9, wherein the antibody is an IgG1. In some embodiments, the IgG1 is a G1m1 or nG1m1 allotype. In some embodiments, the antibody comprises an immunoglobulin Fc region or fragment thereof of a human IgM. In some embodiments, the antibody is a fully human antibody. In some embodiments, the antibody is a full length antibody.

In some embodiments, the antibody or antigen-binding fragment thereof: inhibits binding of a SARS-CoV-2 virus to a host ACE2 receptor; fixes complement to a SARS-CoV-2 virus; induces phagocytosis of a SARS-CoV-2 virus; or any combination thereof.

In some embodiments, the binding of the antibody or antigen-binding fragment thereof neutralizes a SARS-CoV-2 virus by blocking binding of the receptor binding domain (RBD) of the virus with an ACE2 receptor. In some embodiments, the antibody is isolated.

Also provided herein is a composition comprising an antibody provided here. In some embodiments, the composition comprises two, three, or four of the antibodies provided herein.

In some embodiments, the composition comprises
a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

c) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114;

d) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

e) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or f) a first antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, provided herein is a composition comprising a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or c) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, provided herein is a composition comprising a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a fourth antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, the ratio between the first and the second recombinant antibodies is about 1:1. In some embodiments, the ratios between the first, second, and third antibodies are about 1:1:1. In some embodiments, the ratio between the first, second, third, and fourth antibodies is about 1:1:1:1. In some embodiments, the composition neutralizes at least 50% of one or more of the following variants of SARS-CoV-2: U.K. B.1.1.7; South African B.1.351; Brazil P.1; Omicron B.1.1.529 variant; and California B.1.429/427 relative to the neutralization of the USA/WA_CDC-WA1/2020 SARS-CoV-2 by the composition. In some embodiments, the composition neutralizes about 100% of one or more of the following variants of SARS-CoV-2: U.K. B.1.1.7; South African B.1.351; Brazil P.1; Omicron B.1.1.529 variant; and California B.1.429/427 relative to the neutralization of the USA/WA_CDC-WA1/2020 SARS-CoV-2 by the composition.

In some embodiments, the composition further comprises a pharmaceutically acceptable carrier or diluent.

Also provided herein is method of treating or preventing a SARS-CoV-2 infection in a subject, comprising administering a first antibody that neutralizes SARS-CoV-2 via an ACE2 independent mechanism and a second antibody that neutralizes SARS-CoV-2 via an ACE2 dependent mechanism. In some embodiments, the method comprises administering a composition or antibody provided herein to the subject. In some embodiments, the method comprises administering two, three, or four of the antibodies.

In some embodiments, provided herein is a method of treating or preventing a SARS-CoV-2 infection in a subject, comprising administering a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

c) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114;

d) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

e) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or f) a first antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

Also provided herein is a method of treating or preventing a SARS-CoV-2 infection in a subject, comprising administering a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or c) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, provided herein is a method of treating or preventing a SARS-CoV-2 infection in a subject, comprising administering a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and a fourth antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, the administering of the antibody or composition to the subject in need thereof comprises administering the composition into the body of the subject subcutaneously, intravenously, intranasally or intramuscularly.

In some embodiments, the method is for treating a SARS-CoV-2 infection.

Also provided herein are kits for treating or preventing a SARS-CoV-2 infection in a subject comprising a first antibody that specifically binds to a Spike protein of SARS-CoV-2 and neutralizes SARS-CoV-2 via an ACE2 independent mechanism and a second antibody that specifically binds to a Spike protein of SARS-CoV-2 and neutralizes SARS-CoV-2 via an ACE2 dependent mechanism.

In some embodiments, the kit comprises two, three, or four of the antibodies provided herein.

In some embodiments provided herein is a kit for treating or preventing a SARS-CoV-2 infection in a subject comprising a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

c) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114;
d) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;
e) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or
f) a first antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and
a second antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments, provided herein is a kit treating or preventing a SARS-CoV-2 infection in a subject comprising
a) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60,
a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;
b) a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60,
a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or
c) a first antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
a second antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and
a third antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

Also provided herein is a kit for treating or preventing a SARS-CoV-2 infection in a subject comprising
a first antibody comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60,
a second antibody comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66,
a third antibody comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and
a fourth antibody comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

In some embodiments the kit comprises instructions for use according to the methods provided herein.

In some embodiments, the SARS-CoV-2 virus is a SARS-CoV-2 variant.

In some embodiments, the antibody or composition treats or prevents SARS-CoV-2 variant and nonvariant infections with about equivalent efficacies.

In some embodiments, the SARS-CoV-2 variant is the U.K. (B.1.1.7) variant of SARS-CoV-2, the South African (B.1.351) variant of SARS-CoV-2, the California (B.1.429) variant of SARS-CoV-2, the California (B.1.427) variant of SARS-CoV-2, the Brazilian (P.1) variant of SARS-CoV-2, the New York (B.1.526) variant of SARS-CoV-2, the New York (B.1.526.1) variant of SARS-CoV-2, the UK/Nigeria (B.1.525) variant of SARS-CoV-2, the Brazilian (P.2) variant of SARS-CoV-2 or the Omicron (B.1.1.529) variant.

In some embodiments, the inventions described here include antibody compositions with at least first and second recombinant anti-SARS-CoV-2 antibodies that bind distinct epitopes of SARS-CoV-2, wherein at least one of the antibodies is selected from the group consisting of:

(a) an anti-Spike antibody comprising a heavy chain variable region (HCVR) as set forth in the amino acid sequence set forth in SEQ ID NO: 5 or fragment thereof, and a light chain variable region (LCVR) as set forth in the amino acid sequence set forth in SEQ ID NO: 6 or fragment thereof;

(b) an anti-Spike antibody comprising a HCVR as set forth in the amino acid sequence set forth in SEQ ID NO: 3 or fragment thereof, and a LCVR as set forth in the amino acid sequence set forth in SEQ ID NO: 4 or fragment thereof;

(c) an anti-Spike antibody comprising a HCVR as set forth in the amino acid sequence set forth in SEQ ID NO: 1 or fragment thereof, and a LCVR as set forth in the amino acid sequence set forth in SEQ ID NO: 2 or fragment thereof;

(d) an anti-Spike antibody comprising a HCVR as set forth in the amino acid sequence set forth in SEQ ID NO: 7 or fragment thereof, and a LCVR as set forth in the amino acid sequence set forth in SEQ ID NO: 8 or fragment thereof;

(e) an anti-Spike antibody comprising a HCVR as set forth in the amino acid sequence set forth in SEQ ID NO: 9 or fragment thereof, and a LCVR as set forth in the amino acid sequence set forth in SEQ ID NO: 10 or fragment thereof;

(f) an anti-Spike antibody comprising a HCVR as set forth in the amino acid sequence set forth in SEQ ID NO: 11 or fragment thereof, and a LCVR as set forth in the amino acid sequence set forth in SEQ ID NO: 12 or fragment thereof, (g) an anti-Spike antibody comprising a HCVR as set forth in the amino acid sequence set forth in SEQ ID NO: 13 or fragment thereof, and a LCVR as set forth in the amino acid sequence set forth in SEQ ID NO: 14 or fragment thereof, (h) an anti-Spike antibody comprising a HCVR as set forth in the amino acid sequence set forth in SEQ ID NO: 15 or fragment thereof, and a LCVR as set forth in the amino acid sequence set forth in SEQ ID NO: 16 or fragment thereof, (s) an anti-ORF8 antibody comprising a HCVR as set forth in the amino acid sequence set forth in SEQ ID NO: 37 or fragment thereof, and a LCVR as set forth in the amino acid sequence set forth in SEQ ID NO: 38 or fragment thereof; and (t) an anti-ORF8 antibody comprising a HCVR as set forth in the amino acid sequence set forth in SEQ ID NO: 39 or fragment thereof, and a LCVR as set forth in the amino acid sequence set forth in SEQ ID NO: 40 or fragment thereof.

The molar or weight ratios between antibodies or antigen-binding fragments thereof in a composition of the invention that are specific for different epitopes, (i.e., a first, second, third, fourth, fifth, sixth, and so on), generally ranges from about (1:10) to (10:1), but is not limited by this disclosure. Accordingly, for example, the molar or weight ratio between first and second antibodies may be 1:1, or 1:1:1 between first, second, and third antibodies, or 1:1:1:1 between first, second, third, and fourth antibodies.

Antibody compositions of the invention may effectively neutralize non-variant and variant SARS-CoV-2. For example, a composition may neutralize at least 50%, 60%, 70%, 80%, 90%, or 100% of the viral load of one or more of the following variants of SARS-CoV-2: U.K. (alpha, B.1.1.7); South African (beta, B.1.351); Brazil (gamma, P.1); India (delta, B.1.617.2); and California (epsilon, B.1.429/427) relative to the neutralization of the USA/ WA_CDC-WA1/2020 SARS-CoV-2 by the composition.

BRIEF DESCRIPTION OF THE DRAWINGS

FIG. 4B depicts in vitro neutralizing activity of the identified anti-Spike antibody PR194_00232 against the live virus isolate SAR-CoV-2/human/Germany/BavPAt 1/2020, which contains a mutated Spike protein (D614G).

FIGS. 6A-6C depict the concentration-dependent ability of the triple antibody cocktail (IMM20184/IMM20190/ IMM20253) and the two antibody cocktail (IMM20184/ IMM20253) to neutralize pseudoviruses expressing the reference (WA1/2020), alpha/UK, beta/S. African, gamma/ Brazilian, or Epsilon/Californian Spike proteins.

FIGS. 7A-7C depicts the combinatorial activity of the IMM20184/IMM20190/IMM20253 triple combination against pseudoviruses expressing the Spike protein from the reference strain (WA_CDC-WA1/2020), U.K. (B.1.1.7/alpha), South African (B.1.351/beta), Californian (B.1.429/ epsilon), or Brazilian (P.1/P.2/gamma) variants of SARS-CoV-2 (FIG. 7A) and the live virus BavPat1/2020 that contains the D614G mutation (FIG. 7B). Dark gray area represent regions of synergy. Bottom portion of the figure lists the overall and peak HSA scores against each strain.

FIGS. 11A-11D depict in vitro neutralization activity of the triple (IMM20184/IMM20190/IMM20253) and double (IMM20184/IMM20253) combinations of antibodies against three live virus strains as measured by plaque forming assays; the reference strain (WA_CDC-WA1/2020) (FIG. 11A), U.K. (B.1.1.7/alpha) (FIG. 11B), South African (B.1.351/beta) (FIG. 11C).

DETAILED DESCRIPTION

Figure 1:
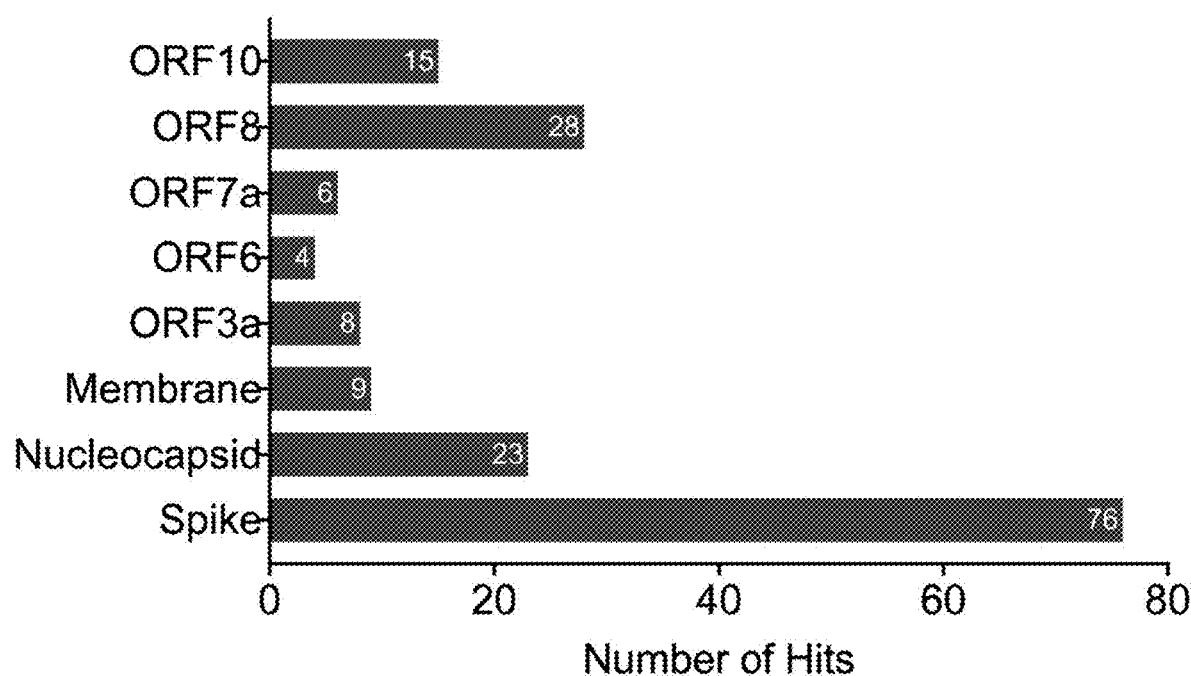
FIG. 1 depicts the breadth of antibodies isolated against a range of SARS-CoV-2 viral proteins.

Antibodies specific for the severe acute respiratory syndrome coronavirus 2 (SARS-CoV-2) virus are described herein. These antibodies may be used to neutralize SARS-CoV-2 by preventing the virus from infecting new host cells. Therefore, the inventions disclosed here also relate to pharmaceutical compositions that contain one or more antibodies of the invention, as well as relate to methods of preventing or treating a SARS-CoV-2 infection in a subject in need thereof. Accordingly, the inventions disclosed herein also relate to methods of administering antibody compositions of the invention to a subject in need thereof.

In some embodiments, the antibodies, compositions, and kits provided herein are especially effective for treating and/or preventing SARS-CoV-2 due to particular novel properties. In some embodiments, provided herein are antibodies that bind to the Spike protein at multiple different locations, for example at multiple non-overlapping epitopes. This is beneficial because SARS-CoV-2 variants may have one or more mutations in the Spike protein to evade the immune system. Thus providing multiple antibodies that bind to multiple different locations in the Spike protein allows binding and neutralization of such variants.

Moreover, some of the antibodies provided herein bind to an ACE2 binding site in the Spike protein, while others bind outside the ACE2 binding site. Without being bound by theory, providing multiple antibodies, some of which target the ACE2 binding site and some of which target regions outside of the ACE2 binding site may combine to provide more effective treatment for SARS-CoV-2.

Accordingly, in some embodiments, provided herein is a method of treating or preventing SARS-CoV-2 comprising administering multiple antibodies that bind to non-overlapping epitopes on the Spike protein. In some embodiments, the method comprises administering an antibody that binds to an ACE2 binding site of the Spike protein and an antibody that binds to an epitope outside of the ACE2 binding site of the Spike protein. In some embodiments, the method comprises administering an antibody that neutralizes SARS-CoV-2 through an ACE2-dependent mechanism and an antibody that neutralizes SARS-CoV-2 through an ACE2-independent mechanism.

In some embodiments, provided herein is a composition comprising antibodies that bind to non-overlapping epitopes on the Spike protein. In some embodiments, the composition comprises an antibody that binds to an ACE2 binding site of the Spike protein and an antibody that binds to an epitope outside of the ACE2 binding site of the Spike protein. In some embodiments, the composition comprises an antibody that neutralizes SARS-CoV-2 through an ACE2-dependent mechanism and an antibody that neutralizes SARS-CoV-2 through an ACE2-independent mechanism.

In some embodiments, provided herein is a kit comprising antibodies that bind to non-overlapping epitopes on the Spike protein. In some embodiments, the kit comprises an antibody that binds to an ACE2 binding site of the Spike protein and an antibody that binds to an epitope outside of the ACE2 binding site of the Spike protein. In some embodiments, the kit comprises an antibody that neutralizes SARS-CoV-2 through an ACE2-dependent mechanism and an antibody that neutralizes SARS-CoV-2 through an ACE2-independent mechanism.

In some aspects, provided herein is an antibody that binds with high affinity to SARS-CoV-2 variants comprising mutated Spike protein. In some embodiment, the mutated Spike protein causes the Spike protein to be pre-cleaved (i.e. cleaved prior to binding the surface of the host cell) or more susceptible to cleavage when binding to the host cell. In some embodiments, such variants correlate with faster viral spread, thus underscoring the utility of the antibodies provided herein for treating and preventing SARS-CoV-2 infections.

Antibodies of the invention are typically monoclonal antibodies, meaning an antibody is produced by a single clonal B-lymphocyte population, a clonal hybridoma cell population, or a clonal population of cells into which the genes of a single antibody, or portions thereof, have been transfected. Monoclonal antibodies are produced by methods known to those of skill in the art, for instance by making hybrid antibody-forming cells from a fusion of myeloma cells with immune lymphocyte cells.

An antibody of the invention may also be an "antigen-binding fragment". An antigen-binding fragment refers to a polypeptide fragment of an immunoglobulin or antibody that binds antigen or competes with intact antibody (i.e., with the intact antibody from which they were derived) for antigen binding (i.e., specific binding to an epitope of SARS-CoV-2). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means. Examples of immunoglobulin variants that are considered antibodies according to the invention include single-domain antibodies (such as VH domain antibodies), Fab fragments, Fab' fragments, F(ab)'2 fragments, single chain Fv proteins ("scFv"), and disulfide stabilized Fv proteins ("dsFv"). A VH single-domain antibody is an immunoglobulin fragment consisting of a heavy chain variable domain. An Fab fragment contains a monovalent antigen-binding immunoglobulin fragment, which can be produced by digestion of whole antibody with the enzyme papain to yield an intact light chain and a portion of one heavy chain. Similarly, an Fab' fragment also contains a monovalent antigen-binding immunoglobulin fragment, which can be produced by digestion of whole antibody with the enzyme pepsin, followed by reduction, to yield an intact light chain and a portion of the heavy chain. Two Fab' fragments are obtained per immunoglobulin molecule. A (Fab')$_2$ fragment is a dimer of two Fab' fragments, that can be obtained by treating whole antibody with the enzyme pepsin without subsequent reduction, so Fab' monomers remain held together by two disulfide bonds. An Fv fragment is a genetically engineered fragment containing the variable region of the light chain and the variable region of the heavy chain expressed as two chains. A single chain ("sc") antibody, such as scFv fragment, is a genetically engineered molecule containing the $V_L$ region of a light chain, the $V_H$ region of a heavy chain, linked by a suitable polypeptide linker as a genetically fused single chain molecule. A dimer of a single chain antibody, such as a scFV2 antibody, is a dimer of a scFV, and may also be known as a "miniantibody". A $dsFv_2$ variant also contains a $V_L$ region of an immunoglobulin and a $V_H$ region, but the chains have been mutated to introduce a disulfide bond to stabilize the association of the chains.

One of skill in the art will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules.

An antibody of the invention is typically a "human" antibody, which may also be referred to as a "fully human" antibody. An antibody which possess a human framework regions and CDRs from a human immunoglobulin is generally be considered to be a human or humanized antibody. For example, a human or humanized antibody may contain the framework and the CDRs of an antibody from the same originating human heavy chain, or human light chain amino acid sequence, or both. Alternatively, the framework regions may originate from one human antibody, and be engineered to include CDRs from a different human antibody.

An antibody according to the invention may also comprise a "tagged" immunoglobulin CH3 domain to facilitate detection of the biologic against a background of endogenous antibodies. More particularly, a tagged CH3 domain is a heterogeneous antibody epitope that has been incorporated into one or more of the AB, EF, or CD structural loops of a human IgG-derived CH3 domain. For example a CH3 tag may be incorporated into the structural context of an IgG1 subclass antibody, other human IgG subclasses, including IgG2, IgG3, and IgG4. Epitope-tagged CH3 domains, also referred to as "CH3 scaffolds" can be incorporated into any antibody of the invention having a heavy chain constant region, generally in the form of an immunoglobulin Fc portion. Examples of CH3 scaffold tags, and methods for incorporating them into antibodies are disclosed in International Patent Application No. PCT/US2019/032780. Antibodies used to detect epitope tagged CH3 scaffolds, and antibodies of the invention, that comprise epitope tagged CH3 scaffolds, are generally referred to herein as "detector antibodies".

Some antibodies of the invention may be described as an "isolated" antibody or "isolated" antigen-binding fragment thereof. An isolated antibody or antigen-binding fragment thereof has been substantially separated or purified away from other biological components environment, such as a cell, proteins and organelles. Ordinarily, an isolated antibody or antigen-binding fragment thereof is prepared by a process involving at least one purification step, although the term "isolated" is not intended to refer to a complete absence of such biological molecules or to an absence of water, buffers, or salts or to components of a pharmaceutical formulation that includes an antibody or antigen-binding fragment of the invention.

In some embodiments of the invention, antibody or antigen-binding fragment thereof is specific for the Spike protein (S) of SARS-CoV-2. Thus, an antibody or antigen-binding fragment thereof may, in one embodiment, bind the 51 subunit of the Spike protein, while in another embodiment, an antibody or antigen-binding fragment thereof binds the S2 subunit. Moreover, some antibodies or antigen-binding fragments thereof bind to the receptor-binding domain (RBD) of the S protein, while other antibodies of the invention bind to non-RBD epitopes of the S protein. RBD-binding antibodies or antigen-binding fragments thereof of the invention may, in certain embodiments, bind a soluble form of the RBD of the S protein. Some antibodies or antigen-binding fragments of the invention bind to sites on the RBD that are resistant to mutational drift. For example, in some embodiments, an antibody or antigen-binding fragment thereof binds the RBD at, or in close proximity of such a site described by Greaney t al. (2021) as the "the E465 patch".

Indeed, among the antibodies of the invention that bind the Spike protein, there are some that bind to highly-conserved epitopes. Accordingly, binding of an antibody or antigen-binding fragment of the invention to a highly-conserved site of the SARS-CoV-2 Spike protein is not affected by point mutations in the Spike protein associated with variants of SARS-Cov-2, Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2.

In certain embodiments of the invention, an isolated antibody or antigen-binding fragment thereof contains a heavy chain variable region (HCVR) and a light chain variable region (LCVR) that is described in Table 1. In some embodiments, provided herein is an antibody comprising a HCDR1, a HCDR2, a HCDR3, a LCDR1, a LCDR2, and a LCDR3 of a heavy chain variable region (HCVR) and a light chain variable region (LCVR) that is described in Table 1. In some embodiments, provided herein is an antibody comprising a HCDR1, a HCDR2, a HCDR3, a LCDR1, a LCDR2, and a LCDR3 set forth in Table 1. In some embodiments, the CDRs are determined using Kabat, Chothia, or contact systems. In some embodiments, the CDRs are determined using the system described in North et al. J.M.B 406(8):228-56 (2011) as set forth in Table 1.

TABLE 1

| Sequence Name | Binds | Description | Amino acid sequence | SEQ ID No. |
|---|---|---|---|---|
| PR193_00018_HC (derived from IMM200184) | S RBD | VH of IMM200184 antibody | EVQLVESGGGLVQPGGSLRLSCSAS GFTFSSFWMSWVRQAPGKGLEWVAT IREDGSEKYYVDSVKGRFSISRDNA KNSLYLQMNSLRAEDTAVYYCARSK WLRGSFDYWGQGTLVTVSS | 1 |
| PR193_00018_LC (derived from IMM200184) | S RBD | VL of IMM200184 antibody | NFMLTQPHSVSESPGKTVTISCTRR SGSIASNYVQWYQQRPGSAPTTVIY EDNQRPSGVPDRFSGSIDSSSNSAS LTISGLQTEDEADYYCQSYDSSNPP GASWVFGGGTKLTVL | 2 |
| PR194_00232_HC (derived from IMM20190) | S RBD | VH of IMM20190 antibody | EVQLVESGGGLVQPGGSLRLSCSAS GFTVSSNYMSWVRQAPRKGLEWVSV IYAGGSTFYADSVKGRFTISRDNSK NTLLLQMNSLRAEDTAVYYCARDRG GYLDYWGQGTLVTVSS | 3 |
| PR194_00232_LC (derived from IMM20190) | S RBD | VL of IMM20190 antibody | DIQMTQSPSSLSASVGDRVTITCRA SQGISNYLAWYQQKPGKVPKLLIYA ASTLQSGVPSRFSGSGSGTDFTLTI SSLQPEDVATYYCQKYNSAPGLTFG GGTKVEIK | 4 |
| PR200_00622_HC (derived from IMM20253) | S RBD | VH of IMM20253 antibody | QVQLVESGGGVVQPGRSLRLSCTAS GFTFSTYGMHWVRQAPGKGLEWVAV ISYDGSSKHYAESVKGRFTISRDNS NNTLYLQMNRLRAEDTAVYYCARDG QPPGWGNYFDYWGQGTLVTVAS | 5 |
| PR200_00622_LC (derived from IMM20253) | S RBD | VL of IMM20253 antibody | SYVLTQPPSVSVAPGKTARITCGGN GIGSKSVYWYQQKPGQAPEVVVYDD SDRPSGIPERFSGSNSGNTATLTIS RVEAGDEADYYCQVWDSSSDPWVFG GGTKLTVL | 6 |
| PR194_00453_HC | S RBD | | QLQLQESGPGLVKPSETLSLTCTVS GGSISSSSSYWGWFRQPPGKGLGWI RSIYYSGSTYYNPSLKSRVTMSVDT SKNQFSLKLSSVTAADTAVYYCARA KFSVWDNYRYPFDYWGQGILVTVSS | 7 |
| PR194_00453_LC | S RBD | | QSVLTQPPSASGTPGQRVTISCSGS SSNIGSNTVNWYQQLPGTAPKLLIY SNNQRPSGVPDRFSGSKSGTSASLA ISGLQSEDEADYYCAAWDDSLNGWV FGGGTKLTVL | 8 |
| PR196_00109_b_HC | S Non-RBD | | QVQLVESGGGVVQPGRSLRLSCAAS GFTFSNYGMHWVRQAPGKGLEWVAV IWYDGSNKYYADSVKGRFTISRDNS KNTLYVQMNSLRAEDTAVYYCARER LEDTAMVNFLDYWGQGTLVTVSS | 9 |
| PR196_00109_b_LC | S Non-RBD | | SYELTQPPSVSVSPGQTASITCSGD KLGHKYASWFQQRPGQSPVLVIYQD AKRPSGIPERFSGSNSGNTATLTIS GTQAMDEADYYCQAWDSSTVVFGGG TKLTVL | 10 |
| PR196_00413_a_HC | S Non-RBD | | QVQLVQSGAEVKKPGSSVKVSCKAS GGTFSSYAITWVRQAPGQGLEWMGG IIPIFGTANYAQKFQGRVTITADES TSTAYMELSSLRSEDTAVYYCASDY GDSPLGYWGQGTLVTVSS | 11 |

TABLE 1-continued

| Sequence Name | Binds | Description | Amino acid sequence | SEQ ID No. |
|---|---|---|---|---|
| PR196_00413_a_LC | S Non-RBD | | DIVMTQSPDSLAVSLGEPASINCTS SQSVLYSSNNKNFLAWYQQKPGQPP KLLIYWASTRESGVPDRFSGSGSGT DFTLTISSLQAEDVAVYYCQQYYSA PLTFGGGTKVEIK | 12 |
| PR194_00292_HC | S Non-RBD | | QVQLQQWGAGLLKPSETLSLTCAVY GGSLSGYYWSWIRQPPGKGLEWIGE INHSGSTNHNPSLKSRVSISVDTSK NQFSLKLSSVTAADTAVYYCARAWK YSSSWYSGGIYYGMDVWGQGTTVTV SS | 13 |
| PR194_00292_LC | S Non-RBD | | QSALTQPASVSGSPGQSITISCSGT SSDVGSYNLVSWYQQHPGKAPKLMI YEGTKRPSGVSNRFSSSKSGNTASL TISGLQAEDEADYYCCSYAGFSTWV FGGGTKLTVL | 14 |
| PR194_00364_b_HC | S Non-RBD | | EVQLVESGGGLVKPGGSLRLSCSAS GFTFTTYTMNWVRQAPGKGLEWVSS ISSTGLSIYYADSVKGRFTISRDNA KNSLYLQMNSLRAEDTAVYYCARDP SPTTIYYYYYMDVWGKGTTVTVSS | 15 |
| PR194_00364_b_LC | S Non-RBD | | QSALTQPASVSGSPGQSITISCTGT SSDVGTYNLVSWYQHYPGKAPKLII YEVSKRPSGVSDRFSGSKSGNTASL TISGLQAEDEADYYCCSYAGSTTGY VVFGGGTKLTVL | 16 |
| PR197_00647_HC | S Non-RBD | | QVQLVESGGGVVQPGRSLRLSCAAS GFTFSSYAMHWVRQAPGKGLQWVTL ISYDGGDKYYADSVRGRFTISRDNS KNTLYLQMNSLRTEDTAVYYCARDR PQTGDWFPPIPTGVLDVWGQGTTVT VSS | 17 |
| PR197_00647_LC | S Non-RBD | | DIQMTQSPSSLSASVGDRVTITCRA SQGISNYLAWFQQKPGKAPKSLIYA ASSLQSGVPSRFSGSESGTDFTLTI SSLQPEDFATYYCQQYHSYPITFGQ GTRLEIK | 18 |
| PR199_00255_HC (derived from IMM20279) | S RBD | VH of IMM20279 antibody | QVQLVESGGGVVQPGRSLRLSCAAS GFTFSTYGMHWVRQAPGKGLEWVAV IWYNGINKHYADSVKGRFTISRDNS KNTLYLQMSSLRVEDTAVYYCARDW GTLTTLFDFWGQGTLVTVSS | 19 |
| PR199_00255_LC (derived from IMM20279) | S RBD | VL of IMM20279 antibody | DIQMTQSPSSLSASVGERATITCRA SQSISSHLNWYQQKPGKAPKFLIYG ASSLQSGVPSRFSGSGSGTDFTLTI SSLQPEDFATYYCQQSYSTPPWTFG QGTKVEIK | 20 |
| PR199_00255_opt_HC | S RBD optimized | | QVQLVESGGGVVQPGRSLRLSCAAS GFTFSTYGMHWVRQAPGKGLEWVAV IWYNGINKYYADSVKGRFTISRDNS KNTLYLQMNSLRAEDTAVYYCARDW GTLTTLFDFWGQGTLVTVSS | 21 |
| PR199_00255_opt_LC | S RBD optimized | | DIQMTQSPSSLSASVGDRVTITCRA SQSISSHLNWYQQKPGKAPKLLIYG ASSLQSGVPSRFSGSGSGTDFTLTI SSLQPEDFATYYCQQSYSTPPWTFG QGTKVEIK | 22 |
| PR201_00151_HC | S RBD | | RVTLRESGPALVKPTQTLTLTCTFS GFSLNTSGMCVSWIRQPPGKALEWL ARIDWDDDKYYSTSLETRLTISKDT SKNQWLTMTNLDPVDTGTYYCARIS IQSRGGGADYWGQGTLVTVSS | 23 |

TABLE 1-continued

| Sequence Name | Binds | Description | Amino acid sequence | SEQ ID No. |
|---|---|---|---|---|
| PR201_00151_LC | S RBD | | DIQMTQSPSSLSASVGDRVTITCRASQSISSYLHWYQQKSGKAPKLLIFVASTLQSGVPSRFSGSGSGTDFTLTISSLQPEDSAAYYCQQSYSPPWTFGQGTKVEIK | 24 |
| PR194_00068_HC | S Non-RBD | | EVQLLESGGGLVQPGGSLRLSCSASGFTFTNYAMSWVRQAPGKGLEWVSTISGSGGSTYYADSVKGRFTISRDNSKSTLFLQMNSLRAEDTAIYYCANSGPTGDLDYWGQGTLVTVSS | 25 |
| PR194_00068_LC | S Non-RBD | | SYELTQPPSVSVSPGQTTLSLTCSGDKLGNKYVCWYQQKPGQSPVLVIYQDTKRPSGIPERVSGSNSGDTATLTISGTQAMDEADYYCQAWDSSTAVFGGGTKLTVL | 26 |
| PR198_00478_HC | ORF3a | | EVQLVESGGGLVKPGGSLRLSCTASGFTFNKAWMSWVRQPPGKGLEWVGRIQSKTDDETTDYAAPVKGRFIVSRDSKNTLYLQMNSLKIEDTAIYYCTSRAHYGSGTSYTPFDYWGQGTLVTVSS | 27 |
| PR198_00478 LC | ORF3a | | DIVMTQSPLSLPVTPGEQASISCRSSQSLLYSNGYNYLDWYLQKPGQSPRLLIYMGSNRASGVPDRFSGSGSGTDFTLKISRVEAEDVGVYYCMQTLQTLFTFGPGTKVDIK | 28 |
| PR210_01029_λ_v1_HC | M | | QVQLQESGPGLVKPSETLSLTCAVYGGSFSGYYWSWIRQPPGKGLEWIAEIDHSGSTNYNPSLKSRVTISVDTSKNQFSLKLRSVTAADTAVYYCARTTSITIFGILVAGGHNCFDSWGQGTLVTVSS | 29 |
| PR210_01029_λ_v1_LC | M | | QSALTQPASVSGSPGQSITISCSGTSSDVGNYDLVSWYQQHPGKAPKVMIYEVTKRPSGVSNRFSGSKSGNTASLTISGLQAEDEADYYCCSYTSSGTFWVFGGGTKLTVL | 30 |
| PR197_00350_HC | NC | | QVQLVQSGAEVKKPGSSVKVSCKASGGTFSNYAINWVRQAPGQGLEWMGGIIPIFGTTNYAQSFQGRVTITADESTSTAYMELSSLRSEDTAVYYCARAGYSSSWYRSTILSYYNYYGLDVWGQGTLVTVSS | 31 |
| PR197_00350_LC | NC | | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQAQQTSFGQGTKLEIK | 32 |
| PR210_01524_HC | NC | | QVQLVESGGGVVQPGRSLRLSCAASGFTFSDYGMHWVRQAPGKGLEWVAVIWYDGSYKYYADSVKGRFTISRDNSKNTVYLQMHSLRAEDTAVYYCARDGQWLRILDYWGQGTLVTVSS | 33 |
| PR210_01524_LC | NC | | EIVLTQSPGTLSLSPGERVTLSCRASQSVRSSSLGWYQQKPGQAPRRLIFGASNRATGIPDRFSGSGSGTDFTLTISRLEPEDFAVYYCQQSGSSLFTFGQGTKLEIK | 34 |
| PR210_00852_HC | NC | | QLQLQESGPGLVKPSETLSLTCTVSGASISSTTYYWGWIRQPPGKGLEWIGSIHYVGSTYYNSSLKSRVTISVDTSKNQFSLKLGSVTAADTAVYYCTLSVAGTFYGLDVWGQGTTVTVSS | 35 |

TABLE 1-continued

| Sequence Name | Binds | Description | Amino acid sequence | SEQ ID No. |
|---|---|---|---|---|
| PR210_00852_LC | NC | | DIQMTQSPSSVSASVGDRVTITCRASQGISSWLAWYQQKPGKAPNLLIYAASSLQSGVPSRFSGSGSGTDFTLTISSLQPEDFATYYCQQANSFPLTFGGGTKVEIK | 36 |
| PR199_00106_b_λ_HC | ORF8 | | EVQLVESGGALVKPGGSLRLSCAASGFTFRNVWMNWVRQAPGKGLEWVGRIKSKTDGGTIDYAAPMKGRLIISRDDSKNMLYLQMSSLKTDDTAVYYCTTHSIRGFEIWGQGTMVTVSS | 37 |
| PR199_00106_b_λ_LC | ORF8 | | SYELTQPPSVSVSPGQTARITCSGDALPKQYAYWYQQKAGQAPVLVIYKDSERPSGIPGRFSGSTSGTTVTLTISGVQAEDEADYYCQSADSSGAPLVFGGGTKLTVL | 38 |
| PR199_00179_κ_HC | ORF8 | | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARDRASGRVGSRFDYWGQGTLVTVSS | 39 |
| PR199_00179_κ_LC | ORF8 | | DIQMTQSPSSLSASVGERATLTCRASQSISSYLNWYQQKPGKAPKLLIYAASSLQSGVPSRFSGSGSGTDFTLTISSLQPEDFATYYCQQSYSTPRVTFGQGTKVEIK | 40 |
| PR197_00705_HC | S RBD | | QVQLQESGPGLVKPSQTLSLTCTVSGDSVSSGDYYWGWIRQHPGKGLEWIGYIYYTGRTFDNPSLKSRLTMSVDTSKNQFSVRLYSVTAADTAVYYCARARDSEGFSQYYFDYWGQGTLVTVSS | 41 |
| PR197_00705_LC | S RBD | | DIQMTQSPSSLSASVGDKVNITCQASEDIDVYLSWYQQKPGKAPKLLIYDASNLETGVPSRFSGSGSGTDFAFTISSLQPEDVATYYCQQYDNLPTFGGGTKVEIK | 42 |
| PR194_00547_r_HC | S Non-S1 | | QVQLVQSGAEVKKPGASVKISCKASGYTFTSYGISWVRQAPGQGLEWMGWISAYNGNTNYAQKLQGRVTMTTDISTSTAYMELRSLKSDDTAVYYCAREVWGAGYYFDYWGQGTLVTVSS | 43 |
| PR194_00547_r_LC | S Non-S1 | | SYELTQPPSVSVSPGQTARITCSGDALPKQYAYWYQQKPGQAPVLVIYKDSERPSGIPERFSGSSSGTTVTLTISGVQAEDEADYYCQSADSSGTYVVFGGGTKLTVL | 44 |
| PR194_00195_HC | S Non-S1 | | QVQLVQSGAEVKKPGSSVKVSCKASGGTFSNYAINWVRQAPGQGLEWMGGIIPIFRTANYAQKFQGRVTITADESTSTACMELSSLRFEDTAVYYCAREYSSSSGFYFDYWGQGTLVTVSS | 45 |
| PR194_00195_LC | S Non-S1 | | QSALTQPASVSGSPGQSITISCSGTSSDVGSYNLVSWYQQHPGKAPKLMIYEGNKRPSGVSNRFSGSKSGNTASLTISGLQAEDEADYYCCSYAGSSAWMFGGGTKLTVL | 46 |
| PR194_00292_HC | S Non-RBD | | QVQLQQWGAGLLKPSETLSLTCAVYGGSLSGYYWSWIRQPPGKGLEWIGEINHSGSTNHNPSLKSRVSISVDTSKNQFSLKLSSVTAADTAVYYCARAWKYSSSWYSGGIYYGMDVWGQGTTVTVSS | 47 |

TABLE 1-continued

| Sequence Name | Binds | Description | Amino acid sequence | SEQ ID No. |
|---|---|---|---|---|
| PR194_00292_LC | S Non-RBD | | QSALTQPASVSGSPGQSITISCSGT SSDVGSYNLVSWYQQHPGKAPKLMI YEGTKRPSGVSNRFSSSKSGNTASL TISGLQAEDEADYYCCSYAGFSTWV FGGGTKLTVL | 48 |
| PR194_00591_HC | S Non-S1 | | QVQLVESGGGVVQPGRSLRLSCAVS GFIFSSHGMHWVRQAPGKGLEWMTV ISYDGSKKHYADSVQGRFIISRDNS KNMVYLQMNDLRAEDTAVYYCAKDA TYCDSITSWCARYSHMDVWGRGTSV TVSS | 49 |
| PR194_00591_LC | S Non-S1 | | LRVWVSWTVDHHLTCSGASSDLGAY NYVSWYQQHPGKAPNLMIYDVNHRP SGVSNRFSGSKSGNTASLTISGLQP EDEADYYCSSYTSRSTLVFGGGTRL TVL | 50 |
| PR196_00042_HC | S Non-S1 | | QVQLQESGPGLVKPSDTLSLICTVS GGSIRSYYWSWIRQPPGKGLQWIGY IYYSGSTNYNPSLKSRVTISVDTSK NQFSLKLSSVTAADTAVYYCASYSG YDWGGFDYWGQGTLVTVSS | 51 |
| PR196_00042_LC | S Non-S1 | | QSVLTQPPSASGTPGQRATISCSGS RSNIGSNTVNWYQQLPGTAPKLLIY SDNQRPSGVPDRFSGSKSGTSASLA VSGLQSEDEADYYCAAWDDSLNGPV FGGGTKLTVL | 52 |
| PR194_00448_HC | S Non-S1 | | QLQLQESGPGLVKPSETLSLTCTVS GGSISNSNYYWGWVRQPPGKGLEWI GSLYYTGSTYYTPSLKSRVAMAVDT SKNLFSLKLSSVTAADTALYYCARL FSSGYYSPLYSFDYWGQGTLVTASS | 53 |
| PR194_00448_LC | S Non-S1 | | SVSGSPGQSITISCTGTTSSDVGGY NFVSWYQQHPGKAPKLMIYDVSNRP SGVSNRFSGSKSGNTASLTISGLRA EDEADYYCSSYTSSSTLIFGGGTKL TVL | 54 |
| PR193_00018_HC | | HCDR1 of IMM200184 | SASGFTFSSFWMS | 55 |
| PR193_00018_HC | | HCDR2 of IMM200184 | TIREDGSEKYYVD | 56 |
| PR193_00018_HC | | HCDR3 of IMM200184 | ARSKWLRGSFDY | 57 |
| PR193_00018_LC | | LCDR1 of IMM200184 | TRRSGSIASNYVQ | 58 |
| PR193_00018_LC | | LCDR2 of IMM200184 | YEDNQRPS | 59 |
| PR193_00018_LC | | LCDR3 of IMM200184 | QSYDSSNPPGASWV | 60 |
| PR194_00232_HC | | HCDR1 of IMM20190 | SASGFTVSSNYMS | 61 |
| PR194_00232_HC | | HCDR2 of IMM20190 | VIYAGGSTF | 62 |
| PR194_00232_HC | | HCDR3 of IMM20190 | ARDRGGYLDY | 63 |
| PR194_00232_LC | | LCDR1 of IMM20190 | RASQGISNYLA | 64 |

TABLE 1-continued

| Sequence Name | Binds | Description | Amino acid sequence | SEQ ID No. |
|---|---|---|---|---|
| PR194_00232_LC | | LCDR2 of IMM20190 | YAASTLQS | 65 |
| PR194_00232_LC | | LCDR3 of IMM20190 | QKYNSAPGLT | 66 |
| PR200_00622_HC | | HCDR1 of IMM20253 | TASGFTFSTYGMH | 67 |
| PR200_00622_HC | | HCDR2 of IMM20253 | VISYDGSSKH | 68 |
| PR200_00622_HC | | HCDR3 of IMM20253 | ARDGQPPGWGNYFDY | 69 |
| PR200_00622_LC | | LCDR1 of IMM20253 | GGNGIGSKSVY | 70 |
| PR200_00622_LC | | LCDR2 of IMM20253 | YDDSDRPS | 71 |
| PR200_00622_LC | | LCDR3 of IMM20253 | QVWDSSSDPWV | 72 |
| PR194_00453_HC | | HCDR1 | TVSGGSISSSSSYWG | 73 |
| PR194_00453_HC | | HCDR2 | SIYYSGSTY | 74 |
| PR194_00453_HC | | HCDR3 | ARAKFSVWDNYRYPFDY | 75 |
| PR194_00453_LC | | LCDR1 | SGSSSNIGSNTVN | 76 |
| PR194_00453_LC | | LCDR2 | YSNNQRPS | 77 |
| PR194_00453_LC | | LCDR3 | AAWDDSLNGWV | 78 |
| PR196_00109_b_HC | | HCDR1 | AASGFTFSNYGMH | 79 |
| PR196_00109_b_HC | | HCDR2 | VIWYDGSNKY | 80 |
| PR196_00109_b_HC | | HCDR3 | ARERLEDTAMVNFLDY | 81 |
| PR196_00109_b_LC | | LCDR1 | SGDKLGHKYAS | 82 |
| PR196_00109_b_LC | | LCDR2 | YQDAKRPS | 83 |
| PR196_00109_b_LC | | LCDR3 | QAWDSSTVV | 84 |
| PR196_00413_a_HC | | HCDR1 | KASGGTFSSYAIT | 85 |
| PR196_00413_a_HC | | HCDR2 | GIIPIFGTAN | 86 |
| PR196_00413_a_HC | | HCDR3 | ASDYGDSPLGY | 87 |
| PR196_00413_a_LC | | LCDR1 | TSSQSVLYSSNNKNFLA | 88 |
| PR196_00413_a_LC | | LCDR2 | YWASTRES | 89 |
| PR196_00413_a_LC | | LCDR3 | QQYYSAPLT | 90 |
| PR194_00292_HC | | HCDR1 | AVYGGSLSGYYWS | 91 |
| PR194_00292_HC | | HCDR2 | EINHSGSTN | 92 |
| PR194_00292_HC | | HCDR3 | ARAWKYSSSWYSGGIYYGMDV | 93 |
| PR194_00292_LC | | LCDR1 | SGTSSDVGSYNLVS | 94 |
| PR194_00292_LC | | LCDR2 | YEGTKRPS | 95 |
| PR194_00292_LC | | LCDR3 | CSYAGFSTWV | 96 |
| PR194_00364_b_HC | | HCDR1 | SASGFTFTTYTMN | 97 |
| PR194_00364_b_HC | | HCDR2 | SISSTGLSIY | 98 |
| PR194_00364_b_HC | | HCDR3 | ARDPSPTTIYYYYMDV | 99 |

TABLE 1-continued

| Sequence Name | Binds | Description | Amino acid sequence | SEQ ID No. |
|---|---|---|---|---|
| PR194_00364_b_LC | | LCDR1 | TGTSSDVGTYNLVS | 100 |
| PR194_00364_b_LC | | LCDR2 | YEVSKRPS | 101 |
| PR194_00364_b_LC | | LCDR3 | CSYAGSTTGYVV | 102 |
| PR197_00647_HC | | HCDR1 | AASGFTFSSYAMH | 103 |
| PR197_00647_HC | | HCDR2 | LISYDGGDKY | 104 |
| PR197_00647_HC | | HCDR3 | ARDRPQTGDWFPPIPTGVLDV | 105 |
| PR197_00647_LC | | LCDR1 | RASQGISNYLA | 106 |
| PR197_00647_LC | | LCDR2 | YAASSLQS | 107 |
| PR197_00647_LC | | LCDR3 | QQYHSYPIT | 108 |
| PR199_00255_HC | | HCDR1 of IMM20279 | AASGFTFSTYGMH | 109 |
| PR199_00255_HC | | HCDR2 of IMM20279 | VIWYNGINKH | 110 |
| PR199_00255_HC | | HCDR3 of IMM20279 | ARDWGTLTTLFDF | 111 |
| PR199_00255_LC | | LCDR1 of IMM20279 | RASQSISSHLN | 112 |
| PR199_00255_LC | | LCDR2 of IMM20279 | YGASSLQS | 113 |
| PR199_00255_LC | | LCDR3 of IMM20279 | QQSYSTPPWT | 114 |
| PR199_00255_opt_HC | | HCDR1 | AASGFTFSTYGMH | 115 |
| PR199_00255_opt_HC | | HCDR2 | VIWYNGINKY | 116 |
| PR199_00255_opt_HC | | HCDR3 | ARDWGTLTTLFDF | 117 |
| PR199_00255_opt_LC | | LCDR1 | RASQSISSHLN | 118 |
| PR199_00255_opt_LC | | LCDR2 | YGASSLQS | 119 |
| PR199_00255_opt_LC | | LCDR3 | QQSYSTPPWT | 120 |
| PR201_00151_HC | | HCDR1 | TFSGFSLNTSGMCVS | 121 |
| PR201_00151_HC | | HCDR2 | RIDWDDDKY | 122 |
| PR201_00151_HC | | HCDR3 | ARISIQSRGGGADY | 123 |
| PR201_00151_LC | | LCDR1 | RASQSISSYLH | 124 |
| PR201_00151_LC | | LCDR2 | FVASTLQS | 125 |
| PR201_00151_LC | | LCDR3 | QQSYSPPWT | 126 |
| PR194_00068_HC | | HCDR1 | SASGFTFTNYAMS | 127 |
| PR194_00068_HC | | HCDR2 | TISGSGGSTY | 128 |
| PR194_00068_HC | | HCDR3 | ANSGPTGDLDY | 129 |
| PR194_00068_LC | | LCDR1 | SGDKLGNKYVC | 130 |
| PR194_00068_LC | | LCDR2 | YQDTKRPS | 131 |
| PR194_00068_LC | | LCDR3 | QAWDSSTAV | 132 |
| PR198_00478_HC | | HCDR1 | TASGFTFNKAWMS | 133 |
| PR198_00478_HC | | HCDR2 | RIQSKTDDETTD | 134 |

TABLE 1-continued

| Sequence Name | Binds | Description | Amino acid sequence | SEQ ID No. |
|---|---|---|---|---|
| PR198_00478_HC | | HCDR3 | TSRAHYGSGTSYTPFDY | 135 |
| PR198_00478 LC | | LCDR1 | RSSQSLLYSNGYNYLD | 136 |
| PR198_00478 LC | | LCDR2 | YMGSNRAS | 137 |
| PR198_00478 LC | | LCDR3 | MQTLQTLFT | 138 |
| PR210_01029_λ_v1_HC | | HCDR1 | AVYGGSFSGYYWS | 139 |
| PR210_01029_λ_v1_HC | | HCDR2 | EIDHSGSTN | 140 |
| PR210_01029_λ_v1_HC | | HCDR3 | ARTTSITIFGILVAGGHNCFDS | 141 |
| PR210_01029_λ_v1_LC | | LCDR1 | SGTSSDVGNYDLVS | 142 |
| PR210_01029_λ_v1_LC | | LCDR2 | MIYEVTKRPS | 143 |
| PR210_01029_λ_v1_LC | | LCDR3 | CSYTSSGTFWV | 144 |
| PR197_00350_HC | | HCDR1 | KASGGTFSNYAIN | 145 |
| PR197_00350_HC | | HCDR2 | GIIPIFGTTN | 146 |
| PR197_00350_HC | | HCDR3 | ARAGYSSSWYRSTILSYYNYYGLDV | 147 |
| PR197_00350_LC | | LCDR1 | RSSQSLLHSNGYNYLD | 148 |
| PR197_00350_LC | | LCDR2 | YLGSNRAS | 149 |
| PR197_00350_LC | | LCDR3 | MQAQQTS | 150 |
| PR210_01524_HC | | HCDR1 | AASGFTFSDYGMH | 151 |
| PR210_01524_HC | | HCDR2 | VIWYDGSYKY | 152 |
| PR210_01524_HC | | HCDR3 | ARDGQWLRILDY | 153 |
| PR210_01524_LC | | LCDR1 | RASQSVRSSSLG | 154 |
| PR210_01524_LC | | LCDR2 | FGASNRAT | 155 |
| PR210_01524_LC | | LCDR3 | QQSGSSLFT | 156 |
| PR210_00852_HC | | HCDR1 | TVSGASISSTTYYWG | 157 |
| PR210_00852_HC | | HCDR2 | SIHYVGSTY | 158 |
| PR210_00852_HC | | HCDR3 | TLSVAGTFYGLDV | 159 |
| PR210_00852_LC | | LCDR1 | RASQGISSWLA | 160 |
| PR210_00852_LC | | LCDR2 | YAASSLQS | 161 |
| PR210_00852_LC | | LCDR3 | QQANSFPLT | 162 |
| PR199_00106_b_λ_HC | | HCDR1 | AASGFTFRNVWMN | 163 |
| PR199_00106_b_λ_HC | | HCDR2 | RIKSKTDGGTID | 164 |
| PR199_00106_b_λ_HC | | HCDR3 | TTHSIRGFEI | 165 |
| PR199_00106_b_λ_LC | | LCDR1 | SGDALPKQYAY | 166 |
| PR199_00106_b_λ_LC | | LCDR2 | YKDSERPS | 167 |
| PR199_00106_b_λ_LC | | LCDR3 | QSADSSGAPLV | 168 |
| PR199_00179_κ_HC | | HCDR1 | AASGFTFSSYSMN | 169 |
| PR199_00179_κ_HC | | HCDR2 | SISSSSSYIY | 170 |
| PR199_00179_κ_HC | | HCDR3 | ARDRASGRVGSRFDY | 171 |
| PR199_00179_κ_LC | | LCDR1 | RASQSISSYLN | 172 |
| PR199_00179_κ_LC | | LCDR2 | YAASSLQS | 173 |

TABLE 1-continued

| Sequence Name | Binds | Description | Amino acid sequence | SEQ ID No. |
|---|---|---|---|---|
| PR199_00179_κ_LC | | LCDR3 | QQSYSTPRVT | 174 |
| PR197_00705_HC | | HCDR1 | TVSGDSVSSGDYYWG | 175 |
| PR197_00705_HC | | HCDR2 | YIYYTGRTF | 176 |
| PR197_00705_HC | | HCDR3 | ARARDSEGFSQYYFDY | 177 |
| PR197_00705_LC | | LCDR1 | QASEDIDVYLS | 178 |
| PR197_00705_LC | | LCDR2 | YDASNLET | 179 |
| PR197_00705_LC | | LCDR3 | QQYDNLPT | 180 |
| PR194_00547_r_HC | | HCDR1 | KASGYTFTSYGIS | 181 |
| PR194_00547_r_HC | | HCDR2 | WISAYNGNTN | 182 |
| PR194_00547_r_HC | | HCDR3 | AREVWGAGYYFDY | 183 |
| PR194_00547_r_LC | | LCDR1 | SGDALPKQYAY | 184 |
| PR194_00547_r_LC | | LCDR2 | YKDSERPS | 185 |
| PR194_00547_r_LC | | LCDR3 | QSADSSGTYVV | 186 |
| PR194_00195_HC | | HCDR1 | KASGGTFSNYAIN | 187 |
| PR194_00195_HC | | HCDR2 | GIIPIFRTAN | 188 |
| PR194_00195_HC | | HCDR3 | AREYSSSGFYFDY | 189 |
| PR194_00195_LC | | LCDR1 | SGTSSDVGSYNLVS | 190 |
| PR194_00195_LC | | LCDR2 | YEGNKRPS | 191 |
| PR194_00195_LC | | LCDR3 | CSYAGSSAWM | 192 |
| PR194_00292_HC | | HCDR1 | AVYGGSLSGYYWS | 193 |
| PR194_00292_HC | | HCDR2 | EINHSGSTN | 194 |
| PR194_00292_HC | | HCDR3 | ARAWKYSSSWYSGGIYYGMDV | 195 |
| PR194_00292_LC | | LCDR1 | SGTSSDVGSYNLVS | 196 |
| PR194_00292_LC | | LCDR2 | YEGTKRPS | 197 |
| PR194_00292_LC | | LCDR3 | CSYAGFSTWV | 198 |
| PR194_00591_HC | | HCDR1 | AVSGFIFSSHGMH | 199 |
| PR194_00591_HC | | HCDR2 | VISYDGSKKH | 200 |
| PR194_00591_HC | | HCDR3 | AKDATYCDSITSWCARYSHMDV | 201 |
| PR194_00591_LC | | LCDR1 | SGASSDLGAYNYVS | 202 |
| PR194_00591_LC | | LCDR2 | YDVNHRPS | 203 |
| PR194_00591_LC | | LCDR3 | SSYTSRSTLV | 204 |
| PR196_00042_HC | | HCDR1 | TVSGGSIRSYYWS | 205 |
| PR196_00042_HC | | HCDR2 | YIYYSGSTN | 206 |
| PR196_00042_HC | | HCDR3 | ASYSGYDWGGFDY | 207 |
| PR196_00042_LC | | LCDR1 | SGSRSNIGSNTVN | 208 |
| PR196_00042_LC | | LCDR2 | YSDNQRPS | 209 |
| PR196_00042_LC | | LCDR3 | AAWDDSLNGPV | 210 |
| PR194_00448_HC | | HCDR1 | TVSGGSISNSNYYWG | 211 |

TABLE 1-continued

| Sequence Name | Binds | Description | Amino acid sequence | SEQ ID No. |
|---|---|---|---|---|
| PR194_00448_HC | | HCDR2 | SLYYTGSTY | 212 |
| PR194_00448_HC | | HCDR3 | ARLFSSGYYSPLYSFDY | 213 |
| PR194_00448_LC | | LCDR1 | TGTTSSDVGGYNFVS | 214 |
| PR194_00448_LC | | LCDR2 | YDVSNRPS | 215 |
| PR194_00448_LC | | LCDR3 | SSYTSSSTLI | 216 |
| CD-2WNG loop epitope with border sequences | | | WESNGNELSDFKTT | 217 |
| CD-2WNG epitope | | | NGNELSDF | 218 |
| CD-4I2X:A epitope with border sequences | | | WEIDGSERQNGKTT | 219 |
| CD-4I2X:A epitope | | | IDGSERQNG | 220 |
| CD-TLK epitope with border sequences | | | WEDNPVYKTT | 221 |
| CD-TLK epitope | | | DNPVY | 222 |
| CD-CD2HV epitope with border sequences | | | WESNIAQPRNYKTT | 223 |
| CD-CD2HV epitope | | | SNIAQPRNY | 224 |
| CD-KRNE epitope with border sequences | | | WESNGQPEKRNENNYKTT | 225 |
| CD-KRNE epitope | | | SNGQPEKRNENNY | 226 |
| CD-LANE epitope with border sequences | | | WESNGQPELANENNYKTT | 227 |
| CD-LANE epitope | | | SNGQPELANENNY | 228 |
| CD-DRR epitope with border sequences | | | WESNGQPDRRYKTT | 229 |
| CD-DRR epitope | | | SNGQPDRRY | 230 |
| CD-DNF-derived epitope with border sequences | | | WESNGQPEDNFKTT | 231 |
| CD-DNF-derived epitope | | | SNGQPEDNF | 232 |
| CD-DQQ epitope with border sequences | | | WESNGQPDQQYKTT | 233 |
| CD-DQQ epitope | | | SNGQPDQQY | 234 |
| CD-OPN epitope with border sequences | | | WETWLNPDPSQKTT | 235 |
| CD-OPN epitope | | | TWLNPDPSQ | 236 |
| CD-Glu epitope with border sequences | | | WEYMPMENNYKTT | 237 |

TABLE 1-continued

| Sequence Name | Binds | Description | Amino acid sequence | SEQ ID No. |
|---|---|---|---|---|
| CD-Glu epitope | | | YMPMENNY | 238 |
| CD-Myc epitope with border sequences | | | WEQKLISEEDLKTT | 239 |
| CD-Myc epitope | | | QKLISEEDL | 240 |
| CD-FLAG epitope with border sequences | | | WEDYKDDDDKTT | 241 |
| CD-FLAG epitope | | | DYKDDDD | 242 |
| CD-HIS epitope with border sequences | | | WESNGHHHHHHYKTT | 243 |
| CD-HIS epitope | | | SNGHHHHHHY | 244 |
| EF-2WNG epitope with border sequences | | | DLTRWDVGNV | 245 |
| EF-2WNG epitope | | | LTRWDV | 246 |
| EF-4I2X:A epitope with border sequences | | | DKDRWERGNV | 247 |
| EF-4I2X:E epitope | | | KDRWER | 248 |
| EF-4I2X:E epitope with border sequences | | | WELDRWDVKTT | 249 |
| EF-4I2X:E epitope | | | LDRWDV | 250 |
| EF-ND epitope with border sequences | | | DNDRWQQGNV | 251 |
| EF-ND epitope | | | NDRWQQ | 252 |

In some embodiments, provided herein is an antibody that binds to a SARS-CoV-2 Spike protein comprising a variable heavy chain (VH) and a variable light chain (VL), wherein the antibody comprises a HCDR1 comprising the amino acid sequence SASGFTFSSFWMS (SEQ ID NO: 55); a HCDR2 comprising the amino acid sequence TIREDGSEKYYVD (SEQ ID NO: 56); and a HCDR3 comprising the amino acid sequence ARSKWLRGSFDY (SEQ ID NO: 57); wherein the antibody comprises a LCDR1 comprising the amino acid sequence TRRSGSIASNYVQ (SEQ ID NO: 58); a LCDR2 comprising the amino acid sequence YEDNQRPS (SEQ ID NO: 59); and a LCDR3 comprising the amino acid sequence QSYDSSNPPGASWV (SEQ ID NO: 60). In some embodiments, the CDRs are defined according to North et al. In some embodiments, the VH comprises the amino acid sequence set forth in SEQ ID NO: 1. In some embodiments, the VL comprises the amino acid sequence set forth in SEQ ID NO: 2. In some embodiments, the VH comprises the amino acid sequence set forth in SEQ ID NO: 1 and the VL comprises the amino acid sequence set forth in SEQ ID NO: 2. In some embodiments, the antibody comprises a HCDR1, HCDR2, and HCDR3 of a heavy chain variable region (HCVR) comprising the amino acid sequence set forth in SEQ ID NO: 1, and a LCDR1, LCDR2, and LCDR3 of a light chain variable region (LCVR) comprising the amino acid sequence is set forth in SEQ ID NO: 2. In some embodiments the antibody comprises one or more CDRs or variable region sequences of IMM20184 (PR193_00018 HC). In some embodiments, the antibody binds to an epitope on the Spike protein outside of the ACE2 binding site. In some embodiments, the antibody neutralizes SARS-CoV-2 through an ACE2-dependent mechanism. In some embodiments, IMM20184 contacts one or more amino acids in the Spike protein selected from the group consisting of N370, A372, F374, K378, S383, and P384. In some embodiments, IMM20184 binds to a conserved epitope. In some embodiments, IMM20184 binds to an epitope of the Spike protein comprising one or more of N370, A372, F374, K378, S383, and P384.

In some embodiments, provided herein is an antibody that binds to a SARS-CoV-2 Spike protein comprising a variable heavy chain (VH) and a variable light chain (VL), wherein the antibody comprises a HCDR1 comprising the amino acid sequence SASGFTVSSNYMS (SEQ ID NO: 61); a HCDR2 comprising the amino acid sequence VIYAGGSTF (SEQ ID NO: 62); and a HCDR3 comprising the amino acid sequence ARDRGGYLDY (SEQ ID NO: 63); wherein the antibody comprises a LCDR1 comprising the amino acid sequence RASQGISNYLA (SEQ ID NO: 64); a LCDR2 comprising the amino acid sequence YAASTLQS (SEQ ID NO: 65); and a LCDR3 comprising the amino acid sequence QKYNSAPGLT (SEQ ID NO: 66). In some embodiments, the CDRs are defined according to North et al. In some embodiments, the VH comprises the amino acid sequence set forth in SEQ ID NO: 3. In some embodiments, the VL comprises the amino acid sequence set forth in SEQ ID NO: 4. In some embodiments, the VH comprises the amino acid sequence set forth in SEQ ID NO: 3 and the VL comprises the amino acid sequence set forth in SEQ ID NO: 4. In some embodiments, the antibody comprises a HCDR1, HCDR2, and HCDR3 of a heavy chain variable region (HCVR) comprising the amino acid sequence set forth in SEQ ID NO: 3, and a LCDR1, LCDR2, and LCDR3 of a light chain variable region (LCVR) comprising the amino acid sequence is set forth in SEQ ID NO: 4. In some embodiments, the antibody comprises one or more CDRs or variable region sequences of IMM20190 (PR194_00232 HC). In some embodiments, the antibody binds to an epitope of the Spike protein in the ACE2 binding site and operates through an ACE2-dependent mechanism. In some embodiments, IMM20190 contacts one or more amino acids of the Spike protein selected from the group consisting of K417, D420, L455, F456, N460, Y473, N487, Y489, N501, and Y505. In some embodiments, IMM20190 binds to a non-conserved epitope. In some embodiments, IMM20190 binds to an epitope of the Spike protein comprising one or more of K417, D420, L455, F456, N460, Y473, N487, Y489, N501, and Y505.

In some embodiments, provided herein is an antibody that binds to a SARS-CoV-2 Spike protein comprising a variable heavy chain (VH) and a variable light chain (VL), wherein the antibody comprises a HCDR1 comprising the amino acid sequence TASGFTFSTYGMH (SEQ ID NO: 67); a HCDR2 comprising the amino acid sequence VISYDGSSKH (SEQ ID NO: 68); and a HCDR3 comprising the amino acid sequence ARDGQPPGWGNYFDY (SEQ ID NO: 69); wherein the antibody comprises a LCDR1 comprising the amino acid sequence GGNGIGSKSVY (SEQ ID NO: 70); a LCDR2 comprising the amino acid sequence YDDSDRPS (SEQ ID NO: 71); and a LCDR3 comprising the amino acid sequence QVWDSSSDPWV (SEQ ID NO: 72). In some embodiments, the CDRs are defined according to North et al. In some embodiments, the VH comprises the amino acid sequence set forth in SEQ ID NO: 5. In some embodiments, the VL comprises the amino acid sequence set forth in SEQ ID NO: 6. In some embodiments, the VH comprises the amino acid sequence set forth in SEQ ID NO: 5 and the VL comprises the amino acid sequence set forth in SEQ ID NO: 6. In some embodiments, the antibody comprises a HCDR1, HCDR2, and HCDR3 of a heavy chain variable region (HCVR) comprising the amino acid sequence set forth in SEQ ID NO: 5, and a LCDR1, LCDR2, and LCDR3 of a light chain variable region (LCVR) comprising the amino acid sequence is set forth in SEQ ID NO: 6. In some embodiments, the antibody comprises one or more CDR sequences or variable region sequences of IMM20253 (PR200_00622 HC). In some embodiments, the antibody binds to a Spike protein with a mutation in the protease cleavage site. In some embodiments, the antibody binds with high affinity to pre-cleaved Spike proteins (i.e. Spike proteins that are cleaved prior to binding to the host cell surface). In some embodiments, the antibody binds with high affinity to Spike proteins with mutations that make a protease site more readily cleavable. In some embodiments, the antibody binds to a Spike protein at an epitope outside of the ACE2 binding site and operates through an ACE2 independent mechanism. In some embodiments, the antibody causes a confirmation change in the Spike protein. In some embodiments, the antibody makes the Spike protein more susceptible to cleavage. In some embodiments IMM20253 contacts one or more amino acid of the Spike protein selected from the group consisting of K356 and R466. In some embodiments, IMM20253 binds to a conserved epitope. In some embodiments, IMM20253 binds to an epitope of the Spike protein comprising K356 and/or R466.

In some embodiments, provided herein is an antibody that binds to a SARS-CoV-2 Spike protein comprising a variable heavy chain (VH) and a variable light chain (VL), wherein the antibody comprises a HCDR1 comprising the amino acid sequence AASGFTFSTYGMH (SEQ ID NO: 109); a HCDR2 comprising the amino acid sequence VIWYNGINKH (SEQ ID NO: 110); and a HCDR3 comprising the amino acid sequence ARDWGTLTTLFDF (SEQ ID NO: 111); wherein the antibody comprises a LCDR1 comprising the amino acid sequence RASQSISSHLN (SEQ ID NO: 112); a LCDR2 comprising the amino acid sequence YGASSLQS (SEQ ID NO: 113); and a LCDR3 comprising the amino acid sequence QQSYSTPPWT (SEQ ID NO: 114). In some embodiments, the VH comprises the amino acid sequence set forth in SEQ ID NO: 19. In some embodiments, the CDRs are defined according to North et al. In some embodiments, the VL comprises the amino acid sequence set forth in SEQ ID NO: 20. In some embodiments, the VH comprises the amino acid sequence set forth in SEQ ID NO: 19 and the VL comprises the amino acid sequence set forth in SEQ ID NO: 20. In some embodiments, the antibody comprises a HCDR1, HCDR2, and HCDR3 of a heavy chain variable region (HCVR) comprising the amino acid sequence set forth in SEQ ID NO: 19, and a LCDR1, LCDR2, and LCDR3 of a light chain variable region (LCVR) comprising the amino acid sequence is set forth in SEQ ID NO: 20. In some embodiments, the antibody comprises one or more CDR sequences or variable region sequences of IMM20279 (PR199_00255_HC). In some embodiments, the antibody binds to an epitope of the Spike protein outside of the ACE2 binding site. In some embodiments, the antibody comprising one or more CDR sequences or variable region sequences of IMM20279 cross-reacts with an antibody comprising one or more CDR sequences or variable region sequences of IMM20184. In some embodiments of the invention, an isolated antibody or antigen-binding fragment thereof binds a SARS-CoV-2 Spike protein, and contains one of the following combinations of a heavy chain variable region (HCVR) and a light chain variable region (LCVR): a HCVR comprising three heavy chain complementarity determining regions (CDRs), (HCDR1, HCDR2 and HCDR3), wherein the amino acid sequence of the HCVR is set forth in SEQ ID NO: 1, and a LCVR comprising three light chain complementarity determining regions (CDRs) (LCDR1, LCDR2 and LCDR3), wherein the amino acid sequence of the LCVR is set forth in SEQ ID NO: 2; a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4; a HCVR comprising three CDRs, (HCDR1, HCDR2 and HCDR3), wherein the amino acid sequence of the HCVR is set forth in SEQ ID NO: 19, and a LCVR comprising three CDRs, (LCDR1, LCDR2 and LCDR3), wherein the amino acid sequence of the LCVR is set forth in SEQ ID NO: 20; a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6; a HCVR comprising three CDRs, (HCDR1, HCDR2 and HCDR3), wherein the amino acid sequence of the HCVR is set forth in SEQ ID NO: 7, and a LCVR comprising three CDRs, (LCDR1, LCDR2 and LCDR3), wherein the amino acid sequence of the LCVR is set forth in SEQ ID NO: 8; or a HCVR comprising three CDRs, (HCDR1, HCDR2 and HCDR3), wherein the amino acid sequence of the HCVR is set forth in SEQ ID NO: 23, and a LCVR comprising three CDRs, (LCDR1, LCDR2 and LCDR3), wherein the amino acid sequence of the LCVR is set forth in SEQ ID NO: 24.

As described above, some antibodies of the invention bind to highly-conserved epitopes, and, thus, are not affected by point mutations in the Spike protein associated with variants of SARS-Cov-2. A nonlimiting list of examples of antibodies or antigen-binding fragments of the invention which bind equivalently to the SARS-CoV-2 reference isolate, USA/WA_CDC-WA1/2020, and each of the aforementioned variant isolates, include: An antibody with a HCVR based on the amino acid sequence set forth in SEQ ID NO: 1 or fragment thereof, and a LCVR based on the amino acid sequence set forth in SEQ ID NO: 2 or fragment thereof; An antibody with a HCVR based on the amino acid sequence set forth in SEQ ID NO: 3 or fragment thereof, and a LCVR based on the amino acid sequence set forth in SEQ ID NO: 4 or fragment thereof; An antibody with a HCVR based on the amino acid sequence set forth in SEQ ID NO: 5 or fragment thereof, and a LCVR based on the amino acid sequence set forth in SEQ ID NO: 6 or fragment thereof; and An antibody with a HCVR based on the amino acid sequence set forth in SEQ ID NO: 19 or fragment thereof, and a LCVR based on the amino acid sequence set forth in SEQ ID NO: 20 or fragment thereof.

The foregoing antibodies of the invention neutralize SARS-CoV-2 and SARS-CoV-2 variants, including variants Alpha (U.K./B.1.1.7), Beta (South African/B.1.351), Gamma (Brazil/P.1), Delta (India/B.1.617.2), B.1.617 (L452R/E484Q) and Epsilon (California/B.1.429/427), either alone, or in combination. In some embodiments, the antibodies neutralize the Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2. More particularly, certain antibodies of the invention bind the SARS-CoV-2 RBD at epitopes, which contain residues that are conserved among variants. In some embodiments, binding to such conserved residues prevents viral escape. In some embodiments, binding to such conserved residues allows binding across variants. Accordingly, a RBD amino acid substitution at a non-conserved or poorly-conserved residue position will have limited or no impact on binding of an antibody of the invention. Such non conserved or poorly-conserved substitutions in the RBD are commonly associated with SARS-CoV-2 variants. Thus, an RBD epitope of some antibodies of the invention may contain at least 1, 2, 3, 4, 5, 6, 7, 8, 9, 10, 11, 12, 13, 14, 15 or more residues at RBD positions 356 (K), 370 (N), 372 (A), 374 (F), 378 (K), 384 (P), 417 (K), 420 (D), 455 (L), 456 (F), 460 (N), 466 (R), 473 (Y), 487 (N), 489 (Y), 501 (N), and 505 (Y). For example, an antibody of the invention may bind an RBD epitope in which the binding energy is relatively higher at residues at 417 (K), 420 (D), 455 (L), 456 (F), 460 (N), 473 (Y), 487 (N), 489 (Y), 501 (N), and 505 (Y). Likewise, another antibody of the invention may bind an RBD epitope in which the binding energy is relatively higher at residues at 370 (N), 372 (A), 374 (F), 378 (K), 384 (P). And yet another antibody of the invention may bind an RBD epitope in which the binding energy is relatively higher at residues at 356 (K) and 466 (R). In some embodiments, the antibody contacts one or more residues at RBD positions 356 (K), 370 (N), 372 (A), 374 (F), 378 (K), 384 (P), 417 (K), 420 (D), 455 (L), 456 (F), 460 (N), 466 (R), 473 (Y), 487 (N), 489 (Y), 501 (N), and 505 (Y). In some embodiments, the antibody contacts one or more of 417 (K), 420 (D), 455 (L), 456 (F), 460 (N), 473 (Y), 487 (N), 489 (Y), 501 (N), and 505 (Y). In some embodiments, the antibody contacts residues at 370 (N), 372 (A), 374 (F), 378 (K), 384 (P). In some embodiments, the epitope is identified using alanine scanning.

In some embodiments, the antibody binds the SARS-CoV-2 RBD at epitopes, which contain residues that are not conserved.

In certain embodiments of the invention, for example, a composition (i.e., a mixture) of two or more of: An antibody with a HCVR based on the amino acid sequence set forth in SEQ ID NO: 1 or fragment thereof, and a LCVR based on the amino acid sequence set forth in SEQ ID NO: 2 or fragment thereof; An antibody with a HCVR based on the amino acid sequence set forth in SEQ ID NO: 3 or fragment thereof, and a LCVR based on the amino acid sequence set forth in SEQ ID NO: 4 or fragment thereof; An antibody with a HCVR based on the amino acid sequence set forth in SEQ ID NO: 5 or fragment thereof, and a LCVR based on the amino acid sequence set forth in SEQ ID NO: 6 or fragment thereof; An antibody with a HCVR based on the amino acid sequence set forth in SEQ ID NO: 19 or fragment thereof, and a LCVR based on the amino acid sequence set forth in SEQ ID NO: 20 or fragment thereof; and An antibody with a HCVR based on the amino acid sequence set forth in SEQ ID NO: 21 or fragment thereof, and a LCVR based on the amino acid sequence set forth in SEQ ID NO: 22 or fragment thereof, additively or synergistically neutralizes SARS-CoV-2, or a variant thereof, such as the Alpha (U.K./B.1.1.7), Beta (South African/B.1.351), Gamma (Brazil/P.1), Delta (India/B.1.617.2), B.1.617 (L452R/E484Q) and Epsilon (California/B.1.429/427). In some embodiments, the antibodies neutralize the Omicron variant. In some embodiments, the antibodies neutralize Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2.

In some embodiments, an antibody of the invention alters the conformation of Spike protein upon binding of the antibody to the Spike protein. More particularly, in certain embodiments, an antibody of the invention binds a Spike protein epitope located on the outside face of the RBD domain of the SARS-CoV-2 RBD. In such embodiments, the epitope may be in close proximity to the N-terminal domain of a second Spike protein within the Spike trimer, and binding of the antibody inactivates the virus' ability to bind cells. Consequently, certain antibodies of the invention neutralize SARS-CoV-2 by the foregoing mechanism. More specifically, binding of such antibodies to the outer face of the RBD imparts its intrinsic neutralization through induction of a conformational change in the Spike protein that prevents virus uptake into the cells without competing for ACE2 binding. An example of an embodiment of the invention that alters conformation of the Spike protein upon binding is an antibody with a heavy chain variable region (HCVR) or fragment thereof and/or a light chain variable region (LCVR) or a fragment thereof derived from an antibody described herein as IMM20253, which contains HCVR and LCVR with amino acid sequences of SEQ ID NOS. 5 and 6, respectively.

In certain embodiments, an antibody of the invention that alters the conformation of Spike protein upon binding of the antibody to the Spike protein as part of its intrinsic neutralization activity, acts additively, and more preferentially synergistically, with other antibodies that compete for ACE2 binding as part of their intrinsic neutralization mechanism. An example of an embodiment of the invention that alters conformation of the Spike protein upon binding and acts additively, and more preferentially synergistically, with antibodies that block ACE2 binding, is an antibody with a heavy chain variable region (HCVR) or fragment thereof and/or a light chain variable region (LCVR) or a fragment thereof derived from an antibody described herein as IMM20253, which contains HCVR and LCVR with amino acid sequences of SEQ ID NOS. 5 and 6, respectively.

As described above, an isolated antibody or antigen-binding fragment thereof of the invention may contain a CH3 scaffold "epitope tag", comprising at least one modification of the wild-type amino acid sequence of the CH3 domain derived from an immunoglobulin Fc region. Accordingly, any of the aforementioned antibodies may have been engineered to contain a CH3 scaffold. The CH3 scaffold of such an isolated antibody or antigen-binding fragment thereof may possess at least one modification of the wild-type sequence occurs within the AB, EF, or CD loops of the CH3 scaffold, including an amino acid substitution, deletion or insertion, for example. In certain embodiments, the epitope tag amino acid sequence contains a sequence derived from SIRPα or Sip. Alternatively, he epitope tag amino acid sequence contains a sequence derived from a constant light chain of an antibody. More particularly, the antibody epitope amino acid sequence of an isolated antibody or antigen-binding fragment thereof that contains a CH3 scaffold with an amino acid sequence set forth in SEQ ID Nos. 3-30, SEQ ID Nos. 33-57, or SEQ ID Nos. 60-67 of International Patent Application No. PCT/US2019/032780.

Compositions

Also provided herein are compositions comprising one or more antibodies provided herein. In some embodiments, provided herein a composition comprising two or more antibodies that bind to a Spike protein, wherein the antibodies bind to different epitopes. In some embodiments, the composition comprises an antibody that operates in an ACE2 independent mechanism and an antibody that operates through an ACE2 dependent mechanism. In some embodiments, the multiple antibodies in the composition act synergistically to treat a SARS-CoV-2 infection in a subject. In some embodiments, the presence of multiple antibodies binding to different epitopes of a SARS-CoV-2 protein allows treatment of variants with mutations in one or more SARS-CoV-2 proteins, such as the Spike protein.

In some embodiments, provided herein is a composition comprising a variable heavy chain (VH) and a variable light chain (VL), wherein the antibody comprises a HCDR1 comprising the amino acid sequence SASGFTFSSFWMS (SEQ ID NO: 55); a HCDR2 comprising the amino acid sequence TIREDGSEKYYVD (SEQ ID NO: 56); and a HCDR3 comprising the amino acid sequence ARSKWLRGSFDY (SEQ ID NO: 57); wherein the antibody comprises a LCDR1 comprising the amino acid sequence TRRSGSIASNYVQ (SEQ ID NO: 58); a LCDR2 comprising the amino acid sequence YEDNQRPS (SEQ ID NO: 59); and a LCDR3 comprising the amino acid sequence QSYDSSNPPGASWV (SEQ ID NO: 60). In some embodiments, the CDRs are defined according to North et al.

In some embodiments, provided herein is a composition comprising a variable heavy chain (VH) and a variable light chain (VL), wherein the antibody comprises a HCDR1 comprising the amino acid sequence SASGFTVSSNYMS (SEQ ID NO: 61); a HCDR2 comprising the amino acid sequence VIYAGGSTF (SEQ ID NO: 62); and a HCDR3 comprising the amino acid sequence ARDRGGYLDY (SEQ ID NO: 63); wherein the antibody comprises a LCDR1 comprising the amino acid sequence RASQGISNYLA (SEQ ID NO: 64); a LCDR2 comprising the amino acid sequence YAASTLQS (SEQ ID NO: 65); and a LCDR3 comprising the amino acid sequence QKYNSAPGLT (SEQ ID NO: 66). In some embodiments, the CDRs are defined according to North et al.

In some embodiments, provided herein is a composition comprising a variable heavy chain (VH) and a variable light chain (VL), wherein the antibody comprises a HCDR1 comprising the amino acid sequence TASGFTFSTYGMH (SEQ ID NO: 67); a HCDR2 comprising the amino acid sequence VISYDGSSKH (SEQ ID NO: 68); and a HCDR3 comprising the amino acid sequence ARDGQPPGWGNYFDY (SEQ ID NO: 69); wherein the antibody comprises a LCDR1 comprising the amino acid sequence GGNGIGSKSVY (SEQ ID NO: 70); a LCDR2 comprising the amino acid sequence YDDSDRPS (SEQ ID NO: 71); and a LCDR3 comprising the amino acid sequence QVWDSSSDPWV (SEQ ID NO: 72). In some embodiments, the CDRs are defined according to North et al.

In some embodiments, provided herein is a composition comprising a variable heavy chain (VH) and a variable light chain (VL), wherein the antibody comprises a HCDR1 comprising the amino acid sequence AASGFTFSTYGMH (SEQ ID NO: 109); a HCDR2 comprising the amino acid sequence VIWYNGINKH (SEQ ID NO: 110); and a HCDR3 comprising the amino acid sequence ARDWGTLTTLFDF (SEQ ID NO: 111); wherein the antibody comprises a LCDR1 comprising the amino acid sequence RASQSISSHLN (SEQ ID NO: 112); a LCDR2 comprising the amino acid sequence YGASSLQS (SEQ ID NO: 113); and a LCDR3 comprising the amino acid sequence QQSYSTPPWT (SEQ ID NO: 114). In some embodiments, the CDRs are defined according to North et al.

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGIS-NYLA (SEQ ID NO: 64), a LCDR2 comprising the amino acid sequence of YAASTLQS (SEQ ID NO: 65), and a LCDR3 comprising the amino acid sequence of QKYN-SAPGLT (SEQ ID NO: 66).

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69), and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a composition comprising a first antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGIS-NYLA (SEQ ID NO: 64), a LCDR2 comprising the amino acid sequence of YAASTLQS (SEQ ID NO: 65), and a LCDR3 comprising the amino acid sequence of QKYN-SAPGLT (SEQ ID NO: 66); and a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a composition comprising a first antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGIS-NYLA (SEQ ID NO: 64), a LCDR2 comprising the amino acid sequence of YAASTLQS (SEQ ID NO: 65), and a LCDR3 comprising the amino acid sequence of QKYN-SAPGLT (SEQ ID NO: 66); and a second antibody comprising a VH comprising a HCDR1 comprising the amino acid sequence of AASGFTFSTYGMH (SEQ ID NO: 109), a HCDR2 comprising the amino acid sequence of VIWYN-GINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a composition comprising a first antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); a second antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a composition comprising a first antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a third antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a composition comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a third antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a fourth antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

Pharmaceutical compositions of the invention contain one or more isolated antibodies or antigen-binding fragments thereof of the invention and a pharmaceutically acceptable carrier or diluent. In one embodiment of the invention, the pharmaceutical composition contains only one of the Spike-binding antibodies described herein. Other pharmaceutical composition of the invention contain a mixture of different Spike-binding antibodies which are described herein, such as, for example, at least 2, at least 3, at least 4, or at least 5, or at least 6 or more Spike-binding antibodies. For example, a pharmaceutical composition of two or more of: An antibody with a HCVR based on the amino acid sequence set forth in SEQ ID NO: 1 or fragment thereof, and a LCVR based on the amino acid sequence set forth in SEQ ID NO: 2 or fragment thereof; An antibody with a HCVR based on the amino acid sequence set forth in SEQ ID NO: 3 or fragment thereof, and a LCVR based on the amino acid sequence set forth in SEQ ID NO: 4 or fragment thereof; An antibody with a HCVR based on the amino acid sequence set forth in SEQ ID NO: 5 or fragment thereof, and a LCVR based on the amino acid sequence set forth in SEQ ID NO: 6 or fragment thereof; an antibody with a HCVR based on the amino acid sequence set forth in SEQ ID NO: 19 or fragment thereof, and a LCVR based on the amino acid sequence set forth in SEQ ID NO: 20 or fragment thereof, and An antibody with a HCVR based on the amino acid sequence set forth in SEQ ID NO: 21 or fragment thereof, and a LCVR based on the amino acid sequence set forth in SEQ ID NO: 22 or fragment thereof, additively or synergistically neutralizes SARS-CoV-2, or a variant thereof, such as the Alpha (U.K./B.1.1.7), Beta (South African/B.1.351), Gamma (Brazil/P.1), Delta (India/B.1.617.2), B.1.617 (L452R/E484Q) and Epsilon (California/B.1.429/427). In some embodiments, the antibodies neutralize Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2.

In some embodiments a pharmaceutical composition of the invention further contains a second therapeutic agent. For example, a pharmaceutical composition of the invention may also contain an anti-inflammatory agent or an antiviral agent.

In some embodiments, the second agent is an antibody. In some aspects, the second agent is casirivimab (REGN10933). In some aspects, the second agent is imdevimab (REGN10987). In some aspects, the second agent is a combination of the neutralizing antibodies, casirivimab and imdevimab (REGEN-COV, previously known as REGN-COV-2) (ClinicalTrials.gov number, NCT04452318 and NCT04425629). The two antibodies can simultaneously bind to two independent epitopes on the RBD (Hansen J. et. al., Studies in humanized mice and convalescent humans yield a SARS-CoV-2 antibody cocktail. 369(6506):1010-1014 (2020); Baum A. et. al, Antibody cocktail to SARS-CoV-2 Spike protein prevents rapid mutational escape seen with individual antibodies, Science 369(6506):1014-1018 (2020)). In some aspects, the second agent is bamlanivimab (LY3819253). In some aspects, the second agent is etesevimab (LY3832479). In some aspects, the second agent is a combination of the neutralizing antibodies, bamlanivimab and etesevimab (ClinicalTrials.gov number, NCT04427501, Dougan M. et. al., Bamlanivimab plus Etesevimab in Mild or Moderate Covid-19. N Engl J med 385(15):1382-1392 (2021)). In some aspects, the second agent is sotrovimab (ClinicalTrials.gov number, NCT04545060, Gupta A. et. al., Early Treatment for Covid-19 with SARS-CoV-2 Neutralizing antibody sotrovimab. N Engl J med 385:1941-1950 (2021)).

As stated above, antibodies and pharmaceutical compositions of the invention can be used in methods for preventing or treating, a SARS-CoV-2 infection in subject. Accordingly, antibodies and pharmaceutical compositions of the invention are useful for treating the disease caused by SARS-CoV-2, commonly referred to as COVID-19, or simply COVID. A pharmaceutical composition of the invention is typically administered to subject in need thereof by injecting the composition into the body of the subject subcutaneously, intravenously or intramuscularly.

Methods of Treatment

Provided herein is a method of treating or preventing a SARS-CoV-2 infection in a subject comprising administering an antibody provided herein to the subject. In some embodiments, the method comprises administering one antibody provided herein. In some embodiments, the method comprises administering two or more antibodies provided herein. In some embodiments, the method comprises administering three or more, or four or more antibodies provided herein.

In some embodiments, provided herein is a method of treating or preventing a SARS-CoV-2 infection in a subject comprising administering an antibody that binds to a Spike protein comprising a variable heavy chain (VH) and a variable light chain (VL), wherein the antibody comprises a HCDR1 comprising the amino acid sequence SASGFTFSSFWMS (SEQ ID NO: 55); a HCDR2 comprising the amino acid sequence TIREDGSEKYYVD (SEQ ID NO: 56); and a HCDR3 comprising the amino acid sequence ARSKWLRGSFDY (SEQ ID NO: 57); wherein the antibody comprises a LCDR1 comprising the amino acid sequence TRRSGSIASNYVQ (SEQ ID NO: 58); a LCDR2 comprising the amino acid sequence YEDNQRPS (SEQ ID NO: 59); and a LCDR3 comprising the amino acid sequence QSYDSSNPPGASWV (SEQ ID NO: 60).

In some embodiments, the method comprises administering an antibody comprising one or more CDR sequences and/or VH and VL sequences of IMM20184. In some embodiments, the method comprises administering an antibody comprising one or more CDR sequences and/or VH and VL sequences of IMM20184 as a monotherapy. In some embodiments, the method comprises administering an antibody comprising one or more CDR sequences and/or VH and VL sequences of IMM20184 as a combination therapy. In some embodiments, the method comprises administering an antibody comprising one or more CDR sequences and/or VH and VL sequences of IMM20184 in combination with one or more additional antibodies provided herein. In some embodiments, the antibody comprising one or more CDR sequences and/or VH and VL sequences of IMM20184 is administered simultaneously with one or more additional antibodies provided herein. In some embodiments, the antibody comprising one or more CDR sequences and/or VH and VL sequences of IMM20184 is administered sequentially with one or more additional antibodies provided herein.

In some embodiments, provided herein is a method of treating or preventing a SARS-CoV-2 infection in a subject comprising administering an antibody that binds to a Spike protein comprising a variable heavy chain (VH) and a variable light chain (VL), wherein the antibody comprises a HCDR1 comprising the amino acid sequence SASGFTVSSNYMS (SEQ ID NO: 61); a HCDR2 comprising the amino acid sequence VIYAGGSTF (SEQ ID NO: 62); and a HCDR3 comprising the amino acid sequence ARDRGGYLDY (SEQ ID NO: 63); wherein the antibody comprises a LCDR1 comprising the amino acid sequence RASQGISNYLA (SEQ ID NO: 64); a LCDR2 comprising the amino acid sequence YAASTLQS (SEQ ID NO: 65); and a LCDR3 comprising the amino acid sequence QKYN-SAPGLT (SEQ ID NO: 66).

In some embodiments, the method comprises administering an antibody comprising one or more CDR sequences and/or VH and VL sequences of IMM20190. In some embodiments, the method comprises administering an antibody comprising one or more CDR sequences and/or VH and VL sequences of IMM20190 as a monotherapy. In some embodiments, the method comprises administering an antibody comprising one or more CDR sequences and/or VH and VL sequences of IMM20190 as a combination therapy. In some embodiments, the method comprises administering an antibody comprising one or more CDR sequences and/or VH and VL sequences of IMM20190 in combination with one or more additional antibodies provided herein. In some embodiments, the antibody comprising one or more CDR sequences and/or VH and VL sequences of IMM20190 is administered simultaneously with one or more additional antibodies provided herein. In some embodiments, the antibody comprising one or more CDR sequences and/or VH and VL sequences of IMM20190 is administered sequentially with one or more additional antibodies provided herein.

In some embodiments, provided herein is a method of treating or preventing a SARS-CoV-2 infection in a subject comprising administering an antibody that binds to a Spike protein comprising a variable heavy chain (VH) and a variable light chain (VL), wherein the antibody comprises a HCDR1 comprising the amino acid sequence TASGFTF-STYGMH (SEQ ID NO: 67); a HCDR2 comprising the amino acid sequence VISYDGSSKH (SEQ ID NO: 68); and a HCDR3 comprising the amino acid sequence ARDGQPPGWGNYFDY (SEQ ID NO: 69); wherein the antibody comprises a LCDR1 comprising the amino acid sequence GGNGIGSKSVY (SEQ ID NO: 70); a LCDR2 comprising the amino acid sequence YDDSDRPS (SEQ ID NO: 71); and a LCDR3 comprising the amino acid sequence QVWDSSSDPWV (SEQ ID NO: 72).

In some embodiments, provided herein is a method of treating or preventing an infection with an Omicron variant of SARS-CoV-2 in a subject comprising administering an antibody that binds to a Spike protein comprising a variable heavy chain (VH) and a variable light chain (VL), wherein the antibody comprises a HCDR1 comprising the amino acid sequence TASGFTFSTYGMH (SEQ ID NO: 67); a HCDR2 comprising the amino acid sequence VISYDGSSKH (SEQ ID NO: 68); and a HCDR3 comprising the amino acid sequence ARDGQPPGWGNYFDY (SEQ ID NO: 69); wherein the antibody comprises a LCDR1 comprising the amino acid sequence GGNGIGSKSVY (SEQ ID NO: 70); a LCDR2 comprising the amino acid sequence YDDSDRPS (SEQ ID NO: 71); and a LCDR3 comprising the amino acid sequence QVWDSSSDPWV (SEQ ID NO: 72). In some embodiments, the method further comprises administering a second antibody.

In some embodiments, the method comprises administering an antibody comprising one or more CDR sequences and/or VH and VL sequences of IMM20253. In some embodiments, the method comprises administering an antibody comprising one or more CDR sequences and/or VH and VL sequences of IMM20253 as a monotherapy. In some embodiments, the method comprises administering an antibody comprising one or more CDR sequences and/or VH and VL sequences of IMM20253 as a combination therapy. In some embodiments, the method comprises administering an antibody comprising one or more CDR sequences and/or VH and VL sequences of IMM20253 in combination with one or more additional antibodies provided herein. In some embodiments, the antibody comprising one or more CDR sequences and/or VH and VL sequences of IMM20253 is administered simultaneously with one or more additional antibodies provided herein. In some embodiments, the antibody comprising one or more CDR sequences and/or VH and VL sequences of IMM20253 is administered sequentially with one or more additional antibodies provided herein.

In some embodiments, provided herein is a method of treating or preventing a SARS-CoV-2 infection in a subject comprising administering an antibody that binds to a Spike protein comprising a variable heavy chain (VH) and a variable light chain (VL), wherein the antibody comprises a HCDR1 comprising the amino acid sequence AASGFTF-STYGMH (SEQ ID NO: 109); a HCDR2 comprising the amino acid sequence VIWYNGINKH (SEQ ID NO: 110); and a HCDR3 comprising the amino acid sequence ARDWGTLTTLFDF (SEQ ID NO: 111); wherein the antibody comprises a LCDR1 comprising the amino acid sequence RASQSISSHLN (SEQ ID NO: 112); a LCDR2 comprising the amino acid sequence YGASSLQS (SEQ ID NO: 113); and a LCDR3 comprising the amino acid sequence QQSYSTPPWT (SEQ ID NO: 114).

In some embodiments, provided herein is a method of treating or preventing an infection with an Omicron variant of SARS-CoV-2 a subject comprising administering an antibody that binds to a Spike protein comprising a variable heavy chain (VH) and a variable light chain (VL), wherein the antibody comprises a HCDR1 comprising the amino acid sequence AASGFTFSTYGMH (SEQ ID NO: 109); a HCDR2 comprising the amino acid sequence VIWYN-GINKH (SEQ ID NO: 110); and a HCDR3 comprising the amino acid sequence ARDWGTLTTLFDF (SEQ ID NO: 111); wherein the antibody comprises a LCDR1 comprising the amino acid sequence RASQSISSHLN (SEQ ID NO: 112); a LCDR2 comprising the amino acid sequence YGASSLQS (SEQ ID NO: 113); and a LCDR3 comprising the amino acid sequence QQSYSTPPWT (SEQ ID NO: 114). In some embodiments, the method further comprises administering a second antibody.

In some embodiments, the method comprises administering an antibody comprising one or more CDR sequences and/or VH and VL sequences of IMM20279. In some embodiments, the method comprises administering an antibody comprising one or more CDR sequences and/or VH and VL sequences of IMM20279 as a monotherapy. In some embodiments, the method comprises administering an antibody comprising one or more CDR sequences and/or VH and VL sequences of IMM20279 as a combination therapy. In some embodiments, the method comprises administering an antibody comprising one or more CDR sequences and/or VH and VL sequences of IMM20279 in combination with one or more additional antibodies provided herein. In some embodiments, the antibody comprising one or more CDR sequences and/or VH and VL sequences of IMM20279 is administered simultaneously with one or more additional antibodies provided herein. In some embodiments, the antibody comprising one or more CDR sequences and/or VH and VL sequences of IMM20279 is administered sequentially with one or more additional antibodies provided herein.

In some embodiments, provided herein is a method of treating or preventing a SARS-CoV-2 infection in a subject comprising administering a combination of two antibodies that comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66).

In some embodiments, provided herein is a method of treating or preventing a SARS-CoV-2 infection in a subject comprising administering a combination of two antibodies that bind to a Spike protein comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69), and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a method of treating or preventing a SARS-CoV-2 infection in a subject comprising administering a combination of two antibodies that comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a method of treating or preventing a SARS-CoV-2 infection in a subject comprising administering a combination of two antibodies that bind to a Spike protein comprising a first antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a method of treating or preventing a SARS-CoV-2 infection in a subject comprising administering a combination of two antibodies that comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a method of treating or preventing a SARS-CoV-2 infection in a subject comprising administering a combination of two antibodies that bind to a Spike protein comprising a first antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a method of treating or preventing a SARS-CoV-2 infection in a subject comprising administering a combination of three antibodies that comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, provided herein is a method of treating or preventing a SARS-CoV-2 infection in a subject comprising administering a combination of three antibodies that bind to a Spike protein comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a method of treating or preventing a SARS-CoV-2 infection in a subject comprising administering a combination of three antibodies that bind to a Spike protein comprising a first antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a third antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, provided herein is a method of treating or preventing a SARS-CoV-2 infection in a subject comprising administering a combination of four antibodies that bind to a Spike protein comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPP-GASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a third antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a fourth antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the method comprises administering one or more of IMM20184, IMM20190, IMM20253, and/or IMM20279 and an additional agent selected from the group consisting of casirivimab, imdevimab, bamlanivimab, etesevimab and sotrovimab.

Also provided herein is a method of treating a SARS-CoV-2 infection in a subject comprising administering two or more antibodies provided herein to the subject. In some embodiments, the SARS-CoV-2 infection is caused by SARS-CoV-2 variant. In some embodiments, the SARS-CoV-2 is the Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2. In some embodiments, the variant has one or more mutations in a Spike protein. In some embodiments, 3 or more, 4 or more, 5 or more, or 6 or more antibodies provided herein are administered to the subject. In some embodiments, the antibodies comprise a HCVR comprising three heavy chain complementarity determining regions (CDRs), (HCDR1, HCDR2 and HCDR3), wherein the amino acid sequence of the HCVR is set forth in SEQ ID NO: 1, and a LCVR comprising three light chain complementarity determining regions (CDRs) (LCDR1, LCDR2 and LCDR3), wherein the amino acid sequence of the LCVR is set forth in SEQ ID NO: 2; a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4; a HCVR comprising three CDRs, (HCDR1, HCDR2 and HCDR3), wherein the amino acid sequence of the HCVR is set forth in SEQ ID NO: 19, and a LCVR comprising three CDRs, (LCDR1, LCDR2 and LCDR3), wherein the amino acid sequence of the LCVR is set forth in SEQ ID NO: 20; a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6; a HCVR comprising three CDRs, (HCDR1, HCDR2 and HCDR3), wherein the amino acid sequence of the HCVR is set forth in SEQ ID NO: 7, and a LCVR comprising three CDRs, (LCDR1, LCDR2 and LCDR3), wherein the amino acid sequence of the LCVR is set forth in SEQ ID NO: 8; or a HCVR comprising three CDRs, (HCDR1, HCDR2 and HCDR3), wherein the amino acid sequence of the HCVR is set forth in SEQ ID NO: 23, and a LCVR comprising three CDRs, (LCDR1, LCDR2 and LCDR3), wherein the amino acid sequence of the LCVR is set forth in SEQ ID NO: 24.

In some embodiments, provided herein is a method of treating an Omicron variant of SARS-CoV-2 in an individual comprising administering two or antibodies provided herein. In some embodiments, the Omicron variant includes a combination of mutations in the Spike protein. In some embodiments, the mutations include a large number of changes that form a ring around the ACE2 binding site. Accordingly, in one aspect an advantage of the present methods is the ability to target epitopes within and outside of the ACE2 binding site such that the treatment is effective in variants, such as Omicron which harbor mutations within the Spike protein including in the ACE2 binding site. In some embodiments, the combinations of antibodies provided herein are especially effective for treating variants such as Omicron because they bind to non-overlapping epitopes. In some embodiments, the Omicron variant has one or more modifications that make the Spike protein more susceptible to cleavage and/or cause pre-cleavage of the Spike protein. In some embodiments, the antibodies provided herein, for example IMM20253, are able to bind to pre-cleaved Spike proteins, or Spike proteins that are more susceptible to cleavage with high affinity.

In some embodiments, provided herein is a method of treating a Delta variant of SARS-CoV-2 in an individual comprising administering two or antibodies provided herein. In some embodiments, the Omicron variant includes a combination of mutations in the Spike protein. In some embodiments, the mutations include a large number of changes that form a ring around the ACE2 binding site. Accordingly, in one aspect an advantage of the present methods is the ability to target epitopes within and outside of the ACE2 binding site such that the treatment is effective in variants, such as Omicron which harbor mutations within the Spike protein including in the ACE2 binding site. In some embodiments, the combinations of antibodies provided herein are especially effective for treating variants such as Delta because they bind to non-overlapping epitopes. In some embodiments, the Delta variant has one or more modifications that make the Spike protein more susceptible to cleavage and/or cause pre-cleavage of the Spike protein. In some embodiments, the antibodies provided herein, for example IMM20253, are able to bind to pre-cleaved Spike proteins, or Spike proteins that are more susceptible to cleavage with high affinity.

In some embodiments, provided herein is a method of treating a SARS-CoV-2 infection in an individual comprising administering antibody IMM20184 to the individual. In some embodiments the antibody comprises a HCVR comprising three heavy chain complementarity determining regions (CDRs), (HCDR1, HCDR2 and HCDR3), wherein the amino acid sequence of the HCVR is set forth in SEQ ID NO: 1, and a LCVR comprising three light chain complementarity determining regions (CDRs) (LCDR1, LCDR2 and LCDR3), wherein the amino acid sequence of the LCVR is set forth in SEQ ID NO: 2. In some embodiments, the antibody comprise a HCDR1, a HCDR2, and an HCDR3 of the HCVR amino acid sequence set forth in SEQ ID NO:1 and a LCDR1, a LCDR2, and a LCDR3 of the LCVR amino acid sequence set forth in SEQ ID NO: 2. In some embodiments, the method comprises administering 2 or more antibodies. In some embodiments, IMM20184 targets an epitope outside the ACE2 binding site and operates via an ACE2 dependent mechanism of action.

In some embodiments, provided herein is a method of treating an Omicron variant of SARS-CoV-2 in an individual comprising administering antibody IMM20253 to the individual. In some embodiments the antibody comprises a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6. In some embodiments, the antibody comprises a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6. In some embodiments, IMM20253 targets an epitope outside the ACE2 binding site and operates via an ACE2 independent mechanism of action. In some embodiments, IMM20253 has high affinity for virus comprising pre-cleaved Spike proteins or Spike proteins that are more susceptible to cleavage, such as Omicron.

In some embodiments, provided herein is a method of treating a Delta variant of SARS-CoV-2 in an individual comprising administering antibody IMM20253 to the individual. In some embodiments the antibody comprises a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6. In some embodiments, the antibody comprises a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6. In some embodiments, IMM20253 targets an epitope outside the ACE2 binding site and operates via an ACE2 independent mechanism of action. In some embodiments, IMM20253 targets an epitope outside the ACE2 binding site and operates via an ACE2 independent mechanism of action. In some embodiments, IMM20253 has high affinity for virus comprising pre-cleaved Spike proteins or Spike proteins that are more susceptible to cleavage, such as Delta.

In some embodiments, provided herein is a method of treating an Omicron variant of SARS-CoV-2 comprising administering antibody MM20190 to the individual. In some embodiments, the antibody comprises a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4. In some embodiments, the antibody comprises a HCDR1, a HCDR2, and a HCDR3 of the HCVR amino acid sequence set forth in SEQ ID NO: 3 and a LCDR1, a LCDR2, and a LCDR3 of the LCVR amino acid sequence set forth in SEQ ID NO:4. In some embodiments, IMM20190, targets an epitope within the ACE2 binding site and operates via an ACE2 dependent mechanism of action.

In some embodiments, provided herein is a method of treating a Delta variant of SARS-CoV-2 comprising administering antibody MM20190 to the individual. In some embodiments, the antibody comprises a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4. In some embodiments, the antibody comprises a HCDR1, a HCDR2, and a HCDR3 of the HCVR amino acid sequence set forth in SEQ ID NO: 3 and a LCDR1, a LCDR2, and a LCDR3 of the LCVR amino acid sequence set forth in SEQ ID NO:4. In some embodiments, IMM20190, targets an epitope within the ACE2 binding site and operates via an ACE2 dependent mechanism of action.

In some embodiments, provided herein is a method of treating an Omicron variant of SARS-CoV-2 in an individual comprising administering antibody IMM20184 and IMM20253 to the individual. In some embodiments, the method comprises administering i) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6 and ii) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6. In some embodiments, the method comprises administering i) an antibody comprising a HCDR1, a HCDR2, and a HCDR3 of the HCVR amino acid sequence set forth in SEQ ID NO:1 and a LCDR1, a LCDR2, and LCDR3 of the LCVR amino acid sequence set forth in SEQ ID NO: 2 and ii) an antibody comprising a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6.

In some embodiments, provided herein is a method of treating a Delta variant of SARS-CoV-2 in an individual comprising administering antibody IMM20184 and IMM20253 to the individual. In some embodiments, the method comprises administering i) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6 and ii) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6. In some embodiments, the method comprises administering i) an antibody comprising a HCDR1, a HCDR2, and a HCDR3 of the HCVR amino acid sequence set forth in SEQ ID NO:1 and a LCDR1, a LCDR2, and LCDR3 of the LCVR amino acid sequence set forth in SEQ ID NO: 2 and ii) an antibody comprising a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6.

In some embodiments, provided herein is a method of treating an Omicron variant of SARS-CoV-2 in an individual comprising administering antibody IMM20184, IMM20253, and IMM20190. In some embodiments, the method comprises administering i) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6 ii) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6; and iii) an antibody comprising a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4. In some embodiments, the method comprises administering i) an antibody comprising a HCDR1, a HCDR2, and a HCDR3 of the HCVR amino acid sequence set forth in SEQ ID NO:1 and a LCDR1, a LCDR2, and a LCDR3 of the LCVR amino acid sequence set forth in SEQ ID NO: 2 ii) an antibody comprising a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6, and iii) an antibody comprising a HCDR1, a HCDR2, and a HCDR3 of the HCVR amino acid sequence set forth in SEQ ID NO: 3 and a LCDR1, a LCDR2, and a LCDR3 of the LCVR amino acid sequence set forth in SEQ ID NO:4.

In some embodiments, provided herein is a method of treating a Delta variant of SARS-CoV-2 in an individual comprising administering antibody IMM20184, IMM20253, and IMM20190. In some embodiments, the method comprises administering i) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6 ii) an antibody comprising a HCVR comprising three CDRs, (HCDR1, HCDR2 and HCDR3), wherein the amino acid sequence of the HCVR is set forth in SEQ ID NO: 5, and a LCVR comprising three CDRs, (LCDR1, LCDR2 and LCDR3), wherein the amino acid sequence of the LCVR is set forth in SEQ ID NO: 6; and iii) an antibody comprising a HCVR comprising three CDRs, (HCDR1, HCDR2 and HCDR3), wherein the amino acid sequence of the HCVR is set forth in SEQ ID NO: 3, and a LCVR comprising three CDRs, (LCDR1, LCDR2 and LCDR3), wherein the amino acid sequence of the LCVR is set forth in SEQ ID NO: 4. In some embodiments, the method comprises administering i) an antibody comprising a HCDR1, a HCDR2, and a HCDR3 of the HCVR amino acid sequence set forth in SEQ ID NO:1 and a LCDR1, a LCDR2, and a LCDR3 of the LCVR amino acid sequence set forth in SEQ ID NO: 2 ii) an antibody comprising a HCDR1, a HCDR2 and a HCDR3 of the HCVR amino acid sequence set forth in SEQ ID NO:5 and a LCDR1, a LCDR2, and a LCDR3 of the LCVR amino acid sequence set forth in SEQ ID NO:6, and iii) an antibody comprising a HCDR1, a HCDR2, and a HCDR3 of the HCVR amino acid sequence set forth in SEQ ID NO: 3 and a LCDR1, a LCDR2, and a LCDR3 of the LCVR amino acid sequence set forth in SEQ ID NO:4.

"Subjects" refers to any person who has been infected with, or has the potential to be infected with the SARS-CoV-2 virus. In some embodiments of the invention those subjects may be of high risk for contracting the virus as a result of being immunocompromised through genetic mutation or drug treatment. For example, subjects may be being treated with immunosuppressive medications as a result of being a solid organ transplant recipient or having a chronic inflammatory disease (e.g. rheumatoid arthritis, psoriasis, Crohn's disease). They may be being treated with chemotherapeutic, radiation, or targeted agents that suppress immune function for treatment of diseases such as cancer. Subjects may also have conditions that place them into high-risk categories for developing severe COVID-19, such as diabetes, chronic pulmonary conditions, chronic cardiovascular conditions, obesity, or pregnancy.

"Preventing" a disease refers to inhibiting the full development of a disease. Other terms, such as "prophylaxis", are also understood to refer to the concept of preventing a disease.

"Treating" refers to a therapeutic intervention that ameliorates, (i.e., reduces the severity), a sign or symptom of a disease or pathological condition after it has begun to develop. In some embodiments of the invention, the antibodies or antigen-binding fragments thereof contained in the pharmaceutical composition treat or prevent the a SARS-CoV-2 infection by neutralizing SARS-CoV-2 virus and/or a SARS-CoV-2 variant. Examples of SARS-CoV-2 variants that are responsive to a method of treatment of the invention include the: Alpha (U.K./B.1.1.7), Beta (South African/B.1.351), Gamma (Brazil/P.1), Delta (India/B.1.617.2), B.1.617 (L452R/E484Q) and Epsilon (California/B.1.429/427). Other examples of SARS-CoV-2 variants that are responsive to a method of treatment of the invention include the CDC Variants of Interest, including the Alpha (U.K./B.1.1.7) variant of SARS-CoV-2, the Beta (South African/B.1.351) variant of SARS-CoV-2, the Gamma (Brazilian/P.1) variant of SARS-CoV-2, the Delta (India/B.1.617.2), B.1.617 (L452R/E484Q)), the Epsilon (California/B.1.429/427, New York/B.1.526/526.1) variant of SARS-CoV-2, the UK/Nigeria (B.1.525) variant of SARS-CoV-2, the Brazilian (P.2) variant of SARS-CoV-2, the lambda (C.37) variant of SARS-CoV-2, or the Omicron (B.1.1.529) variant of SARS-CoV-2.

In certain embodiments, an effective amount of an antibody or antibody composition of the invention to prevent or treat SARS-CoV-2 infection does not result in complete protection from a SARS-CoV-2 disease but results in a lower titer or reduced number of SARS-CoV-2 viruses compared to an untreated subject. In certain embodiments, the effective amount results in a 0.5-fold, 1-fold, 2-fold, 4-fold, 6-fold, 8-fold, 10-fold, 15-fold, 20-fold, 25-fold, 50-fold, 75-fold, 100-fold, 125-fold, 150-fold, 175-fold, 200-fold, 300-fold, 400-fold, 500-fold, 750-fold, or 1,000-fold or greater reduction in titer of SARS-CoV-2 virus relative to an untreated subject. In some embodiments, the effective amount results in a reduction in titer of SARS-CoV-2 virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs. Benefits of a reduction in the titer, number or total burden of SARS-CoV-2 virus include, but are not limited to, less severe symptoms of the infection, fewer symptoms of the infection, reduction in the length of the disease associated with the infection, reduction in the length of viral shedding, and prevention of the onset or diminution of severity of diseases occurring secondary to SARS-CoV-2 virus infections.

Kits

Also, provided herein are kits for treating or preventing a SARS-CoV-2 infection in a subject comprising one or more antibodies provided herein. In some embodiments, the kit comprises two antibodies that bind to a Spike protein. In some embodiments, the kit comprises three or more antibodies that bind to a Spike protein. In some embodiments, the kit comprises four or more antibodies that bind to a Spike protein. In some embodiments, the anti-Spike antibodies are in different compositions in the kit. In some embodiments, the anti-Spike antibodies are in the same composition.

In some embodiments, the kit comprises one or more of IMM20184, IMM20190, IMM20253, and/or IMM20279 and an additional agent. In some embodiments, the kit comprises one or more of IMM20184, IMM20190, IMM20253, and/or IMM20279 and an additional agent selected from the group consisting of casirivimab, imdevimab, bamlanivimab, etesevimab and sotrovimab. In some embodiments, the kit comprises an anti-Spike antibody comprising a variable heavy chain (VH) and a variable light chain (VL), wherein the antibody comprises a HCDR1 comprising the amino acid sequence SASGFTFSSFWMS (SEQ ID NO: 55); a HCDR2 comprising the amino acid sequence TIREDGSEKYYVD (SEQ ID NO: 56); and a HCDR3 comprising the amino acid sequence ARSKWLRGSFDY (SEQ ID NO: 57); wherein the antibody comprises a LCDR1 comprising the amino acid sequence TRRSGSIASNYVQ (SEQ ID NO: 58); a LCDR2 comprising the amino acid sequence YEDNQRPS (SEQ ID NO: 59); and a LCDR3 comprising the amino acid sequence QSYDSSNPPGASWV (SEQ ID NO: 60). In some embodiments, the CDRs are defined according to North et al.

In some embodiments, the kit comprises an anti-Spike antibody comprising a variable heavy chain (VH) and a variable light chain (VL), wherein the antibody comprises a HCDR1 comprising the amino acid sequence SASGFTVSSNYMS (SEQ ID NO: 61); a HCDR2 comprising the amino acid sequence VIYAGGSTF (SEQ ID NO: 62); and a HCDR3 comprising the amino acid sequence ARDRGGYLDY (SEQ ID NO: 63); wherein the antibody comprises a LCDR1 comprising the amino acid sequence RASQGISNYLA (SEQ ID NO: 64); a LCDR2 comprising the amino acid sequence YAASTLQS (SEQ ID NO: 65); and a LCDR3 comprising the amino acid sequence QKYNSAPGLT (SEQ ID NO: 66). In some embodiments, the CDRs are defined according to North et al.

In some embodiments, the kit comprises an anti-Spike antibody comprising a variable heavy chain (VH) and a variable light chain (VL), wherein the antibody comprises a HCDR1 comprising the amino acid sequence TASGFTFSTYGMH (SEQ ID NO: 67); a HCDR2 comprising the amino acid sequence VISYDGSSKH (SEQ ID NO: 68); and a HCDR3 comprising the amino acid sequence ARDGQPPGWGNYFDY (SEQ ID NO: 69); wherein the antibody comprises a LCDR1 comprising the amino acid sequence GGNGIGSKSVY (SEQ ID NO: 70); a LCDR2 comprising the amino acid sequence YDDSDRPS (SEQ ID NO: 71); and a LCDR3 comprising the amino acid sequence QVWDSSSDPWV (SEQ ID NO: 72). In some embodiments, the CDRs are defined according to North et al.

In some embodiments, the kit comprises an anti-Spike antibody comprising a variable heavy chain (VH) and a variable light chain (VL), wherein the antibody comprises a HCDR1 comprising the amino acid sequence AASGFTFSTYGMH (SEQ ID NO: 109); a HCDR2 comprising the amino acid sequence VIWYNGINKH (SEQ ID NO: 110); and a HCDR3 comprising the amino acid sequence ARDWGTLTTLFDF (SEQ ID NO: 111); wherein the antibody comprises a LCDR1 comprising the amino acid sequence RASQSISSHLN (SEQ ID NO: 112); a LCDR2 comprising the amino acid sequence YGASSLQS (SEQ ID NO: 113); and a LCDR3 comprising the amino acid sequence QQSYSTPPWT (SEQ ID NO: 114). In some embodiments, the CDRs are defined according to North et al.

In some embodiments, the kit comprises an anti-Spike antibody comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66).

In some embodiments, the kit comprises a combination of two anti-Spike antibodies comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPPGASWV (SEQ ID NO: 60); and a second antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69), and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, the kit comprises a combination of two anti-Spike antibodies comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPP-GASWV (SEQ ID NO: 60); and a second antibody comprising a VH comprising a HCDR1 comprising the amino acid sequence of AASGFTFSTYGMH (SEQ ID NO: 109), a HCDR2 comprising the amino acid sequence of VIWYN-GINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the kit comprises a combination of two anti-Spike antibodies comprising a first antibody comprising a VH comprising a HCDR1 comprising the amino acid sequence of SASGFTVSSNYMS (SEQ ID NO: 61), a HCDR2 comprising the amino acid sequence of VIYAGG-STF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a second antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, the kit comprises a combination of two anti-Spike antibodies comprising a first antibody comprising a VH comprising a HCDR1 comprising the amino acid sequence of SASGFTVSSNYMS (SEQ ID NO: 61), a HCDR2 comprising the amino acid sequence of VIYAGG-STF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a second antibody comprising a VH comprising a HCDR1 comprising the amino acid sequence of AASGFTF-STYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the kit comprises a combination of two anti-Spike antibodies comprising a first antibody comprising a VH comprising a HCDR1 comprising the amino acid sequence of TASGFTFSTYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a second antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the kit comprises a combination of three anti-Spike antibodies comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPP-GASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72).

In some embodiments, the kit comprises a combination of three anti-Spike antibodies comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPP-GASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); and a third antibody comprising a VH comprising a HCDR1 comprising the amino acid sequence of AASGFTF-STYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the kit comprises a combination of three anti-Spike antibodies comprising a first antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a second antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a third antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114).

In some embodiments, the kit comprises a combination of four anti-Spike antibodies comprising a first antibody comprising a VH comprising a HCDR1 comprising the amino acid sequence of SASGFTFSSFWMS (SEQ ID NO: 55), a HCDR2 comprising the amino acid sequence of TIREDGSEKYYVD (SEQ ID NO: 56), and a HCDR3 comprising the amino acid sequence of ARSKWLRGSFDY (SEQ ID NO: 57); and a VL comprising a LCDR1 comprising the amino acid sequence of TRRSGSIASNYVQ (SEQ ID NO: 58), a LCDR2 comprising the amino acid sequence of YEDNQRPS (SEQ ID NO: 59), and a LCDR3 comprising the amino acid sequence of QSYDSSNPP-GASWV (SEQ ID NO: 60); a second antibody comprising the amino acid sequence of SASGFTVSSNYMS (SEQ ID NO: 61), a HCDR2 comprising the amino acid sequence of VIYAGGSTF (SEQ ID NO: 62), and a HCDR3 comprising the amino acid sequence of ARDRGGYLDY (SEQ ID NO: 63); and a VL comprising a LCDR1 comprising the amino acid sequence of RASQGISNYLA (SEQ ID NO: 64), a LCDR2 comprising the amino acid sequence of YAASTLQS (SEQ ID NO: 65), and a LCDR3 comprising the amino acid sequence of QKYNSAPGLT (SEQ ID NO: 66); a third antibody comprising a VH comprising a HCDR1 comprising the amino acid sequence of TASGFTF-STYGMH (SEQ ID NO: 67), a HCDR2 comprising the amino acid sequence of VISYDGSSKH (SEQ ID NO: 68), and a HCDR3 comprising the amino acid sequence of ARDGQPPGWGNYFDY (SEQ ID NO: 69); and a VL comprising a LCDR1 comprising the amino acid sequence of GGNGIGSKSVY (SEQ ID NO: 70), a LCDR2 comprising the amino acid sequence of YDDSDRPS (SEQ ID NO: 71), and a LCDR3 comprising the amino acid sequence of QVWDSSSDPWV (SEQ ID NO: 72); and a fourth antibody comprising a VH comprising a HCDR1 comprising the amino acid sequence of AASGFTFSTYGMH (SEQ ID NO: 109), a HCDR2 comprising the amino acid sequence of VIWYNGINKH (SEQ ID NO: 110), and a HCDR3 comprising the amino acid sequence of ARDWGTLTTLFDF (SEQ ID NO: 111); and a VL comprising a LCDR1 comprising the amino acid sequence of RASQSISSHLN (SEQ ID NO: 112), a LCDR2 comprising the amino acid sequence of YGASSLQS (SEQ ID NO: 113), and a LCDR3 comprising the amino acid sequence of QQSYSTPPWT (SEQ ID NO: 114). In some embodiments, the kit comprises an anti-Spike antibody provided in Table 1 and one or more additional antibodies. In some embodiments, the kit comprises a combination of casirivimab and imdevimab (RE-GEN-COV, previously known as REGN-COV-2). In some embodiments, the kit comprises a combination of bamlanivimab and etesevimab. In some embodiments, the kit comprises sotrovimab.

Embodiments

Embodiment 1. An antibody composition comprising at least first and second recombinant anti-SARS-CoV-2 antibodies that bind distinct epitopes of SARS-CoV-2, wherein at least one of the antibodies is selected from the group consisting of:
(a) an anti-Spike antibody comprising
  a heavy chain variable region (HCVR) as set forth in the amino acid sequence set forth in SEQ ID NO: 5 or fragment thereof, and
  a light chain variable region (LCVR) as set forth in the amino acid sequence set forth in SEQ ID NO: 6 or fragment thereof;
(b) an anti-Spike antibody comprising
  a HCVR as set forth in the amino acid sequence set forth in SEQ ID NO. 3 or fragment thereof, and
  a LCVR as set forth in the amino acid sequence set forth in SEQ ID NO: 4 or fragment thereof;
(c) an anti-Spike antibody comprising
  a HCVR as set forth in the amino acid sequence set forth in SEQ ID NO: 1 or fragment thereof, and
  a LCVR as set forth in the amino acid sequence set forth in SEQ ID NO: 2 or fragment thereof;

(d) an anti-Spike antibody comprising
  a HCVR as set forth in the amino acid sequence set forth in SEQ ID NO: 7 or fragment thereof, and
  a LCVR as set forth in the amino acid sequence set forth in SEQ ID NO: 8 or fragment thereof;
(e) an anti-Spike antibody comprising
  a HCVR as set forth in the amino acid sequence set forth in SEQ ID NO. 9 or fragment thereof, and
  a LCVR as set forth in the amino acid sequence set forth in SEQ ID NO: 10 or fragment thereof;
(f) an anti-Spike antibody comprising
  a HCVR as set forth in the amino acid sequence set forth in SEQ ID NO: 11 or fragment thereof, and
  a LCVR as set forth in the amino acid sequence set forth in SEQ ID NO: 12 or fragment thereof;
(g) an anti-Spike antibody comprising
  a HCVR as set forth in the amino acid sequence set forth in SEQ ID NO. 13 or fragment thereof, and
  a LCVR as set forth in the amino acid sequence set forth in SEQ ID NO: 14 or fragment thereof;
(h) an anti-Spike antibody comprising
  a HCVR as set forth in the amino acid sequence set forth in SEQ ID NO: 15 or fragment thereof, and
  a LCVR as set forth in the amino acid sequence set forth in SEQ ID NO: 16 or fragment thereof;
(i) an anti-Spike antibody comprising
  a HCVR as set forth in the amino acid sequence set forth in SEQ ID NO: 17 or fragment thereof, and
  a LCVR as set forth in the amino acid sequence set forth in SEQ ID NO: 18 or fragment thereof;
(j) an anti-Spike antibody comprising
  a HCVR as set forth in the amino acid sequence set forth in SEQ ID NO. 19 or fragment thereof, and
  a LCVR as set forth in the amino acid sequence set forth in SEQ ID NO: 20 or fragment thereof;
(k) an anti-Spike antibody comprising
  a HCVR as set forth in the amino acid sequence set forth in SEQ ID NO: 21 or fragment thereof, and
  a LCVR as set forth in the amino acid sequence set forth in SEQ ID NO: 22 or fragment thereof;
(l) an anti-Spike antibody comprising
  a HCVR as set forth in the amino acid sequence set forth in SEQ ID NO: 23 or fragment thereof, and
  a LCVR as set forth in the amino acid sequence set forth in SEQ ID NO: 24 or fragment thereof;
(m) an anti-Spike antibody comprising
  a HCVR as set forth in the amino acid sequence set forth in SEQ ID NO: 25 or fragment thereof, and
  a LCVR as set forth in the amino acid sequence set forth in SEQ ID NO: 26 or fragment thereof;
(n) an anti-ORF3a antibody comprising
  a HCVR as set forth in the amino acid sequence set forth in SEQ ID NO: 27 or fragment thereof, and
  a LCVR as set forth in the amino acid sequence set forth in SEQ ID NO: 28 or fragment thereof;
(o) an anti-Membrane antibody comprising
  a HCVR as set forth in the amino acid sequence set forth in SEQ ID NO. 29 or fragment thereof, and
  a LCVR as set forth in the amino acid sequence set forth in SEQ ID NO: 30 or fragment thereof;
(p) an anti-Nucleocapsid antibody comprising
  a HCVR as set forth in the amino acid sequence set forth in SEQ ID NO: 31 or fragment thereof, and
  a LCVR as set forth in the amino acid sequence set forth in SEQ ID NO: 32 or fragment thereof;
(q) an anti-Nucleocapsid antibody comprising
  a HCVR as set forth in the amino acid sequence set forth in SEQ ID NO: 33 or fragment thereof, and
  a LCVR as set forth in the amino acid sequence set forth in SEQ ID NO: 34 or fragment thereof;
(r) an anti-Nucleocapsid antibody comprising
  a HCVR as set forth in the amino acid sequence set forth in SEQ ID NO. 35 or fragment thereof, and
  a LCVR as set forth in the amino acid sequence set forth in SEQ ID NO: 36 or fragment thereof;
(s) an anti-ORFS antibody comprising
  a HCVR as set forth in the amino acid sequence set forth in SEQ ID NO: 37 or fragment thereof, and
  a LCVR as set forth in the amino acid sequence set forth in SEQ ID NO: 38 or fragment thereof; and
(t) an anti-ORF8 antibody comprising
  a HCVR as set forth in the amino acid sequence set forth in SEQ ID NO: 39 or fragment thereof, and
  a LCVR as set forth in the amino acid sequence set forth in SEQ ID NO: 40 or fragment thereof.

Embodiment 2. The antibody composition of embodiment 1, comprising first and second antibodies selected from the group consisting of:
(a) the anti-Spike antibody comprising
  a heavy chain variable region (HCVR) as set forth in the amino acid sequence set forth in SEQ ID NO: 5 or fragment thereof, and
  a light chain variable region (LCVR) as set forth in the amino acid sequence set forth in SEQ ID NO: 6 or fragment thereof;
(b) the anti-Spike antibody comprising
  a HCVR as set forth in the amino acid sequence set forth in SEQ ID NO: 3 or fragment thereof, and
  a LCVR as set forth in the amino acid sequence set forth in SEQ ID NO: 4 or fragment thereof;
(c) the anti-Spike antibody comprising
  a HCVR as set forth in the amino acid sequence set forth in SEQ ID NO: 1 or fragment thereof, and
  a LCVR as set forth in the amino acid sequence set forth in SEQ ID NO: 2 or fragment thereof; and
(d) the anti-Spike antibody comprising
  a HCVR as set forth in the amino acid sequence set forth in SEQ ID NO: 19 or fragment thereof, and
  a LCVR as set forth in the amino acid sequence set forth in SEQ ID NO: 20 or fragment thereof.

Embodiment 3. The antibody composition of embodiment 2, wherein the ratio between the first and the second antibodies is about 1:1.

Embodiment 4 The antibody composition of embodiment 1, comprising first. second, and third recombinant anti-SARS-CoV-2 antibodies, wherein:
(a) the first recombinant antibody is the anti-Spike antibody comprising
  a heavy chain variable region (HCVR) as set forth in the amino acid sequence set forth in SEQ ID NO: 5 or fragment thereof, and
  a light chain variable region (LCVR) as set forth in the amino acid sequence set forth in SEQ ID NO. 6 or fragment thereof;
(b) the second recombinant antibody is the anti-Spike antibody comprising
  a HCVR as set forth in the amino acid sequence set forth in SEQ ID NO: 3 or fragment thereof, and
  a LCVR as set forth in the amino acid sequence set forth in SEQ ID NO: 4 or fragment thereof; and
(c) the third recombinant antibody is the anti-Spike antibody comprising a HCVR as set forth in the amino acid sequence set forth in SEQ ID NO. 1 or fragment thereof, and
a LCVR as set forth in the amino acid sequence set forth in SEQ ID NO: 2 or fragment thereof.

Embodiment 5. The antibody composition of embodiment 1, comprising first, second, and third recombinant anti-SARS-CoV-2 antibodies, wherein;
(a) the first recombinant antibody is the anti-Spike antibody comprising
a heavy chain variable region (HCVR) as set forth in the amino acid sequence set forth in SEQ ID NO: 19 or fragment thereof, and
a light chain variable region (LCVR) as set forth in the amino acid sequence set forth in SEQ ID NO. 20 or fragment thereof;
(b) the second recombinant antibody is the anti-Spike antibody comprising
a HCVR as set forth in the amino acid sequence set forth in SEQ ID NO: 3 or fragment thereof, and
a LCVR as set forth in the amino acid sequence set forth in SEQ ID NO: 4 or fragment thereof; and
(c) the third recombinant antibody is the anti-Spike antibody comprising
a HCVR as set forth in the amino acid sequence set forth in SEQ ID NO: 1 or fragment thereof, and
a LCVR as set forth in the amino acid sequence set forth in SEQ ID NO: 2 or fragment thereof.

Embodiment 6. The antibody composition of embodiment 4 or 5, wherein the ratios between the first, second. and third antibodies are about 1:1:1.

Embodiment 7. The antibody composition of embodiment 1, comprising first, second, third, and fourth antibodies selected from the group consisting of
(a) the anti-Spike antibody comprising
a heavy chain variable region (HCVR) as set forth in the amino acid sequence set forth in SEQ ID NO. 5 or fragment thereof, and
a light chain variable region (LCVR) as set forth in the amino acid sequence set forth in SEQ ID NO: 6 or fragment thereof;
(b) the anti-Spike antibody comprising
a HCVR as set forth in the amino acid sequence set forth in SEQ ID NO. 3 or fragment thereof, and
a LCVR as set forth in the amino acid sequence set forth in SEQ ID NO: 4 or fragment thereof;
(c) the anti-Spike antibody comprising
a HCVR as set forth in the amino acid sequence set forth in SEQ ID NO: 1 or fragment thereof, and
a LCVR as set forth in the amino acid sequence set forth in SEQ ID NO: 2 or fragment thereof; and
(d) the anti-Spike antibody comprising
a HCVR as set forth in the amino acid sequence set forth in SEQ ID NO: 19 or fragment thereof, and
a LCVR as set forth in the amino acid sequence set forth in SEQ ID NO: 20 or fragment thereof.

Embodiment 8 The antibody composition of embodiment 7, wherein the ratio between the first, second, third, and fourth antibodies is about 1:1:1:1.

Embodiment 9. The antibody composition of any one of claims 1-8. wherein the antibody composition neutralizes at least 50% of one or more of the following variants of SARS-CoV-2: U.K. B.1.1.7: South African B.1.351: Brazil P.1; and California B.1.429/427 relative to the neutralization of the USA/WA_CDC-WA1/2020 SARS-CoV-2 by the composition.

Embodiment 10. The antibody composition of any one of embodiments 1-8, wherein the antibody composition neutralizes about 100% of one or more of the following variants of SARS-CoV-2: U.K. B.1.1.7; South African B.1.351: Brazil P.1; and California B.1.429/427 relative to the neutralization of the USA/WA_CDC-WA 1/2020 SARS-CoV-2 by the composition.

Embodiment 11. The antibody composition of any one of embodiments 1-10, wherein the epitopes of the antibodies in the composition are non-overlapping.

Embodiment 12. A method of treating or preventing a SARS-CoV-2 infection in a subject in need thereof, comprising administering an amount of the antibody composition of any one of embodiments 1-11 sufficient to treat the SARS-CoV-2 infection Embodiment 13. The method of claim 12, wherein antibodies or antigen-binding fragments thereof in the antibody composition treat the SARS-CoV-2 infection by effecting at least one of the following actions:
inhibiting binding of SARS-CoV-2 viruses to host ACE2 receptors;
inducing clearance of SARS-CoV-2 viruses by fixing complement to the viruses; and
inducing phagocytosis of the of SARS-CoV-2 viruses virus Embodiment 14. An isolated antibody or antigen-binding fragment thereof that binds a SARS-CoV-2 Spike protein comprising one of the following combinations of a heavy chain variable region (HCVR) and a light chain variable region (LCVR):
a HCVR comprising three heavy chain complementarity determining regions (CDRs), (HCDR1, HCDR2 and HCDR3), wherein the amino acid sequence of the HCVR is set forth in SEQ ID NO: 1, and a LCVR comprising three light chain complementarity determining regions (CDRs) (LCDR1, LCDR2 and LCDR3), wherein the amino acid sequence of the LCVR is set forth in SEQ ID NO: 2;
a HCVR comprising three CDRs, (HCDR1, HCDR2 and HCDR3), wherein the amino acid sequence of the HCVR is set forth in SEQ ID NO. 3, and a LCVR comprising three CDRs, (LCDR1, LCDR2 and LCDR3), wherein the amino acid sequence of the LCVR is set forth in SEQ ID NO: 4;
a HCVR comprising three CDRs, (HCDR1, HCDR2 and HCDR3), wherein the amino acid sequence of the HCVR is set forth in SEQ ID NO. 5, and a LCVR comprising three CDRs, (LCDR1. LCDR2 and LCDR3), wherein the amino acid sequence of the LCVR is set forth in SEQ ID NO: 6;
a HCVR comprising three CDRs, (HCDR1, HCDR2 and HCDR3). wherein the amino acid sequence of the HCVR is set forth in SEQ ID NO: 7, and a LCVR comprising three CDRs, (LCDR1. LCDR2 and LCDR3), wherein the amino acid sequence of the LCVR is set forth in SEQ ID NO: 8;
a HCVR comprising three CDRs, (HCDR1, HCDR2 and HCDR3), wherein the amino acid sequence of the HCVR is set forth in SEQ ID NO: 9, and a LCVR comprising three CDRs, (LCDR1, LCDR2 and LCDR3), wherein the amino acid sequence of the LCVR is set forth in SEQ ID NO: 10;
a HCVR comprising three CDRs, (HCDR1, HCDR2 and HCDR3), wherein the amino acid sequence of the HCVR is set forth in SEQ ID NO: 11, and a LCVR comprising three CDRs, (LCDR1, LCDR2 and LCDR3), wherein the amino acid sequence of the LCVR is set forth in SEQ ID NO: 12;

a HCVR comprising three CDRs, (HCDR1. HCDR2 and HCDR3), wherein the amino acid sequence of the HCVR is set forth in SEQ ID NO: 13. and a LCVR comprising three CDRs, (LCDR1, LCDR2 and LCDR3), wherein the amino acid sequence of the LCVR is set forth in SEQ ID NO: 14 a HCVR comprising three CDRs, (HCDR1, HCDR2 and HCDR3), wherein the amino acid sequence of the HCVR is set forth in SEQ ID NO: 15, and a LCVR comprising three CDRs, (LCDR1, LCDR2 and LCDR3), wherein the amino acid sequence of the LCVR is set forth in SEQ ID NO: 16 a HCVR comprising three CDRs, (HCDR1, HCDR2 and HCDR3), wherein the amino acid sequence of the HCVR is set forth in SEQ ID NO: 17, and a LCVR comprising three CDRs, (LCDR1, LCDR2 and LCDR3), wherein the amino acid sequence of the LCVR is set forth in SEQ ID NO: 18 a HCVR comprising three CDRs, (HCDR1, HCDR2 and HCDR3), wherein the amino acid sequence of the HCVR is set forth in SEQ ID NO. 19, and a LCVR comprising three CDRs, (LCDR1, LCDR2 and LCDR3), wherein the amino acid sequence of the LCVR is set forth in SEQ ID NO: 20;

a HCVR comprising three CDRs, (HCDR1, HCDR2 and HCDR3), wherein the amino acid sequence of the HCVR is set forth in SEQ ID NO: 21. and a LCVR comprising three CDRs, (LCDR1. LCDR2 and LCDR3), wherein the amino acid sequence of the LCVR is set forth in SEQ ID NO: 22;

a HCVR comprising three CDRs, (HCDR1, HCDR2 and HCDR3), wherein the amino acid sequence of the HCVR is set forth in SEQ ID NO: 23, and a LCVR comprising three CDRs, (LCDR1, LCDR2 and LCDR3), wherein the amino acid sequence of the LCVR is set forth in SEQ ID NO: 24; or a HCVR comprising three CDRs, (HCDR1, HCDR2 and HCDR3), wherein the amino acid sequence of the HCVR is set forth in SEQ ID NO: 25 and a LCVR comprising three CDRs, (LCDR1, LCDR2 and LCDR3), wherein the amino acid sequence of the LCVR is set forth in SEQ ID NO: 26.

Embodiment 15. An isolated antibody or antigen-binding fragment thereof that binds a SARS-CoV-2 nucleocapsid protein comprising one of the following combinations of a heavy chain variable region (HCVR) and a light chain variable region (LCVR)

a HCVR comprising three CDRs, HCDR1, HCDR2 and HCDR3, wherein the amino acid sequence of the HCVR is set forth in SEQ ID NO: 31; and a LCVR comprising three CDRs, LCDR1, LCDR2 and LCDR3, wherein the amino acid sequence of the LCVR is set forth in SEQ ID NO: 32;

a HCVR comprising three CDRs, HCDR1, HCDR2 and HCDR3, wherein the amino acid sequence of the HCVR is set forth in SEQ ID NO: 33; and a LCVR comprising three CDRs, LCDR1, LCDR2 and LCDR3, wherein the amino acid sequence of the LCVR is set forth in SEQ ID NO: 34; and a HCVR comprising three CDRs, HCDR1, HCDR2 and HCDR3, wherein the amino acid sequence of the HCVR is set forth in SEQ ID NO: 35; and a LCVR comprising three CDRs, LCDR1, LCDR2 and LCDR3. wherein the amino acid sequence of the LCVR is set forth in SEQ ID NO: 36.

Embodiment 16. An isolated antibody or antigen-binding fragment thereof that binds a SARS-CoV-2 membrane protein comprising:
a heavy chain variable region (HCVR) comprising three CDRs, HCDR1, HCDR2 and HCDR3, wherein the amino acid sequence of the HCVR is set forth in SEQ ID NO: 29; and
a light chain variable region (LCVR) comprising three CDRs, LCDR1, LCDR2 and LCDR3, wherein the amino acid sequence of the LCVR is set forth in SEQ ID NO: 30.

Embodiment 17. An isolated antibody or antigen-binding fragment thereof that binds a SARS-CoV-2 open reading frame protein (ORF)3a protein comprising:
a HCVR comprising three CDRs, HCDR1, HCDR2 and HCDR3, wherein the amino acid sequence of the HCVR is set forth in SEQ ID NO: 27; and a LCVR comprising three CDRs, LCDR1, LCDR2 and LCDR3. wherein the amino acid sequence of the LCVR is set forth in SEQ ID NO: 28.

Embodiment 18. An isolated antibody or antigen-binding fragment thereof that binds a SARS-CoV-2 open reading frame protein (ORF)8 protein comprising one of the following combinations of a heavy chain variable region (HCVR) and a light chain variable region (LCVR):
a HCVR comprising three CDRs, HCDR1, HCDR2 and HCDR3, wherein the amino acid sequence of the HCVR is set forth in SEQ ID NO: 37; and
a LCVR comprising three CDRs, LCDR1. LCDR2 and LCDR3, wherein the amino acid sequence of the LCVR is set forth in SEQ ID NO: 38; and
a HCVR comprising three CDRs, HCDR1, HCDR2 and HCDR3. wherein the amino acid sequence of the HCVR is set forth in SEQ ID NO: 39 and
a LCVR comprising three CDRs, LCDR1. LCDR2 and LCDR3, wherein the amino acid sequence of the LCVR is set forth in SEQ ID NO: 40.

Embodiment 19. The isolated antibody or antigen-binding fragment thereof of any one of embodiments 13-18. wherein the antibody comprises a CH3 scaffold. comprising at least one modification of the wild-type amino acid sequence of the CH3 domain derived from an immunoglobulin Fc region.

Embodiment 20. The isolated antibody or antigen-binding fragment thereof of embodiment 19. wherein at least one modification of the wild-type sequence occurs within the AB, EF, or CD loops of the CH3 scaffold.

Embodiment 21. The isolated antibody or antigen-binding fragment thereof of embodiment 20, wherein the at least one modification is an amino acid substitution, deletion or insertion.

Embodiment 22. The isolated antibody or antigen-binding fragment thereof of embodiment 21. wherein the at least one antibody epitope amino acid sequence is located within the AB loop.

Embodiment 23. The isolated antibody or antigen-binding fragment thereof of embodiment 22, wherein the antibody epitope amino acid sequence comprises a sequence derived from SIRPα or SIRPγ.

Embodiment 24. The isolated antibody or antigen-binding fragment thereof of embodiment 23. wherein the antibody epitope amino acid sequence comprises a sequence derived from a constant light chain of an antibody.

Embodiment 25. The isolated antibody or antigen-binding fragment thereof of embodiments 24, wherein the antibody epitope amino acid sequence comprises a sequence selected from the group consisting of SEQ ID Nos. 33-57 of International Patent Application No. PCT/US2019/032780.

Embodiment 26 The isolated antibody or antigen-binding fragment thereof of any one of embodiments 19-25, wherein the EF and CD loops comprise only wild-type amino acid sequences.

Embodiment 27. The isolated antibody or antigen-binding fragment thereof of embodiment 26. wherein the at least one antibody epitope amino acid sequence is located within the EF loop.

Embodiment 28. The isolated antibody or antigen-binding fragment thereof of embodiment 27, wherein the antibody epitope amino acid sequence comprises a sequence derived from SIRPα or SIRPγ.

Embodiment 29. The isolated antibody or antigen-binding fragment thereof of embodiment 28. wherein the antibody epitope amino acid sequence comprises a sequence derived from a constant light chain of an antibody.

Embodiment 30. The isolated antibody or antigen-binding fragment thereof of embodiment 27, wherein the antibody epitope amino acid sequence comprises a sequence selected from the group consisting of SEQ ID Nos. 60-67 of International Patent Application No: PCT/US2019/032780.

Embodiment 31. The isolated antibody or antigen-binding fragment thereof of any one of embodiment 25-30. wherein the AB and CD loops comprise only the wild-type amino acid sequences.

Embodiment 32. The isolated antibody or antigen-binding fragment thereof of embodiment 20, wherein the antibody epitope amino acid sequence is located within the CD loop.

Embodiment 33. The isolated antibody or antigen-binding fragment thereof of embodiment 32, wherein the antibody epitope amino acid sequence comprises a sequence derived from SIRPα or SIRPγ.

Embodiment 34. The isolated antibody or antigen-binding fragment thereof of embodiment 32, wherein the antibody epitope amino acid sequence comprises a sequence derived from a constant light chain of an antibody.

Embodiment 35. The isolated antibody or antigen-binding fragment thereof of embodiment 32. wherein the antibody epitope amino acid sequence comprises a sequence selected from the group consisting of SEQ ID Nos. 3-30 of International Patent Application No: PCT/US2019/032780.

Embodiment 36. The isolated antibody or antigen-binding fragment thereof of any one of embodiments 32-35, wherein the AB and EF loops comprise only the wild-type amino acid sequences of the immunoglobulin heavy chain.

Embodiment 37. The isolated antibody or antigen-binding fragment thereof of any one of embodiments 19-36, wherein the CH3 scaffold is derived from a human immunoglobulin Fc region.

Embodiment 38. The isolated antibody or antigen-binding fragment thereof of embodiment 37. wherein the immunoglobulin Fc region is an IgG1, IgG2, IgG3, or IgG4.

Embodiment 39. The isolated antibody or antigen-binding fragment thereof of embodiment 38. wherein the human antibody is an IgG1.

Embodiment 40. The isolated antibody or antigen-binding fragment thereof of embodiment 39, wherein the IgG1 is a G1m1 or nG1m1 allotype.

Embodiment 41. The isolated antibody or antigen-binding fragment thereof of any one of embodiments 14-40. comprises an immunoglobulin Fc region or fragment thereof of a human IgG1, IgG2, IgG3, IgG4, IgM, IgD, IgA1, IgA2 or IgE.

Embodiment 42. An isolated antigen-binding fragment of any one of embodiments 14-18, wherein the antigen-binding fragment is a variable heavy (VH) single domain monoclonal antibody.

Embodiment 43. An isolated antigen-binding fragment of any one of embodiments 14-18, wherein the antigen-binding fragment is a single chain (sc)Fv-Fc fragment.

Embodiment 44. An isolated antigen-binding fragment of any one of embodiments 14-18, wherein the isolated antigen-binding fragment comprises an Fv, scFv, Fab, F(ab')2, or Fab' fragment, diabody. or any fragment whose half-life has been increased.

Embodiment 45. The isolated antibody or antigen-binding fragment thereof of any one of embodiments 14-44, wherein binding of the antibody or antigen-binding fragment thereof:
inhibits binding of a SARS-CoV-2 virus to a host ACE2 receptor;
fixes complement to a SARS-CoV-2 virus;
induces phagocytosis of a SARS-CoV-2 virus, or
any combination thereof.

Embodiment 46. The isolated antibody or antigen-binding fragment of any one of embodiments 14-44, wherein the binding of the antibody or antigen-binding fragment thereof neutralizes a SARS-CoV-2 virus by blocking binding of the receptor binding domain (RBD) of the virus with an ACE2 receptor.

Embodiment 47. The isolated antibody or antigen-binding fragment thereof of any one of embodiments 14-46. wherein the SARS-CoV-2 virus is a SARS-CoV-2 variant.

Embodiment 48. The isolated antibody or antigen-binding fragment thereof of embodiment 47, wherein the SARS-CoV-2 variant is the U.K. (B.1.1.7) variant of SARS-CoV-2, the South African (B.1.351) variant of SARS-CoV-2, the California (B.1.429) variant of SARS-CoV-2, the California (B 1.427) variant of SARS-CoV-2, the Brazilian (P.1) variant of SARS-CoV-2, the New York (B.1.526) variant of SARS-CoV-2, the New York (B 1.526.1) variant of SARS-CoV-2, the UK/Nigeria (B.1.525) variant of SARS-CoV-2, or the Brazilian (P.2) variant of SARS-CoV-2.

Embodiment 49. A pharmaceutical composition comprising an isolated antibody or antigen-binding fragment thereof of embodiment 14 and a pharmaceutically acceptable carrier or diluent.

Embodiment 50. The pharmaceutical composition of embodiment 49, further comprising at least 1. at least 2, at least 3, at least 4, or at least 5 additional isolated antibodies or antigen-binding fragments thereof of embodiment 14.

Embodiment 51. The pharmaceutical composition of embodiment 49 or 50, further comprising at least 1. at least 2. or at least 3 additional isolated antibodies or antigen-binding fragments thereof of claim 15.

Embodiment 52. The pharmaceutical composition of any one of embodiments 49-51. further comprising the isolated antibody or antigen-binding fragment thereof of claim 16.

Embodiment 53. The pharmaceutical composition of any one of embodiments 49-52, further comprising the isolated antibody or antigen-binding fragment thereof of claim 17.

Embodiment 54. The pharmaceutical composition of any one of embodiments 49-53, wherein at least one antibody or antigen-binding fragment thereof comprises an immunoglobulin Fc region or fragment thereof of a human IgG1, IgG2, IgG3, or IgG4.

Embodiment 55. The pharmaceutical composition of any one of embodiments 49-53, wherein at least one antibody or antigen-binding fragment thereof comprises an immunoglobulin Fc region or fragment thereof of a human IgM.

Embodiment 56. The pharmaceutical composition of any one of embodiments 49-53, wherein at least one antibody or antigen-binding fragment thereof comprises an immunoglobulin Fc region or fragment thereof of a human IgD.

Embodiment 57. The pharmaceutical composition of any one of embodiments 49-53, wherein at least one antibody or antigen-binding fragment thereof comprises an immunoglobulin Fc region or fragment thereof of a human IgA1 or IgA2.

Embodiment 58. The pharmaceutical composition of any one of embodiments 49-53. wherein at least one antibody or antigen-binding fragment thereof comprises an immunoglobulin Fc region or fragment thereof of a human IgE.

Embodiment 59. The pharmaceutical composition of any one of embodiments 49-58, wherein at least one antibody or antigen-binding fragment thereof is a polyreactive antibody.

Embodiment 60. The pharmaceutical composition of any one of embodiments 49-59, further comprising a second therapeutic agent.

Embodiment 61. The pharmaceutical composition of embodiment 60, wherein the second therapeutic agent is selected from the group consisting of: an anti-inflammatory agent, and an antiviral agent.

Embodiment 62. A method for treating or preventing a SARS-CoV-2 infection in a subject in need thereof, comprising administering an effective amount of any one of the pharmaceutical compositions of embodiments 49-61.

Embodiment 63. The method of embodiment 62, wherein the one or more antibodies or antigen-binding fragments thereof contained in the pharmaceutical composition treat or prevent the a SARS-CoV-2 infection by neutralizing the SARS-CoV-2 virus.

Embodiment 64. The method of embodiment 63, wherein the SARS-CoV-2 virus is a SARS-CoV-2 variant Embodiment 65. The method of embodiment 64, wherein the SARS-CoV-2 variant is the U.K. (B.1.1.7) variant of SARS-CoV-2, the South African (B 1.351) variant of SARS-CoV-2, the California (B.1.429) variant of SARS-CoV-2, the California (B.1.427) variant of SARS-CoV-2, the Brazilian (P.1) variant of SARS-CoV-2, the New York (B.1.526) variant of SARS-CoV-2, the New York (B.1.526.1) variant of SARS-CoV-2, the UK/Nigeria (B.1.525) variant of SARS-CoV-2, the Brazilian (P.2) variant of SARS-CoV-2, or the Omicron (B.1.529) variant.

Embodiment 66. The method of embodiments 64 or 65, wherein the pharmaceutical composition treats or prevents SARS-CoV-2 variant and nonvariant infections with equivalent efficacies.

Embodiment 67. The method of treatment of any one of embodiments 62-66, wherein the administering of the pharmaceutical composition to the subject in need thereof comprises injecting the composition into the body of the subject subcutaneously, intravenously or intramuscularly.

Examples

Example 1. Evaluation of the breadth of patients' humoral responses against SARS-CoV-2. The overall spectrum of the productive antibody response to SARS-CoV-2 was examined using an automated, high-throughput hybridoma library generation and screening platform [Puligedda et al. 2014] after isolating memory B cells acquired from blood samples of COVID-19 convalescent patients who demonstrated a high antibody titer to N and/or S proteins.

Collection of patient samples. Blood samples were drawn from convalescing COVID-19 patient volunteers deemed eligible for donating convalescent plasma as set forth in the U.S. Food and Drug Administration (FDA)'s Recommendations [FDA 2020]. Patients displayed no PCR-detectable viremia and maximal IgG (2880) titer of class switched, virus-specific antibodies.

Generation of hybridoma libraries. Hybridomas were generated from the memory B cells isolated from the donors by following protocols for isolating and expanding primary B cells as well as electrofusion methods described in U.S. patents [Dessain & Weinberg 2002, Dessain & Adekar 2009]. Hybridomas stably expressing human mAbs were generated by electrofusion of expanded B-cells to the B5-6T myeloma cell line, which expresses an ectopic human telomerase gene that stabilizes human chromosomes in the hybrid cells created. Fused hybridomas were plated into 96-well plates in growth medium with HAT selection of stable hybridomas for 7 days. After 7 days, growth media were switched to media with HT for stable selected hybridoma growth. Hybridomas were cultured in a 37° C. incubator for 14-21 days during which time they were imaged for monoclonality and monitored for isotype- and sub-class-specific Ig secretion. Supernatants from monoclonal wells expressing measurable levels of Ig were cherry-picked and submitted for target-based screening.

Screening Assays For Antiviral Antibodies. The naturally occurring human antibodies (IgM, IgG, and IgA isotypes) secreted by those hybridomas were screened for reactivity against a panel of SARS-CoV-2 proteins. Antibody screening assays were developed for three SARS-CoV-2 structural proteins (S, N, M) and a panel of accessory ORF proteins of SARS-CoV-2. In addition to the reference Spike (S) protein corresponding to that found on the USA/WA_CDC-WA1/2020 virus, counterscreening was carried out on Spike proteins, or Spike protein domains, corresponding to the Spike proteins present on the surface of viral variants. The breadth of variants tested are described in Table 2.

TABLE 2

SARS-CoV-2 Spike Screening Proteins

| SARS-CoV-2 Viral Target | Assay System | | Variants Tested |
|---|---|---|---|
| Spike (S) | HTRF | Cell-based | |
| 1 Trimer-stabilized FL (non-S1) | √ | | A352S, E406Q, K417N, N439K, K444R, L452R, Y453F, A475V, E484Q, E484K, F486S, N501Y, D614G, S. African |
| 2 S1 domain (non-RBD) | √ | | partial (K417N, E484K, N501Y); Brazilian (K417T, E484K, |
| 3 Receptor binding domain (RBD) | √ | | N501Y); S. African (K417N, E484K, N501Y, D614G); Spanish (A222S, D614G); U.K. part sequence for the closest related V gene was used to generate a full-length version of each gene. The gene sequences were codon optimized to create expression constructs for recombinant production and testing of antibodies. Final sequences were translated and analyzed for potential stop codons and frame shifts.

Example 3. Recombinant production of antibodies. Heavy and light chain pairs from 103 clones, from which productive immunoglobulin RNA sequences were determined, were expressed as recombinant antibodies.

Production of paired light and heavy chains. Variable domains yielding productive uninterrupted protein sequences were analyzed for number of reads and the degree of somatic hypermutations (SHM) in comparison to the closest immunoglobulin germline. Hybridoma hit sequences with at least one chain that had more than 2% of SHM were advanced to HC/LC pairing and the recombinant production of antibodies. Immunoglobulin expression fragments were cloned into the pcDNA3.4-based vectors and expressed in 293F cells. Affinity and binding pattern of recombinant antibodies were compared to the original antibody-containing hybridoma supernatants in BLI, HTRF and cell-based assay. Antibody-containing supernatants or purified antibodies were advanced to downstream assays. If multiple heavy or light chain sequences were detected within one well, their CDRs were aligned and compared for potential PCR errors. In cases where multiple sequences within a well were different, i.e., originated from separate clones, all potential combinations of light and heavy chains were recombinantly produced and tested in downstream assays. Wells that yielded a single HC/LC pair were advanced to recombinant expression and downstream assays. 5' fragments of the constant regions were sequenced to identify the isotype of the antibody and compared to the experimentally identified isotype of hybridoma supernatants. The resulting isotype of the heavy or light chain was assigned based on two or more positive readings from experimental (ex. ELISA and FACS) assays and sequencing.

A combined analysis of Ig isotype and their level of SHM of virus-specific antibodies revealed several key properties of the productive antiviral response. First, among all "mutated" immunoglobulins that had more than 2% of their nucleotide sequence deviated from the closest germline, there was an unusually high (26.4%) proportion of mutated IgMs, having a mean SHM rate of 5.73%. The functional basis of this phenomenon is not known, but one could speculate that these IgMs came from non-switched memory B cells that had undergone affinity maturation. Second, a subset of such somatically hypermutated IgMs recognized full-length Spike, but not the soluble RBD or 51 subunit of Spike protein. And third, while the predominant isotype among class-switched antibodies was, as expected, IgG it was possible to capture a panel of fairly mutated virus-specific IgAs. It is plausible that these antibodies play a major role in mucosal neutralization of the incoming virus and may be of particular use for prophylaxis of viral infection and for vaccine design.

Example 4. Identified anti-Spike antibodies from convalescent COVID-19 patients exhibit potent binding to Spike proteins mimicking a range of different viral variants. Purified recombinant antibodies were assessed, in the HTRF assay described above, using either soluble RBD or 51 domains containing mutations found in naturally occurring viral variants, as well as mutations predicted to decrease binding of neutralizing antibodies. Table 3 depicts the binding of identified anti-Spike antibodies, expressed as fold-binding over background. As anticipated, binding of some antibodies, such as PR201_00151 and PR194_00232, are negatively affected by specific mutations within the Spike domain (e.g. K417N). In contrast, binding by antibodies like PR199_00255, PR193_00018, and PR200_00622 are unaffected by the range of mutations analyzed, including variants containing single point mutations, as well as multiple point mutations that mimic the naturally occurring Spike proteins found on the B.1.1.7 and B.1.351 virus isolates. A subset of antibodies, such as PR199_00255 and PR200_00622, also bind to Spike protein found on SARS-CoV-1, suggesting that they bind to a highly conserved epitope.

Binding of the antibodies PR913_00018, PR194_00232, and PR200_00622 were further characterized in the HTRF assay to determine $EC_{50}$ of binding to a wide range of single and multi-point mutations, including to the B.1.1.7, B.1.429, P.1, and B.1.351 variants. Each of the antibodies bound to the Wuhan/Washington reference Spike RBD protein with $EC_{50}$s in the HTRF assay of between 45-68 pM. Mutations that mapped to the ACE2 binding site on the RBD appear to disrupt the binding affinity of PR199_00232, whereas no mutation, or combination of mutations, tested disrupted the ability of either PR193_00018 or PR200_00622 to bind to the RBD. The ability of these two antibodies to bind to the wide range of variants suggests that their epitopes are maintained even in the face of the viral drift that has occurred to date.

The impact of mutational drift on the binding of each of PR193_0018, PR194_00232, and PR200_00622 antibodies was evaluated using a series of Spike proteins containing either single point mutations or complex point mutations that recapitulate the spectrum of mutations in naturally occurring variants that have emerged across the globe. PR194_00232 is the most sensitive of the three antibodies to mutational drift within the Spike protein. Mutations, such as K417N and N501Y, mutations known to exist in naturally occurring variants, and consistent with the alanine scanning data, significantly decrease the ability of PR194_00232 to bind the Spike protein. Whereas other naturally occurring mutations, such as L452R, E484Q, or D614G do not impact binding relative to binding to the Washington reference Spike protein. In contrast, binding of PR193_0018 and PR200_00622 are not significantly impacted by any of the single point mutations tested. In fact, binding by PR193_0018 and PR200_00622 to specific variant Spike proteins (e.g., E484K and E484Q) appears to be modestly enhanced over the reference Spike. Similar observations were made when binding of PR193_0018, PR194_00232, and PR200_00622 was tested against RBD domain proteins containing the full complement of mutations known to exist in four different variants. Of particular interest is the binding to RBDs corresponding to the South African (B.1.351) and U.K. (B.1.1.7) variants. As predicted by the K417N and N501Y single point mutation data, binding of PR194_00232 to both the U.K. and S.A. variants is weaker than observed against the reference strain Spike protein.

TABLE 3

Binding of Antibodies to Variant Forms of Recombinant Spike Protein

| Ab # | Epitope | D614G | N439K | E406Q | K417N | N501Y | Y453F | A352S | A475V | DHV69/70, DY144, N501Y, A570D, D614G, P681H | DHV69/70, Y453F, D614G | A222S, D614G | K417N, E484K, N501Y, D614G |
|---|---|---|---|---|---|---|---|---|---|---|---|---|---|
| PR193_00018 | RBD | 4.930 | 4.427 | 6.581 | 3.637 | 4.921 | 4.737 | 4.616 | 4.419 | 4.150 | 5.613 | 5.429 | 4.637 |
| PR194_00068 | Non-RBD | 1.119 | 1.064 | 1.002 | 1.056 | 0.932 | 1.005 | 0.894 | 0.989 | 1.198 | 1.224 | 1.186 | 1.230 |
| PR194_00232 | RBD | 4.837 | 5.952 | 8.811 | 2.252 | 4.303 | 5.943 | 6.749 | 7.474 | 3.910 | 8.180 | 8.470 | 1.123 |
| PR194_00292 | Non-RBD | 1.064 | 1.057 | 0.967 | 1.028 | 0.996 | 0.974 | 0.940 | 1.023 | 2.372 | 2.594 | 1.017 | 2.257 |
| PR194_00364_b | Non-RBD | 2.469 | 1.016 | 0.918 | 1.060 | 0.948 | 0.977 | 0.917 | 1.019 | 3.631 | 3.054 | 3.052 | 4.546 |
| PR194_00453 | RBD | 9.552 | 1.052 | 0.990 | 1.099 | 1.034 | 0.987 | 1.111 | 1.064 | 9.059 | 9.447 | 9.212 | 9.574 |
| PR196_00413_a | Non-RBD | 9.921 | 1.070 | 1.023 | 1.059 | 1.079 | 1.061 | 1.073 | 1.007 | 6.394 | 9.676 | 8.740 | 9.002 |
| PR197_00647 | Non-RBD | 8.299 | 1.036 | 1.032 | 1.033 | 1.056 | 1.106 | 1.038 | 0.999 | 1.103 | 1.072 | 9.539 | 7.725 |
| PR199_00255 | RBD | 11.231 | 6.087 | 10.864 | 7.286 | 6.150 | 1.032 | 8.258 | 7.645 | 7.291 | 9.631 | 9.296 | 9.477 |
| PR200_00622 | RBD | 6.100 | 5.049 | 7.598 | 4.680 | 5.113 | 4.670 | 5.142 | 5.222 | 5.922 | 7.003 | 6.644 | 6.278 |
| PR201_00151 | RBD | 7.246 | 6.027 | 8.298 | 1.089 | 6.156 | 5.479 | 7.058 | 5.700 | 4.220 | 6.531 | 7.294 | 1.049 |

Antibodies were evaluated for ability to bind to recombinant Spike protein in an HTRF assay, binding was expressed as a fold over background. Single point mutations (except D614G) were expressed in the context of soluble RBD domain, all others were expressed in context of soluble S1 domain. No binding was anticipated to RBD domain constructs by antibodies that bind to epitopes outside the RBD domain.

TABLE 4

EC50 of Binding to Variant Forms of Recombinant Spike Protein.

| | | EC50 (pM) HTRF assay (relative to RBD) | | |
|---|---|---|---|---|
| Mutation | Location | PR194_00232 IMM20190 | PR200_00622 IMM20253 | PR193_00018 IMM20184 |
| REF | RBD | 68.2 | 52.7 | 44.8 |
| N439K | RBD | 68.9 | 53.4 | 51.0 |
| E406Q | RBD | 67.7 | 40.6 | 26.1 |
| K417N | RBD | >500 | 67.4 | 43.7 |
| N501Y | RBD | 279 | 58.5 | 39.8 |
| Y453F | RBD | 64.6 | 62.6 | 49.4 |
| A352S | RBD | 21.9 | 31.7 | 26.3 |
| A475V | RBD | 72.4 | 33.0 | 27.9 |
| E484Q | RBD | 52.4 | 23.8 | 21.6 |
| E484K | RBD | 33.4 | 31.6 | 20.5 |
| L452R | RBD | 31.8 | 34.0 | 43.6 |
| K444R | RBD | 25.8 | 26.1 | 19.4 |
| F486S | RBD | 33.4 | 25.9 | 22.1 |
| K417N, E484K, N501Y | RBD | Inactive | 19.7 | 14.5 |
| K417T, E484K, N501Y | RBD | Inactive | 23.6 | 18.3 |
| REF | S1 | 56.0 | 49.1 | 31.8 |
| D614G | S1 | 62.7 | 62.4 | 39.7 |
| A222S, D614G | S1 | 49.1 | 44.9 | 26.9 |
| K417N, E484K, N501Y, D614G | S1 | 230 | 24.8 | 26.7 |
| ΔHV69/70, N501Y, D614G | S1 | 396 | 21.6 | 14.3 |
| ΔH69/70, ΔY144, N501Y, A570D, D614G, P681H | S1, RBD | >500 | 62.4 | 45.5 |
| ΔH69/70, Y453F, D614G | S1, RBD | 47.2 | 66.4 | 31.6 |

Figure 2:
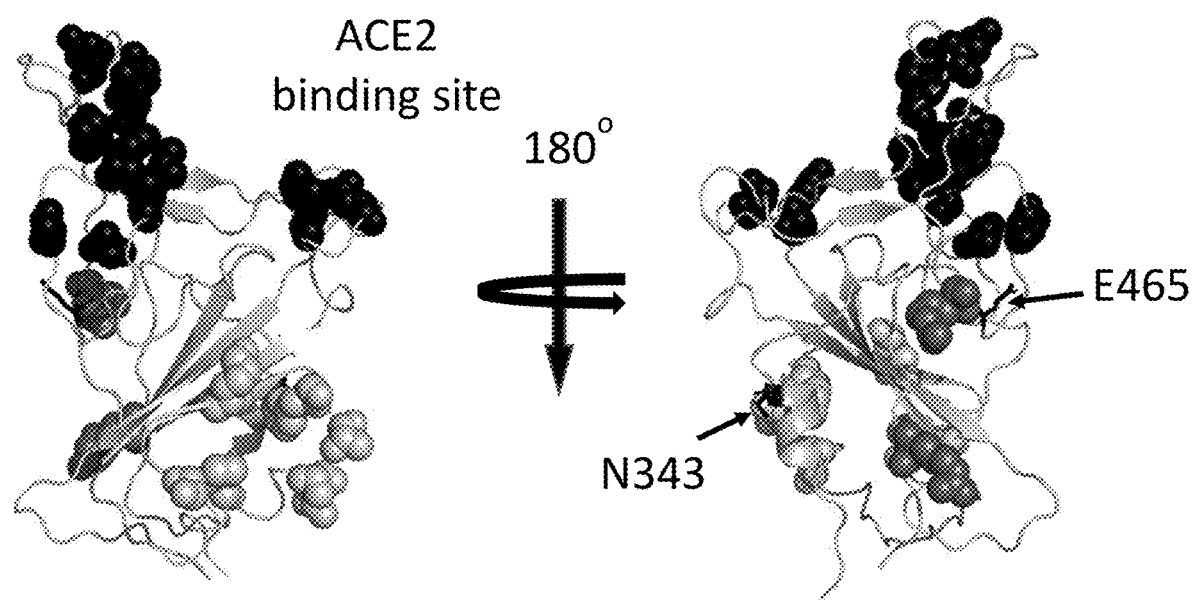
FIG. 2 depicts the epitopes for IMM20190 (black sphere, left panel), IMM20184 (light gray, left panel), and IMM20253 (dark gray, right panel), as determined by alanine scanning. ACE2 binding site and two other residues [N343 represents a site of potential glycosylation and E465 (Greaney et al 2021)]
Figure 3A:
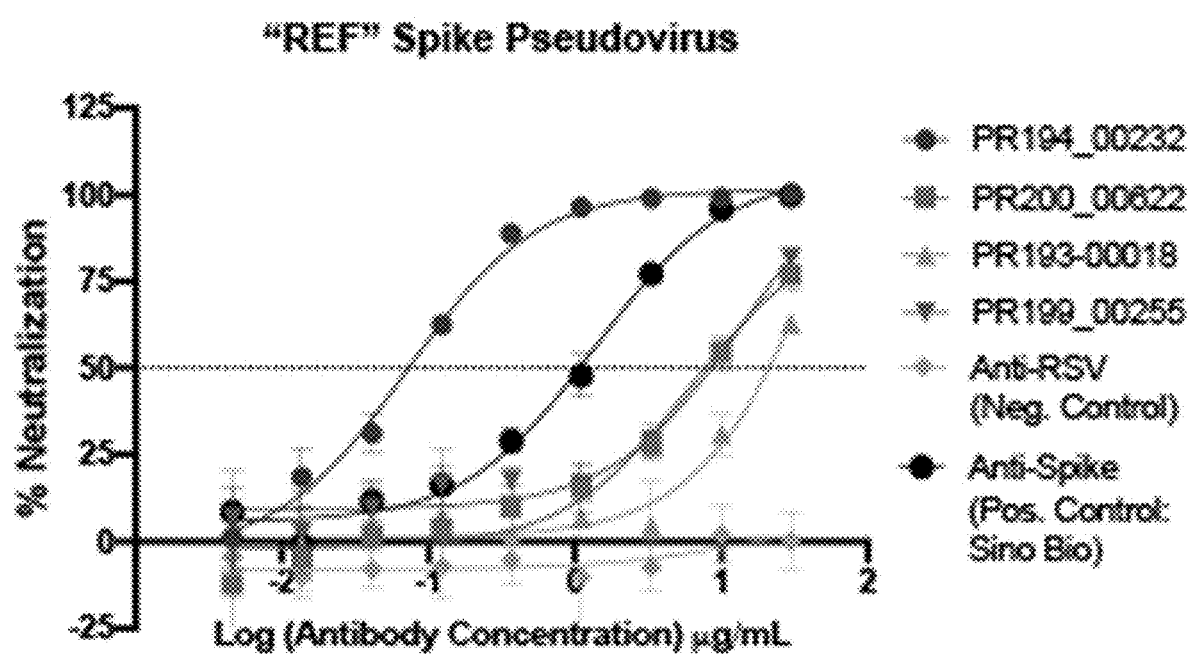
FIGS. 3A-3D depict in vitro pseudovirus neutralization activity of PR193_00018 (IMM20184), PR194_00232 (IMM20190), PR200_00622 (IMM20253), and PR190_00255 (IMM20279) against pseudoviruses expressing four different variations of Spike (FIGS. 3A-3D).
Figure 3B:
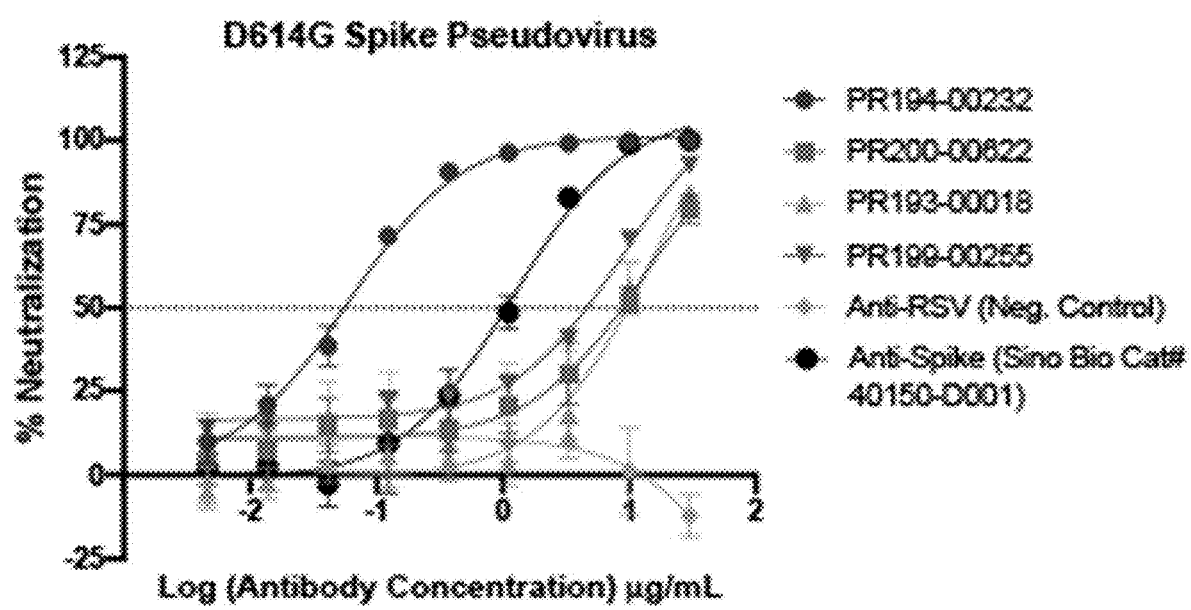
Figure 3C:
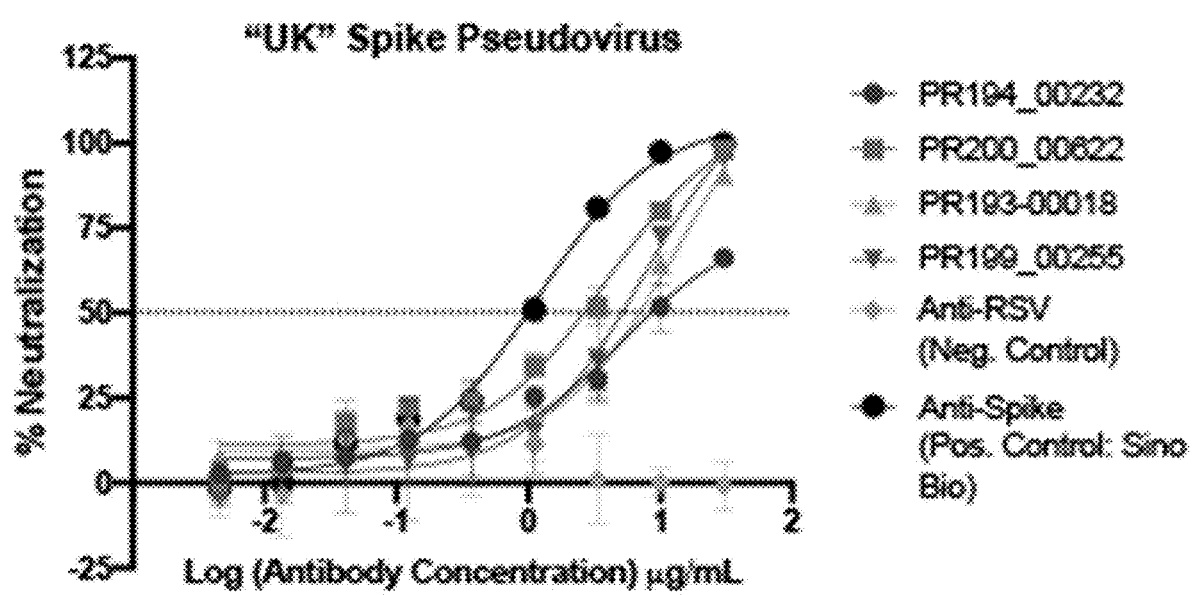
Figure 3D:
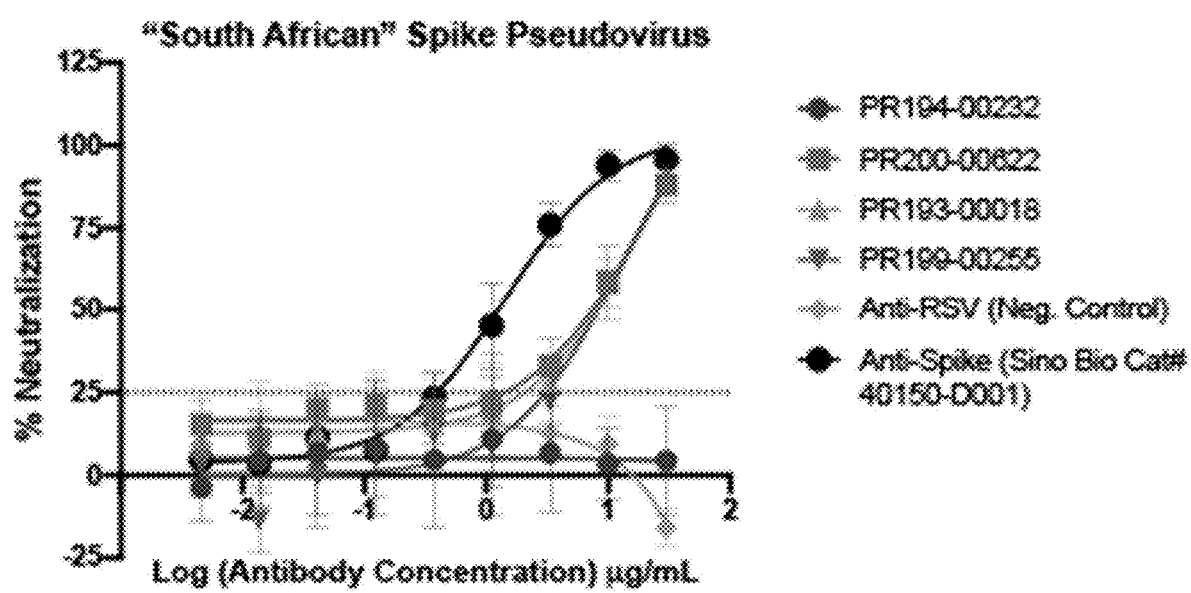

Example 5. Identified anti-Spike antibodies bind to non-overlapping epitopes within the RBD of SARS-Co-V-2 Spike. Purified recombinant forms of the PR193_00018, PR194_00232, and PR200_00622 failed to compete with each other for binding to the SARS-CoV-2 RBD when assessed via biolayer interferometry on an Octet QKe instrument. These data suggested the three antibodies bind to non-overlapping epitopes on the SARS-CoV-2 RBD. Alanine scanning of the RBD was performed to identify residues critical for binding of each of the antibodies. Consistent with each of the antibodies binding to non-overlapping epitopes, non-overlapping sets of residues were identified as being critical for binding of the antibodies (Table 5). Those residues map to unique regions of three dimensional structure of the RBD, consistent with the ability of the antibodies to fail to compete with each other for binding (FIG. 2)

TABLE 5

Identification of critical residues for Ab binding.
Binding Reactivity (% WT)

| Mutation | IMM20190 Fab | IMM20184 Fab | IMM20253 Fab HS | COV010 MAb | COV003 MAb |
|---|---|---|---|---|---|
| K356A | 82.2 (6) | 61.5 (6) | 7.1 (4) | 86.3 (4) | 45.7 (8) |
| N370A | 63.4 (5) | 7.5 (3) | 72.4 (4) | 65.9 (12) | 66.4 (2) |
| A372S | 127.3 (42) | 3 (2) | 99.9 (16) | 97.1 (8) | 72.6 (4) |
| F374A | 64.8 (7) | 7.4 (1) | 70.8 (8) | 87.4 (4) | 53 (1) |
| K378A | 87.9 (3) | 6.7 (0) | 66.9 (17) | 57.7 (10) | 64.6 (2) |
| S383A | 110.8 (1) | 0.4 (2) | 86.3 (2) | 41 (2) | 94.7 (9) |
| P384A | 111.5 (1) | 2.1 (1) | 112 (12) | 54 (7) | 107.9 (11) |
| K417A | 5.6 (6) | 96.2 (32) | 113 (20) | 120 (2) | 116.1 (7) |
| D420A | 4.6 (2) | 65.5 (14) | 69 (6) | 76.5 (7) | 48.1 (5) |
| L455A | 4.5 (7) | 170.6 (27) | 114 (13) | 175.3 (15) | 119.3 (50) |
| F456A | 2.3 (2) | 79.7 (2) | 64.8 (4) | 97.4 (8) | 84.8 (2) |
| N460A | 9.4 (6) | 76.3 (20) | 89 (12) | 117.2 (24) | 112.4 (1) |
| R466A | 70.8 (19) | 78.7 (15) | 5 (1) | 57.8 (10) | 26 (3) |
| Y473A | 1 (7) | 83.5 (26) | 65.3 (7) | 92.1 (14) | 35.4 (19) |
| N487A | 12.6 (6) | 84.5 (7) | 67 (31) | 83.8 (2) | 65.8 (0) |
| Y489A | 3.1 (4) | 73 (6) | 65 (12) | 99.3 (21) | 73.9 (1) |
| N501A | 12.9 (1) | 93.4 (5) | 80.1 (14) | 94.1 (8) | 84.7 (1) |
| Y505A | 0.3 (4) | 130 (9) | 108.2 (11) | 131.9 (13) | 119.9 (6) |

Figure 4A:
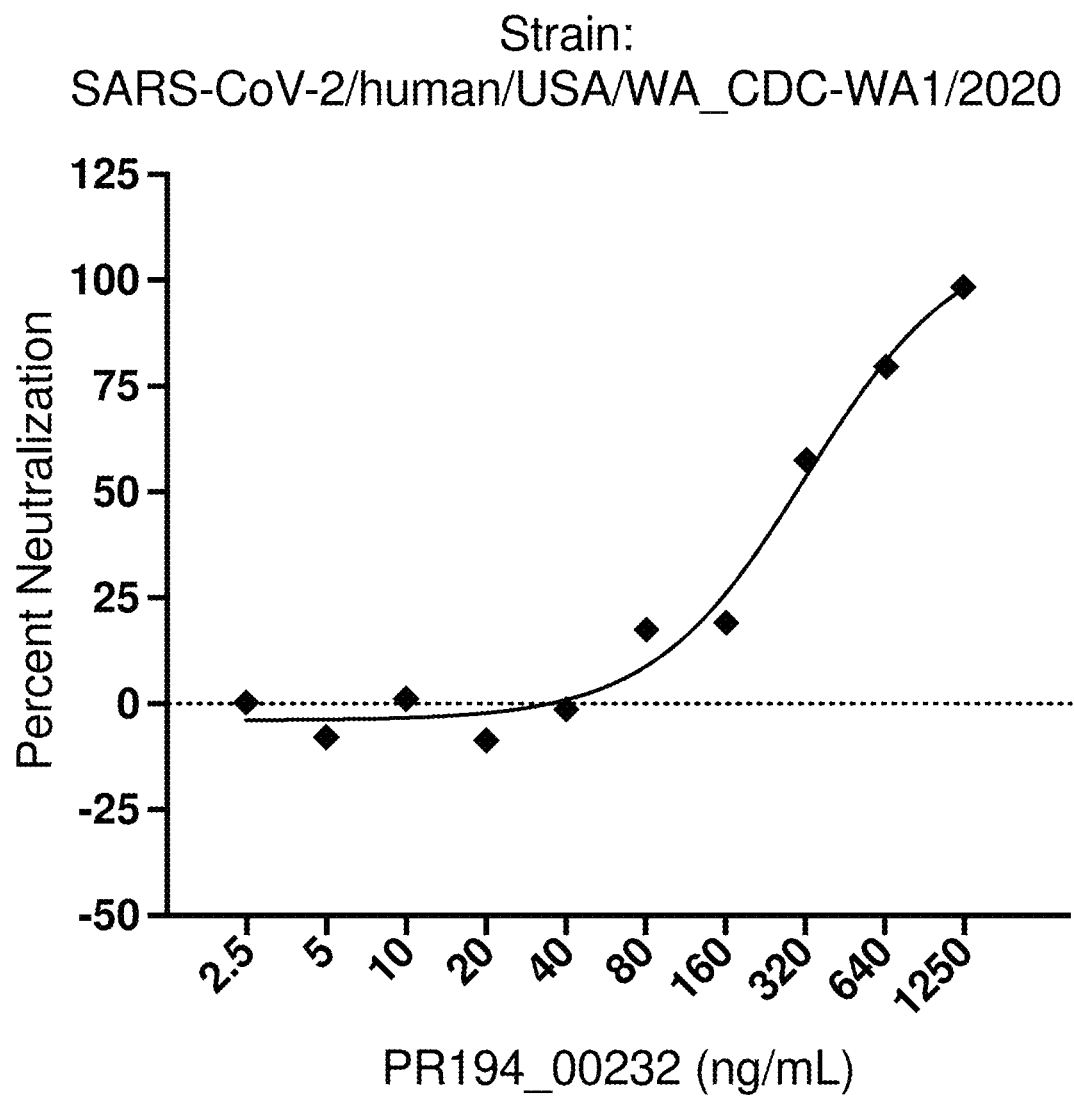
FIGS. 4A-4B depict in vitro neutralizing activity of the identified anti-Spike antibody PR194_00232 against FIG. 4A the live virus isolate SAR-CoV-2/human/USA/ WA_CDC-WA1/2020, which contains a reference Spike protein.
Figure 4B:
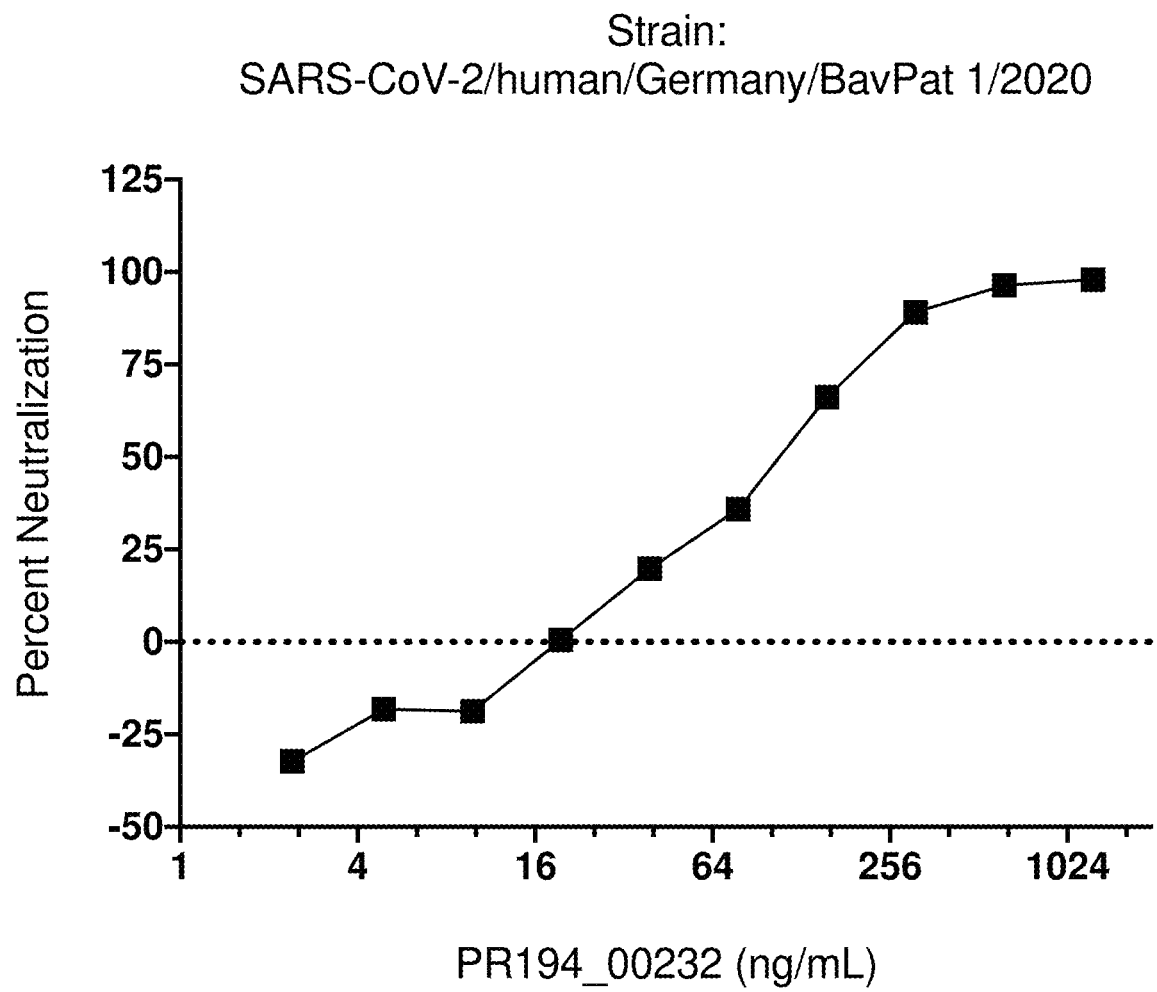

Mean binding reactivities (and ranges) are listed for all identified critical residues. Critical residues for Ab binding (boxed) were residues whose mutations were negative for binding to test Abs, but positive for binding to control Ab Example 6. Identified anti-Spike antibodies neutralize SARS-CoV-2 pseudovirus. The functional consequence of antibodies binding to Spike was assessed in assays using pseudotyped replication-incompetent lentivirus which were used to infect HEK293 cells overexpressing Angiotensin converting enzyme 2 (ACE2). Spike-expressing pseudovirus was generated with System Bioscience's pPACK-SPIKE packaging system (System Biosciences, Cat #CVD19-500A-1) as per manufacturer's protocol. Briefly, $8\times10^6$ 293TN Producer cells (System Biosciences, LV900A-1) were plated in T150 flasks overnight. Plasmids encoding lentiviral packaging proteins and Spike were added 1 mL of plain DMEM for each T150 being transfected. 55 mL of PureFection reagent (System Biosciences; Cat #LV750A-1) was added to each 1 mL tube, vortexed for 10 seconds, and incubated at room temperature for 15 minutes. The plasmid and PureFection mixture were added to a T150 flask containing 293TN cells and placed in a 37° C. incubator containing 5% $CO_2$ for 48 hours. Pseudovirus-containing supernatants were harvested at 48 hours and passed through a 0.45 micron PVDF filter to remove cellular debris. 5×PEG-it Virus Precipitation Solution (System Biosciences, Cat #LV810A-1) was added to supernatants and incubated 4° C. overnight. Pseudovirus-containing supernatants with 1×PEG-it Virus Precipitation Solution were then spun at 1500×g for 30 minutes. Pseudovirus-containing pellets were resuspended in plain DMEM to achieve at 10× concentration and frozen at −80° C. in single use aliquots.

Pseudovirus infection and neutralization assays were performed by using standard methods. Pseudoviruses were produced with the pPACK-SPIKE packaging kit, $10^4$ ACE2-293T cells were plated in the inner 60 wells of a white opaque 96 well flat bottom plate (Corning; Cat #3917) in 1004 of ACE2-293T media overnight in a 37° C. incubator containing 5% $CO_2$. To determine infectivity of each lot of pseudovirus, pseudovirus-containing supernatants were thawed from −80° C. and two-fold dilutions were performed. 100 mL of pseudovirus at various dilutions was added to ACE2-293T cells. To test neutralization activity of antibodies, indicated antibody concentrations were pre-incubated with pseudovirus for 1 hour in a 37° C. incubator containing 5% $CO_2$. Then, 1004 of antibody/pseudovirus mixture was added to ACE2-293T cells. After 72 hours, cells and media were equilibrated to room temperature for 20 minutes. 100 mL of media was removed and replaced with 1004 of Bright-Glo Luciferase Assay Reagent (Promega, Cat #E2620). Luminescence was measured on the EnSpire Plate Reader (PerkinElmer).

Initial testing with pseudovirus was performed using antibody-containing supernatants, 3-4 log dilutions of 26 unique anti-Spike antibodies were tested for their ability to block infection in comparison to an anti-RSV negative control and a commercially available anti-Spike positive control.

Neutralization activity of a subset of antibodies (FIGS. 3A-3D) was confirmed using SARS-CoV-2 luciferase reporter virus particles (RVP's) (Integral Molecular) based on the manufacturer's instructions. In brief, RVP's were thawed for 2-3 minutes in a 37° C. water bath. The recommended amount of RVP's was added to the inner wells of a white opaque 96 well plate (Corning; Cat #3917) or 384 well plate (Greiner Bio-One; Cat #781080). Media containing the indicated amount of antibody was added to each well, resulting in a final volume of 100 mL per well (96 well plate) or 25 mL per well (384 well plate). The antibody/RVP mixture was pre-incubated for 1 hour in a 37° C. incubator containing 5% $CO_2$. ACE2-293T target cells were added to each well ($2\times10^4$ cells in 100 mL for a 96 well plate or $0.9\times10^4$ cells for a 384 well plate) and incubated for 72 hours. Media was removed from all wells, equal volumes of PBS and *Renilla*-Glo Luciferase Assay Reagent (Promega; Cat #E2720) were added to each well (60 mL total for a 96 well plate or 30 mL total for a 384 well plate). After 10 minutes, luminescence was measured on the EnSpire Plate Reader (PerkinElmer). Percent neutralization was calculated with the following equation: [(RLU of Virus+ cells)−(RLU of Experimental Sample)]/[(RLU of Virus+ cells)−(RLU of cells only)].

The PR194_00232 antibody that exhibited potent neutralization against pseudovirus expressing both the reference (SARS-CoV-2/human/USA/WA_CDC-WA1/2020) and D614G (SARS-CoV-2/human/Germany/BavPat 1/2020) were also assessed in neutralization assays using live virus of each of the isolates (FIGS. 4A and 4B).

Full dose response of purified antibodies confirmed strong neutralizing activity by antibodies such as PR194_00232. The D614G variant is a widespread mutation [Plante et al. 2020] found in a number of different isolates. Antibodies such as PR194_00232, that bound to the soluble protein and neutralized pseudovirus expressing the D614G Spike, were also able to neutralize the live virus with comparable IC50 values (FIG. 4B).

Figure 5A:
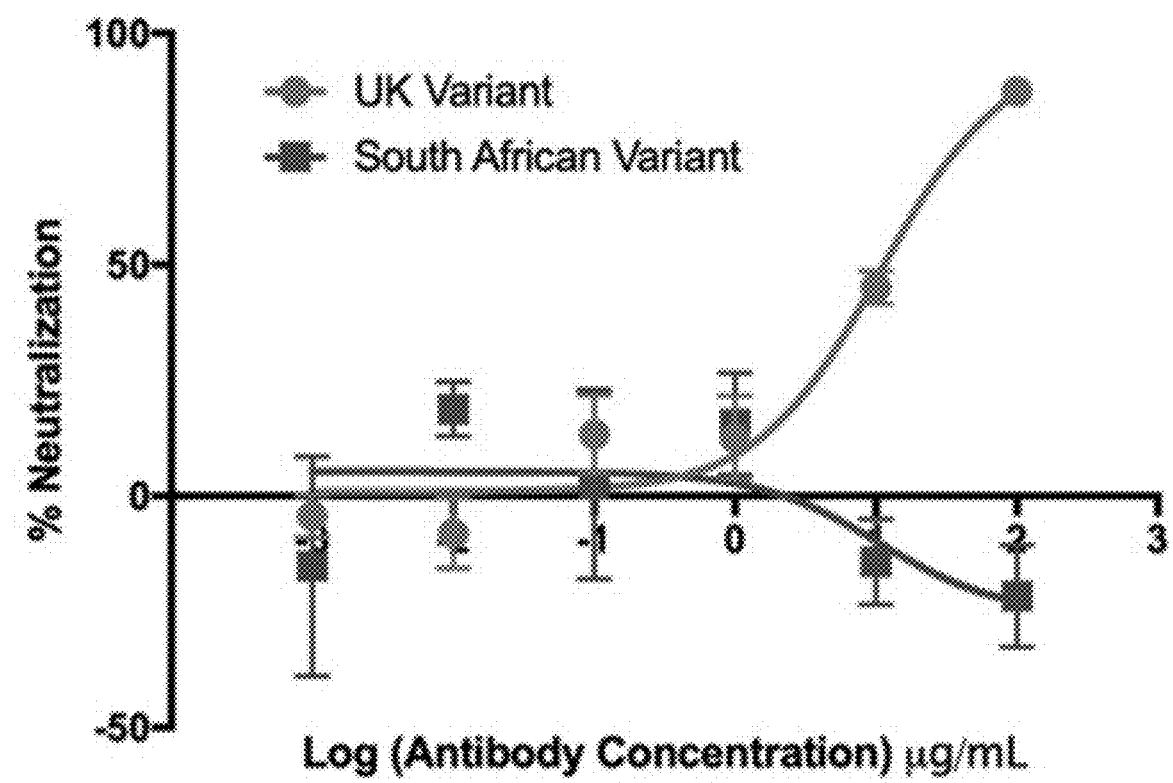
FIGS. 5A-5C. depict in vitro neutralization activity of identified anti-Spike antibodies, as noted, against pseudovirus expressing the Spike protein from either the U.K. (B.1.1.7) or South African (B.1.351) variant of SARS-CoV-2
Figure 5B:
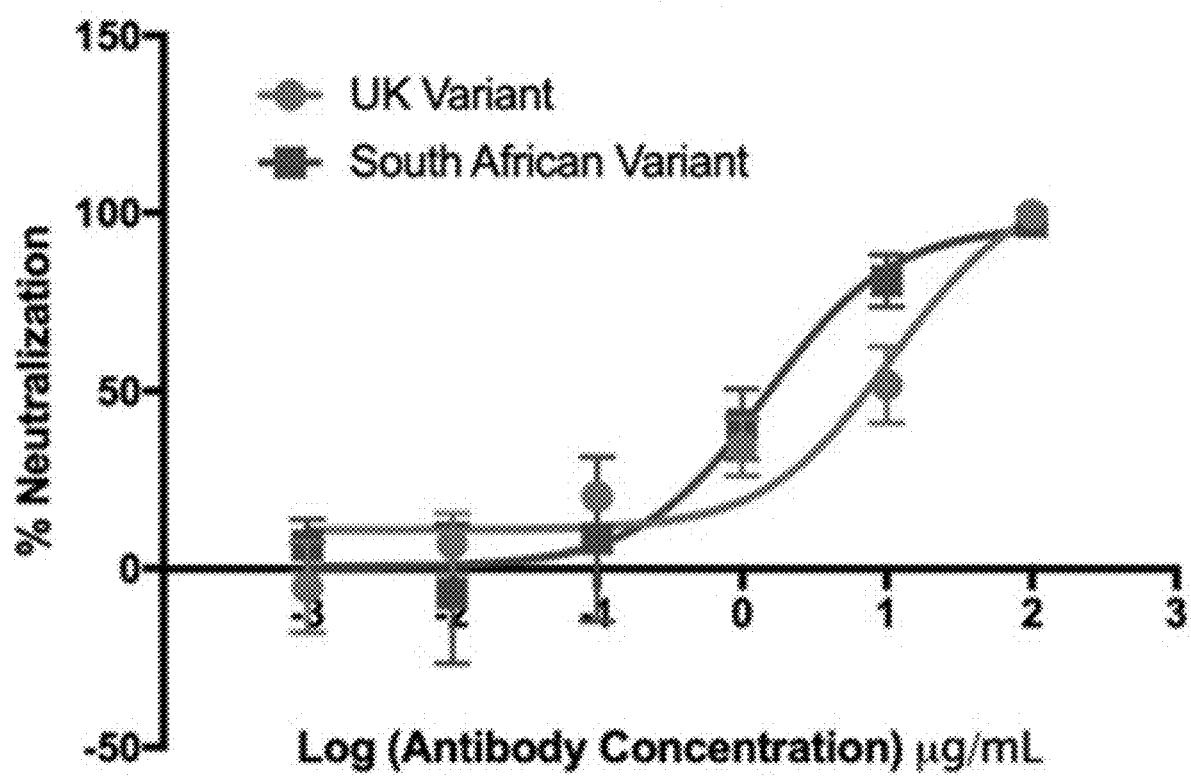
Figure 5C:
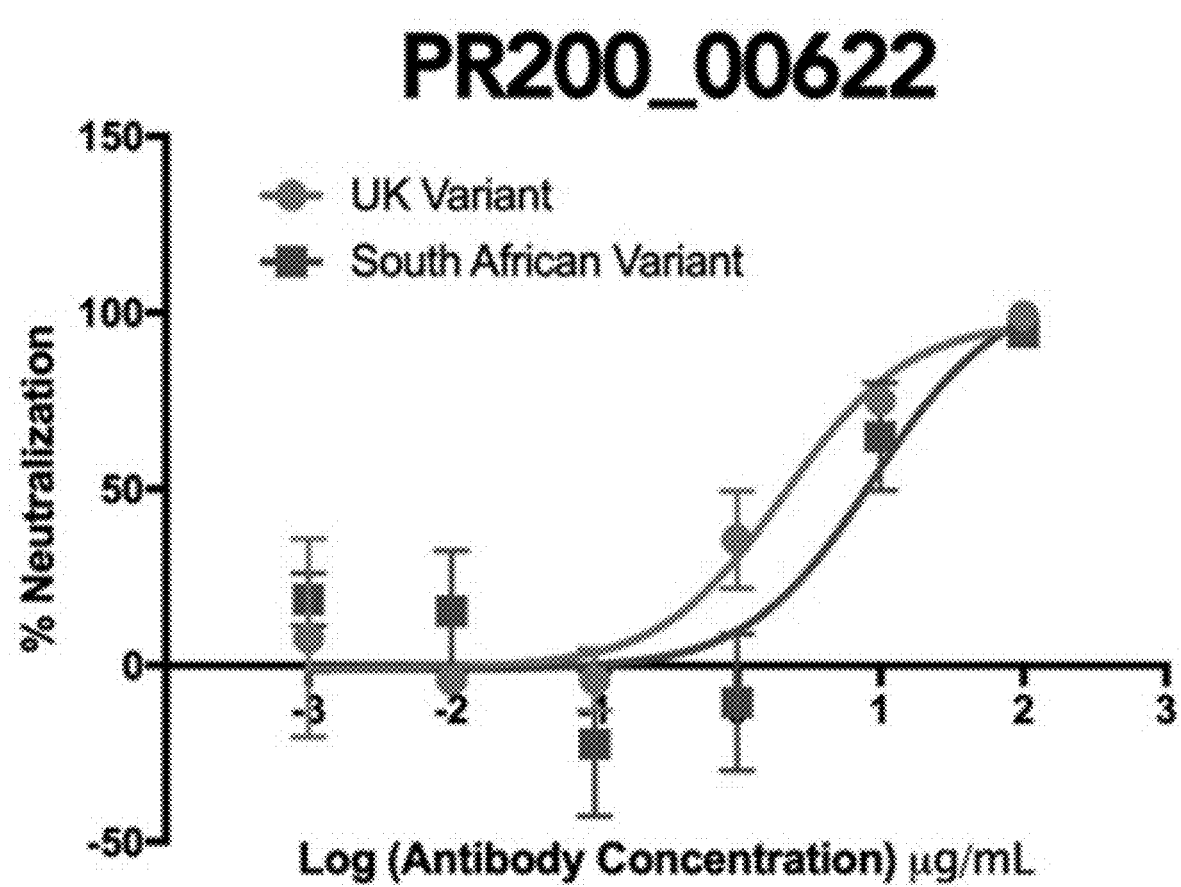

Pseudovirus particles expressing Spike proteins that mimic the U.K. (B.1.1.7) and South African (B.1.351) isolates are neutralized by antibodies which retain binding to the mutated Spikes (Tables 3 &4). This is exemplified by the antibodies PR193_00018 and PR200_00622 (FIGS. 5B and 5C). In contrast, antibodies that lose binding affinity for the mutated Spikes have a decreased neutralization potency; PR193_00232 (FIG. 5A) retains neutralization activity against the UK variant pseudovirus but is unable to effectively neutralize the S. African pseudovirus.

Example 7. A cocktail of three anti-SARS-CoV-2 anti-Spike antibodies elicit combinatorial effects. With the objective of producing an antibody composition that is able to neutralize both current, and future, variants, including, but not limited to, CDC Variants of Concern/Interest (alpha/B.1.1.7; beta/B.1.351; gamma/P.1; delta/B.1.617.2; epsilon/B.1.429/427), antibodies selective for non-overlapping epitopes on the SARS-CoV-2 Spike protein were assessed in pair-wise, and three-way combinations to identify additive, or preferably synergistic, neutralization.

Figure 6A:
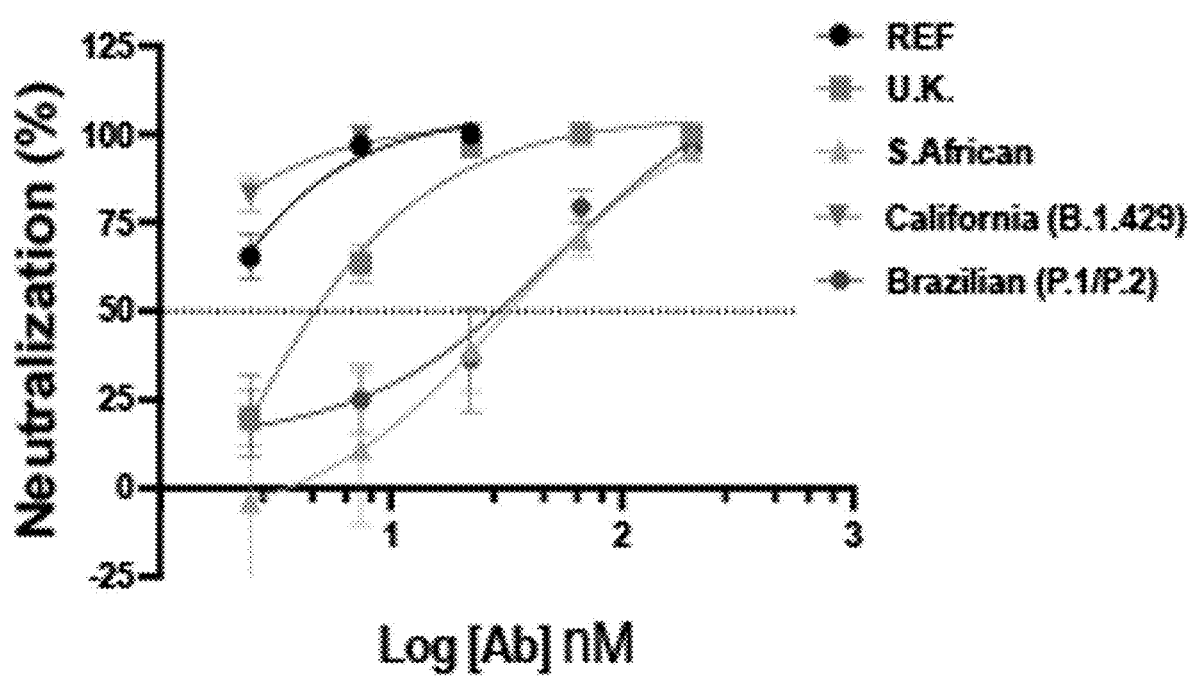
Figure 6B:
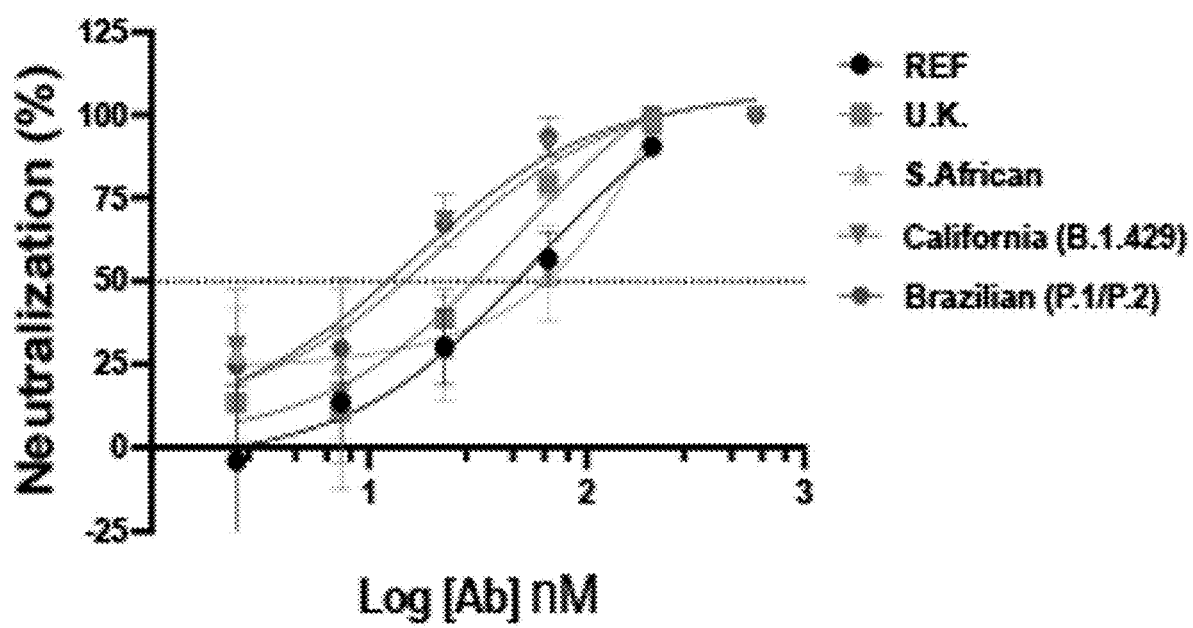

More specifically, the antibodies PR194_00232 (IMM20190), PR193_00018 (IMM20184), and PR200_00622 (IMM20253) were assessed in combinations to evaluate the combinatorial impact on neutralization of pseudovirus expressing a range of different variations of the Spike protein (FIGS. 6A-6C). IC50 values for the triple combination and double combination comprising IMM20184 and IMM20253 were determined using RVPs, as described above.

As depicted in FIGS. 6A-6C the triple combination of antibodies neutralized pseudoviruses corresponding to the USA/WA_CDC-WA1/2020 (reference sequence) and the CDC variants of concern (alpha/U.K./B.1.1.7, beta/South African/B.1.351, gamma/Brazil/P.1 and epsilon/California/B.1.429/427). In these pseudovirus assays, the $IC_{50}$s for neutralization of the reference and California variants were not determined due to the potency exhibited against those variants; concentrations sufficiently low enough to obtain below 50% neutralization were not tested. Neutralization of the U.K., Brazilian, and South African were achieved with $IC_{50}$s of 0.7 nM, 31 nM, and 23 nM, respectively, in these assays. The impact of IMM20190 on neutralization of the reference, CA, and UK variants can be observed by comparing the $IC_{50}$s achieved with the double combination of IMM20184/IMM20253 against the same pseudoviruses. In the absence of IMM20190, the reference California and U.K. variant pseudoviruses are neutralized with higher $IC_{50}$s, corresponding to 37 nM, 15 nM and 25 nM respectively. In the case of the S. African and Brazilian, the lack of IMM20190 does not dramatically alter the $IC_{50}$s, consistent with IMM20184/IMM20253 providing the majority of the neutralization activity.

To determine combinatorial impact of the antibodies pseudovirus neutralization experiments were set up as described above, except that for combinations of two antibodies, one test article was titrated in the background of each concentration in a serial dilution of the other test article. Single antibody titrations were included as controls. For combinations of three antibodies, one test article was titrated in the background of each concentration in a serial dilution of a 1:1 mixture of the other two test articles. To evaluate antibody synergy in the combinations, the observed combination response matrix of pseudovirus neutralization was used as input for the online SynergyFinder platform (4), where quadruplicate data points were input separately. The highest single agent (HSA) reference model was applied, which quantifies synergy as the excess over the maximum response of a single drug in the combination. Synergy between antibodies in each combination is reported as an overall synergy score (the average of observed synergy across the dose combination matrix) as well as a peak HSA score (the highest synergy score calculated across the dose combination matrix). Synergy scores of less than −10, between −10 and 10, and greater than 10 indicate antagonistic, additive, and synergistic antibody combinations, respectively. While peak HSA scores report on synergy at the most optimal combination concentrations, the overall synergy score is less affected by outlier data points.

Figure 7A:
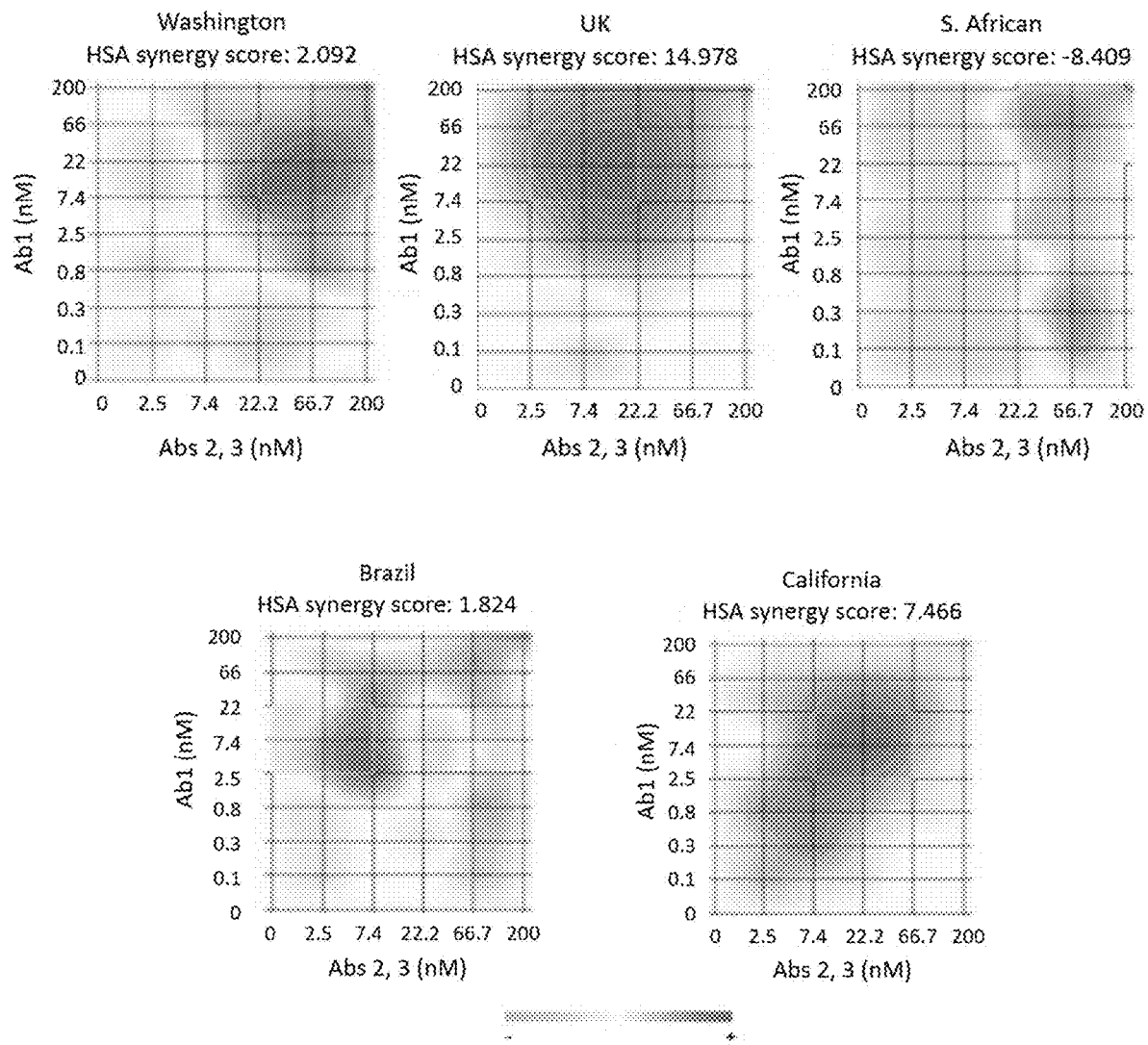
Figure 7B:
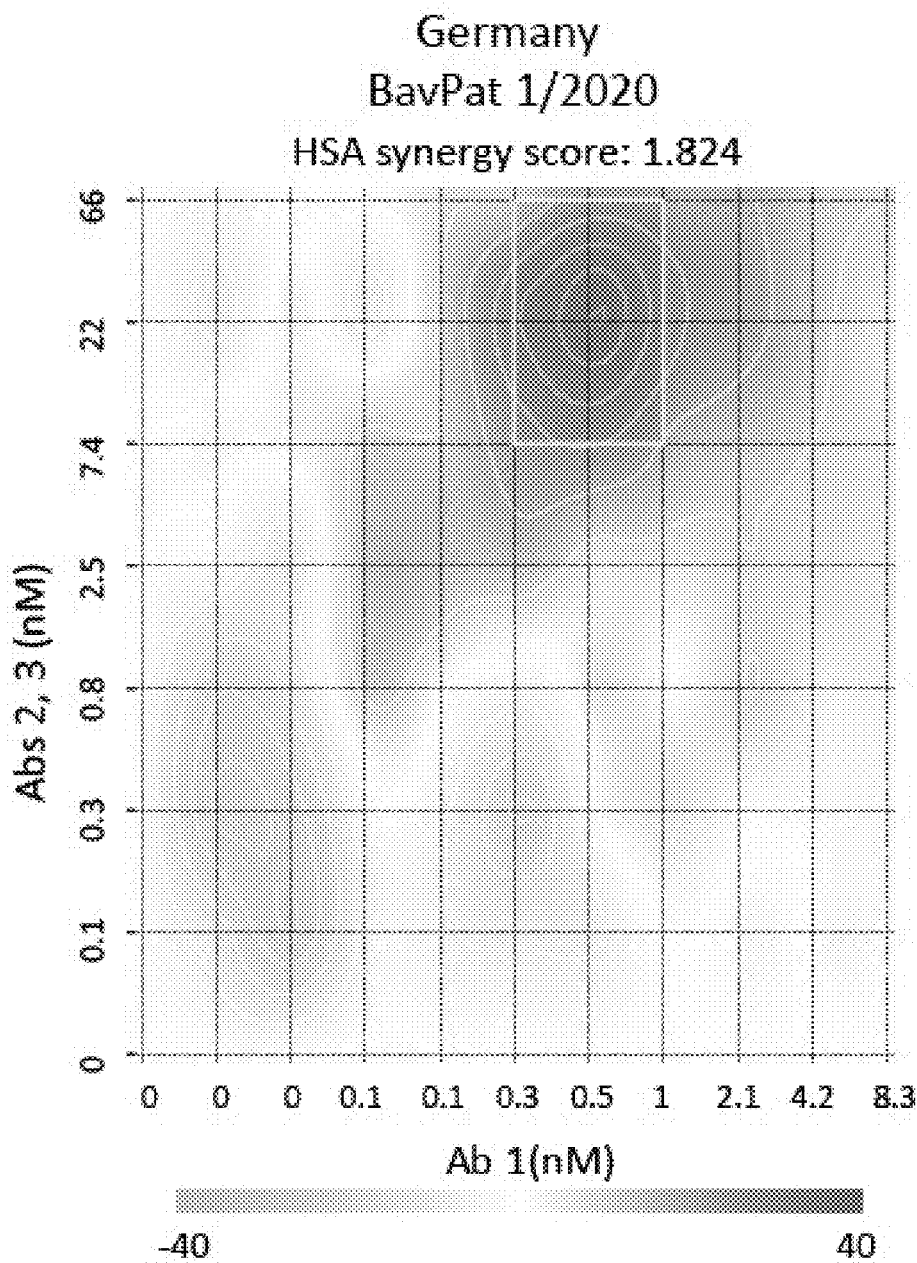

As depicted in FIGS. 7A-7C, the triple antibody combination of IMM20184/IMM20190/IMM20253, also known as IMM-BCP-01, synergized with each other to neutralize pseudovirus expressing the WA1/2020 reference, alpha/UK/B.1.1.7, Beta/S. African/B.1.351, Gamma/Brazil/P.1, and epsilon/Californian/B.1.429 spike proteins. Peak synergy scores ranged from 19.8 against the gamma variant to 61.1 against the alpha variant. Synergy was maintained against the alpha/UK variant across the entire concentration range tested. Overall additivity was observed against the other pseudoviruses. Synergy was observed against the live virus isolate Germany BavPat 1/2020 at defined ratios, with overall additivity being observed across the concentrations tested (FIG. 7B).

Figure 8:
FIG. 8 depicts the crystal structure of the SARS-CoV-2 RBD (RCSB PDB: 7A97) represented in cartoon with the epitopes of IMM20184, IMM20190, and IMM20253 depicted in black spheres. The locations of residues L452, T478, and E484, which are mutated in B.1.617.1/kappa (L452R E484Q) and B.1.617.2/delta (L452R T478K), are depicted in gray spheres. The residues mutated in the delta and kappa SARS-CoV-2 variants lie outside of the IMM-20184, IMM20190, and IMM20253 epitopes.

Example 8. Predicted activity against new variants. As the SARS-CoV-2 virus continues to mutate it will be imperative to predict, and confirm, the ability of antibodies to neutralize newly arising variants. As depicted in FIG. 8 the residues critical for binding of IMM20184, IMM20190, and IMM20253 are spatially distinct from the residues mutated in the RBD of the B.1.617.2 (delta), B.1.617.3 (kappa), and C.37 (lambda) variants. Based upon the location of the L452R T478K mutations in the B.1.617.2 variant, the L452R E484Q mutations in the B.1.617.3 variant, and the L452Q F490S mutations in the lambda variant, it was predicted that the triple antibody combination would be able to neutralize those variants in a manner at least equivalent to the reference WA1/2020 strain.

Figure 9:
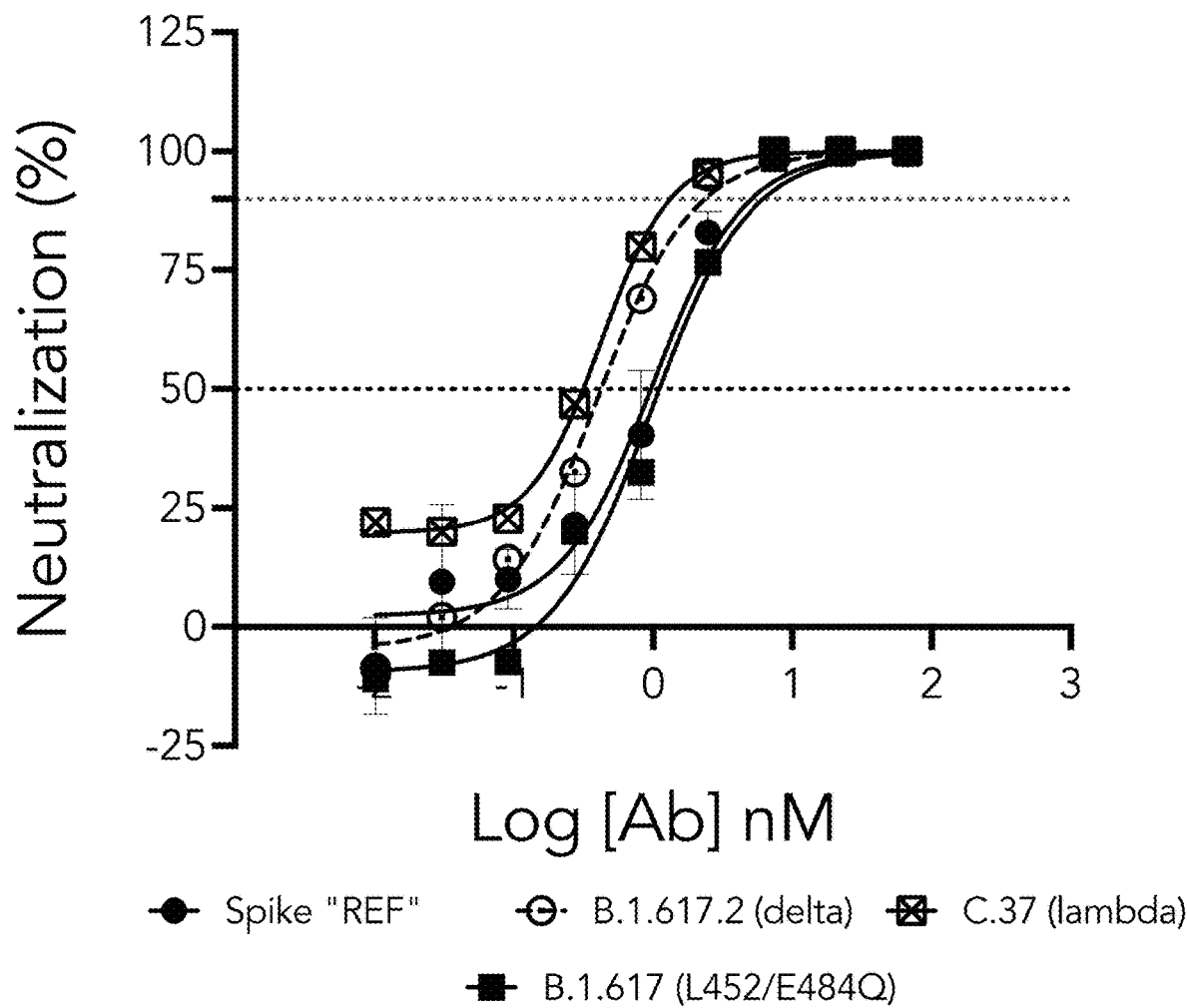
FIG. 9 depicts the in vitro neutralization activity of triple antibody cocktail (IMM20184/IMM20190/IMM20253) against pseudovirus expressing either the WA1/2020 (REF), B1.617 (L452R, E484Q), B.1.617.2 (delta), or lambda (C.37) Spike proteins.

Pseudovirus neutralization assays were performed with RVPs, as described above, that express the B.1.617.2, B.1.617.3, or C.37 variants. Consistent with the prediction, IMM-BCP-01 neutralized the pseudoviruses in a manner that was at least equivalent to the reference WA1/2020 variant (Table 6). Neutralization curves (FIG. 9).

Figure 10:
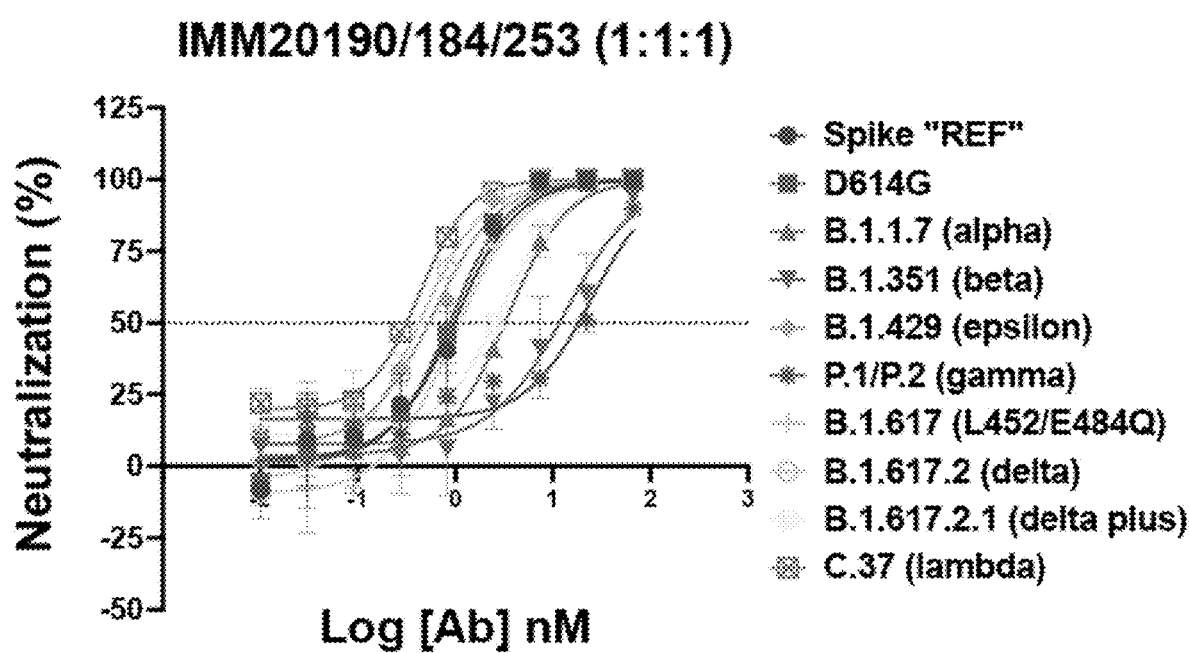
FIG. 10 depicts in vitro neutralization activity triple antibody cocktail (IMM20184/IMM20190/IMM20253) against pseudovirus expressing the Spike protein from the reference strain (WA_CDC-WA1/2020), D614G, B.1.1.7 (alpha/U.K.), B.1.351 (beta/S. African), P.1/P.2 (gamma/ Brazilian), B.1.429 (Epsilon/Californian), B.1.617.1 (L452/ E484Q), B.1.617.2 (delta/India), B.1.617.2 Ay.2 (Delta Plus), or C.37 (lambda) variants of SARS-CoV-2.
Figure 11A:
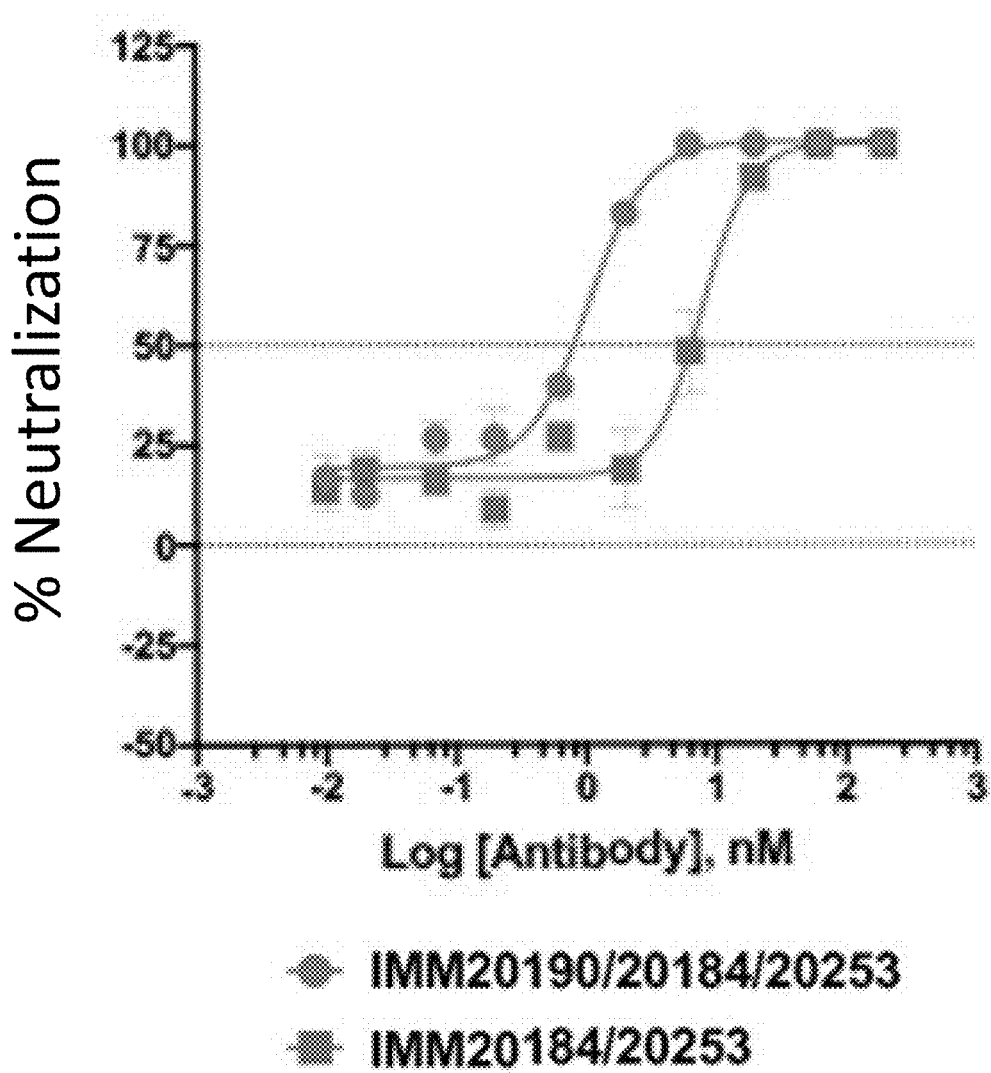
Figure 11B:
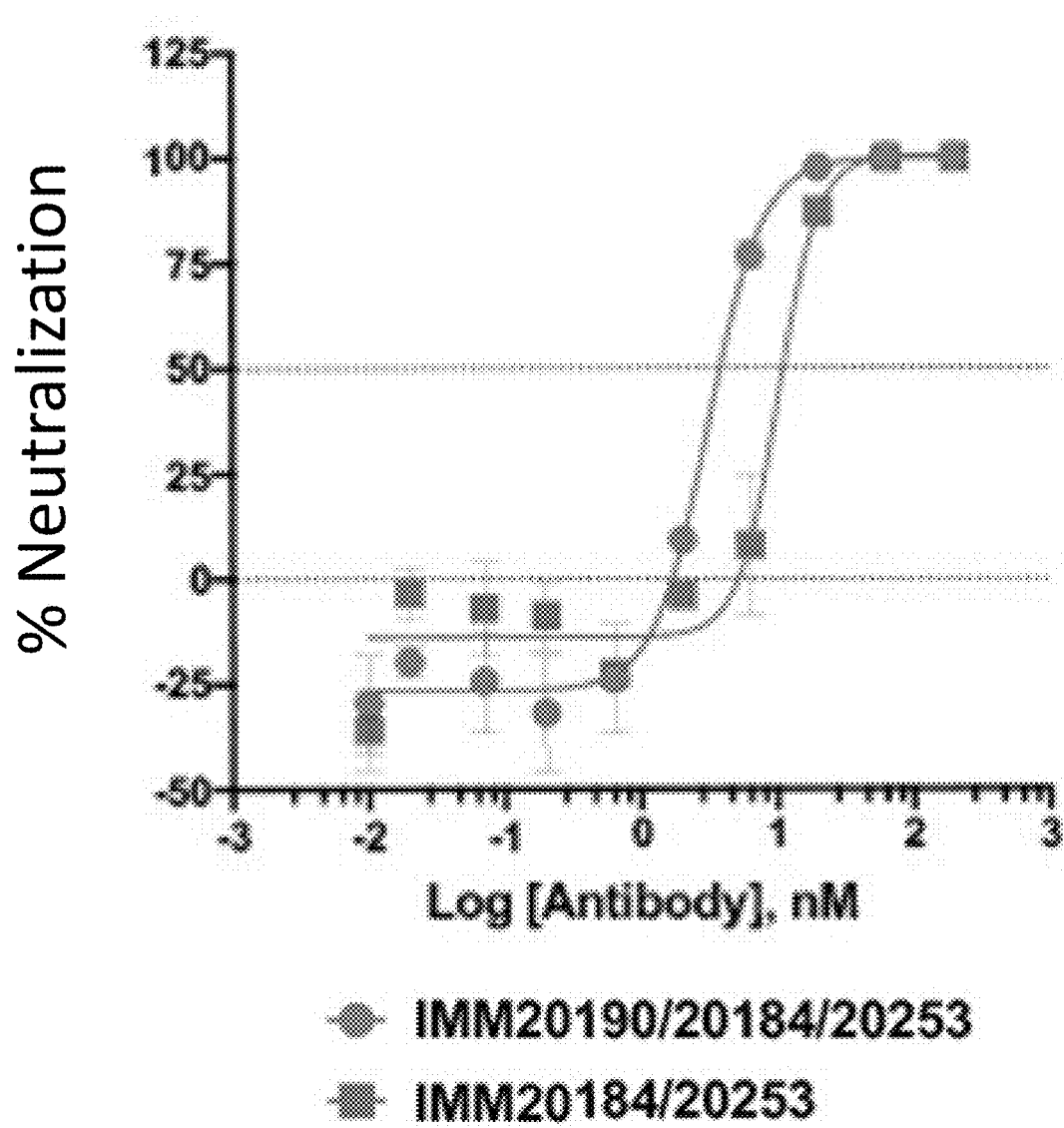
Figure 11C:
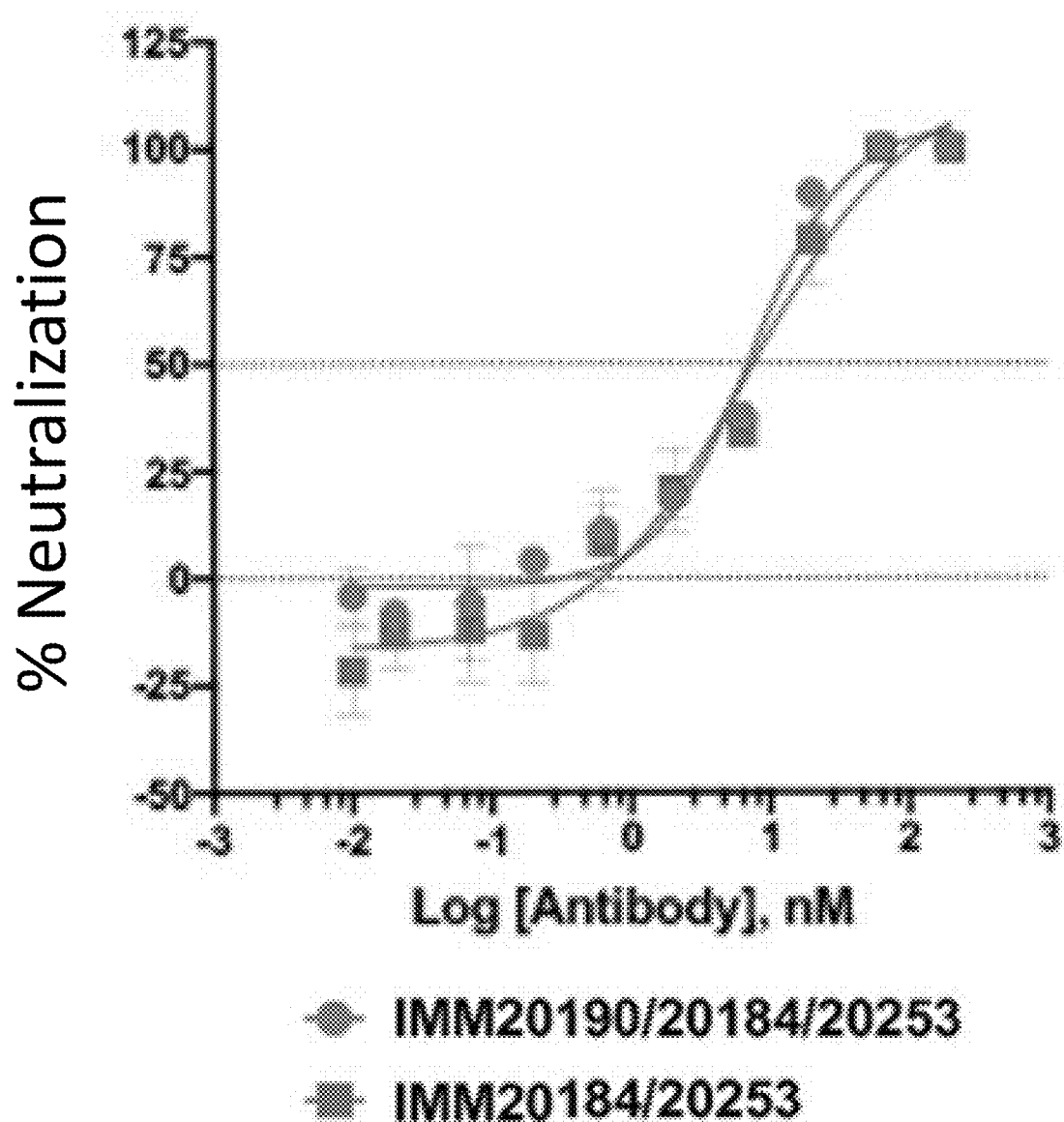

Activity of the triple antibody cocktail against the B.1.617.2 and B.1.617.3 variants is depicted in the context of other variants in FIG. 10. Consistent with the known epitopes of the antibodies, and positions of RBD-localized mutations in the different variants, the triple antibody cocktail exhibits neutralizing activity across all variants tested.

IMM20190 binds to a large epitope that encompasses two distinct regions on the RBD (FIG. 2). K417 and N501, residues known to be mutated in different variants, represent residues in each of the two binding sites. Mutation of one of those sites (N501Y), as observed in the alpha/B.1.1.7 variant, is sufficient to maintain IMM20190 activity (FIGS. 5A-5C) and provides for improved synergy with IMM20184/IMM20253. The delta plus/B.1.617.2.ay1/2 variant contains a K417N mutation. As predicted by our understanding of the IMM20190 epitope, and borne out by the results depicted in Table 6, the K417N mutation causes a partial loss of neutralization potential, the magnitude of the effect is in line with that observed against the alpha. Mutation of both K417 and N501, as observed in the beta/B.1.351 and gamma/P.1 variants, more fully abrogates IMM20190 activity, and neutralization is achieved through the IMM20184/IMM20253 antibodies. Those are reflected in the results depicted FIG. 10 and the IC50/90 values derived from those data (Table 6).

TABLE 6

IC50 & IC90 Values (nM) for IMM-BCP-01 Against Reference and Variants

|  | Pseudovirus | | Live Virus | |
| --- | --- | --- | --- | --- |
|  | IC50 | IC90 | IC50 | IC90 |
| REF (WA1/2020) | 1.0 | 5.2 | 1.1 | 3.4 |
| D614G | 0.9 | 4.2 | NT | NT |
| Alpha | 3.4 | 16.1 | 3.1 | 8.7 |
| Beta | 13.5 | 87.4 | 7.4 | 41.7 |
| Gamma | 24.8 | 129 | NT | NT |
| Delta | 0.4 | 2.3 | NT | NT |
| Delta plus | 3.0 | 15.2 | NT | NT |
| Epsilon | 0.6 | 3.4 | NT | NT |
| Lambda | 0.4 | 1.5 | NT | NT |
| Kappa (L452/E484Q/D614G) | 1.0 | 5.7 | NT | NT |

NT = Not Tested

The broad panel of neutralization data, combined with our understanding of the IMM-BCP-01 epitopes, provides us with confidence on predicting the impact of any newly emerging variants on the efficacy of the IMM-BCP-01 cocktail.

Example 9. Triple combination is active against live virus
To confirm results obtained with pseudovirus testing we performed neutralization assays on four different live virus variants under BSL3 conditions: USA/WA_CDC-WA1/2020 (reference sequence), Germany/BavPat 1/2020 (D614G), UK (B.1.1.7), and South African (B.1.351). In all cases, neutralization of the live virus recapitulated data obtained in pseudovirus neutralization assays (FIGS. 11A-11D and Table 6). Assays using the Germany/BavPat1/2020 strain were performed in a manner sufficient to assess combinatorial effects via the HSA algorithm. Data demonstrated an overall additive effect, with peak HSA scores reaching levels of synergy (FIG. 7B)

Figure 12:
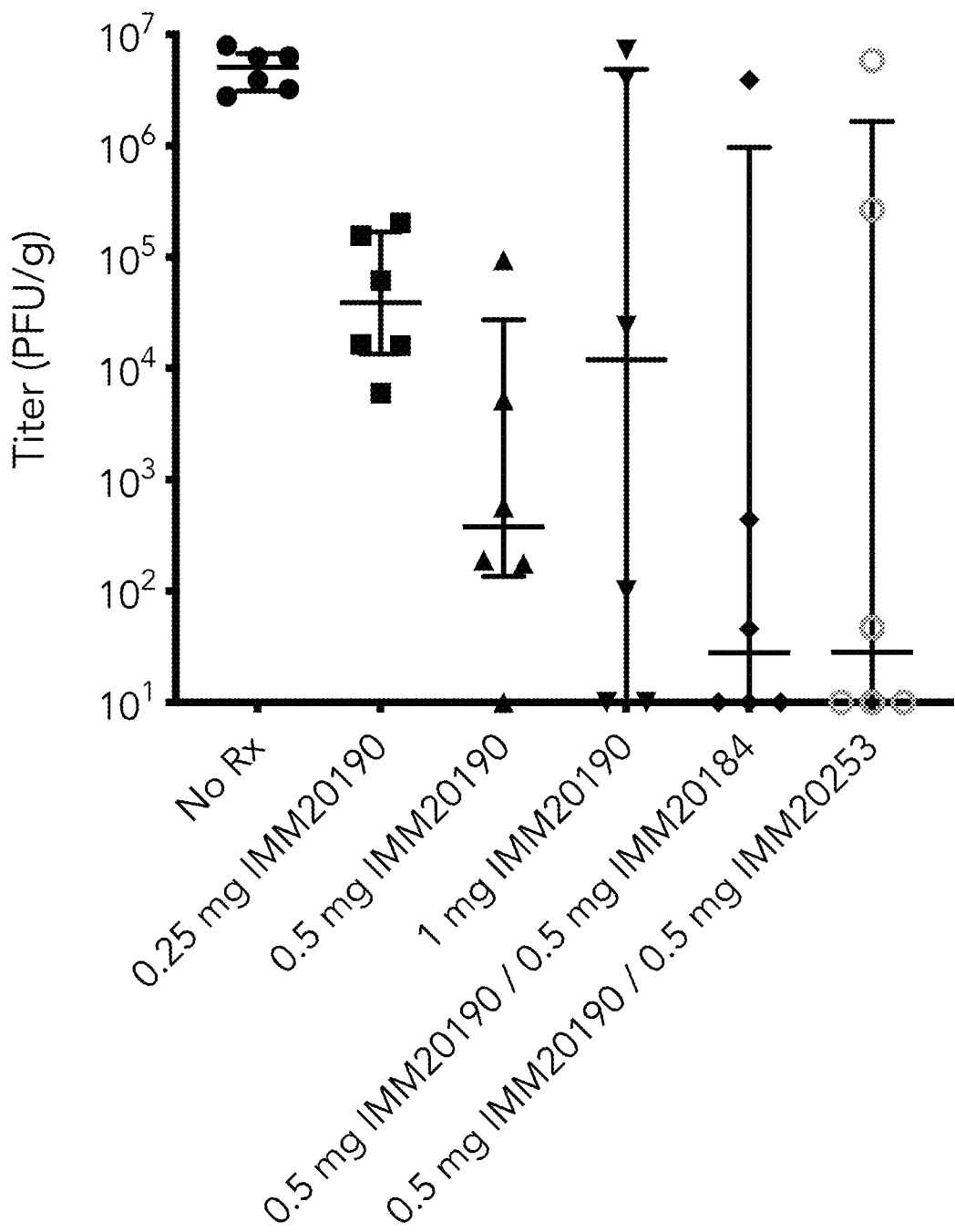
FIG. 12 depicts lung titer per gram tissue, as measured by plaque forming units, as an assessment of in vivo activity of the identified anti-Spike antibody PR194_00232, alone and in combination with either PR193_00018 or PR200_00622, against the live virus isolate SAR-CoV-2/human/USA/ WA_CDC-WA1/2020, when dosed in the prophylactic setting.

Example 10. Abs neutralize virus in a hamster model of SARS-CoV-2. Antibodies capable of neutralizing live virus in vitro were assessed for the ability to neutralize virus in vivo using a hamster model of SARS-CoV-2 infection. Hamsters treated with increasing doses of PR194_00232 were infected with SARS-CoV-2 (SARS-CoV-2/human/USA/WA_CDC-WA1/2020) and viral load in the lungs were assessed at Day 4 post inoculation of the virus using standard tissue culture infectivity assays and plaque counting. PR194_00232 was able to neutralize virus, relative to no-treatment controls, in a dose-dependent manner when dosed in the prophylactic setting (FIG. 12). Consistent with PR193_00018 and PR200_00622 working combinatorially with PR194_00232 to clear the virus, combinations consisting of PR194_00232/PR193_0018 and PR194_00232/PR200_00622 appear more effective at clearing the virus than PR194_00232 alone.

Figure 13:
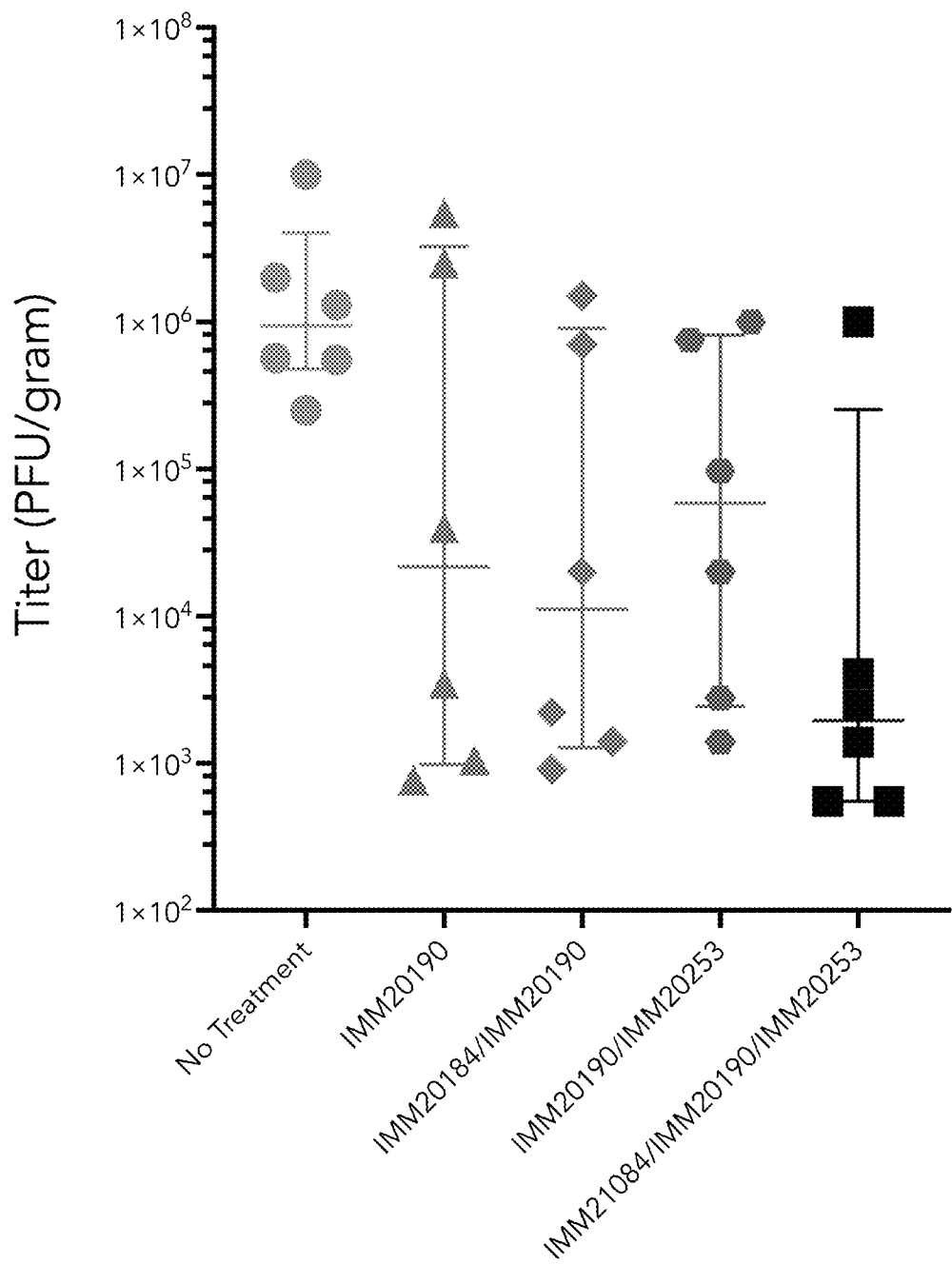
FIG. 13 depicts lung titer per gram tissue, as measured by plaque forming units, as an assessment of in vivo activity of various combinations of anti-Spike antibodies, dosed in a therapeutic setting, in the hamster model of COVID-19. Error bars represent the median+/−95% CI.

When dosed in the therapeutic setting (FIG. 13), a roughly 3-log clearance of virus, relative to no treatment, was observed in 5 out of 6 animals treated with this antibody cocktail. In contrast, other dose groups exhibited a more variable response with only three animals in any other group ever reaching maximal clearance. These data suggest that optimal viral clearance requires all three antibodies to be part of the cocktail.

Figure 14:
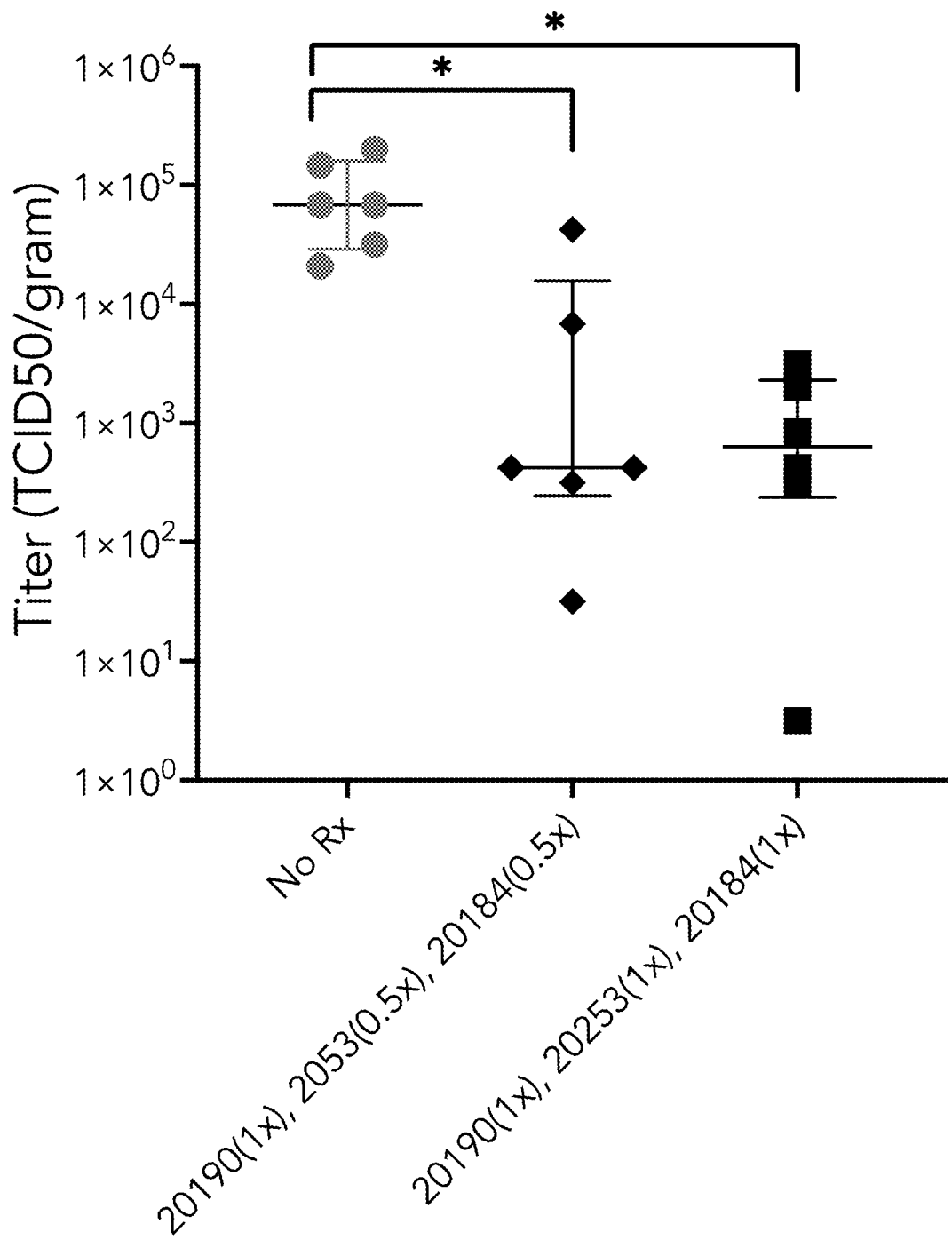
FIG. 14 depicts lung titer per gram tissue, measured by TCID50 assays, as an assessment of in vivo activity of the triple combination of IMM20184/IMM20190/IMM20253, at two different ratios, dosed in a therapeutic setting, in hamster model of COVID-19. Error bars represent the median+/−interquartile range.

In a follow-up study, the triple combination dosed at equimolar ratios (0.25 mg each) resulted in a statistically significant decrease in viral load in the lungs at day 4 post-inoculation, as measured with TCID50 assays (FIG. 14). To that end, in the same study doses of IMM20184 and IMM20253 were decreased to 0.125 mg each and we observed an increase in the median level of viral load in the lung compared to the cohort treated with the 1:1:1 ratio. These data provide additional support that IMM20184 and IMM20253 are contributing to in vivo efficacy, even in the context of the USA/WA_CDC-WA1/2020 viral isolate which is highly sensitive to neutralization by IMM20190 in vitro.

Figure 15:
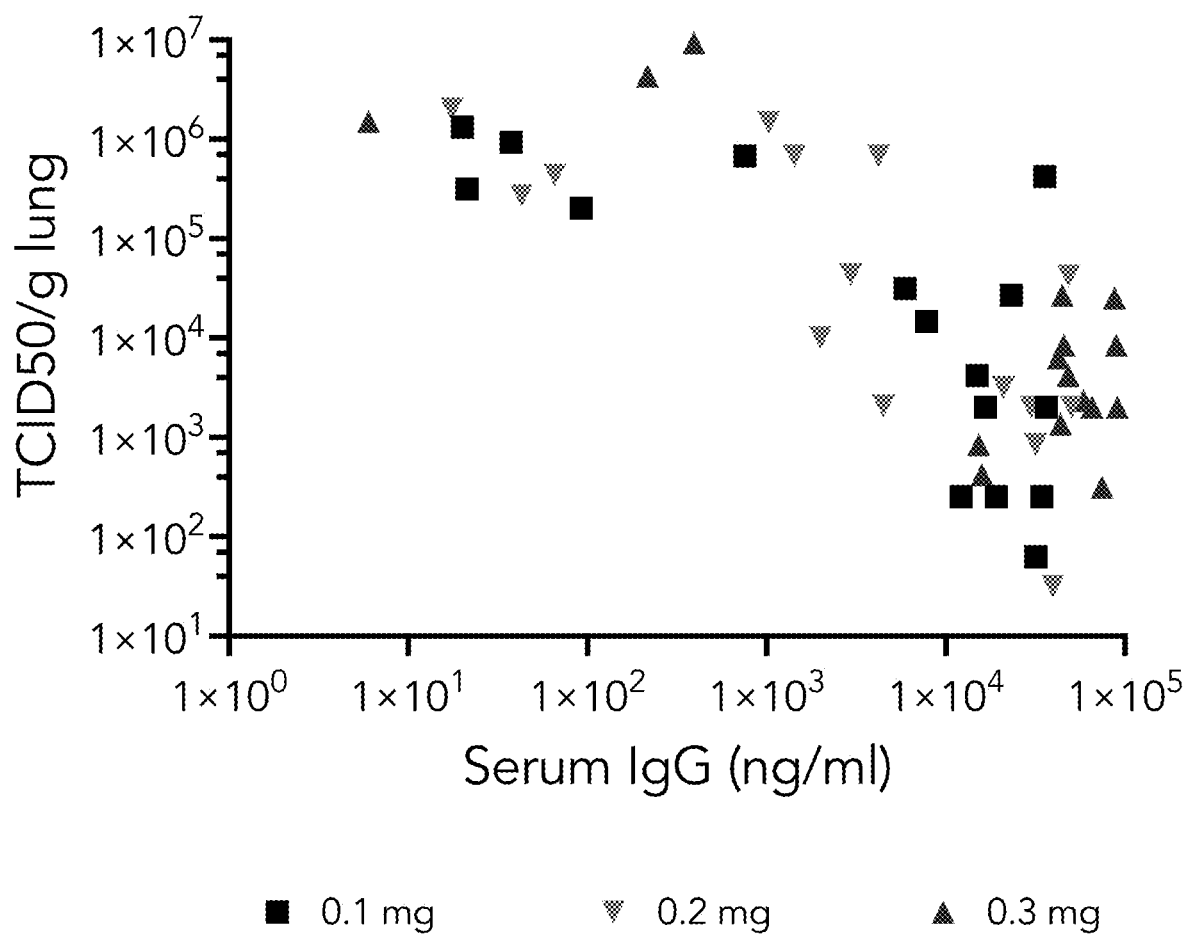
FIG. 15 depicts correlation of viral lung titer per gram tissue, as measured by TCID50 assays, plotted against serum concentration of triple antibody cocktail (IMM20184/190/ 253, 1:1:1 ratio) at day 4 post administration of antibodies in a therapeutic setting. Antibody cocktail was administered at three dose levels, 0.1 mg each, 0.2 mg each, 0.3 mg each.

Variability observed in the efficacy of IMM-BCP-01 in various studies led to retrospective correlation of systemic exposure post-intraperitoneal injection with overall viral clearance (FIG. 15). Syrian golden Hamsters were inoculated with $3.3 \times 10^5$ TCID50 doses of WA1/2020 live virus in the nasal turbinates ($1.65 \times 10^5$ per nare). IMM-BCP-01 was administered i.p. 6 hours post-inoculation at three different dose levels. Dose levels were 0.1 mg each (0.3 mg total), 0.2 mg each (0.6 mg total), or 0.3 mg each (0.9 mg total). Animals were euthanized at Day 4 and viral titers in lung determined by TCID50 assays. Levels of IgG in serum at time of euthanasia were determined by anti-huIgG ELISA to correlate IgG exposure with overall viral clearance. Data support the idea that i.p. injections led to variable levels of exposure and correlated with viral clearance. Serum levels of approximately 3-5 ug/mL at day 4 were sufficient to achieve viral clearance and were obtained by all three dose levels tested.

Figure 16A:
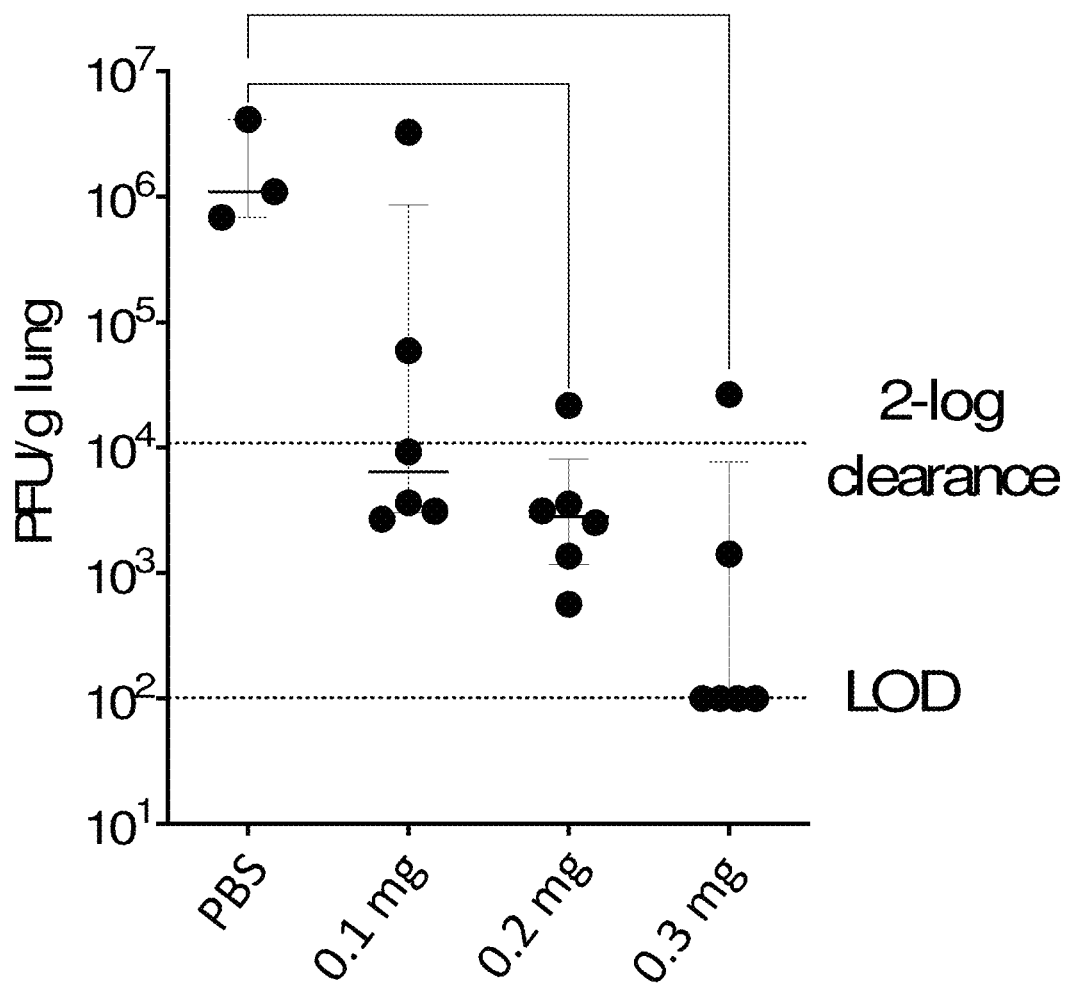
FIGS. 16A-16B depict lung titer per gram of tissue, as measured by plaque forming units. Hamsters infected with either the FIG. 16A WA1/2020 or FIG. 16B Beta isolate were treated in prophylactic setting with a dose response of triple antibody cocktail (IMM20184/IMM20190/ IMM20253, 1:1:1)
Figure 16B:
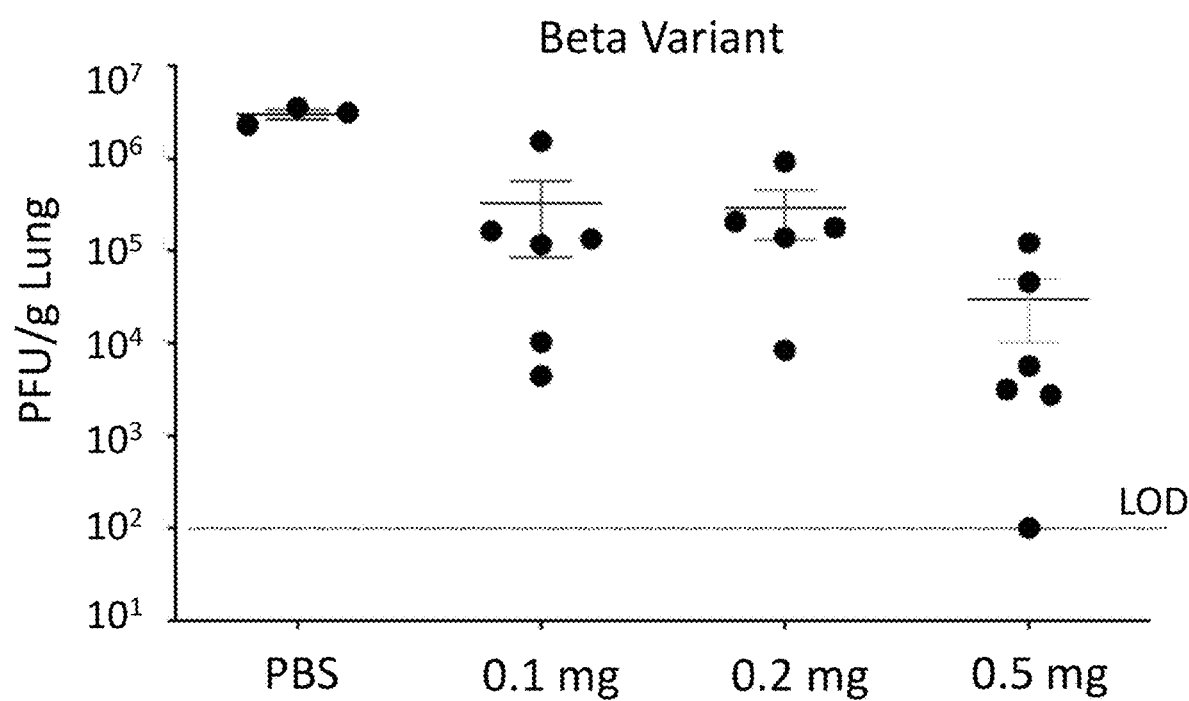

IMM-BCP-01 is able to clear virus from the lungs of hamsters infected with variants of concern. Hamsters were dosed prophylactically with IMM-BCP-01 one day prior to inoculation with either the Alpha (FIG. 16A) or Beta (FIG. 16B) variant and lung titers were determined on day 4 post-inoculation. IMM-BCP-01 at the lowest doses tested provided levels of viral clearance that match, or exceed, those obtained by antibodies with demonstrated clinical efficacy. In addition, increased doses of IMM-BCP-01 led to a dose-dependent improvement in viral clearance, with ≥four-log clearance of WA1/2020 and 2.5 log clearance of Beta at the highest doses tested. All doses tested represent clinically relevant doses.

Figure 17:
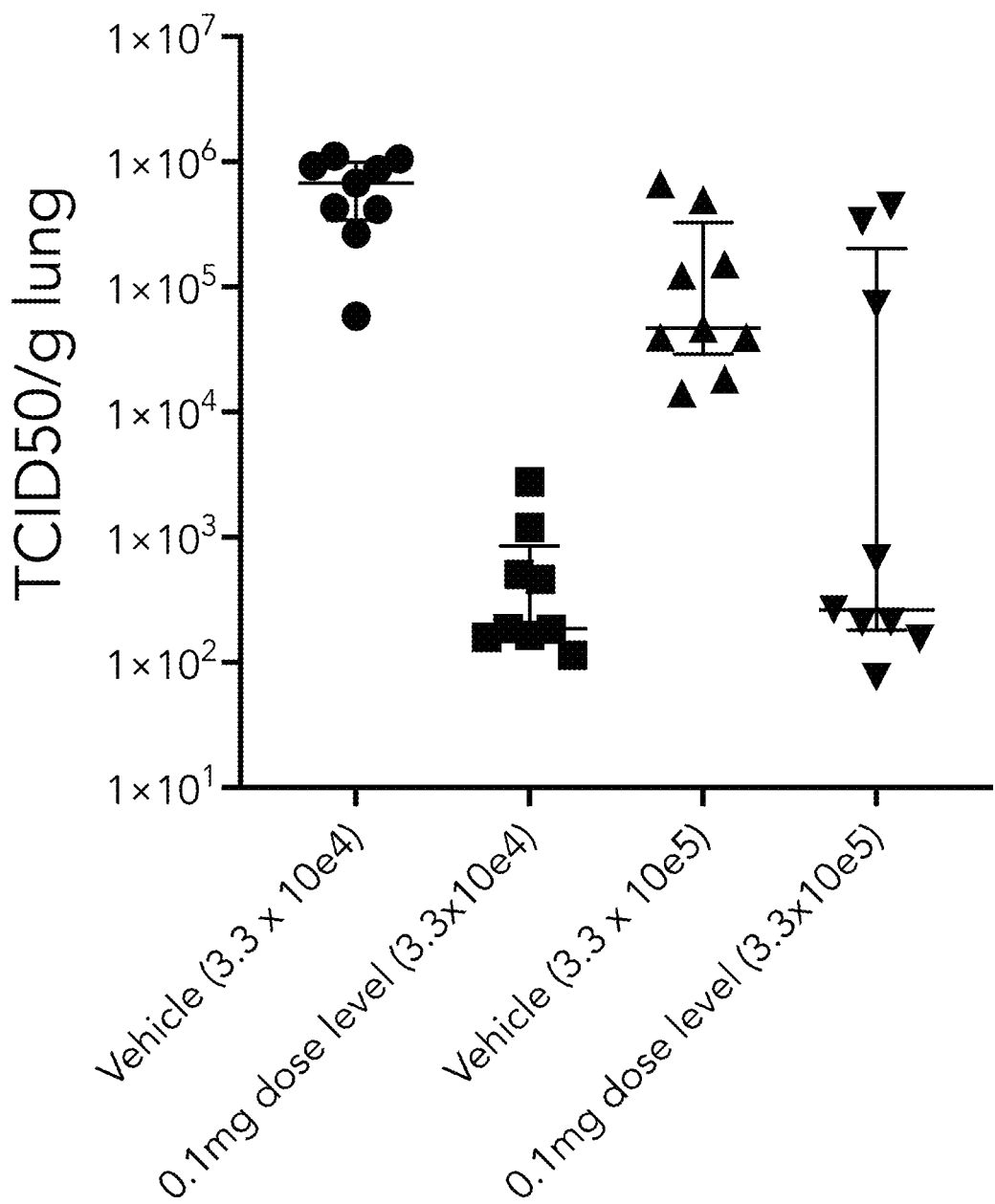
FIG. 17 depicts anti-viral activity of a triple antibody cocktail (IMM20184/190/253, 1:1:1 ratio), dosed at 0.1 mg each, into Syrian hamsters that were inoculated with either $3.3 \times 10^4$ or $3.3 \times 10^5$ virus. Viral titers in lungs were assessed four days post-inoculation via TCID50 assays. Antibody was administered in a therapeutic setting.

Robust activity of the cocktail was observed regardless of inoculation titer used (FIG. 17). Syrian hamsters were inoculated with either $3.3 \times 10^5$ TCID50 doses of WA1/2020 live virus in the nasal turbinates ($1.65 \times 10^5$ per nare) or $3.3 \times 10^4$ TCID50 doses of WA1/2020 live virus in the nasal turbinates ($1.65 \times 10^4$ per nare). Animals were then treated 6 hours post-inoculation with either vehicle or IMM-BCP-01 at 0.1 mg each dose level. Robust viral clearance was observed, relative to the vehicle control, for both inoculation levels.

TABLE 7

Binding Constants of IMM20184, IMM20190, & IMM20253 for Isolated RBD and Trimer

| Ligand | Analyte | Kon (1/ms) | Koff (1/s) | KD (M) |
|---|---|---|---|---|
| IMM20184 | Trimer | 3.12E+04 | 2.29E−04 | 7.35E−09 |
|  | RBD | 5.95E+04 | 1.31E−03 | 2.20E−09 |
| IMM20190 | Trimer | 2.95E+04 | 1.95E−04 | 6.59E−09 |
|  | RBD | 2.02E+05 | 3.76E−04 | 1.87E−09 |
| IMM20253 | Trimer | 8.13E+04 | 1.17E−04 | 1.44E−09 |
|  | RBD | 1.39E+06 | 2.18E−04 | 1.57E−10 |

TABLE 8

Phagocytosis Scores of Various anti-RBD Abs

| IMM # | Target | Score at 0.6 nM |
|---|---|---|
| IMM20184 | Spike (RBD) | 56.6 |
| IMM20190 | Spike (RBD) | 48.1 |
| IMM20198 | Spike (RBD) | 37.9 |
| IMM20242 | Spike (RBD) | 1.26 |
| IMM20253 | Spike (RBD) | 49.5 |
| IMM20254 | Spike (RBD) | 48.9 |
| IMM20279 | Spike (RBD) | 43.3 |
| COM00035 | Positive Control | 50.1 |
| Anti-RSV | Negative Control | 1.38 |

Figure 18A:
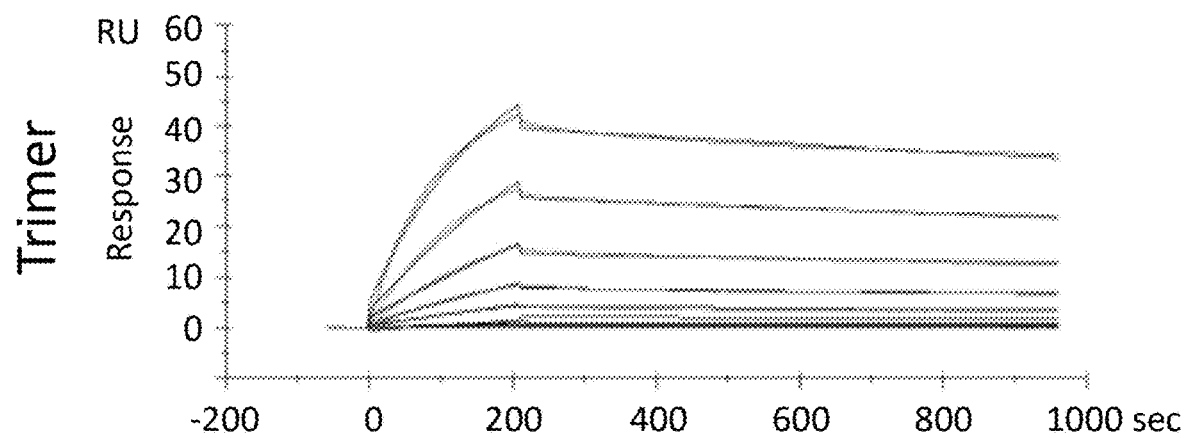
FIGS. 18A-18C depict the ability of IMM20184, IMM20190, and IMM20253 to bind to the isolated RBD and intact trimer of SARS-CoV-2 reference strain (WA1/2020) as measured by surface plasmon resonance.
Figure 18A:
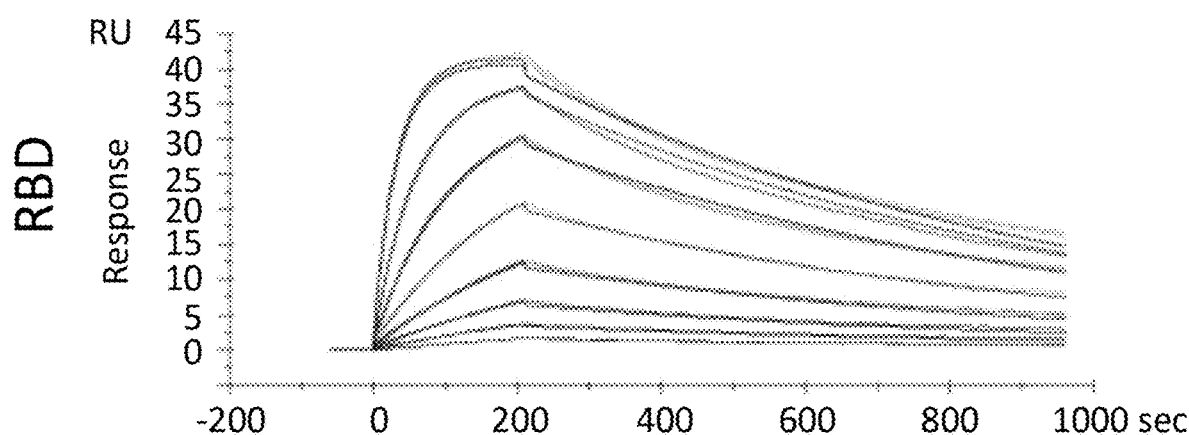
Figure 18B:
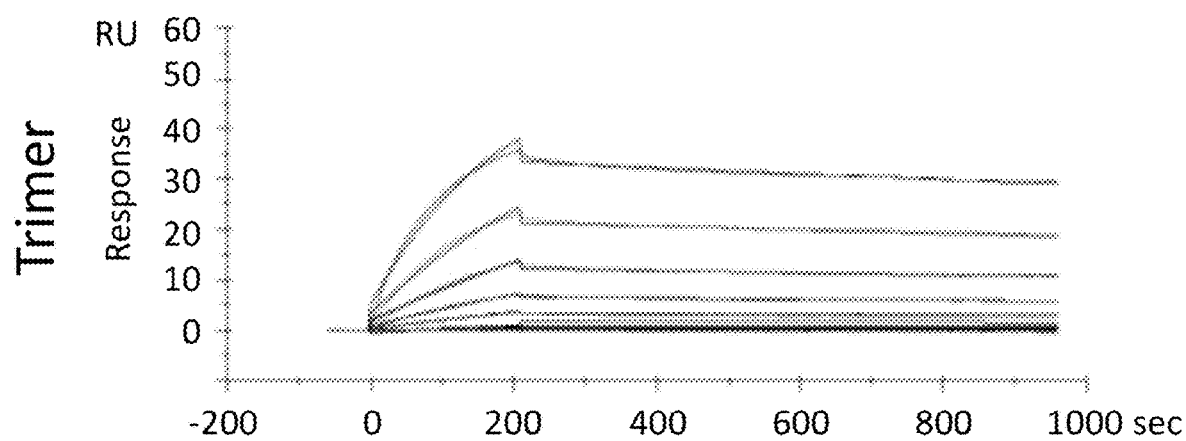
Figure 18B:
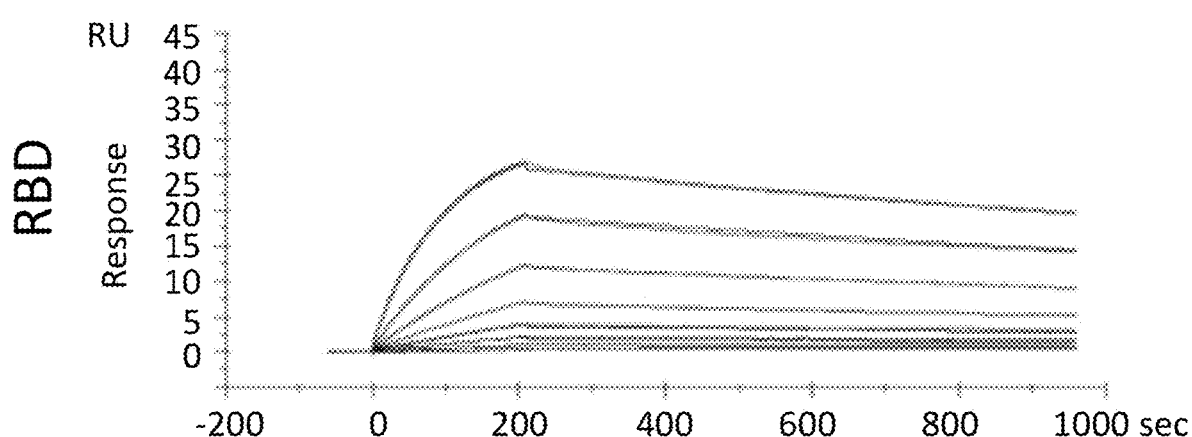
Figure 18C:
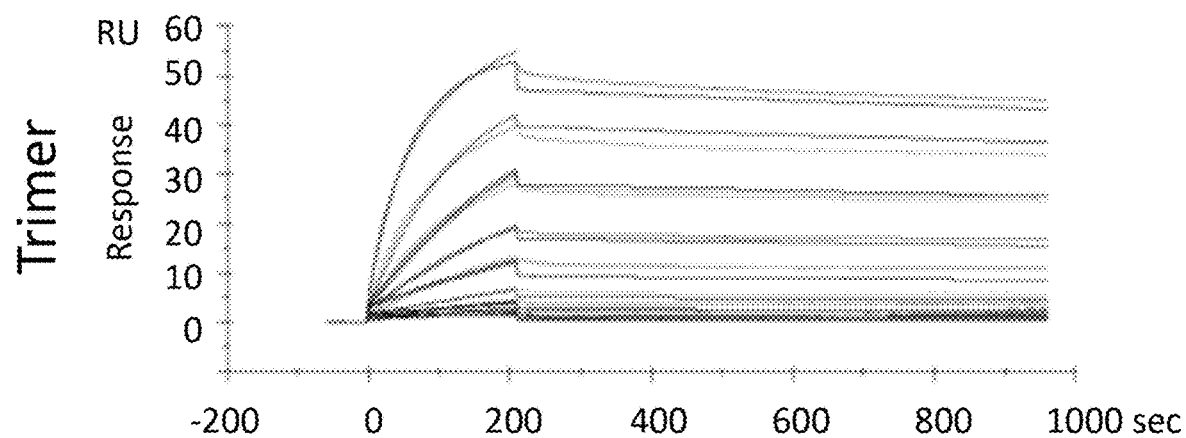
Figure 18C:
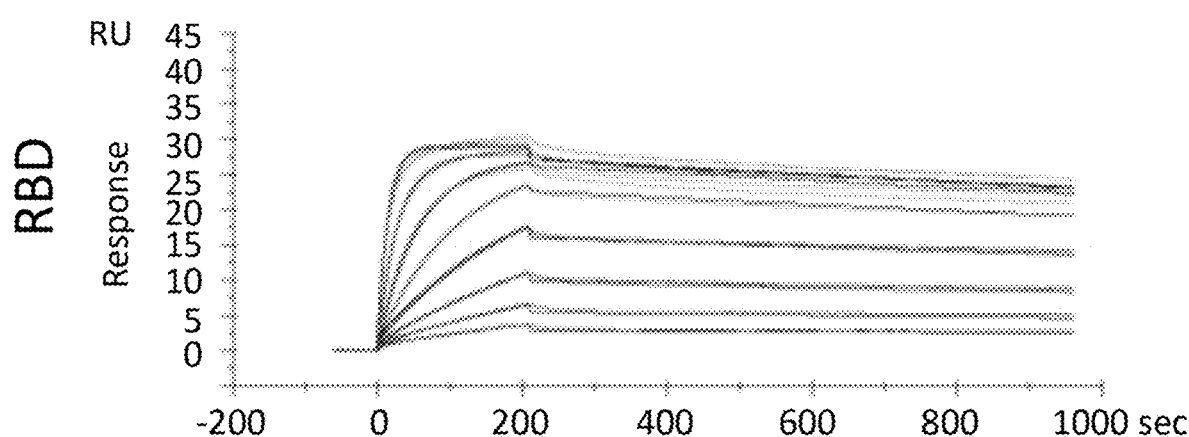

Example 11. Antibodies Elicit Mechanisms that Could Enhance Viral Neutralization and Clearance. Each of the antibodies comprising IMM-BCP-01 (IMM20184, IMM20190, and IMM20253) bind to both isolated RBD and Spike trimer when assessed by surface plasmon resonance (FIGS. 18A-18C). These data suggest that IMM20184 can bind avidly to the Spike trimer, as signified by the decrease off-rate (Table 7), and cross-link two Spike monomers.

Figure 19A:
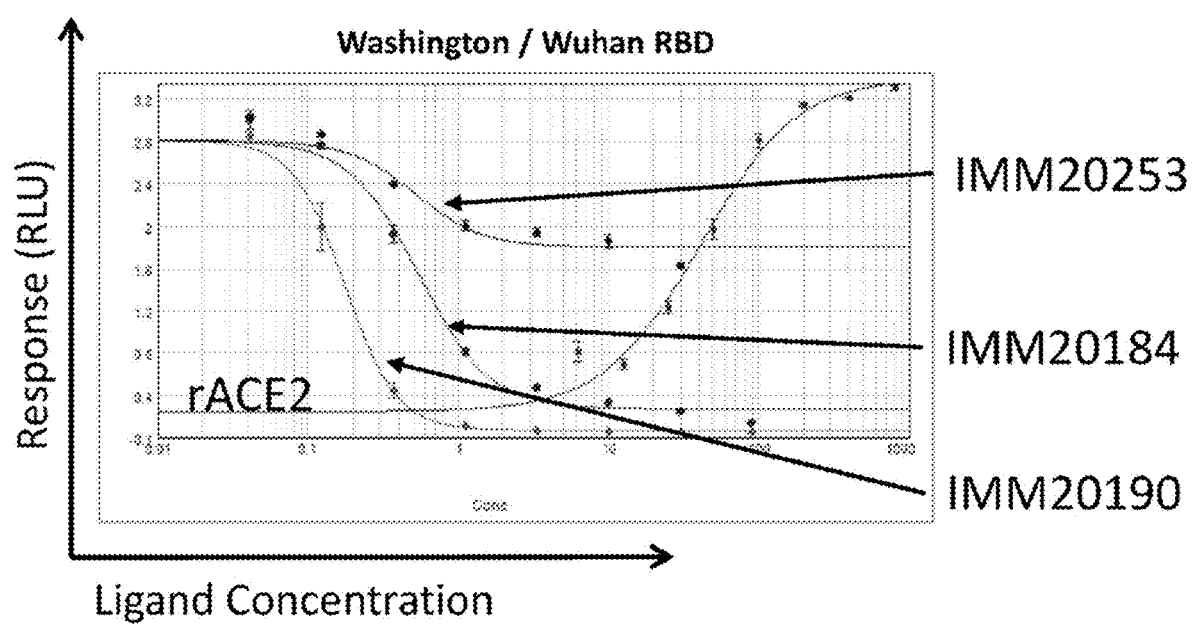
FIGS. 19A-19C depict the ability of IMM20184, IMM20190, and IMM20253 to block binding of ACE2 to isolated RBD corresponding to FIG. 19A WA1/2020, FIG. 19B Alpha, FIG. 19C Beta viral isolate
Figure 19B:
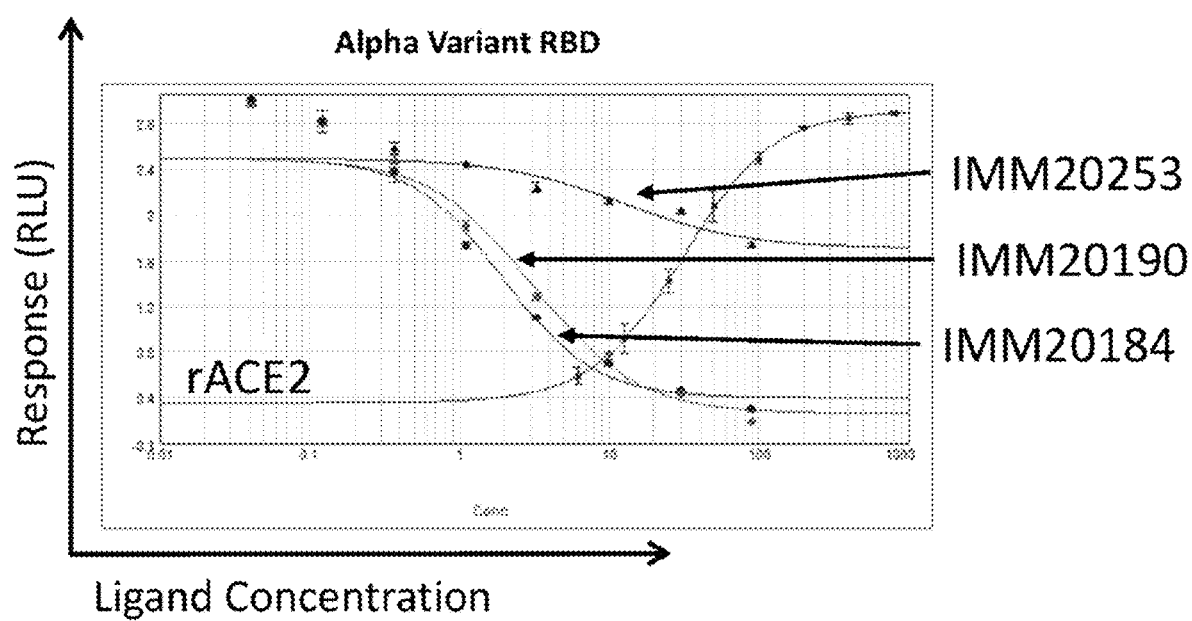
Figure 19C:
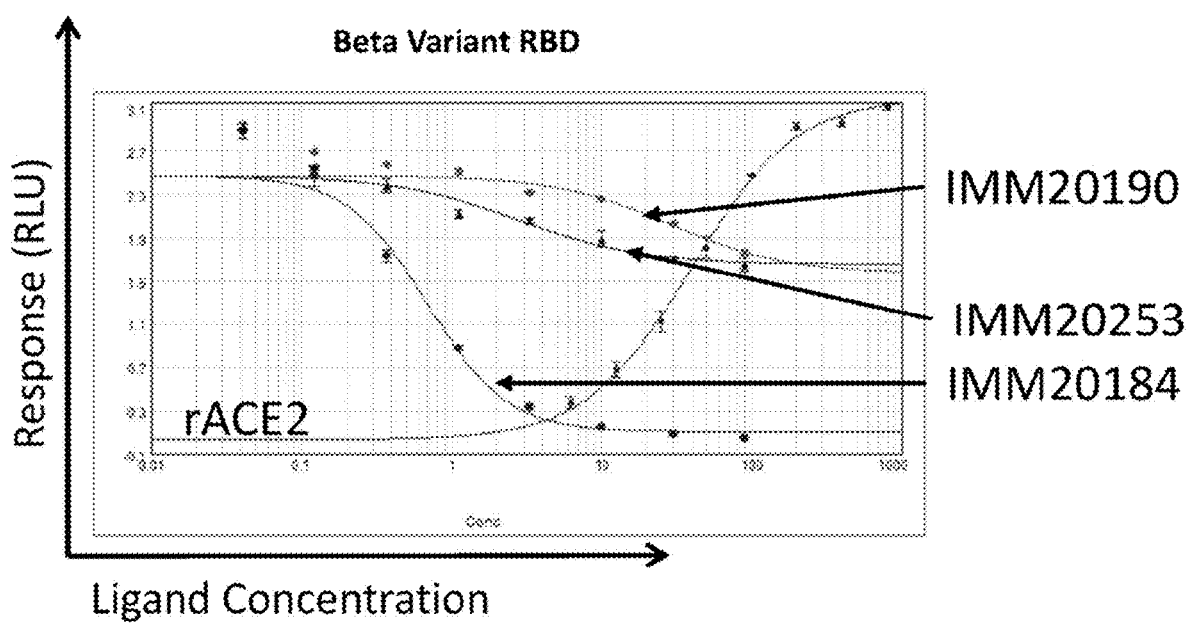

Consistent with its epitope overlapping with the ACE2 binding site, IMM20190 is able to compete binding of ACE2 to isolated RBD protein from the REF and Alpha variant (FIG. 19A and FIG. 19B), but its ability to compete ACE2 binding to the Beta variant is decreased (FIG. 19C), consistent with its known decreased binding and neutralization potency. IMM20184 effectively competes binding of ACE2 to all three isolated RBD (FIGS. 19A-C), despite binding to an epitope that is outside of known ACE2 binding site (FIG. 2). Despite exhibiting neutralization activity against both pseudovirus and live virus, IMM20253 is unable to effectively compete for ACE2 binding (FIGS. 19A-C). This suggests the neutralization is due to a mechanism distinct from direct ACE2 competition.

Figure 20A:
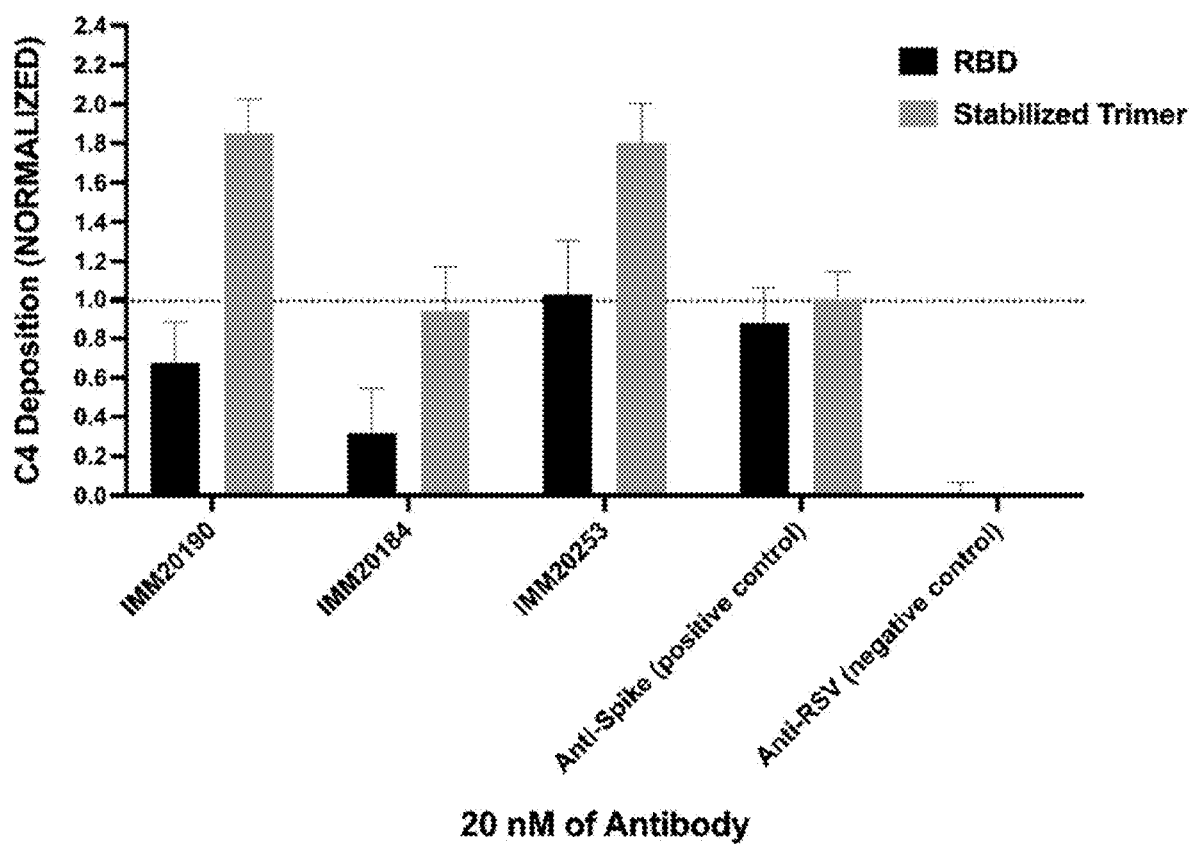
FIGS. 20A-20C depicts in vitro complement fixation activity of PR193_0018 (IMM20184), PR194_00190 (IMM20190), PR200_00253 (IMM20253), the two antibody cocktail of IMM20184/IMM20253, and the triple antibody cocktail (IMM20184/IMM20190/IMM20253) relative to control antibodies when assessed at defined FIGS. 20A and 20B concentrations and in a concentration-dependent FIG. 20C manners.
Figure 20B:
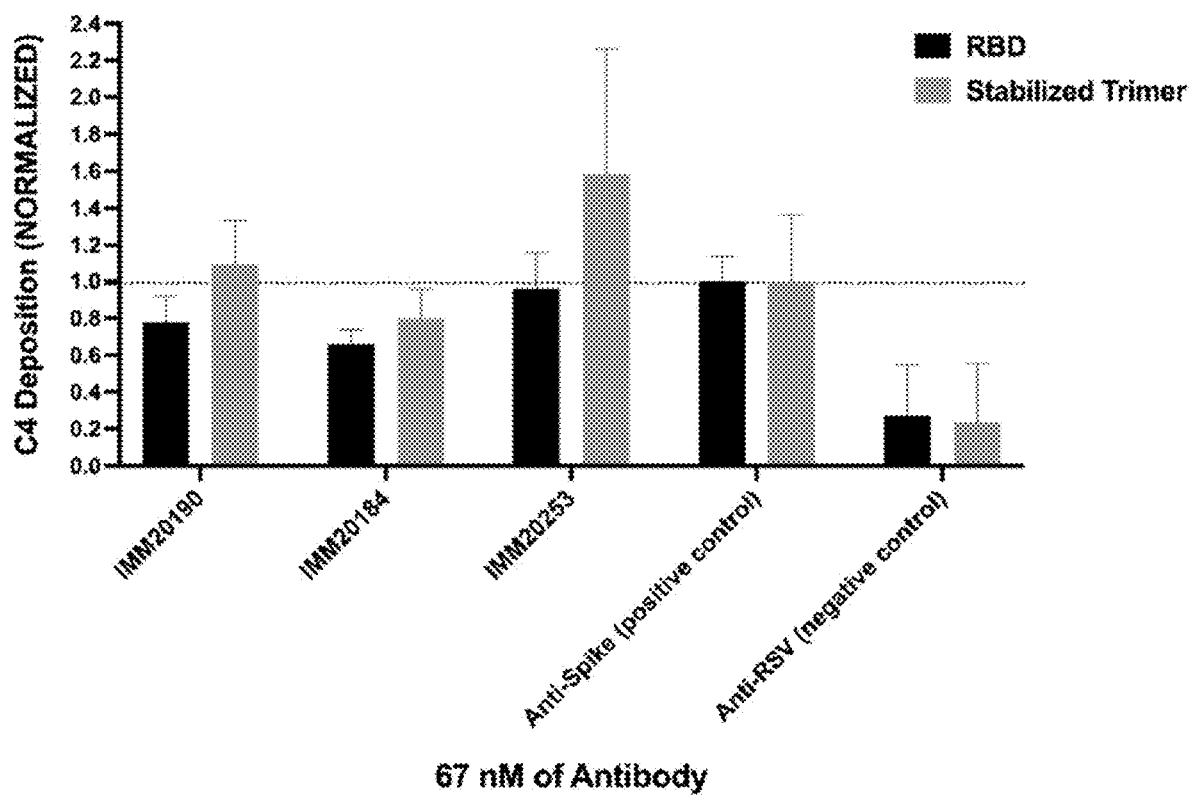
Figure 20C:
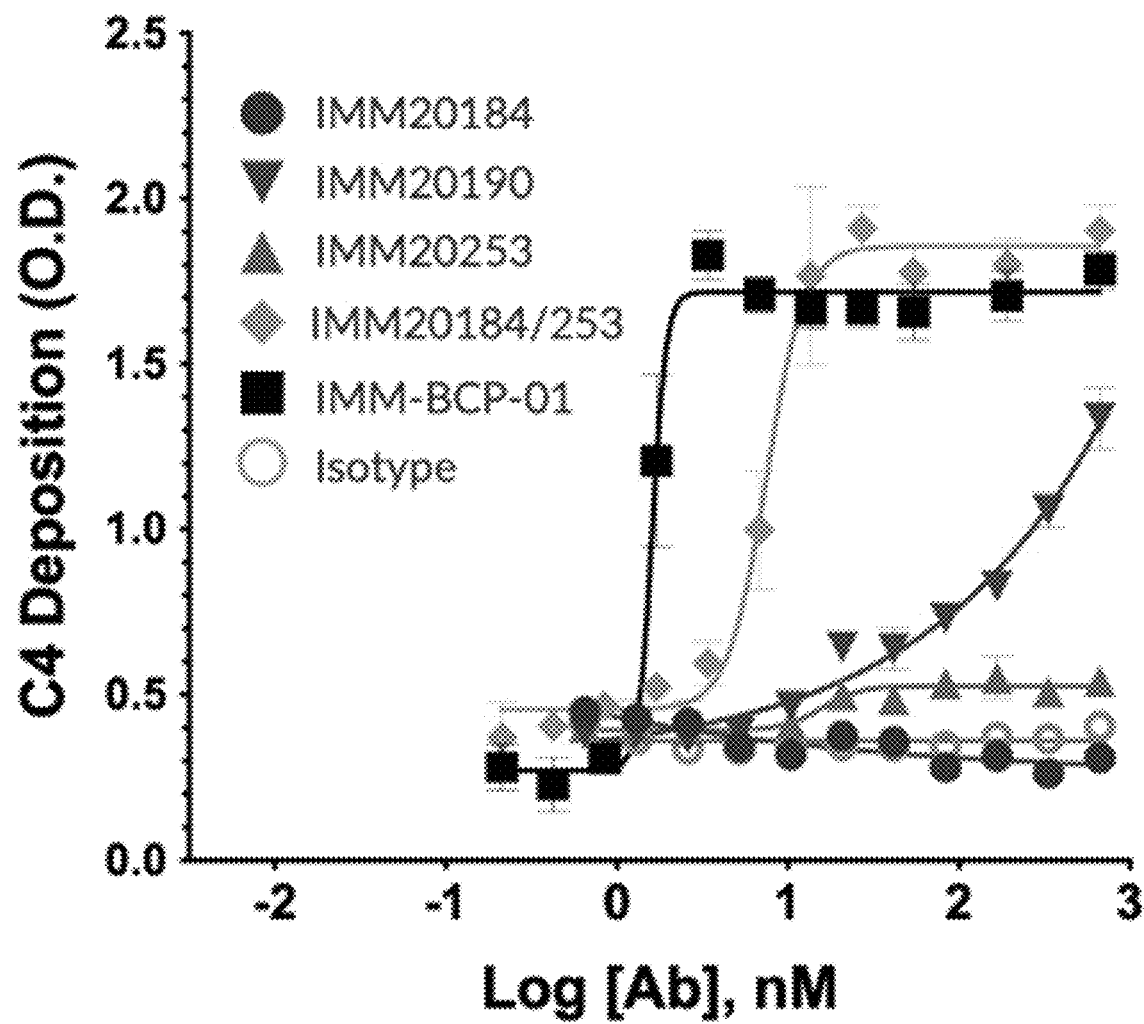

IMM20184, IMM20190 and IMM20253 were assessed for the ability to fix complement using standard assays [Nikitin et al., 2019]. As depicted in FIGS. 20A and 20B, all three antibodies comprising IMM-BCP-01 were able to fix complement, albeit to different levels when assessed at defined concentrations. All three antibodies demonstrated a preference for fixing complement upon binding to the stabilized trimer as compared to the isolated RBD. When assessed in a concentration-dependent manner (FIG. 20C), the combination of IMM20184 and IMM20253 induced an enhanced level of complement fixation beyond what was observed by either antibody alone. That activity was further enhanced by addition of IMM20190 to the antibody cocktail. These data suggesting the antibodies comprising IMM-BCP-01 elicit a combinatorial, or synergistic, activation of complement fixation upon binding Spike.

Figure 21:
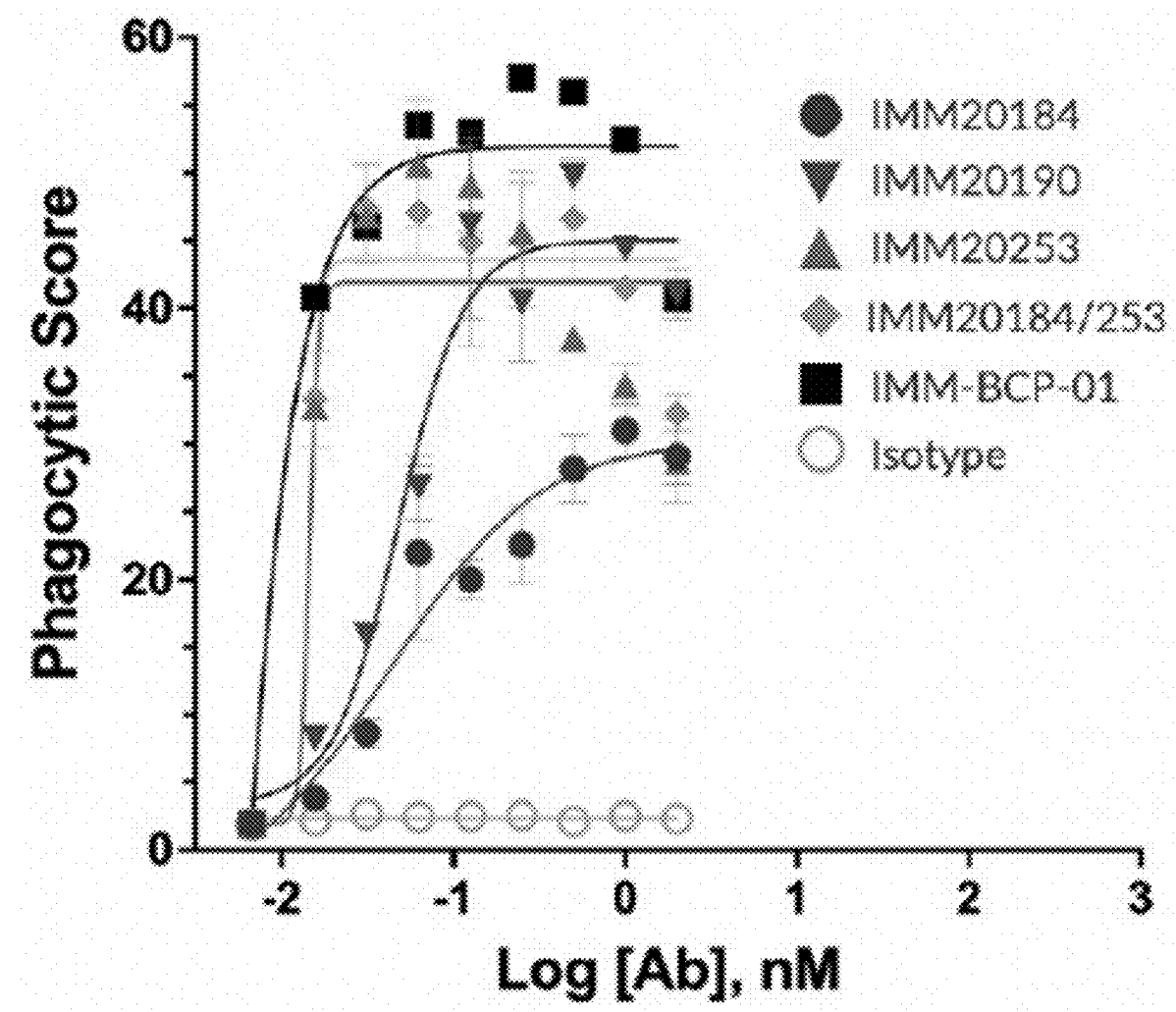
FIG. 21 depicts in vitro phagocytosis activity of IMM20184, IMM20190, IMM20253, the IMM20184/IMM20253 two-antibody cocktail, and IMM-BCP-01 (three antibody cocktail) relative to isotype control antibodies when assessed across a range of concentrations.
Figure 22:
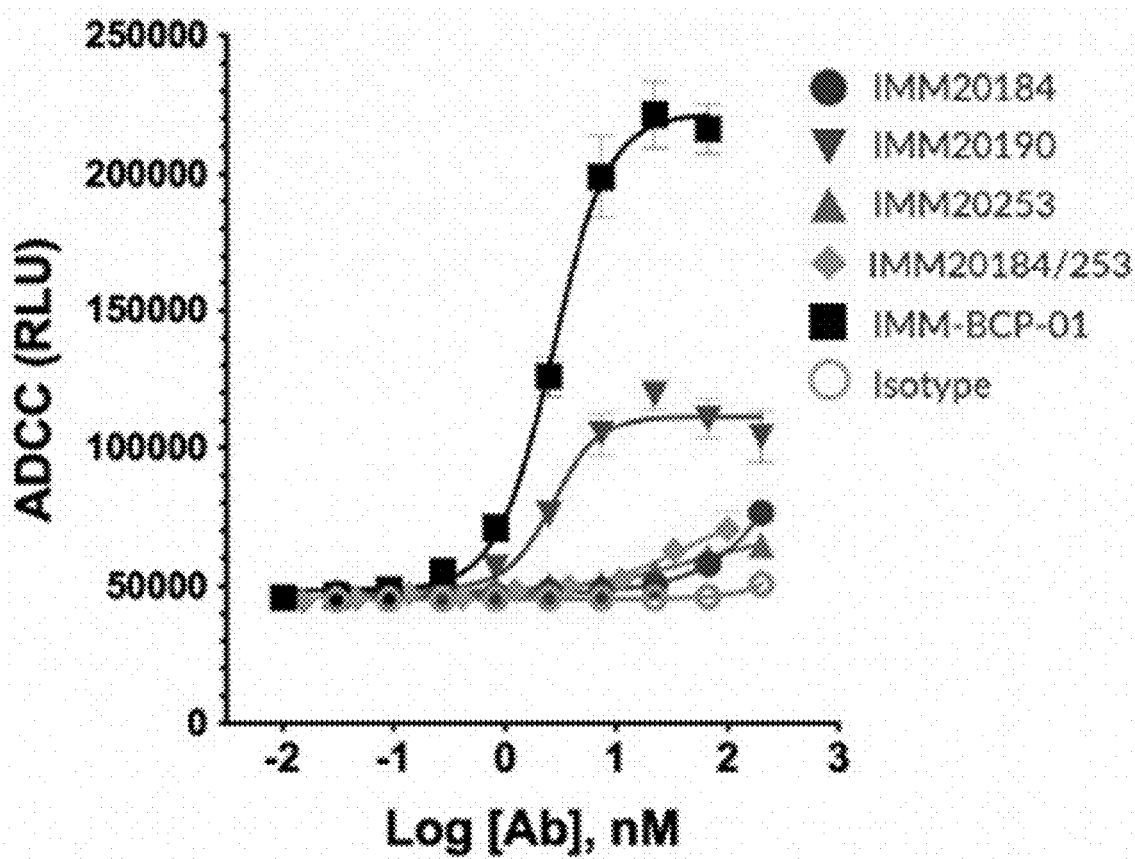
FIG. 22 depicts antibody-dependent cellular cytotoxicity activity of IMM20184, IMM20190, IMM20253, the two antibody cocktail of IMM20184/IMM20253, and the triple antibody cocktail (IMM20184/IMM20190/IMM20253; IMM-BCP-01) relative to isotype control antibodies when assessed in a concentration-dependent manner.

Select antibodies were also assessed for the ability to phagocytosis at a defined concentration and using methods described previously [Shi et al., 2014]. As listed in Table 8, antibodies elicited a range of phagocytosis scores, with higher values representing a more robust ability to induce phagocytosis. Each of the antibodies comprising IMM-BCP-01 was further evaluated in the ability to induce phagocytosis in a concentration-dependent manner against the full-length trimer, both as individual antibodies and as cocktails of two or three antibodies (FIG. 21). All three antibodies induce phagocytosis of the full-length trimer in concentration-dependent manners, with IMM20253 inducing the most robust activation of phagocytosis as assessed in vitro. IMM-BCP-01 exhibited enhanced activity, over a wider concentration range, as compared to any of the individual antibodies and the IMM20184/IMM20253 two antibody combination.

IMM-BCP-01 induces a more robust antibody-dependent cellular cytotoxicity than any of the individual component antibodies when assessed in vitro using Promega's ADCC Reporter Bioassay and S-expressing CHO-K1 target cells at a 2:1 effector:target cell ratio and manufacturer protocols.

Taken together these data suggest that the IMM-BCP-01 cocktail robustly induces multiple effector functions in a manner that is enhanced by the presence of two or more of its constituent antibodies as compared to the individual antibodies alone.

Example 12. IMM20253 may neutralize SARS-CoV-2 through a mechanism that alters Spike protein conformation. As depicted in FIG. 2, IMM20253 binds to an epitope that is on the outside face of the RBD domain of the SARS-CoV-2 RBD. When in the closed conformation, the epitope is in close proximity to the N-terminal domain of a second Spike protein within the Spike trimer. A recent paper [Sun et al, 2021] describes the isolation of nanobodies (Nb), defined as class III Nb, that bind to epitopes that appear to overlap with the IMM20253 epitope. Biochemical characterization the Class III Nb demonstrates that binding of the Nb to the Spike protein induces a conformational change to the post-fusion conformation. This presumably inactivates the virus' ability to bind cells and provides a mechanism for the neutralization observed in vitro. Like the Class III Nbs, IMM20253 is unable to directly compete for ACE2 binding (FIGS. 20A-20C), but is able to neutralize both reference and alpha variant live virus as a single agent when measured as a function of virus internalization (Table 9). Together, these data suggest that IMM20253 binding to the outer face of the RBD may impart its intrinsic neutralization through induction of a conformational change in the Spike protein that prevents virus uptake into the cells without competing for ACE2 binding. Interestingly, IMM20253 appears to be approximately 30-times more potent against the alpha strain than the delta strain. This may be a function of the internalization kinetics of the two different variants. This difference may also underlie the strong synergy observed between the IMM20184/IMM20190/IMM20253 in the context of neutralizing the alpha variant (FIGS. 7A-7C). It should be noted that like Greaney et al [Greany e al], Sun et al describe the region around the IMM20253 epitope as being of therapeutic interest, one to which antibodies are not known to exist [Greany et al] and one that is going to be difficult for antibodies to access [Sun et al]. Consistent with these assertions, the CoVIC consortium analyzed over 300 antibodies that bind to the RBD domain of the SARS-CoV-2 Spike protein and failed to identify an antibody that bound to the IMM20253 epitope. These points all highlight the uniqueness of the IMM20253 antibody [Hastie et al].

Figure 23A:
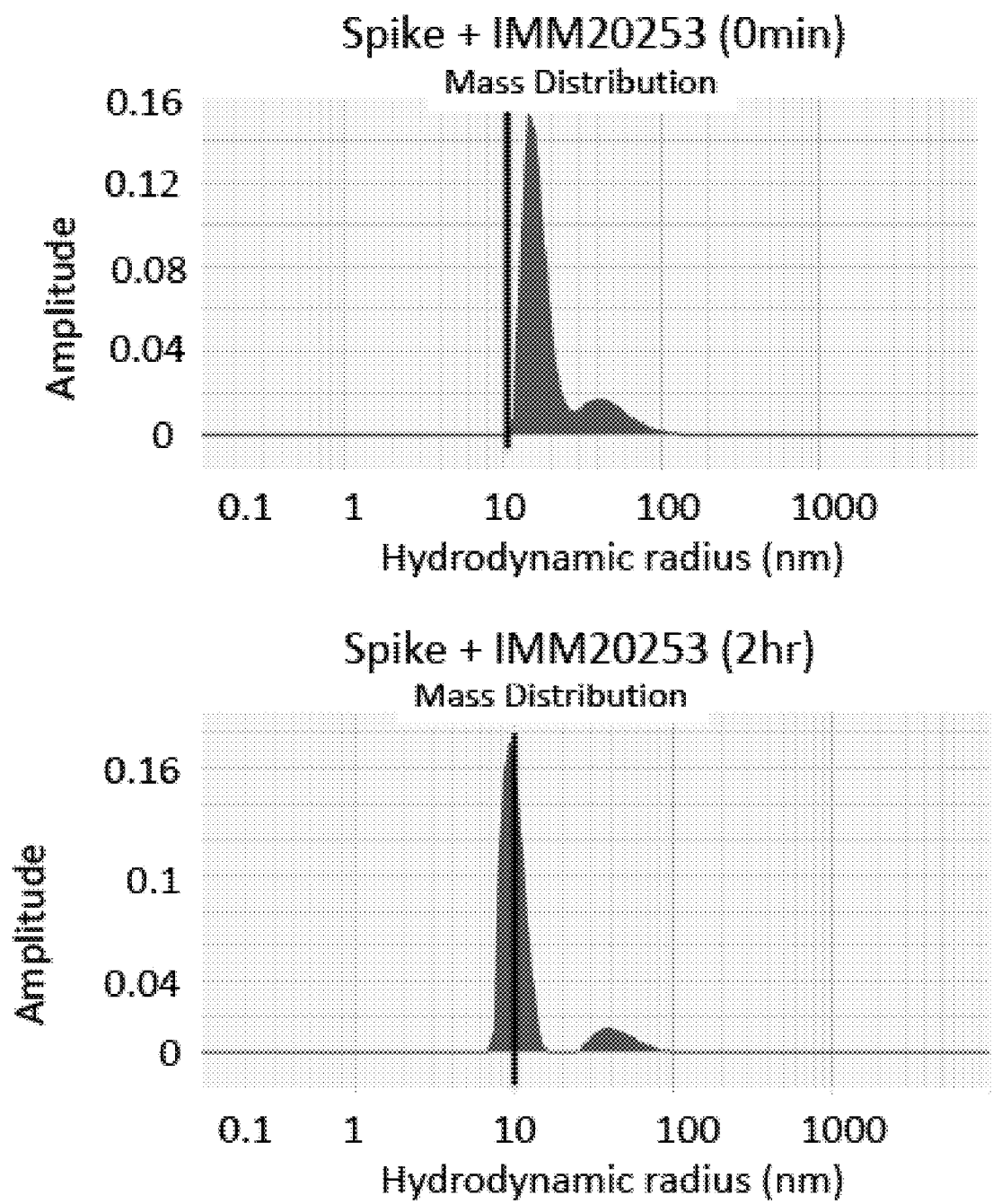
FIGS. 23A-23B depict time-dependent conformational change in Spike protein, as measured by dynamic light scattering, upon binding of IMM20253 or IMM20190.
Figure 23B:
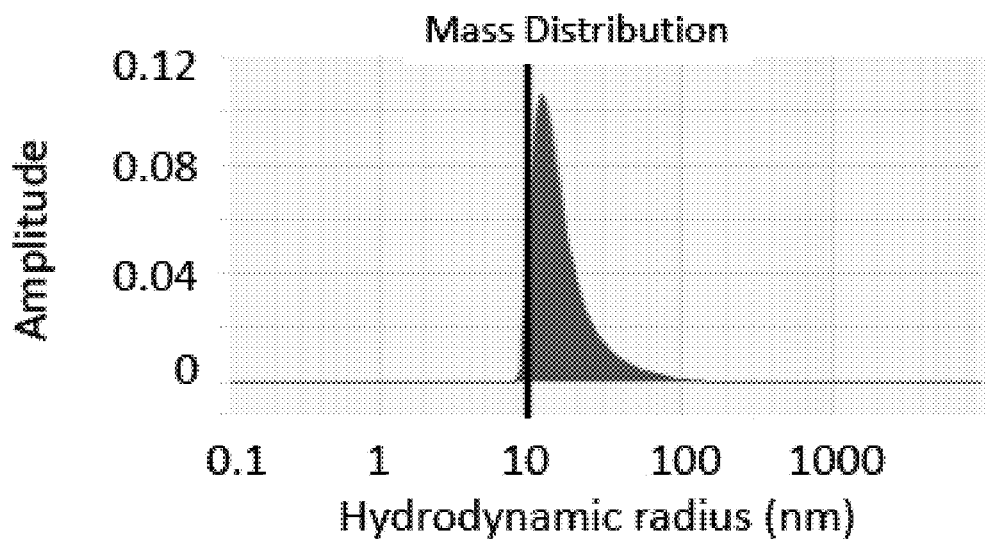
Figure 23B:
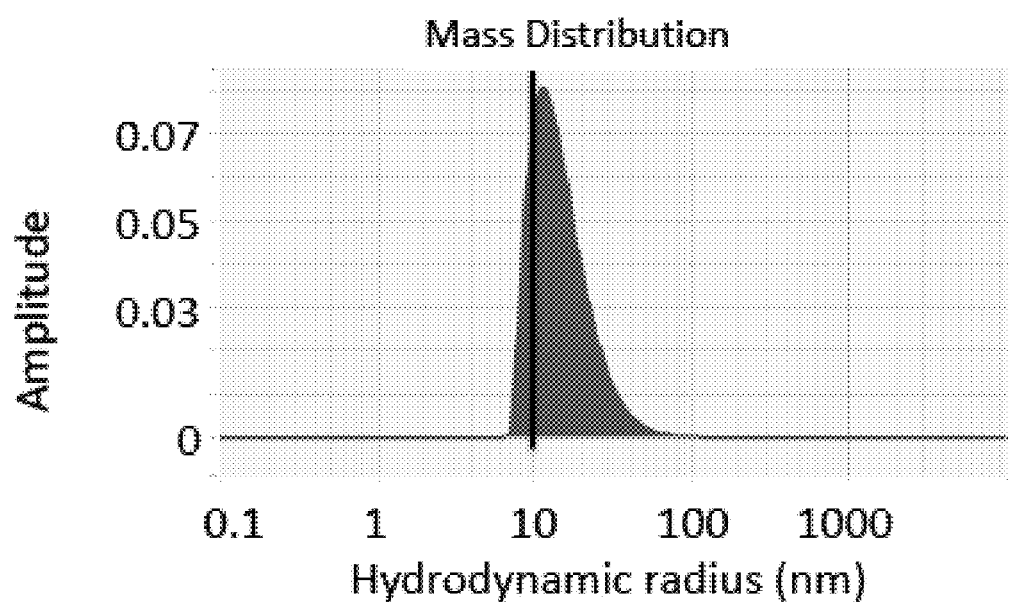

As outlined in FIGS. 23A-23B, binding of IMM20253, but not IMM20190, induces a time-dependent conformational changed in the trimeric Spike protein. Dynamic light scattering (DLS) analysis performed at t=0 and t=2 hours, demonstrates that IMM20253 binding results in the complex adopting a conformation with a smaller hydrodynamic radius. In contrast, the IMM20190/Spike trimer complex maintains a similar hydrodynamic radius throughout the two hour incubation.

Figure 24:
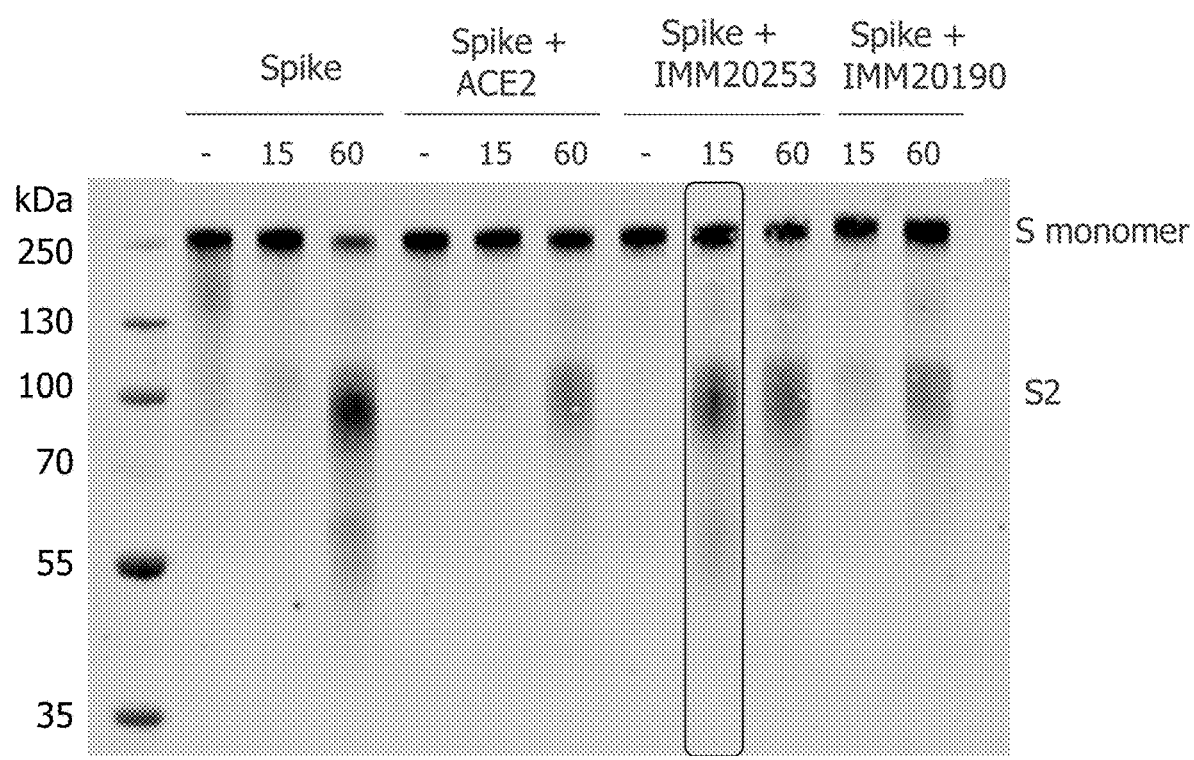
FIG. 24 depicts time-dependent protease digestion of Spike and Spike in complex with ACE2, IMM20253, or IMM20190.

The conformational change induced by IMM20253 results in an increased protease sensitivity of the Spike protein (FIG. 24). Cleavage of Spike, when incubated in the presence of thrombin protease, is observed at t=1 hour. Similar results are observed when Spike is complexed with either ACE2 or IMM20190. In contrast, proteolytic cleavage of Spike, and release of S2, is observed within 15 minutes when Spike is complexed with the IMM20253. Without being bound by theory, this data suggests that the IMM20253 antibody is particularly effective against variants that have pre-cleaved Spike proteins and/or variants that are more susceptible to cleavage.

Figure 25A:
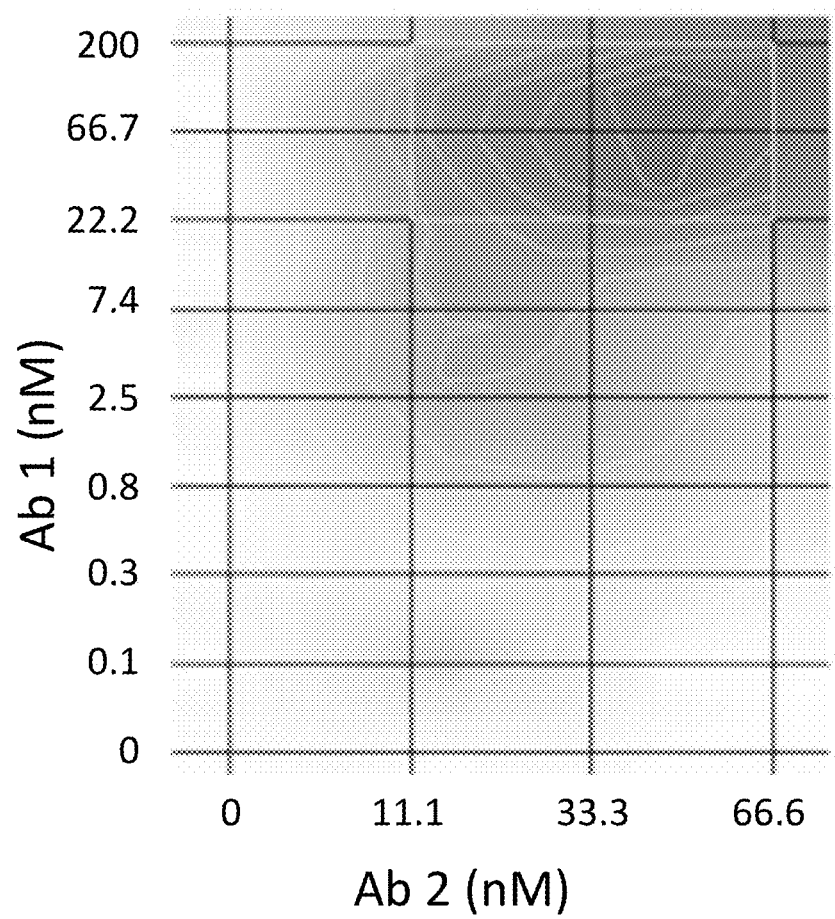
FIGS. 25A-25C depict the combinatorial neutralization activity of IMM20253 in combination with IMM20184, REGN987, or REGN933 against pseudoviruses expressing the Spike protein from the Delta Plus (B.1.617.2 ay1/2) variant. Dark grey area represent regions of synergy. Bottom portion of the figure lists the overall HSA scores for each combination.
Figure 25B:
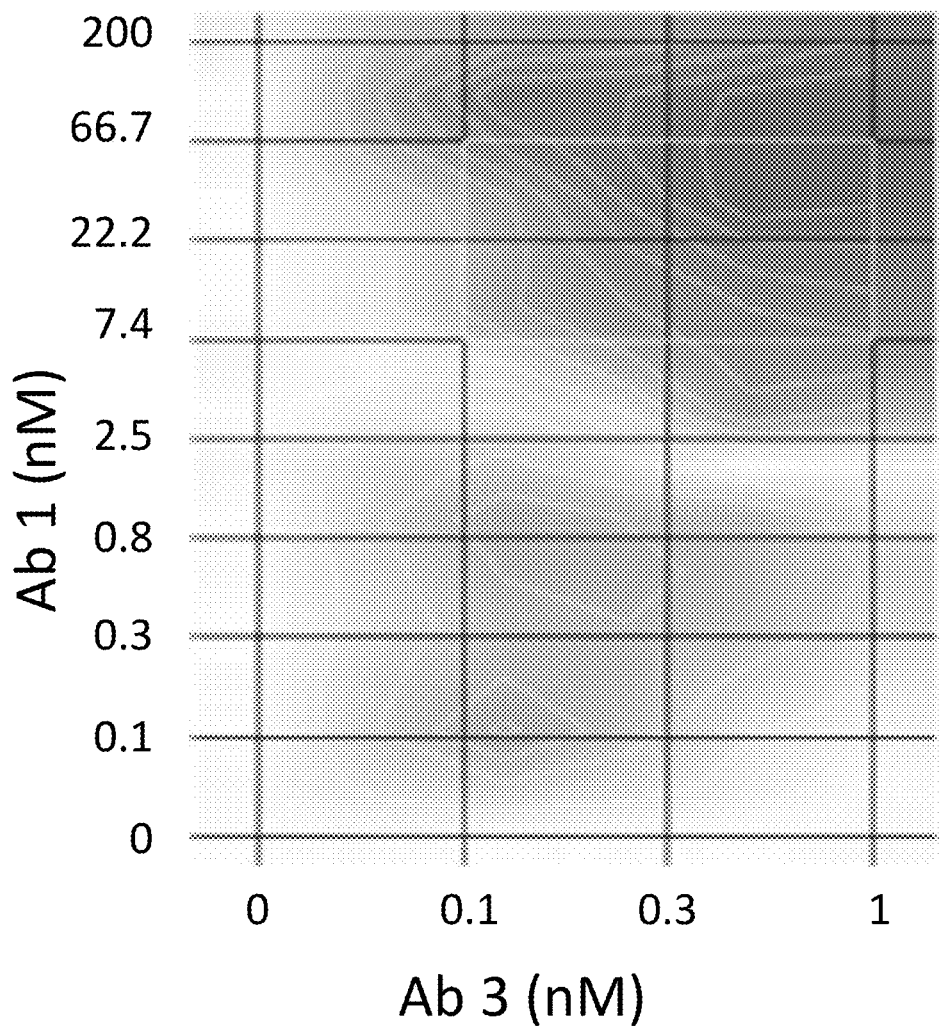
Figure 25C:
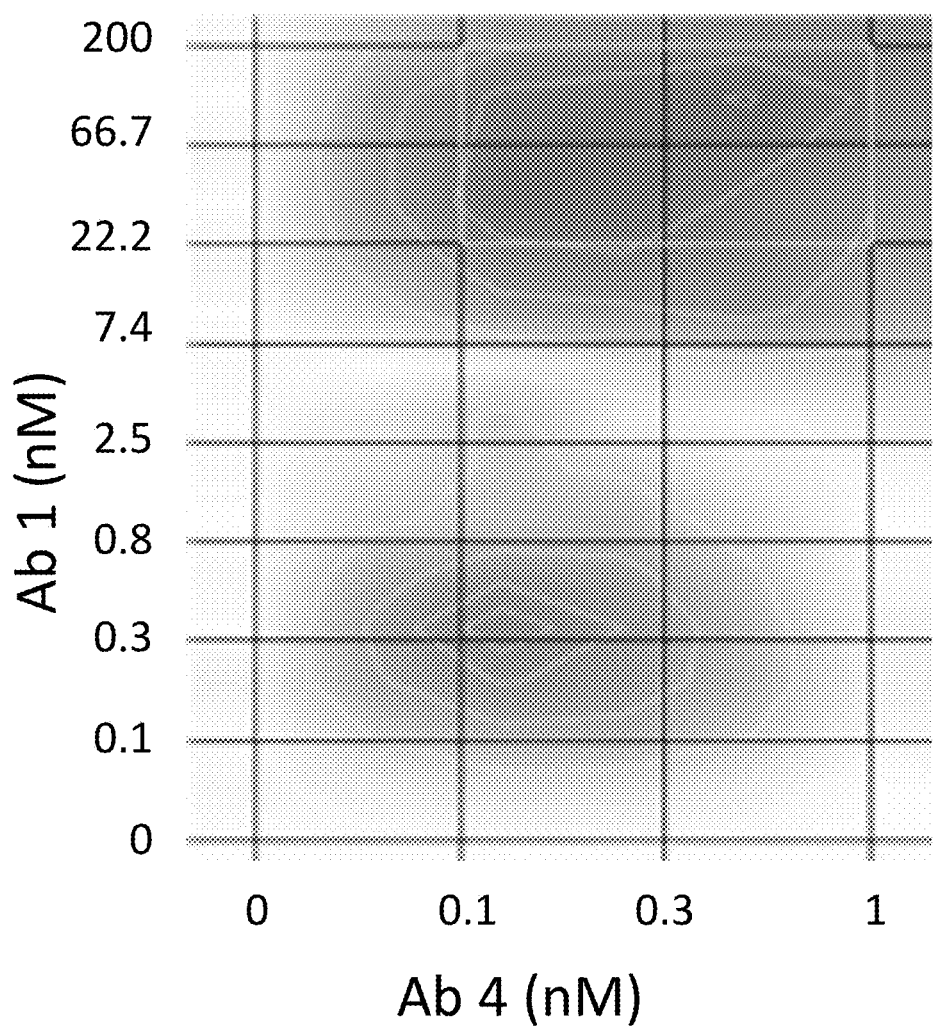

IMM20184, induces synergy with other ACE2-competing enzymes. IMM20253, IMM20184, or IMM20253/IMM20184 combines with one or more of the following antibodies to induce combinatorial, preferably synergistic, viral neutralization in vitro and promote in vivo viral clearance. Examples of antibodies that combine to induce the combinatorial effect with IMM20253, IMM20184 or IMM20253/IMM20184 include, but are not limited to, sotrovimab, casirivimab, imdevimab, bamlanivimab, etesevimab, tixagevimab, cilgavimab, ADG2, ADG10, ADG20, ADG30, and CR3022. As depicted in FIGS. 25A-25C, IMM20253 works in combination with IMM20184, as well as in-house generated versions of REGN987 (imdevimab) and REGN933 (casirivimab) when assayed against B.1.617.2 ay2 pseudovirus. Under the conditions tested all three combinations displayed synergistic neutralization at defined concentrations achievable in vivo (HSA score ≥10). Under the conditions tested, the IMM20253/IMM20184 combination achieved an overall HSA score indicative of synergy (12.5). IMM20253/REGN933 achieved an overall HSA score of 9.5, suggestive of additivity (HSA score between −10 and 10). The IMM20253/REGN933 combination demonstrated an overall HSA score of 5.6, consistent with additive activity under the conditions tested. All three antibodies (IMM20184, REGN933 and REGN987)

TABLE 9

Neutralization capacity of all single, double, and triple combinations of IMM20184, IMM20190, and IMM20253 in a virus internalization assay.

| antibody/combination | virus batch nr | virus type | WHO label | Pango lineage | IC50 (nM) | IC80 (nM) | IC90 (nM) |
|---|---|---|---|---|---|---|---|
| IMM20184 | VC-210180028 | SARS-CoV-2 (UK strain) | Alpha | B.1.1.7 | 43.32 | >393.7 | >393.7 |
| IMM20190 | VC-210180028 | SARS-CoV-2 (UK strain) | Alpha | B.1.1.7 | 2.66 | 13.67 | >393.7 |
| IMM20253 | VC-210180028 | SARS-CoV-2 (UK strain) | Alpha | B.1.1.7 | 1.38 | 61.11 | 218.95 |
| Combo 1 (IMM20184/IMM20190) | VC-210180028 | SARS-CoV-2 (UK strain) | Alpha | B.1.1.7 | 0.98 | 3.60 | 6.62 |
| Combo 2 (IMM20184/IMM20253) | VC-210180028 | SARS-CoV-2 (UK strain) | Alpha | B.1.1.7 | 5.72 | 21.08 | 37.28 |
| Combo 3 (IMM20190/IMM20253) | VC-210180028 | SARS-CoV-2 (UK strain) | Alpha | B.1.1.7 | 0.85 | 8.49 | 16.62 |
| Combo 4 (IMM20184/IMM20253) | VC-210180028 | SARS-CoV-2 (UK strain) | Alpha | B.1.1.7 | 0.44 | 2.85 | 5.80 |
| IMM20184 | VC-210180051 | SARS-CoV-2 (BavPat-1) | n/a | n/a (wild type) | 33.81 | 125.56 | 235.94 |
| IMM20190 | VC-210180051 | SARS-CoV-2 (BavPat-1) | n/a | n/a (wild type) | 0.35 | 1.43 | 3.06 |
| IMM20253 | VC-210180051 | SARS-CoV-2 (BavPat-1) | n/a | n/a (wild type) | 39.38 | 150.68 | 289.21 |
| Combo 1 (IMM20184/IMM20190) | VC-210180051 | SARS-CoV-2 (BavPat-1) | n/a | n/a (wild type) | 0.37 | 1.41 | 3.50 |
| Combo 2 (IMM20184/IMM20253) | VC-210180051 | SARS-CoV-2 (BavPat-1) | n/a | n/a (wild type) | 3.89 | 36.42 | 78.50 |
| Combo 3 (IMM20190/IMM20253) | VC-210180051 | SARS-CoV-2 (BavPat-1) | n/a | n/a (wild type) | 0.35 | 1.28 | 3.34 |
| Combo 4 (IMM20184/IMM20253) | VC-210180051 | SARS-CoV-2 (BavPat-1) | n/a | n/a (wild type) | 0.24 | 1.20 | 2.81 |

Figure 26:
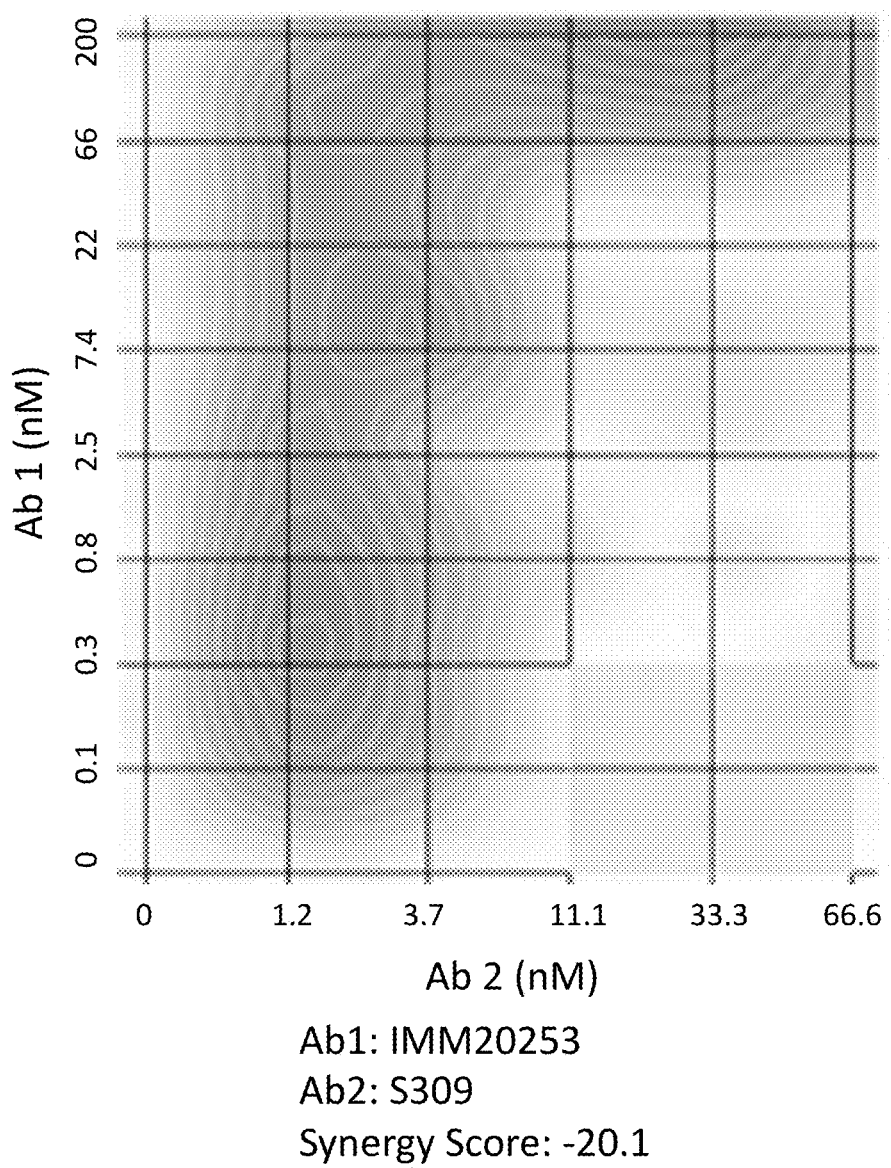
FIG. 26 depicts the combinatorial neutralization activity of IMM20253 in combination with S309 against pseudoviruses expressing the Spike protein from the Delta Plus (B.1.617.2 ay1/2) variant. Grey areas represent areas of antagonism between the two antibodies. Bottom portion of the figure lists the overall HSA score for the combination.
Figure 27A:
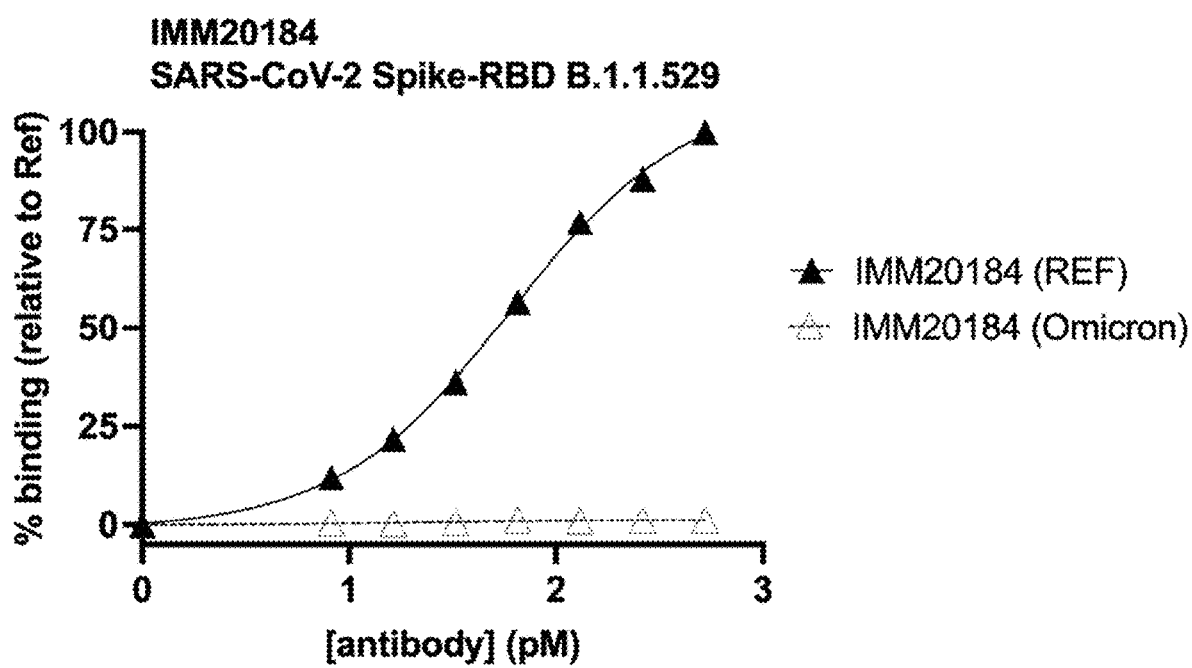
FIG. 27A-27D depict the in vitro binding activity of individual antibodies FIG. 27A IMM20184, FIG. 27B IMM20190, FIG. 27C IMM20253, and FIG. 27D IMM20279 to the SARS-CoV-2 Spike-RBD Omicron variant relative to the reference strain.
Figure 27B:
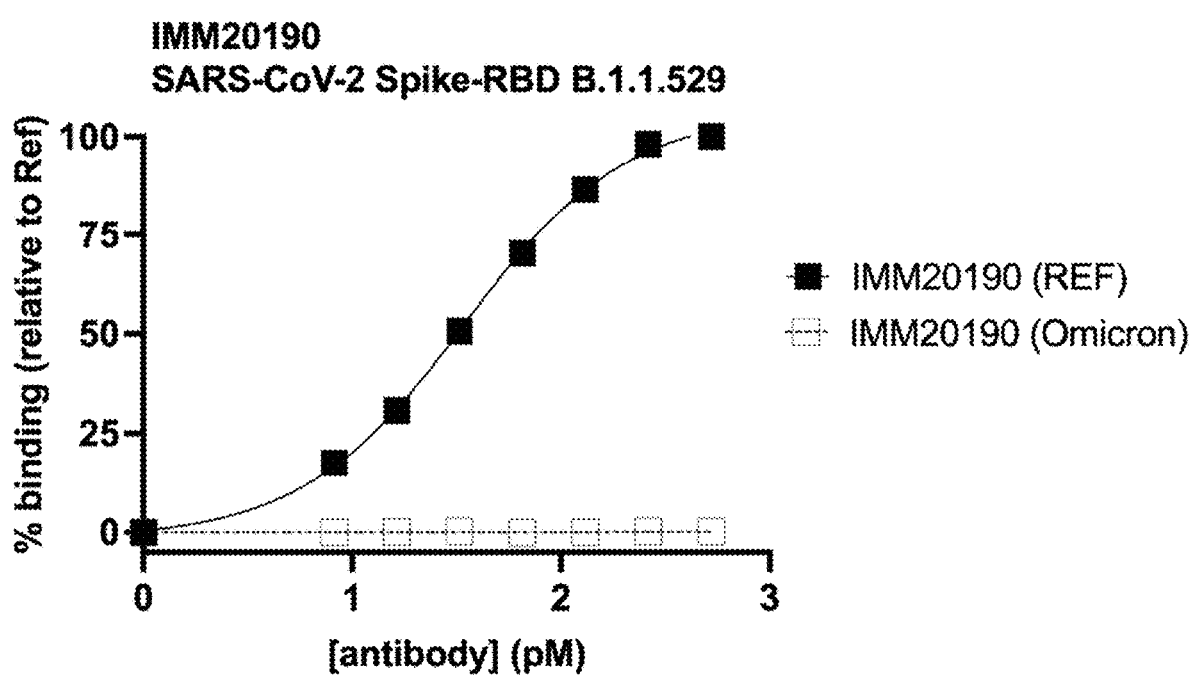
Figure 27C:
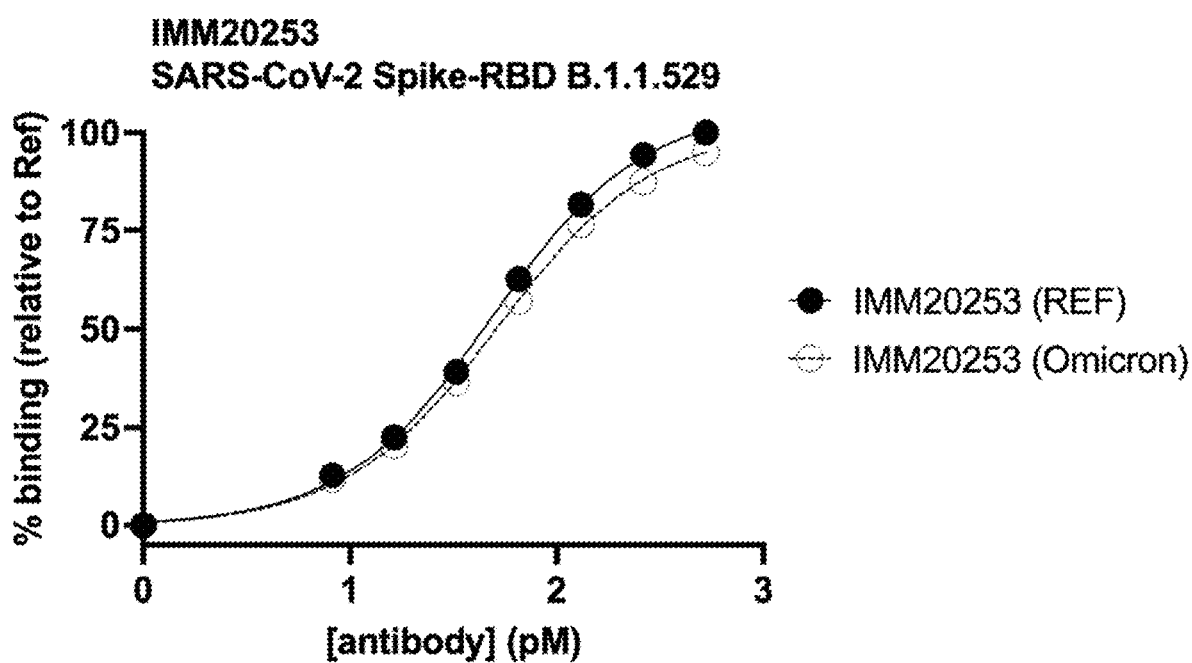
Figure 27D:
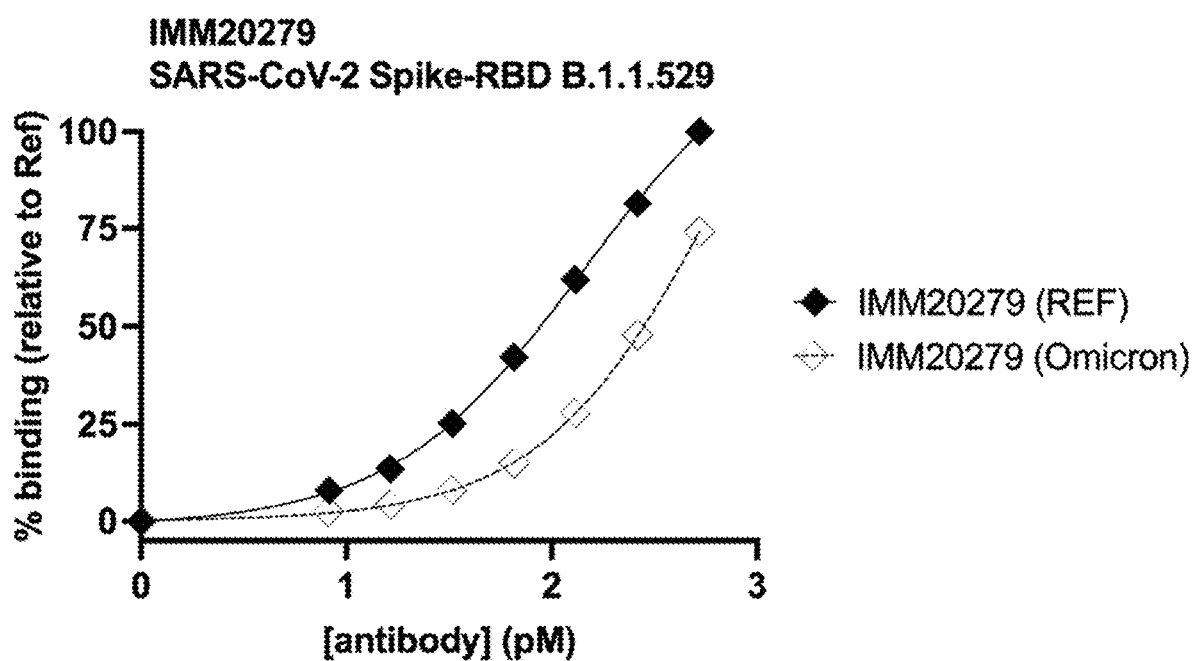
Figure 28:
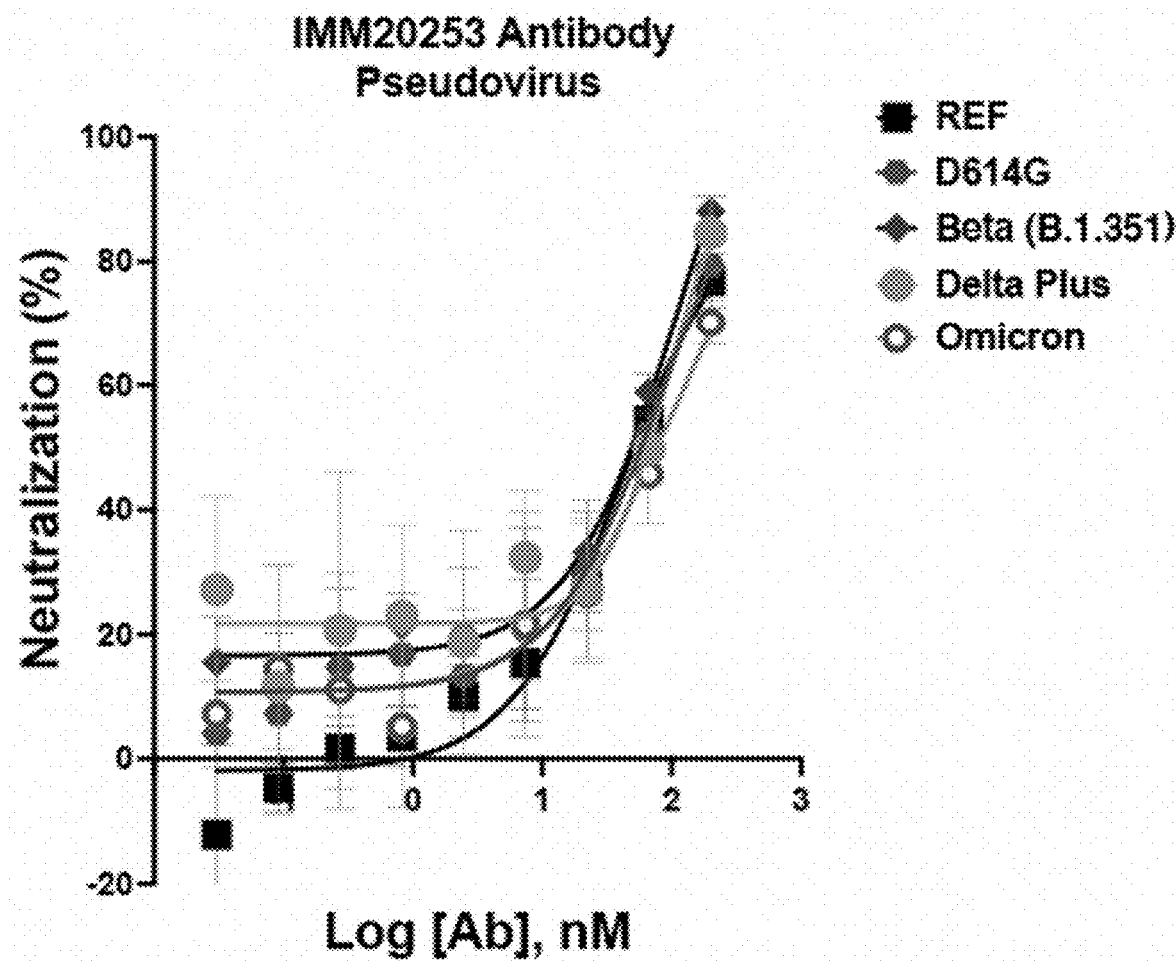
FIG. 28 depicts the in vitro neutralization activity of the IMM20253 antibody against pseudovirus expressing the Spike protein from the reference strain (SARS-CoV-2/human/USA/WA_CDC-WA1/2020), DG14G (SARS-CoV-2/human/Germany/BavPat 1/2020), B.1.351 (beta/S. African), B.1.617.2 Ay.2 (Delta Plus) and B.1.1.529 (Omicron) variants of SARS-CoV-2.

Example 13. IMM20253, alone or in combination with IMM20184, induces synergy with other ACE2-competitive antibodies. Binding of either IMM20253, IMM20184, or the combination of the two antibodies (IMM20253/IMM20184), induces combinatorial effects, preferably synergy, when combined with the ACE2-competitive antibody IMM20190. Combinations of IMM20253, IMM20184, or IMM20253/ block ACE2 binding. In contrast, IMM20253 in combination with in-house generated S309 (sotrovimab) resulted in strong antagonism across all concentrations tested (FIG. 26). S309 is thought to work through a non-ACE2 dependent neutralization mechanism. This suggests that IMM20253's non-ACE2 dependent neutralization mechanism may enhance neutralization in combination with antibodies that work via an ACE2- dependent neutralization mechanism, but may antagonize other non-ACE2 dependent mechanisms of neutralization.

Example 14. IMM20253 and IMM20279 and exhibit potent binding to the Spike protein of the Omicron variant. Individual antibodies were assessed, in the HTRF assay described above, using the full length Spike protein and soluble RBD domains of the Spike protein containing mutations found in the Omicron variant. FIGS. 27A-27D depict the binding of the individual antibodies to the Spike-RBD of the Omicron variant, expressed as percentage binding, relative to the binding to the reference strain. Binding of the antibodies IMM20190 and IMM20184 (FIGS. 27A and 27B), are negatively affected by the mutations within the Spike domain of the Omicron variant. In contrast, binding by the IMM20253 (FIG. 27 C) and IMM20279 (FIG. 27 D) antibodies are unaffected by the range of mutations within the Spike protein of the Omicron variant. The binding affinity of the IMM20279 antibody to the RBD as well as the full-length Spike protein is comparable to that of the reference strain (FIG. 27 D).

Example 15. IMM20253 antibody neutralizes SARS-CoV-2 pseudovirus expressing the Omicron variant. The functional consequence of the IMM20253 antibody binding to Spike was assessed. Pseudovirus infection and neutralization assays were performed by using standard methods described above. The IMM20253 antibody exhibited potent neutralization against pseudovirus expressing the Spike protein from the B.1.1.529 (Omicron) variant (FIG. 28). The neutralization activity was comparable to the activity against pseudovirus expressing the Spike protein from the reference strain (SARS-CoV-2/human/USA/WA_CDC-WA1/2020), D614G (SARS-CoV-2/human/Germany/BavPat 1/2020), B.1.351 (beta/S. African), B.1.617.2 Ay.2 (Delta Plus) variants of SARS-CoV-2 (FIG. 28).

REFERENCES

Berlin D A, Gulick R M, Martinez F J. Severe Covid-19. N Engl J Med. 2020 [cited 5 Nov. 2020]. doi:10.1056/nejmcp2009575

Bonsignori, M., Pollara, J., Moody, M. A., Alpert, M. D., Chen, X., Hwang, K.-K., Gilbert, P. B., Huang, Y., Gurley, T. C., Kozink, D. M., et al. (202). Antibody-dependent cellular cytotoxicity-mediating antibodies from an HIV-1 vaccine efficacy trial target multiple epitopes and preferentially use the VH1 gene family. J. Virol. 86, 11521-11532.

Braun J, Loyal L, Frentsch M, Wendisch D, Georg P, Kurth F, et al. SARS-CoV-2-reactive T cells in healthy donors and patients with COVID-19. Nature. 2020. doi:10.1038/s41586-020-2598-9

Callaway B E. The coronavirus is mutating—does it matter? Nature. 2020; 585.

Cao Y, Su B, Guo X, Sun W. Deng Y, Bao L. et al. Potent neutralizing antibodies against SARS-CoV-2 identified by high-throughput single-cell sequencing of convalescent patients' B cells. Cell. 2020. doi:10.1016/j.cell.2020.05.025

Chakraborty I, Maity P. COVID-19 outbreak: Migration, effects on society, global environment and prevention. Sci Total Environ. 2020; 728: 138882. doi:10.1016/j.scitotenv.2020.138882

Dessain, S. K., and Chumakov. K. (2014). Human monoclonal antibodies that neutralize vaccine and wild-type poliovirus strains. Antiviral Res. 108, 36-43.

Degorce, F., Card, A., Soh, S., Trinquet, E., Knapik, G. P., Xie, B. (2009) HTRF: A technology tailored for drug discovery—A review of theoretical aspects and recent applications. Current Chemical Genomics, 22-32.

Dessain, S. K., and Weinberg, R. A. (2002). US7491530132.

Dessain, S. K., and Adekar, S. P. (2009). U.S. Pat. No. 8,999,707B2.

Editorial. Progress report on the coronavirus pandemic. Nature. 2020; 584: 325-325. FDA (2020). Guidance for Industry: FDA s Recommendations for Investigational COVID-19 Conavalescent Plasma.

Fehr, A. R., and Perlman, S. (2015). Coronaviruses: An overview of their replication and pathogenesis. In Coronaviruses: Methods and Protocols, (Springer New York), pp. 1-23.

Ferretti A P, Kula T, Wang Y, Nguyen D M V, Weinheimer A, Dunlap G S, et al. Unbiased Screens Show CD8+ T Cells of COVID-19 Patients Recognize Shared Epitopes in SARS-CoV-2 that Largely Reside outside the Spike Protein. Immunity. 2020 [cited 5 Nov. 2020]. doi: 10.1016/j.immuni.2020.10.006

Greany A J, Loes A N, Crawfor K H D, Starr T N, Malone K D, Chu H Y, and Bloom J D. Comprehensive mapping of mutations in the SARS-CoV-2 receptor binding domain that affect recognition by polyclonal human plasma antibodies. Cell Host Microbe. 2021; 29: 463-476

Grifoni A, Weiskopf D, Ramirez S I, Mateus S, Dan J M, Moderbacher C R, et al. Targets of T Cell Responses to SARS-CoV-2 Coronavirus in Humans with COVID-19 Disease and Unexposed Individuals. Cell. 2020; 181: 1489-1501.e15. doi:10.1016/j.cell.2020.05.01:5

Hastie K M, Li H, Bedinger D, Schendel S E, Dennison S M, Li K, et al Defining Variant-resistant Epitopes Targeted by SARS-CoV-2 Antibodies: A Global Consortium Study. Science. 2021. doi10.1126/science.abh2315

Jacobsen, H. I., Poulsen, T. T., Dahlman, A., Kjær, I., Koefoed, K., Sen, J. W., Weilguny, D., Bjerregaard, B., Andersen, C. R., Horak, I. D., et al. (2015). Pan-HER, an antibody mixture simultaneously targeting EGFR, HERZ and HER3, effectively overcomes tumor heterogeneity and plasticity. Clin. Cancer Res. 21, 4110-4122.

Korber B, Fischer W M, Gnanakaran S, Yoon H, Theiler J, Abfalterer W, et al. Tracking Changes in SARS-CoV-2 Spike: Evidence that D614G Increases Infectivity of the COVID-19 Virus. Cell. 2020; 182: 812-827.e19. doi: 10.1016/j.cell.2020.06.043

Lan, J., Ge, J., Yu, J., Shan, S., Zhou, H., Fan, S., Zhang, Q., Shi, X., Wang, Q., Zhang, L., et al. (2020). Structure of the SARS-CoV-2 Spike receptor-binding domain bound to the ACE2 receptor. Nature 581, 215-220.

Levites Y, O'Nuallain B, Puligedda R D, Ondrejcak T, Adekar S P, Chen C, et al. A human monoclonal IgG that binds Aβ assemblies and diverse amyloids exhibits anti-amyloid. activities in vitro and in vivo. J Neurosci. 2015; 35: 6265-6276. doi: 10.1523/JNEUROSCI.5109-14.2015

Li Q, Wu J, Nie J, Zhang L, Hao H, Liu S, et al. The Impact of Mutations in SARS-CoV-2 Spike on Viral infectivity and Antigenicity. Cell. 2020; 182: 1284-1294.e9. doi: 10.1016/j.cell.2020.07.012

Morens D M, Fauci A S. Emerging Pandemic Diseases: How We Got to COVID-19. Cell. Cell Press; 2020. pp. 1077-1092. doi:10.1016/j.cell.2020.08.021

Nikitin, P. A., Rose, E. L., Byun, T. S., Parry, G. C., and Panicker, S. (2019). C1s inhibition by BIVV009 (Sutimlimab) Prevents Complement-Enhanced Activation of Autoimmune Human B Cells in Vitro. J. Immunol. 202, 1200-1209.

Puligedda, R. D., Kouiavskaia, D., Adekar, S. P., Sharma, R., Devi Kattala, C. Rezapkin, G., Bidzhieva, B., Dessain, S. K., and Chumakov, K. Human monoclonal antibodies that neutralize vaccine and wild-type poliovirus strains. Antiviral Res, 2014; 108: 36-43.

Puligedda, R. D., Sharma, R., Al-Salem, F. H., Kouiavskaia, D., Velu, A. B., Kattala, C. D., Prendergast, G. C., Lynch, D. R., Chumakov, K., and Dessain, S. K. (2019). Capture and display of antibodies secreted by hybridoma cells enables fluorescent on-cell screening. MAbs 11, 546-558.

Puligedda, R. D., Vigdorovich, V., Kouiayskaia, D., Kattala, C. D., Zhao, J., Al-Saleem, F. H., Chumakov, K., Sather, D. N., and Dessain, S. K. (2020). Human IgA Monoclonal Antibodies That Neutralize Poliovirus, Produced by Hybridomas and Recombinant Expression. Antibodies 9, 5.

Robbiani, D. F., Gaebler, C., Muecksch, F., Lorenzi, J. C. C., Wang, Z., Cho, A., Agudelo, M., Barnes, C. O., Finkin, S., Hagglof, T., et al. (2020). Convergent Antibody Responses to BARS-CoV-2 Infection in Convalescent Individuals. BioRxiv 2020.05.13.092619.

Shi, J., Rose, E. L., Singh, A., Hussain, S., Stagliano, N. B., Parry, G. C., and Panicker, S. (2014). TNT003, an inhibitor of the serine protease C1s, prevents complement activation induced by cold agglutinins. Blood 123, 4015-4022.

Stamper C T, Dugan H L, Li L, Asby N W, Halfmann P J, Guthmiller J J, et al. Distinct B well subsets give rise to antigen-specific antibody responses against SARS-CoV-2. Res SquareResearch Sq. 2020.

Sun D, Sang Z, Kim Y J, Xiang Y, Cohen T, Belford A K, Huet A, Conway J F, Sun J, Taylor D J, Scheidman-Duhovny D, Zhang C. Huang W, Shi Y. Potent neutralizing nanobodies resist convergent circulating variants of SARS-CoV-2 by targeting diverse and conserved epitopes. Nat. Comm. 12, 4676.

Tursi, S. A., Puligedda, R. D., Szabo, P., Nicastro, L. K., Miller, A. L., Qiu, C., Gallucci., S., Relkin, N. H., Buttaro, Dessain, S. K., et al. (2020). *Salmonella* Typhimurium biofilm disruption by a human antibody that binds a pan-amyloid epitope on curli. Nat. Commun. 11.

Von Holle, T. A., and Anthony Moody, M. (2019). Influenza and antibody-dependent cellular cytotoxicity. Front. Immunol. 10, 1-8.

WHO Coronavirus Disease (COVID-19) Dashboard WHO Coronavirus Disease (COVID-19) Dashboard. [cited 9 Nov. 2020].

Zhou, P., Yang, X. Lou, Wang, X. G., Hu, B., Zhang, L., Zhang, W., Si, H. R., Zhu, Y., Li, B., Huang, C. L., et al. (2020. pneumonia outbreak associated with a new coronavirus of probable bat origin. Nature 579, 270-273.

What is claimed:

1. An antibody or antigen binding fragment that binds a severe acute respiratory syndrome coronavirus 2 (SARS-CoV-2) Spike protein, wherein the antibody or antigen binding fragment thereof comprises
- a HCVR comprising the amino acid sequence set forth in SEQ ID NO: 1, and a LCVR comprising the amino acid sequence is set forth in SEQ ID NO: 2;
- a HCVR comprising the amino acid sequence set forth in SEQ ID NO: 3, and a LCVR comprising the amino acid sequence is set forth in SEQ ID NO: 4;
- a HCVR comprising the amino acid sequence set forth in SEQ ID NO: 5, and a LCVR comprising the amino acid sequence is set forth in SEQ ID NO: 6;
- a HCVR comprising the amino acid sequence set forth in SEQ ID NO: 7, and a LCVR comprising the amino acid sequence is set forth in SEQ ID NO: 8;
- a HCVR comprising the amino acid sequence set forth in SEQ ID NO: 9, and a LCVR comprising the amino acid sequence is set forth in SEQ ID NO: 10;
- a HCVR comprising the amino acid sequence set forth in SEQ ID NO: 11, and a LCVR comprising the amino acid sequence is set forth in SEQ ID NO: 12;
- a HCVR comprising the amino acid sequence set forth in SEQ ID NO: 13, and a LCVR comprising the amino acid sequence is set forth in SEQ ID NO: 14;
- a HCVR comprising the amino acid sequence set forth in SEQ ID NO: 15, and a LCVR comprising the amino acid sequence is set forth in SEQ ID NO: 16;
- a HCVR comprising the amino acid sequence set forth in SEQ ID NO: 17, and a LCVR comprising the amino acid sequence is set forth in SEQ ID NO: 18;
- a HCVR comprising the amino acid sequence set forth in SEQ ID NO: 19, and a LCVR comprising the amino acid sequence is set forth in SEQ ID NO: 20;
- a HCVR comprising the amino acid sequence set forth in SEQ ID NO: 21, and a LCVR comprising the amino acid sequence is set forth in SEQ ID NO: 22;
- a HCVR comprising the amino acid sequence set forth in SEQ ID NO: 23, and a LCVR comprising the amino acid sequence is set forth in SEQ ID NO: 24; or
- a HCVR comprising the amino acid sequence set forth in SEQ ID NO: 25 and a LCVR comprising the amino acid sequence is set forth in SEQ ID NO: 26.

2. An antibody or antigen binding fragment that binds to a severe acute respiratory syndrome coronavirus 2 (SARS-CoV-2) Spike protein, wherein the antibody or antigen binding fragment thereof comprises
- a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60;
- a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;
- a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72; or
- a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

3. The antibody or antigen-binding fragment thereof of claim 1, wherein the antibody is an Fc IgG1, IgG2, IgG3, IgG4, IgM, IgD, IgA1, IgA2 or IgE isotype.

4. The antibody or antigen-binding fragment thereof of claim 3, wherein the antibody is an IgG1 isotype.

5. The antibody or antigen-binding fragment thereof of claim 3, wherein the IgG1 is a G1m1 or nG1m1 allotype.

6. The antibody of claim 1, wherein the antibody is a full length antibody.

7. The antibody or antigen-binding fragment thereof of claim 1, wherein binding of the antibody or antigen-binding fragment thereof:
- inhibits binding of a SARS-CoV-2 virus to a host angiotensin converting enzyme 2 (ACE2) receptor;
- fixes complement to a SARS-CoV-2 virus;
- induces phagocytosis of a SARS-CoV-2 virus; or
- any combination thereof.

8. The antibody or antigen-binding fragment of claim 1, wherein the binding of the antibody or antigen-binding fragment thereof neutralizes a SARS-CoV-2 virus by blocking binding of the receptor binding domain (RBD) of the virus with an ACE2 receptor.

9. The antibody or antigen-binding fragment thereof of claim 1, wherein the SARS-CoV-2 virus is a SARS-CoV-2 variant.

10. The antibody or antigen-binding fragment thereof of claim 9, wherein the SARS-CoV-2 variant is the U.K. (B.1.1.7) variant of SARS-CoV-2, the South African (B.1.351) variant of SARS-CoV-2, the California (B.1.429) variant of SARS-CoV-2, the California (B.1.427) variant of SARS-CoV-2, the Brazilian (P.1) variant of SARS-CoV-2, the New York (B.1.526) variant of SARS-CoV-2, the New York (B.1.526.1) variant of SARS-CoV-2, the UK/Nigeria (B.1.525) variant of SARS-CoV-2, the Brazilian (P.2) variant of SARS-CoV-2 or the Omicron (B.1.1.529) variant.

11. The antibody or antigen binding fragment thereof of claim 1, wherein the antibody is isolated.

12. A composition comprising the antibody or antigen binding fragment thereof of claim 1.

13. A composition comprising two, three, or four of the antibodies or antigen binding fragments thereof of claim 2.

14. The composition of claim 13 comprising
a) a first antibody or antigen binding fragment thereof comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
  a second antibody or antigen binding fragment thereof comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

b) a first antibody or antigen binding fragment thereof comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
  a second antibody or antigen binding fragment thereof comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

c) a first antibody or antigen binding fragment thereof comprising a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60, and
  a second antibody or antigen binding fragment thereof comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114;

d) a first antibody or antigen binding fragment thereof comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
  a second antibody or antigen binding fragment thereof comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72;

e) a first antibody or antigen binding fragment thereof comprising a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66, and
  a second antibody or antigen binding fragment thereof comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114; or f) a first antibody or antigen binding fragment thereof comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72, and
  a second antibody or antigen binding fragment thereof comprising a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

15. A method of treating or preventing a SARS-CoV-2 infection in a subject, comprising administering an antibody or fragment thereof that binds to a SARS-CoV-2 Spike protein, wherein the antibody comprises:
  a VH comprising a HCDR1 comprising the amino acid sequence of SEQ ID NO:55, a HCDR2 comprising the amino acid sequence of SEQ ID NO:56, and a HCDR3 comprising the amino acid sequence of SEQ ID NO:57; and a VL comprising a LCDR1 comprising the amino acid sequence of SEQ ID NO:58, a LCDR2 comprising the amino acid sequence of SEQ ID NO:59, and a LCDR3 comprising the amino acid sequence of SEQ ID NO:60;
  a VH comprising a HCDR1 comprising the amino acid sequence of SEQ ID NO:61, a HCDR2 comprising the amino acid sequence of SEQ ID NO:62, and a HCDR3 comprising the amino acid sequence of SEQ ID NO:63; and a VL comprising a LCDR1 comprising the amino acid sequence of SEQ ID NO:64 a LCDR2 comprising the amino acid sequence of SEQ ID NO:65, and a LCDR3 comprising the amino acid sequence of SEQ ID NO:66;

a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72; or a VH comprising a HCDR1 comprising the amino acid sequence of SEQ ID NO:109, a HCDR2 comprising the amino acid sequence of SEQ ID NO:110, and a HCDR3 comprising the amino acid sequence of SEQ ID NO:111; and a VL comprising a LCDR1 comprising the amino acid sequence of SEQ ID NO:112, a LCDR2 comprising the amino acid sequence of SEQ ID NO:113, and a LCDR3 comprising the amino acid sequence of SEQ ID NO:114.

16. The method of treating or preventing a SARS-CoV-2 infection in a subject thereof of claim 15, comprising administering an antibody or antigen binding fragment thereof comprising:
 a HCVR comprising the amino acid sequence set forth in SEQ ID NO: 1, and a LCVR comprising the amino acid sequence is set forth in SEQ ID NO: 2;
 a HCVR comprising the amino acid sequence set forth in SEQ ID NO: 3, and a LCVR comprising the amino acid sequence is set forth in SEQ ID NO: 4;
 a HCVR comprising the amino acid sequence set forth in SEQ ID NO: 5, and a LCVR comprising the amino acid sequence is set forth in SEQ ID NO: 6;
 a HCVR comprising the amino acid sequence set forth in SEQ ID NO: 7, and a LCVR comprising the amino acid sequence is set forth in SEQ ID NO: 8;
 a HCVR comprising the amino acid sequence set forth in SEQ ID NO: 9, and a LCVR comprising the amino acid sequence is set forth in SEQ ID NO: 10;
 a HCVR comprising the amino acid sequence set forth in SEQ ID NO: 11, and a LCVR comprising the amino acid sequence is set forth in SEQ ID NO: 12;
 a HCVR comprising the amino acid sequence set forth in SEQ ID NO: 13, and a LCVR comprising the amino acid sequence is set forth in SEQ ID NO: 14;
 a HCVR comprising the amino acid sequence set forth in SEQ ID NO: 15, and a LCVR comprising the amino acid sequence is set forth in SEQ ID NO: 16;
 a HCVR comprising the amino acid sequence set forth in SEQ ID NO: 17, and a LCVR comprising the amino acid sequence is set forth in SEQ ID NO: 18;
 a HCVR comprising the amino acid sequence set forth in SEQ ID NO: 19, and a LCVR comprising the amino acid sequence is set forth in SEQ ID NO: 20;
 a HCVR comprising the amino acid sequence set forth in SEQ ID NO: 21, and a LCVR comprising the amino acid sequence is set forth in SEQ ID NO: 22;
 a HCVR comprising the amino acid sequence set forth in SEQ ID NO: 23, and a LCVR comprising the amino acid sequence is set forth in SEQ ID NO: 24; or
 a HCVR comprising the amino acid sequence set forth in SEQ ID NO: 25 and a LCVR comprising the amino acid sequence is set forth in SEQ ID NO: 26.

17. The method of treating or preventing a SARS-CoV-2 infection in a subject thereof of claim 15, comprising administering an antibody or antigen binding fragment thereof comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72.

18. The method of claim 16, wherein the SARS-CoV-2 virus is a SARS-CoV-2 variant, and the SARS-CoV-2 variant is the U.K. (B.1.1.7) variant of SARS-CoV-2, the South African (B.1.351) variant of SARS-CoV-2, the California (B.1.429) variant of SARS-CoV-2, the California (B.1.427) variant of SARS-CoV-2, the Brazilian (P.1) variant of SARS-CoV-2, the New York (B.1.526) variant of SARS-CoV-2, the New York (B.1.526.1) variant of SARS-CoV-2, the UK/Nigeria (B.1.525) variant of SARS-CoV-2, the Brazilian (P.2) variant of SARS-CoV-2 or the Omicron (B.1.1.529) variant.

19. The method of claim 16, wherein the antibody or antigen-binding fragment thereof is an Fc IgG1, IgG2, IgG3, IgG4, IgM, IgD, IgA1, IgA2 or IgE isotype.

20. The method of claim 19, wherein the antibody or antigen-binding fragment thereof is an IgG1 isotype.

21. The method of claim 19, wherein the IgG1 is a G1m1 or nG1m1 allotype.

22. The method of claim 16, wherein the antibody or antigen-binding fragment thereof, wherein the antibody is a full length antibody.

23. The method of claim 16, wherein binding of the antibody or antigen-binding fragment thereof:
 inhibits binding of a SARS-CoV-2 virus to a host ACE2 receptor;
 fixes complement to a SARS-CoV-2 virus;
 induces phagocytosis of a SARS-CoV-2 virus; or
 any combination thereof.

24. The method of claim 16, wherein the binding of the antibody or antigen-binding fragment thereof neutralizes a SARS-CoV-2 virus by blocking binding of the receptor binding domain (RBD) of the virus with an ACE2 receptor.

25. The method of claim 16, wherein the SARS-CoV-2 virus is a SARS-CoV-2 variant.

26. The method of claim 16, wherein the SARS-CoV-2 variant is the U.K. (B.1.1.7) variant of SARS-CoV-2, the South African (B.1.351) variant of SARS-CoV-2, the California (B.1.429) variant of SARS-CoV-2, the California (B.1.427) variant of SARS-CoV-2, the Brazilian (P.1) variant of SARS-CoV-2, the New York (B.1.526) variant of SARS-CoV-2, the New York (B.1.526.1) variant of SARS-CoV-2, the UK/Nigeria (B.1.525) variant of SARS-CoV-2, the Brazilian (P.2) variant of SARS-CoV-2 or the Omicron (B.1.1.529) variant.

27. The method of claim 15, wherein the antibody or antigen-binding fragment thereof is an Fc IgG1, IgG2, IgG3, IgG4, IgM, IgD, IgA1, IgA2 or IgE isotype.

28. The method of claim 15, wherein the antibody or antigen-binding fragment thereof is an IgG1 isotype.

29. The method of claim 15, wherein the antibody or antigen-binding fragment thereof, wherein the antibody is a full length antibody.

30. The antibody or antigen-binding fragment thereof of claim 2, wherein the antibody is an Fc IgG1, IgG2, IgG3, IgG4, IgM, IgD, IgA1, IgA2 or IgE isotype.

31. The antibody or antigen-binding fragment thereof of claim 2, wherein the antibody is an IgG1 isotype.

32. The antibody of claim 2, wherein the antibody is a full length antibody.

33. The antibody or antigen binding fragment thereof of claim 1 comprising a HCVR comprising the amino acid sequence set forth in SEQ ID NO: 5, and a LCVR comprising the amino acid sequence is set forth in SEQ ID NO: 6.

34. The antibody or antigen binding fragment thereof of claim 2 comprising a VH comprising a HCDR1 comprising the amino acid sequence of SEQ ID NO:67, a HCDR2 comprising the amino acid sequence of SEQ ID NO:68, and a HCDR3 comprising the amino acid sequence of SEQ ID NO:69; and a VL comprising a LCDR1 comprising the amino acid sequence of SEQ ID NO:70, a LCDR2 comprising the amino acid sequence of SEQ ID NO:71, and a LCDR3 comprising the amino acid sequence of SEQ ID NO:72.

35. A composition comprising the antibody or antigen binding fragment thereof of claim 2, wherein the antibody or antibody fragment thereof is isolated.

\* \* \* \* \*

```
SEQUENCE LISTING

<160> NUMBER OF SEQ ID NOS: 252

<210> SEQ ID NO 1
<211> LENGTH: 119
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Thr Ile Arg Glu Asp Gly Ser Glu Lys Tyr Tyr Val Asp Ser Val
    50                  55                  60

Lys Gly Arg Phe Ser Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Lys Trp Leu Arg Gly Ser Phe Asp Tyr Trp Gly Gln Gly
            100                 105                 110

Thr Leu Val Thr Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Synthetic Construct
```

```
<400> SEQUENCE: 2

Asn Phe Met Leu Thr Gln Pro His Ser Val Ser Glu Ser Pro Gly Lys
1               5                   10                  15

Thr Val Thr Ile Ser Cys Thr Arg Arg Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ser Asn Pro Pro Gly Ala Ser Trp Val Phe Gly Gly Gly Thr Lys Leu
            100                 105                 110

Thr Val Leu
        115

<210> SEQ ID NO 3
<211> LENGTH: 116
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Val Ser Ser Asn
            20                  25                  30

Tyr Met Ser Trp Val Arg Gln Ala Pro Arg Lys Gly Leu Glu Trp Val
        35                  40                  45

Ser Val Ile Tyr Ala Gly Gly Ser Thr Phe Tyr Ala Asp Ser Val Lys
    50                  55                  60

Gly Arg Phe Thr Ile Ser Arg Asp Asn Ser Lys Asn Thr Leu Leu Leu
65                  70                  75                  80

Gln Met Asn Ser Leu Arg Ala Glu Asp Thr Ala Val Tyr Tyr Cys Ala
                85                  90                  95

Arg Asp Arg Gly Gly Tyr Leu Asp Tyr Trp Gly Gln Gly Thr Leu Val
            100                 105                 110

Thr Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45
```

```
Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Gly
                85                  90                  95

Leu Thr Phe Gly Gly Gly Thr Lys Val Glu Ile Lys
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: Synthetic Construct

<400> SEQUENCE: 5

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Ser Lys His Tyr Ala Glu Ser Val
    50                  55                  60

Lys Gly Arg Phe Thr Ile Ser Arg Asp Asn Ser Asn Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Gly Gln Pro Pro Gly Trp Gly Asn Tyr Phe Asp Tyr Trp
            100                 105                 110

Gly Gln Gly Thr Leu Val Thr Val Ala Ser
            115                 120
```

<210> SEQ ID NO 6
<211> LENGTH: 108
<212> TYPE: PRT
<213> ORGANISM: Artificial Sequence
<220> FEATURE:
<223> OTHER INFORMATION: Synthetic Construct

<400> SEQUENCE: 6

```
Ser Tyr Val Leu Thr Gln Pro Pro Ser Val Ser Val Ala Pro Gly Lys
1               5                   10                  15

Thr Ala Arg Ile Thr Cys Gly Gly Asn Gly Ile Gly Ser Lys Ser Val
                20                  25                  30

Tyr Trp Tyr Gln Gln Lys Pro Gly Gln Ala Pro Glu Val Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Pro
                85                  90                  95

Trp Val Phe Gly Gly Gly Thr Lys Leu Thr Val Leu
            100                 105
```

<210> SEQ ID NO 7

```
<211> LENGTH: 125
<212> TYPE: PRT
<213> ORGANISM: Artificial Sequence
<220> FEATURE:
<223> OTHER INFORMATION: Synthetic Construct

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Ser Tyr Trp Gly Trp Phe Arg Gln Pro Pro Gly Lys Gly Leu Gly
        35                  40                  45

Trp Ile Arg Ser Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Lys Phe Ser Val Trp Asp Asn Tyr Arg Tyr Pro Phe
            100                 105                 110

Asp Tyr Trp Gly Gln Gly Ile Leu Val Thr Val Ser Ser
        115                 120                 125

<210> SEQ ID NO 8
<211> LENGTH: 110
<212> TYPE: PRT
<213> ORGANISM: Artificial Sequence
<220> FEATURE:
<223> OTHER INFORMATION: Synthetic Construct

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 9
<211> LENGTH: 123
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30
```

```
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Arg Glu Arg Leu Glu Asp Thr Ala Met Val Asn Phe Leu Asp Tyr
            100                 105                 110

Trp Gly Gln Gly Thr Leu Val Thr Val Ser Ser
        115                 120
```

<210> SEQ ID NO 10
<211> LENGTH: 106
<212> TYPE: PRT
<213> ORGANISM: Artificial Sequence
<220> FEATURE:
<223> OTHER INFORMATION: Synthetic Construct

<400> SEQUENCE: 10

```
Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly His Lys Tyr Ala
                20                  25                  30

Ser Trp Phe Gln Gln Arg Pro Gly Gln Ser Pro Val Leu Val Ile Tyr
            35                  40                  45

Gln Asp Ala Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic Construct

<400> SEQUENCE: 11

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Thr Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Tyr Gly Asp Ser Pro Leu Gly Tyr Trp Gly Gln Gly Thr
            100                 105                 110
```

Leu Val Thr Val Ser Ser
        115

<210> SEQ ID NO 12
<211> LENGTH: 113
<212> TYPE: PRT
<213> ORGANISM: Artificial Sequence
<220> FEATURE:
<223> OTHER INFORMATION: Synthetic Construct

<400> SEQUENCE: 12

Asp Ile Val Met Thr Gln Ser Pro Asp Ser Leu Ala Val Ser Leu Gly
1               5                   10                  15

Glu Pro Ala Ser Ile Asn Cys Thr Ser Ser Gln Ser Val Leu Tyr Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Leu Thr Phe Gly Gly Gly Thr Lys Val Glu Ile
            100                 105                 110

Lys

<210> SEQ ID NO 13
<211> LENGTH: 127
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn His Asn Pro Ser Leu Lys
    50                  55                  60

Ser Arg Val Ser Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Trp Lys Tyr Ser Ser Ser Trp Tyr Ser Gly Gly Ile Tyr Tyr
            100                 105                 110

Gly Met Asp Val Trp Gly Gln Gly Thr Thr Val Thr Val Ser Ser
        115                 120                 125

<210> SEQ ID NO 14
<211> LENGTH: 110
<212> TYPE: PRT
<213> ORGANISM: Artificial Sequence
<220> FEATURE:
<223> OTHER INFORMATION: Synthetic Construct -continued

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Ser Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Phe
                85                  90                  95

Ser Thr Trp Val Phe Gly Gly Thr Lys Leu Thr Val Leu
            100                 105                 110

<210> SEQ ID NO 15
<211> LENGTH: 124
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Thr Phe Thr Thr Tyr
            20                  25                  30

Thr Met Asn Trp Val Arg Gln Ala Pro Gly Lys Gly Leu Glu Trp Val
        35                  40                  45

Ser Ser Ile Ser Ser Thr Gly Leu Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Pro Thr Thr Ile Tyr Tyr Tyr Tyr Met Asp
            100                 105                 110

Val Trp Gly Lys Gly Thr Thr Val Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Thr Tyr
            20                  25                  30

Asn Leu Val Ser Trp Tyr Gln His Tyr Pro Gly Lys Ala Pro Lys Leu
        35                  40                  45

Ile Ile Tyr Glu Val Ser Lys Arg Pro Ser Gly Val Ser Asp Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Thr Thr Gly Tyr Val Val Phe Gly Gly Gly Thr Lys Leu Thr Val Leu
            100                 105                 110

<210> SEQ ID NO 17
<211> LENGTH: 128
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Gln Trp Val
            35                  40                  45

Thr Leu Ile Ser Tyr Asp Gly Asp Lys Tyr Tyr Ala Asp Ser Val
 50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Pro Gln Thr Gly Asp Trp Phe Pro Pro Ile Pro Thr
            100                 105                 110

Gly Val Leu Asp Val Trp Gly Gln Gly Thr Thr Val Thr Val Ser Ser
        115                 120                 125

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Ile
                85                  90                  95

Thr Phe Gly Gln Gly Thr Arg Leu Glu Ile Lys
            100                 105

<210> SEQ ID NO 19
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asn Gly Ile Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Val Glu Asp Thr Ala Val Tyr Tyr Cys
                85                  90                  95

Ala Arg Asp Trp Gly Thr Leu Thr Leu Phe Asp Phe Trp Gly Gln
            100                 105                 110

Gly Thr Leu Val Thr Val Ser Ser
        115                 120

<210> SEQ ID NO 20
<211> LENGTH: 108
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
1               5                   10                  15

Glu Arg Ala Thr Ile Thr Cys Arg Ala Ser Gln Ser Ile Ser Ser His
            20                  25                  30

Leu Asn Trp Tyr Gln Gln Lys Pro Gly Lys Ala Pro Lys Phe Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105

<210> SEQ ID NO 21
<211> LENGTH: 120
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45
```

Ala Val Ile Trp Tyr Asn Gly Ile Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Trp Gly Thr Leu Thr Thr Leu Phe Asp Phe Trp Gly Gln
               100                 105                 110

Gly Thr Leu Val Thr Val Ser Ser
               115                 120

<210> SEQ ID NO 22
<211> LENGTH: 108
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser His
                20                  25                  30

Leu Asn Trp Tyr Gln Gln Lys Pro Gly Lys Ala Pro Lys Leu Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
               100                 105

<210> SEQ ID NO 23
<211> LENGTH: 122
<212> TYPE: PRT
<213> ORGANISM: Artificial Sequence
<220> FEATURE:
<223> OTHER INFORMATION: Synthetic Construct

<400> SEQUENCE: 23

Arg Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Asn Thr Ser
                20                  25                  30

Gly Met Cys Val Ser Trp Ile Arg Gln Pro Pro Gly Lys Ala Leu Glu
         35                  40                  45

Trp Leu Ala Arg Ile Asp Trp Asp Asp Lys Tyr Tyr Ser Thr Ser
     50                  55                  60

Leu Glu Thr Arg Leu Thr Ile Ser Lys Asp Thr Ser Lys Asn Gln Val
 65                  70                  75                  80

Val Leu Thr Met Thr Asn Leu Asp Pro Val Asp Thr Gly Thr Tyr Tyr
                85                  90                  95

Cys Ala Arg Ile Ser Ile Gln Ser Arg Gly Gly Ala Asp Tyr Trp
         100                 105                 110

Gly Gln Gly Thr Leu Val Thr Val Ser Ser
               115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Ser Gly Lys Ala Pro Lys Leu Leu Ile
        35                  40                  45

Phe Val Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Ala Tyr Tyr Cys Gln Gln Ser Tyr Ser Pro Pro Trp
                85                  90                  95

Thr Phe Gly Gln Gly Thr Lys Val Glu Ile Lys
            100                 105
```

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Ile Tyr Tyr Cys
                85                  90                  95

Ala Asn Ser Gly Pro Thr Gly Asp Leu Asp Tyr Trp Gly Gln Gly Thr
            100                 105                 110

Leu Val Thr Val Ser Ser
        115
```

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

```
Ser Tyr Glu Leu Thr Gln Pro Pro Ser Val Ser Val Ser Pro Gly Gln
1               5                   10                  15
```

```
Thr Thr Leu Ser Leu Thr Cys Ser Gly Asp Lys Leu Gly Asn Lys Tyr
            20                  25                  30

Val Cys Trp Tyr Gln Gln Lys Pro Gly Gln Ser Pro Val Leu Val Ile
            35                  40                  45

Tyr Gln Asp Thr Lys Arg Pro Ser Gly Ile Pro Glu Arg Val Ser Gly
 50                  55                  60

Ser Asn Ser Gly Asp Thr Ala Thr Leu Thr Ile Ser Gly Thr Gln Ala
 65                  70                  75                  80

Met Asp Glu Ala Asp Tyr Tyr Cys Gln Ala Trp Asp Ser Ser Thr Ala
                 85                  90                  95

Val Phe Gly Gly Gly Thr Lys Leu Thr Val Leu
            100                 105
```

<210> SEQ ID NO 27
<211> LENGTH: 126
<212> TYPE: PRT
<213> ORGANISM: Artificial Sequence
<220> FEATURE:
<223> OTHER INFORMATION: Synthetic Construct

<400> SEQUENCE: 27

```
Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Asn Lys Ala
            20                  25                  30

Trp Met Ser Trp Val Arg Gln Pro Pro Gly Lys Gly Leu Glu Trp Val
            35                  40                  45

Gly Arg Ile Gln Ser Lys Thr Asp Asp Glu Thr Thr Asp Tyr Ala Ala
 50                  55                  60

Pro Val Lys Gly Arg Phe Ile Val Ser Arg Asp Asp Ser Lys Asn Thr
 65                  70                  75                  80

Leu Tyr Leu Gln Met Asn Ser Leu Lys Ile Glu Asp Thr Ala Ile Tyr
                 85                  90                  95

Tyr Cys Thr Ser Arg Ala His Tyr Gly Ser Gly Thr Ser Tyr Thr Pro
            100                 105                 110

Phe Asp Tyr Trp Gly Gln Gly Thr Leu Val Thr Val Ser Ser
            115                 120                 125
```

<210> SEQ ID NO 28
<211> LENGTH: 112
<212> TYPE: PRT
<213> ORGANISM: Artificial Sequence
<220> FEATURE:
<223> OTHER INFORMATION: Synthetic Construct

<400> SEQUENCE: 28

```
Asp Ile Val Met Thr Gln Ser Pro Leu Ser Leu Pro Val Thr Pro Gly
 1               5                  10                  15

Glu Gln Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
            35                  40                  45

Pro Arg Leu Leu Ile Tyr Met Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                 85                  90                  95
```

```
Leu Gln Thr Leu Phe Thr Phe Gly Pro Gly Thr Lys Val Asp Ile Lys
                100                 105                 110
```

<210> SEQ ID NO 29
<211> LENGTH: 128
<212> TYPE: PRT
<213> ORGANISM: Artificial Sequence
<220> FEATURE:
<223> OTHER INFORMATION: Synthetic Construct

<400> SEQUENCE: 29

```
Gln Val Gln Leu Gln Glu Ser Gly Pro Gly Leu Val Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Ala Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Thr Thr Ser Ile Thr Ile Phe Gly Ile Leu Val Ala Gly Gly His
                100                 105                 110

Asn Cys Phe Asp Ser Trp Gly Gln Gly Thr Leu Val Thr Val Ser Ser
            115                 120                 125
```

<210> SEQ ID NO 30
<211> LENGTH: 111
<212> TYPE: PRT
<213> ORGANISM: Artificial Sequence
<220> FEATURE:
<223> OTHER INFORMATION: Synthetic Construct

<400> SEQUENCE: 30

```
Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Val Gly Asn Tyr
            20                  25                  30

Asp Leu Val Ser Trp Tyr Gln Gln His Pro Gly Lys Ala Pro Lys Val
        35                  40                  45

Met Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Thr Ser Ser
                85                  90                  95

Gly Thr Phe Trp Val Phe Gly Gly Gly Thr Lys Leu Thr Val Leu
                100                 105                 110
```

<210> SEQ ID NO 31
<211> LENGTH: 132
<212> TYPE: PRT
<213> ORGANISM: Artificial Sequence
<220> FEATURE:
<223> OTHER INFORMATION: Synthetic Construct

<400> SEQUENCE: 31

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Asn Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Ser Phe
    50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Tyr Ser Ser Ser Trp Tyr Arg Ser Thr Ile Leu Ser
            100                 105                 110

Tyr Tyr Asn Tyr Tyr Gly Leu Asp Val Trp Gly Gln Gly Thr Leu Val
            115                 120                 125

Thr Val Ser Ser
    130

<210> SEQ ID NO 32
<211> LENGTH: 110
<212> TYPE: PRT
<213> ORGANISM: Artificial Sequence
<220> FEATURE:
<223> OTHER INFORMATION: Synthetic Construct

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Gln Thr Ser Phe Gly Gln Gly Thr Lys Leu Glu Ile Lys
            100                 105                 110

<210> SEQ ID NO 33
<211> LENGTH: 119
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Tyr Tyr Ala Asp Ser Val
    50                  55                  60

```
Lys Gly Arg Phe Thr Ile Ser Arg Asp Asn Ser Lys Asn Thr Val Tyr
 65                  70                  75                  80

Leu Gln Met His Ser Leu Arg Ala Glu Asp Thr Ala Val Tyr Tyr Cys
                 85                  90                  95

Ala Arg Asp Gly Gln Trp Leu Arg Ile Leu Asp Tyr Trp Gly Gln Gly
            100                 105                 110

Thr Leu Val Thr Val Ser Ser
            115
```

<210> SEQ ID NO 34
<211> LENGTH: 108
<212> TYPE: PRT
<213> ORGANISM: Artificial Sequence
<220> FEATURE:
<223> OTHER INFORMATION: Synthetic Construct

<400> SEQUENCE: 34

```
Glu Ile Val Leu Thr Gln Ser Pro Gly Thr Leu Ser Leu Ser Pro Gly
 1               5                  10                  15

Glu Arg Val Thr Leu Ser Cys Arg Ala Ser Gln Ser Val Arg Ser Ser
             20                  25                  30

Ser Leu Gly Trp Tyr Gln Gln Lys Pro Gly Gln Ala Pro Arg Arg Leu
         35                  40                  45

Ile Phe Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ser Gly Ser Ser Leu
                 85                  90                  95

Phe Thr Phe Gly Gln Gly Thr Lys Leu Glu Ile Lys
            100                 105
```

<210> SEQ ID NO 35
<211> LENGTH: 121
<212> TYPE: PRT
<213> ORGANISM: Artificial Sequence
<220> FEATURE:
<223> OTHER INFORMATION: Synthetic Construct

<400> SEQUENCE: 35

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Ala Ser Ile Ser Ser Thr
             20                  25                  30

Thr Tyr Tyr Trp Gly Trp Ile Arg Gln Pro Pro Gly Lys Gly Leu Glu
         35                  40                  45

Trp Ile Gly Ser Ile His Tyr Val Gly Ser Thr Tyr Tyr Asn Ser Ser
 50                  55                  60

Leu Lys Ser Arg Val Thr Ile Ser Val Asp Thr Ser Lys Asn Gln Phe
 65                  70                  75                  80

Ser Leu Lys Leu Gly Ser Val Thr Ala Ala Asp Thr Ala Val Tyr Tyr
                 85                  90                  95

Cys Thr Leu Ser Val Ala Gly Thr Phe Tyr Gly Leu Asp Val Trp Gly
            100                 105                 110

Gln Gly Thr Thr Val Thr Val Ser Ser
            115                 120
```

```
<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Arg Asn Val
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Ile Asp Tyr Ala Ala
    50                  55                  60

Pro Met Lys Gly Arg Leu Ile Ile Ser Arg Asp Asp Ser Lys Asn Met
65                  70                  75                  80

Leu Tyr Leu Gln Met Ser Ser Leu Lys Thr Asp Asp Thr Ala Val Tyr
                85                  90                  95

Tyr Cys Thr Thr His Ser Ile Arg Gly Phe Glu Ile Trp Gly Gln Gly
            100                 105                 110

Thr Met Val Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Synthetic Construct

<400> SEQUENCE: 38

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30
```

Tyr Trp Tyr Gln Gln Lys Ala Gly Gln Ala Pro Val Leu Val Ile Tyr
            35                  40                  45

Lys Asp Ser Glu Arg Pro Ser Gly Ile Pro Gly Arg Phe Ser Gly Ser
 50                  55                  60

Thr Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ala Pro
                85                  90                  95

Leu Val Phe Gly Gly Gly Thr Lys Leu Thr Val Leu
            100                 105

<210> SEQ ID NO 39
<211> LENGTH: 122
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Ser Gly Arg Val Gly Ser Arg Phe Asp Tyr Trp
            100                 105                 110

Gly Gln Gly Thr Leu Val Thr Val Ser Ser
            115                 120

<210> SEQ ID NO 40
<211> LENGTH: 108
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
1               5                   10                  15

Glu Arg Ala Thr Leu Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys

<210> SEQ ID NO 41
<211> LENGTH: 124
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Val Ser Ser Gly
            20                  25                  30

Asp Tyr Tyr Trp Gly Trp Ile Arg Gln His Pro Gly Lys Gly Leu Glu
        35                  40                  45

Trp Ile Gly Tyr Ile Tyr Tyr Thr Gly Arg Thr Phe Asp Asn Pro Ser
    50                  55                  60

Leu Lys Ser Arg Leu Thr Met Ser Val Asp Thr Ser Lys Asn Gln Phe
65                  70                  75                  80

Ser Val Arg Leu Tyr Ser Val Thr Ala Ala Asp Thr Ala Val Tyr Tyr
                85                  90                  95

Cys Ala Arg Ala Arg Asp Ser Glu Gly Phe Ser Gln Tyr Tyr Phe Asp
            100                 105                 110

Tyr Trp Gly Gln Gly Thr Leu Val Thr Val Ser Ser
        115                 120

<210> SEQ ID NO 42
<211> LENGTH: 106
<212> TYPE: PRT
<213> ORGANISM: Artificial Sequence
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
1               5                   10                  15

Asp Lys Val Asn Ile Thr Cys Gln Ala Ser Gln Asp Ile Asp Val Tyr
            20                  25                  30

Leu Ser Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Ala Phe Thr Ile Ser Ser Leu Gln Pro
65                  70                  75                  80

Glu Asp Val Ala Thr Tyr Tyr Cys Gln Gln Tyr Asp Asn Leu Pro Thr
                85                  90                  95

Phe Gly Gly Gly Thr Lys Val Glu Ile Lys
            100                 105

<210> SEQ ID NO 43
<211> LENGTH: 120
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ala
1               5                   10                  15

```
Ser Val Lys Ile Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Ile Ser Thr Ser Thr Ala Tyr
65                  70                  75                  80

Met Glu Leu Arg Ser Leu Lys Ser Asp Asp Thr Ala Val Tyr Tyr Cys
                85                  90                  95

Ala Arg Glu Val Trp Gly Ala Gly Tyr Tyr Phe Asp Tyr Trp Gly Gln
            100                 105                 110

Gly Thr Leu Val Thr Val Ser Ser
        115                 120
```

<210> SEQ ID NO 44
<211> LENGTH: 108
<212> TYPE: PRT
<213> ORGANISM: Artificial Sequence
<220> FEATURE:
<223> OTHER INFORMATION: Synthetic Construct

<400> SEQUENCE: 44

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
            100                 105
```

<210> SEQ ID NO 45
<211> LENGTH: 121
<212> TYPE: PRT
<213> ORGANISM: Artificial Sequence
<220> FEATURE:
<223> OTHER INFORMATION: Synthetic Construct

<400> SEQUENCE: 45

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Arg Thr Ala Asn Tyr Ala Gln Lys Phe
    50                  55                  60

Gln Gly Arg Val Thr Ile Thr Ala Asp Glu Ser Thr Ser Thr Ala Cys
65                  70                  75                  80

Met Glu Leu Ser Ser Leu Arg Phe Glu Asp Thr Ala Val Tyr Tyr Cys
```

```
                85                  90                  95

Ala Arg Glu Tyr Ser Ser Ser Gly Phe Tyr Phe Asp Tyr Trp Gly
            100                 105                 110

Gln Gly Thr Leu Val Thr Val Ser Ser
            115                 120

<210> SEQ ID NO 46
<211> LENGTH: 110
<212> TYPE: PRT
<213> ORGANISM: Artificial Sequence
<220> FEATURE:
<223> OTHER INFORMATION: Synthetic Construct

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Ala Trp Met Phe Gly Gly Gly Thr Lys Leu Thr Val Leu
            100                 105                 110

<210> SEQ ID NO 47
<211> LENGTH: 127
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn His Asn Pro Ser Leu Lys
    50                  55                  60

Ser Arg Val Ser Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Trp Lys Tyr Ser Ser Trp Tyr Ser Gly Gly Ile Tyr Tyr
            100                 105                 110

Gly Met Asp Val Trp Gly Gln Gly Thr Thr Val Thr Val Ser Ser
        115                 120                 125

<210> SEQ ID NO 48
<211> LENGTH: 110
<212> TYPE: PRT
<213> ORGANISM: Artificial Sequence
<220> FEATURE:
```

<223> OTHER INFORMATION: Synthetic Construct

<400> SEQUENCE: 48

```
Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Ser Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Phe
                85                  90                  95

Ser Thr Trp Val Phe Gly Gly Gly Thr Lys Leu Thr Val Leu
            100                 105                 110
```

<210> SEQ ID NO 49
<211> LENGTH: 129
<212> TYPE: PRT
<213> ORGANISM: Artificial Sequence
<220> FEATURE:
<223> OTHER INFORMATION: Synthetic Construct

<400> SEQUENCE: 49

```
Gln Val Gln Leu Val Glu Ser Gly Gly Val Val Gln Pro Gly Arg
1               5                   10                  15

Ser Leu Arg Leu Ser Cys Ala Val Ser Gly Phe Ile Phe Ser Ser His
            20                  25                  30

Gly Met His Trp Val Arg Gln Ala Pro Gly Lys Gly Leu Glu Trp Met
        35                  40                  45

Thr Val Ile Ser Tyr Asp Gly Ser Lys Lys His Tyr Ala Asp Ser Val
    50                  55                  60

Gln Gly Arg Phe Ile Ile Ser Arg Asp Asn Ser Lys Asn Met Val Tyr
65                  70                  75                  80

Leu Gln Met Asn Asp Leu Arg Ala Glu Asp Thr Ala Val Tyr Tyr Cys
                85                  90                  95

Ala Lys Asp Ala Thr Tyr Cys Ser Ile Thr Ser Trp Cys Ala Arg
            100                 105                 110

Tyr Ser His Met Asp Val Trp Gly Arg Gly Thr Ser Val Thr Val Ser
        115                 120                 125

Ser
```

<210> SEQ ID NO 50
<211> LENGTH: 103
<212> TYPE: PRT
<213> ORGANISM: Artificial Sequence
<220> FEATURE:
<223> OTHER INFORMATION: Synthetic Construct

<400> SEQUENCE: 50

```
Leu Arg Val Trp Val Ser Trp Thr Val Asp His His Leu Thr Cys Ser
1               5                   10                  15

Gly Ala Ser Ser Asp Leu Gly Ala Tyr Asn Tyr Val Ser Trp Tyr Gln
            20                  25                  30

Gln His Pro Gly Lys Ala Pro Asn Leu Met Ile Tyr Asp Val Asn His
        35                  40                  45
```

```
Arg Pro Ser Gly Val Ser Asn Arg Phe Ser Gly Ser Lys Ser Gly Asn
        50                  55                  60

Thr Ala Ser Leu Thr Ile Ser Gly Leu Gln Pro Glu Asp Glu Ala Asp
 65                  70                  75                  80

Tyr Tyr Cys Ser Ser Tyr Thr Ser Arg Ser Thr Leu Val Phe Gly Gly
                 85                  90                  95

Gly Thr Arg Leu Thr Val Leu
            100
```

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

```
Gln Val Gln Leu Gln Glu Ser Gly Pro Gly Leu Val Lys Pro Ser Asp
 1               5                  10                  15

Thr Leu Ser Leu Ile Cys Thr Val Ser Gly Gly Ser Ile Arg Ser Tyr
             20                  25                  30

Tyr Trp Ser Trp Ile Arg Gln Pro Pro Gly Lys Gly Leu Gln Trp Ile
         35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Tyr Ser Gly Tyr Asp Trp Gly Gly Phe Asp Tyr Trp Gly Gln Gly
            100                 105                 110

Thr Leu Val Thr Val Ser Ser
        115
```

<210> SEQ ID NO 52
<211> LENGTH: 110
<212> TYPE: PRT
<213> ORGANISM: Artificial Sequence
<220> FEATURE:
<223> OTHER INFORMATION: Synthetic Construct

<400> SEQUENCE: 52

```
Gln Ser Val Leu Thr Gln Pro Pro Ser Ala Ser Gly Thr Pro Gly Gln
 1               5                  10                  15

Arg Ala Thr Ile Ser Cys Ser Gly Ser Arg Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asp Asn Gln Arg Pro Ser Gly Val Pro Asp Arg Phe Ser
 50                  55                  60

Gly Ser Lys Ser Gly Thr Ser Ala Ser Leu Ala Val Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110
```

<210> SEQ ID NO 53
<211> LENGTH: 125
<212> TYPE: PRT
<213> ORGANISM: Artificial Sequence
<220> FEATURE:
<223> OTHER INFORMATION: Synthetic Construct

<400> SEQUENCE: 53

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Asn Tyr Tyr Trp Gly Trp Val Arg Gln Pro Pro Gly Lys Gly Leu Glu
        35                  40                  45

Trp Ile Gly Ser Leu Tyr Tyr Thr Gly Ser Thr Tyr Tyr Thr Pro Ser
    50                  55                  60

Leu Lys Ser Arg Val Ala Met Ala Val Asp Thr Ser Lys Asn Leu Phe
65                  70                  75                  80

Ser Leu Lys Leu Ser Ser Val Thr Ala Ala Asp Thr Ala Leu Tyr Tyr
                85                  90                  95

Cys Ala Arg Leu Phe Ser Ser Gly Tyr Tyr Ser Pro Leu Tyr Ser Phe
            100                 105                 110

Asp Tyr Trp Gly Gln Gly Thr Leu Val Thr Ala Ser Ser
        115                 120                 125
```

<210> SEQ ID NO 54
<211> LENGTH: 103
<212> TYPE: PRT
<213> ORGANISM: Artificial Sequence
<220> FEATURE:
<223> OTHER INFORMATION: Synthetic Construct

<400> SEQUENCE: 54

```
Ser Val Ser Gly Ser Pro Gly Gln Ser Ile Thr Ile Ser Cys Thr Gly
1               5                   10                  15

Thr Thr Ser Ser Asp Val Gly Gly Tyr Asn Phe Val Ser Trp Tyr Gln
            20                  25                  30

Gln His Pro Gly Lys Ala Pro Lys Leu Met Ile Tyr Asp Val Ser Asn
        35                  40                  45

Arg Pro Ser Gly Val Ser Asn Arg Phe Ser Gly Ser Lys Ser Gly Asn
    50                  55                  60

Thr Ala Ser Leu Thr Ile Ser Gly Leu Arg Ala Glu Asp Glu Ala Asp
65                  70                  75                  80

Tyr Tyr Cys Ser Ser Tyr Thr Ser Ser Ser Thr Leu Ile Phe Gly Gly
                85                  90                  95

Gly Thr Lys Leu Thr Val Leu
            100
```

<210> SEQ ID NO 55
<211> LENGTH: 13
<212> TYPE: PRT
<213> ORGANISM: Artificial Sequence
<220> FEATURE:
<223> OTHER INFORMATION: Synthetic Construct

<400> SEQUENCE: 55

```
Ser Ala Ser Gly Phe Thr Phe Ser Ser Phe Trp Met Ser
1               5                   10
```

<210> SEQ ID NO 56

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 56

Thr Ile Arg Glu Asp Gly Ser Glu Lys Tyr Tyr Val Asp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Ala Arg Ser Lys Trp Leu Arg Gly Ser Phe Asp Tyr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Thr Arg Arg Ser Gly Ser Ile Ala Ser Asn Tyr Val Gln
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Tyr Glu Asp Asn Gln Arg Pro Ser
1               5

<210> SEQ ID NO 60
<211> LENGTH: 14
<212> TYPE: PRT
<213> ORGANISM: Artificial Sequence
<220> FEATURE:
<223> OTHER INFORMATION: Synthetic Construct

<400> SEQUENCE: 60

Gln Ser Tyr Asp Ser Ser Asn Pro Pro Gly Ala Ser Trp Val
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic Construct

<400> SEQUENCE: 61

Ser Ala Ser Gly Phe Thr Val Ser Ser Asn Tyr Met Ser
1               5                   10

<210> SEQ ID NO 62
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 62

Val Ile Tyr Ala Gly Gly Ser Thr Phe
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Ala Arg Asp Arg Gly Gly Tyr Leu Asp Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Construct

<400> SEQUENCE: 64

Arg Ala Ser Gln Gly Ile Ser Asn Tyr Leu Ala
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Synthetic Construct

<400> SEQUENCE: 65

Tyr Ala Ala Ser Thr Leu Gln Ser
1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gln Lys Tyr Asn Ser Ala Pro Gly Leu Thr
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic Construct

<400> SEQUENCE: 67

Thr Ala Ser Gly Phe Thr Phe Ser Thr Tyr Gly Met His
1               5                   10

<210> SEQ ID NO 68
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 68

Val Ile Ser Tyr Asp Gly Ser Ser Lys His
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

Ala Arg Asp Gly Gln Pro Pro Gly Trp Gly Asn Tyr Phe Asp Tyr
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Synthetic Construct

<400> SEQUENCE: 70

Gly Gly Asn Gly Ile Gly Ser Lys Ser Val Tyr
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Tyr Asp Asp Ser Asp Arg Pro Ser
1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Gln Val Trp Asp Ser Ser Ser Asp Pro Trp Val
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

<400> SEQUENCE: 73

Thr Val Ser Gly Gly Ser Ile Ser Ser Ser Ser Tyr Trp Gly
1               5                   10                  15

<210> SEQ ID NO 74
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 74

Ser Ile Tyr Tyr Ser Gly Ser Thr Tyr
1               5

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

Ala Arg Ala Lys Phe Ser Val Trp Asp Asn Tyr Arg Tyr Pro Phe Asp
1               5                   10                  15

Tyr

<210> SEQ ID NO 76
<211> LENGTH: 13
<212> TYPE: PRT
<213> ORGANISM: Artificial Sequence
<220> FEATURE:
<223> OTHER INFORMATION: Synthetic Construct

<400> SEQUENCE: 76

Ser Gly Ser Ser Ser Asn Ile Gly Ser Asn Thr Val Asn
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Tyr Ser Asn Asn Gln Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Ala Ala Trp Asp Asp Ser Leu Asn Gly Trp Val
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic Construct

<400> SEQUENCE: 79

Ala Ala Ser Gly Phe Thr Phe Ser Asn Tyr Gly Met His
1               5                   10

<210> SEQ ID NO 80
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 80

Val Ile Trp Tyr Asp Gly Ser Asn Lys Tyr
1               5                   10

<210> SEQ ID NO 81
<211> LENGTH: 16
<212> TYPE: PRT
<213> ORGANISM: Artificial Sequence
<220> FEATURE:
<223> OTHER INFORMATION: Synthetic Construct

<400> SEQUENCE: 81

Ala Arg Glu Arg Leu Glu Asp Thr Ala Met Val Asn Phe Leu Asp Tyr
1               5                   10                  15

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

<400> SEQUENCE: 82

Ser Gly Asp Lys Leu Gly His Lys Tyr Ala Ser
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct

<400> SEQUENCE: 83

Tyr Gln Asp Ala Lys Arg Pro Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Construct

<400> SEQUENCE: 84

Gln Ala Trp Asp Ser Ser Thr Val Val
1               5

<210> SEQ ID NO 85
<211> LENGTH: 13
<212> TYPE: PRT
<213> ORGANISM: Artificial Sequence
<220> FEATURE:
<223> OTHER INFORMATION: Synthetic Construct

<400> SEQUENCE: 85

Lys Ala Ser Gly Gly Thr Phe Ser Ser Tyr Ala Ile Thr
1               5                   10

<210> SEQ ID NO 86
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 86

Gly Ile Ile Pro Ile Phe Gly Thr Ala Asn
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Construct

<400> SEQUENCE: 87

Ala Ser Asp Tyr Gly Asp Ser Pro Leu Gly Tyr
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Synthetic Construct

<400> SEQUENCE: 88

Thr Ser Ser Gln Ser Val Leu Tyr Ser Ser Asn Asn Lys Asn Phe Leu
1               5                   10                  15

Ala

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Tyr Trp Ala Ser Thr Arg Glu Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Gln Gln Tyr Tyr Ser Ala Pro Leu Thr
1               5

<210> SEQ ID NO 91
<211> LENGTH: 13
<212> TYPE: PRT
<213> ORGANISM: Artificial Sequence
<220> FEATURE:
<223> OTHER INFORMATION: Synthetic Construct

<400> SEQUENCE: 91

Ala Val Tyr Gly Gly Ser Leu Ser Gly Tyr Tyr Trp Ser
1               5                   10

<210> SEQ ID NO 92
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 92

Glu Ile Asn His Ser Gly Ser Thr Asn
1               5

<210> SEQ ID NO 93
<211> LENGTH: 21
<212> TYPE: PRT
<213> ORGANISM: Artificial Sequence
<220> FEATURE:
<223> OTHER INFORMATION: Synthetic Construct

<400> SEQUENCE: 93

Ala Arg Ala Trp Lys Tyr Ser Ser Ser Trp Tyr Ser Gly Gly Ile Tyr
1               5                   10                  15

Tyr Gly Met Asp Val
            20

<210> SEQ ID NO 94
<211> LENGTH: 14
<212> TYPE: PRT
<213> ORGANISM: Artificial Sequence
<220> FEATURE:
<223> OTHER INFORMATION: Synthetic Construct

<400> SEQUENCE: 94

Ser Gly Thr Ser Ser Asp Val Gly Ser Tyr Asn Leu Val Ser
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95

Tyr Glu Gly Thr Lys Arg Pro Ser
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic Construct

<400> SEQUENCE: 96

Cys Ser Tyr Ala Gly Phe Ser Thr Trp Val
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Ser Ala Ser Gly Phe Thr Phe Thr Thr Tyr Thr Met Asn
1               5                   10

<210> SEQ ID NO 98
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 98

Ser Ile Ser Ser Thr Gly Leu Ser Ile Tyr
1               5                   10

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Ala Arg Asp Pro Ser Pro Thr Thr Ile Tyr Tyr Tyr Tyr Met Asp
1               5                   10                  15

Val

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

Thr Gly Thr Ser Ser Asp Val Gly Thr Tyr Asn Leu Val Ser
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Tyr Glu Val Ser Lys Arg Pro Ser
1               5

<210> SEQ ID NO 102
<211> LENGTH: 12
<212> TYPE: PRT
<213> ORGANISM: Artificial Sequence
<220> FEATURE:
<223> OTHER INFORMATION: Synthetic Construct

<400> SEQUENCE: 102

Cys Ser Tyr Ala Gly Ser Thr Thr Gly Tyr Val Val
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic Construct

<400> SEQUENCE: 103

Ala Ala Ser Gly Phe Thr Phe Ser Ser Tyr Ala Met His
1               5                   10
```

```
<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Leu Ile Ser Tyr Asp Gly Gly Asp Lys Tyr
1               5                   10

<210> SEQ ID NO 105
<211> LENGTH: 21
<212> TYPE: PRT
<213> ORGANISM: Artificial Sequence
<220> FEATURE:
<223> OTHER INFORMATION: Synthetic Construct

<400> SEQUENCE: 105

Ala Arg Asp Arg Pro Gln Thr Gly Asp Trp Phe Pro Pro Ile Pro Thr
1               5                   10                  15

Gly Val Leu Asp Val
            20

<210> SEQ ID NO 106
<211> LENGTH: 11
<212> TYPE: PRT
<213> ORGANISM: Artificial Sequence
<220> FEATURE:
<223> OTHER INFORMATION: Synthetic Construct

<400> SEQUENCE: 106

Arg Ala Ser Gln Gly Ile Ser Asn Tyr Leu Ala
1               5                   10

<210> SEQ ID NO 107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 107

Tyr Ala Ala Ser Ser Leu Gln Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Construct

<400> SEQUENCE: 108

Gln Gln Tyr His Ser Tyr Pro Ile Thr
1               5

<210> SEQ ID NO 109
<211> LENGTH: 13
<212> TYPE: PRT
<213> ORGANISM: Artificial Sequence
<220> FEATURE:
<223> OTHER INFORMATION: Synthetic Construct

<400> SEQUENCE: 109

Ala Ala Ser Gly Phe Thr Phe Ser Thr Tyr Gly Met His
1               5                   10
```

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Val Ile Trp Tyr Asn Gly Ile Asn Lys His
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic Construct

<400> SEQUENCE: 111

Ala Arg Asp Trp Gly Thr Leu Thr Thr Leu Phe Asp Phe
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic Construct

<400> SEQUENCE: 112

Arg Ala Ser Gln Ser Ile Ser Ser His Leu Asn
1               5                   10

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

Tyr Gly Ala Ser Ser Leu Gln Ser
1               5

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Gln Gln Ser Tyr Ser Thr Pro Pro Trp Thr
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic Construct

<400> SEQUENCE: 115

Ala Ala Ser Gly Phe Thr Phe Ser Thr Tyr Gly Met His
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Val Ile Trp Tyr Asn Gly Ile Asn Lys Tyr
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic Construct

<400> SEQUENCE: 117

Ala Arg Asp Trp Gly Thr Leu Thr Thr Leu Phe Asp Phe
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Construct

<400> SEQUENCE: 118

Arg Ala Ser Gln Ser Ile Ser Ser His Leu Asn
1               5                   10

<210> SEQ ID NO 119
<211> LENGTH: 8
<212> TYPE: PRT
<213> ORGANISM: Artificial Sequence
<220> FEATURE:
<223> OTHER INFORMATION: Synthetic Construct

<400> SEQUENCE: 119

Tyr Gly Ala Ser Ser Leu Gln Ser
1               5

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct

<400> SEQUENCE: 120

Gln Gln Ser Tyr Ser Thr Pro Pro Trp Thr
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Synthetic Construct

<400> SEQUENCE: 121

Thr Phe Ser Gly Phe Ser Leu Asn Thr Ser Gly Met Cys Val Ser
1               5                   10                  15

```
<210> SEQ ID NO 122
<211> LENGTH: 9
<212> TYPE: PRT
<213> ORGANISM: Artificial Sequence
<220> FEATURE:
<223> OTHER INFORMATION: Synthetic Construct

<400> SEQUENCE: 122

Arg Ile Asp Trp Asp Asp Asp Lys Tyr
1               5

<210> SEQ ID NO 123
<211> LENGTH: 14
<212> TYPE: PRT
<213> ORGANISM: Artificial Sequence
<220> FEATURE:
<223> OTHER INFORMATION: Synthetic Construct

<400> SEQUENCE: 123

Ala Arg Ile Ser Ile Gln Ser Arg Gly Gly Gly Ala Asp Tyr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic Construct

<400> SEQUENCE: 124

Arg Ala Ser Gln Ser Ile Ser Ser Tyr Leu His
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Phe Val Ala Ser Thr Leu Gln Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Construct

<400> SEQUENCE: 126

Gln Gln Ser Tyr Ser Pro Pro Trp Thr
1               5

<210> SEQ ID NO 127
<211> LENGTH: 13
<212> TYPE: PRT
<213> ORGANISM: Artificial Sequence
<220> FEATURE:
<223> OTHER INFORMATION: Synthetic Construct

<400> SEQUENCE: 127

Ser Ala Ser Gly Phe Thr Phe Thr Asn Tyr Ala Met Ser
1               5                   10

<210> SEQ ID NO 128
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Thr Ile Ser Gly Ser Gly Gly Ser Thr Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Construct

<400> SEQUENCE: 129

Ala Asn Ser Gly Pro Thr Gly Asp Leu Asp Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic Construct

<400> SEQUENCE: 130

Ser Gly Asp Lys Leu Gly Asn Lys Tyr Val Cys
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Synthetic Construct

<400> SEQUENCE: 131

Tyr Gln Asp Thr Lys Arg Pro Ser
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic Construct

<400> SEQUENCE: 132

Gln Ala Trp Asp Ser Ser Thr Ala Val
1               5

<210> SEQ ID NO 133
<211> LENGTH: 13
<212> TYPE: PRT
<213> ORGANISM: Artificial Sequence
<220> FEATURE:
<223> OTHER INFORMATION: Synthetic Construct

<400> SEQUENCE: 133

Thr Ala Ser Gly Phe Thr Phe Asn Lys Ala Trp Met Ser
1               5                   10

<210> SEQ ID NO 134
<211> LENGTH: 12
```

<210> SEQ ID NO 134
<211> LENGTH: (not shown)
<212> TYPE: PRT
<213> ORGANISM: Artificial Sequence
<220> FEATURE:
<223> OTHER INFORMATION: Synthetic Construct

<400> SEQUENCE: 134

Arg Ile Gln Ser Lys Thr Asp Asp Glu Thr Thr Asp
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Synthetic Construct

<400> SEQUENCE: 135

Thr Ser Arg Ala His Tyr Gly Ser Gly Thr Ser Tyr Thr Pro Phe Asp
1               5                   10                  15
Tyr

<210> SEQ ID NO 136
<211> LENGTH: 16
<212> TYPE: PRT
<213> ORGANISM: Artificial Sequence
<220> FEATURE:
<223> OTHER INFORMATION: Synthetic Construct

<400> SEQUENCE: 136

Arg Ser Ser Gln Ser Leu Leu Tyr Ser Asn Gly Tyr Asn Tyr Leu Asp
1               5                   10                  15

<210> SEQ ID NO 137
<211> LENGTH: 8
<212> TYPE: PRT
<213> ORGANISM: Artificial Sequence
<220> FEATURE:
<223> OTHER INFORMATION: Synthetic Construct

<400> SEQUENCE: 137

Tyr Met Gly Ser Asn Arg Ala Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic Construct

<400> SEQUENCE: 138

Met Gln Thr Leu Gln Thr Leu Phe Thr
1               5

<210> SEQ ID NO 139
<211> LENGTH: 13
<212> TYPE: PRT
<213> ORGANISM: Artificial Sequence
<220> FEATURE:
<223> OTHER INFORMATION: Synthetic Construct

<400> SEQUENCE: 139

Ala Val Tyr Gly Gly Ser Phe Ser Gly Tyr Tyr Trp Ser
1               5                   10

<210> SEQ ID NO 140

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 140

Glu Ile Asp His Ser Gly Ser Thr Asn
1               5

<210> SEQ ID NO 141
<211> LENGTH: 22
<212> TYPE: PRT
<213> ORGANISM: Artificial Sequence
<220> FEATURE:
<223> OTHER INFORMATION: Synthetic Construct

<400> SEQUENCE: 141

Ala Arg Thr Thr Ser Ile Thr Ile Phe Gly Ile Leu Val Ala Gly Gly
1               5                   10                  15

His Asn Cys Phe Asp Ser
            20

<210> SEQ ID NO 142
<211> LENGTH: 14
<212> TYPE: PRT
<213> ORGANISM: Artificial Sequence
<220> FEATURE:
<223> OTHER INFORMATION: Synthetic Construct

<400> SEQUENCE: 142

Ser Gly Thr Ser Ser Asp Val Gly Asn Tyr Asp Leu Val Ser
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic Construct

<400> SEQUENCE: 143

Met Ile Tyr Glu Val Thr Lys Arg Pro Ser
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic Construct

<400> SEQUENCE: 144

Cys Ser Tyr Thr Ser Ser Gly Thr Phe Trp Val
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic Construct

<400> SEQUENCE: 145

Lys Ala Ser Gly Gly Thr Phe Ser Asn Tyr Ala Ile Asn
1               5                   10
```

<210> SEQ ID NO 146
<211> LENGTH: 10
<212> TYPE: PRT
<213> ORGANISM: Artificial Sequence
<220> FEATURE:
<223> OTHER INFORMATION: Synthetic Construct

<400> SEQUENCE: 146

Gly Ile Ile Pro Ile Phe Gly Thr Thr Asn
1               5                   10

<210> SEQ ID NO 147
<211> LENGTH: 25
<212> TYPE: PRT
<213> ORGANISM: Artificial Sequence
<220> FEATURE:
<223> OTHER INFORMATION: Synthetic Construct

<400> SEQUENCE: 147

Ala Arg Ala Gly Tyr Ser Ser Ser Trp Tyr Arg Ser Thr Ile Leu Ser
1               5                   10                  15

Tyr Tyr Asn Tyr Tyr Gly Leu Asp Val
            20                  25

<210> SEQ ID NO 148
<211> LENGTH: 16
<212> TYPE: PRT
<213> ORGANISM: Artificial Sequence
<220> FEATURE:
<223> OTHER INFORMATION: Synthetic Construct

<400> SEQUENCE: 148

Arg Ser Ser Gln Ser Leu Leu His Ser Asn Gly Tyr Asn Tyr Leu Asp
1               5                   10                  15

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149

Tyr Leu Gly Ser Asn Arg Ala Ser
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic Construct

<400> SEQUENCE: 150

Met Gln Ala Gln Gln Thr Ser
1               5

<210> SEQ ID NO 151
<211> LENGTH: 13
<212> TYPE: PRT
<213> ORGANISM: Artificial Sequence
<220> FEATURE:
<223> OTHER INFORMATION: Synthetic Construct

<400> SEQUENCE: 151

Ala Ala Ser Gly Phe Thr Phe Ser Asp Tyr Gly Met His

```
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct

<400> SEQUENCE: 152

```
Val Ile Trp Tyr Asp Gly Ser Tyr Lys Tyr
1               5                   10
```

<210> SEQ ID NO 153
<211> LENGTH: 12
<212> TYPE: PRT
<213> ORGANISM: Artificial Sequence
<220> FEATURE:
<223> OTHER INFORMATION: Synthetic Construct

<400> SEQUENCE: 153

```
Ala Arg Asp Gly Gln Trp Leu Arg Ile Leu Asp Tyr
1               5                   10
```

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

```
Arg Ala Ser Gln Ser Val Arg Ser Ser Ser Leu Gly
1               5                   10
```

<210> SEQ ID NO 155
<211> LENGTH: 8
<212> TYPE: PRT
<213> ORGANISM: Artificial Sequence
<220> FEATURE:
<223> OTHER INFORMATION: Synthetic Construct

<400> SEQUENCE: 155

```
Phe Gly Ala Ser Asn Arg Ala Thr
1               5
```

<210> SEQ ID NO 156
<211> LENGTH: 9
<212> TYPE: PRT
<213> ORGANISM: Artificial Sequence
<220> FEATURE:
<223> OTHER INFORMATION: Synthetic Construct

<400> SEQUENCE: 156

```
Gln Gln Ser Gly Ser Ser Leu Phe Thr
1               5
```

<210> SEQ ID NO 157
<211> LENGTH: 15
<212> TYPE: PRT
<213> ORGANISM: Artificial Sequence
<220> FEATURE:
<223> OTHER INFORMATION: Synthetic Construct

<400> SEQUENCE: 157

```
Thr Val Ser Gly Ala Ser Ile Ser Ser Thr Thr Tyr Tyr Trp Gly
1               5                   10                  15
```

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Ser Ile His Tyr Val Gly Ser Thr Tyr
1               5

<210> SEQ ID NO 159
<211> LENGTH: 13
<212> TYPE: PRT
<213> ORGANISM: Artificial Sequence
<220> FEATURE:
<223> OTHER INFORMATION: Synthetic Construct

<400> SEQUENCE: 159

Thr Leu Ser Val Ala Gly Thr Phe Tyr Gly Leu Asp Val
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct

<400> SEQUENCE: 160

Arg Ala Ser Gln Gly Ile Ser Ser Trp Leu Ala
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Tyr Ala Ala Ser Ser Leu Gln Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162

Gln Gln Ala Asn Ser Phe Pro Leu Thr
1               5

<210> SEQ ID NO 163
<211> LENGTH: 13
<212> TYPE: PRT
<213> ORGANISM: Artificial Sequence
<220> FEATURE:
<223> OTHER INFORMATION: Synthetic Construct

<400> SEQUENCE: 163

Ala Ala Ser Gly Phe Thr Phe Arg Asn Val Trp Met Asn
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic Construct

<400> SEQUENCE: 164

Arg Ile Lys Ser Lys Thr Asp Gly Gly Thr Ile Asp
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Synthetic Construct

<400> SEQUENCE: 165

Thr Thr His Ser Ile Arg Gly Phe Glu Ile
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Ser Gly Asp Ala Leu Pro Lys Gln Tyr Ala Tyr
1               5                   10

<210> SEQ ID NO 167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 167

Tyr Lys Asp Ser Glu Arg Pro Ser
1               5

<210> SEQ ID NO 168
<211> LENGTH: 11
<212> TYPE: PRT
<213> ORGANISM: Artificial Sequence
<220> FEATURE:
<223> OTHER INFORMATION: Synthetic Construct

<400> SEQUENCE: 168

Gln Ser Ala Asp Ser Ser Gly Ala Pro Leu Val
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Synthetic Construct

<400> SEQUENCE: 169

Ala Ala Ser Gly Phe Thr Phe Ser Ser Tyr Ser Met Asn
1               5                   10

```
<210> SEQ ID NO 170
<211> LENGTH: 10
<212> TYPE: PRT
<213> ORGANISM: Artificial Sequence
<220> FEATURE:
<223> OTHER INFORMATION: Synthetic Construct

<400> SEQUENCE: 170

Ser Ile Ser Ser Ser Ser Ser Tyr Ile Tyr
1               5                   10

<210> SEQ ID NO 171
<211> LENGTH: 15
<212> TYPE: PRT
<213> ORGANISM: Artificial Sequence
<220> FEATURE:
<223> OTHER INFORMATION: Synthetic Construct

<400> SEQUENCE: 171

Ala Arg Asp Arg Ala Ser Gly Arg Val Gly Ser Arg Phe Asp Tyr
1               5                   10                  15

<210> SEQ ID NO 172
<211> LENGTH: 11
<212> TYPE: PRT
<213> ORGANISM: Artificial Sequence
<220> FEATURE:
<223> OTHER INFORMATION: Synthetic Construct

<400> SEQUENCE: 172

Arg Ala Ser Gln Ser Ile Ser Ser Tyr Leu Asn
1               5                   10

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 173

Tyr Ala Ala Ser Ser Leu Gln Ser
1               5

<210> SEQ ID NO 174
<211> LENGTH: 10
<212> TYPE: PRT
<213> ORGANISM: Artificial Sequence
<220> FEATURE:
<223> OTHER INFORMATION: Synthetic Construct

<400> SEQUENCE: 174

Gln Gln Ser Tyr Ser Thr Pro Arg Val Thr
1               5                   10

<210> SEQ ID NO 175
<211> LENGTH: 15
<212> TYPE: PRT
<213> ORGANISM: Artificial Sequence
<220> FEATURE:
<223> OTHER INFORMATION: Synthetic Construct

<400> SEQUENCE: 175

Thr Val Ser Gly Asp Ser Val Ser Ser Gly Asp Tyr Tyr Trp Gly
1               5                   10                  15

<210> SEQ ID NO 176
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 176

Tyr Ile Tyr Tyr Thr Gly Arg Thr Phe
1               5

<210> SEQ ID NO 177
<211> LENGTH: 16
<212> TYPE: PRT
<213> ORGANISM: Artificial Sequence
<220> FEATURE:
<223> OTHER INFORMATION: Synthetic Construct

<400> SEQUENCE: 177

Ala Arg Ala Arg Asp Ser Glu Gly Phe Ser Gln Tyr Tyr Phe Asp Tyr
1               5                   10                  15

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct

<400> SEQUENCE: 178

Gln Ala Ser Glu Asp Ile Asp Val Tyr Leu Ser
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Synthetic Construct

<400> SEQUENCE: 179

Tyr Asp Ala Ser Asn Leu Glu Thr
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic Construct

<400> SEQUENCE: 180

Gln Gln Tyr Asp Asn Leu Pro Thr
1               5

<210> SEQ ID NO 181
<211> LENGTH: 13
<212> TYPE: PRT
<213> ORGANISM: Artificial Sequence
<220> FEATURE:
<223> OTHER INFORMATION: Synthetic Construct

<400> SEQUENCE: 181

Lys Ala Ser Gly Tyr Thr Phe Thr Ser Tyr Gly Ile Ser
1               5                   10

<210> SEQ ID NO 182
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 182

Trp Ile Ser Ala Tyr Asn Gly Asn Thr Asn
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Synthetic Construct

<400> SEQUENCE: 183

Ala Arg Glu Val Trp Gly Ala Gly Tyr Tyr Phe Asp Tyr
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic Construct

<400> SEQUENCE: 184

Ser Gly Asp Ala Leu Pro Lys Gln Tyr Ala Tyr
1               5                   10

<210> SEQ ID NO 185
<211> LENGTH: 8
<212> TYPE: PRT
<213> ORGANISM: Artificial Sequence
<220> FEATURE:
<223> OTHER INFORMATION: Synthetic Construct

<400> SEQUENCE: 185

Tyr Lys Asp Ser Glu Arg Pro Ser
1               5

<210> SEQ ID NO 186
<211> LENGTH: 11
<212> TYPE: PRT
<213> ORGANISM: Artificial Sequence
<220> FEATURE:
<223> OTHER INFORMATION: Synthetic Construct

<400> SEQUENCE: 186

Gln Ser Ala Asp Ser Ser Gly Thr Tyr Val Val
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Synthetic Construct

<400> SEQUENCE: 187

Lys Ala Ser Gly Gly Thr Phe Ser Asn Tyr Ala Ile Asn
1               5                   10

<210> SEQ ID NO 188
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 188

Gly Ile Ile Pro Ile Phe Arg Thr Ala Asn
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Synthetic Construct

<400> SEQUENCE: 189

Ala Arg Glu Tyr Ser Ser Ser Ser Gly Phe Tyr Phe Asp Tyr
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Synthetic Construct

<400> SEQUENCE: 190

Ser Gly Thr Ser Ser Asp Val Gly Ser Tyr Asn Leu Val Ser
1               5                   10

<210> SEQ ID NO 191
<211> LENGTH: 8
<212> TYPE: PRT
<213> ORGANISM: Artificial Sequence
<220> FEATURE:
<223> OTHER INFORMATION: Synthetic Construct

<400> SEQUENCE: 191

Tyr Glu Gly Asn Lys Arg Pro Ser
1               5

<210> SEQ ID NO 192
<211> LENGTH: 10
<212> TYPE: PRT
<213> ORGANISM: Artificial Sequence
<220> FEATURE:
<223> OTHER INFORMATION: Synthetic Construct

<400> SEQUENCE: 192

Cys Ser Tyr Ala Gly Ser Ser Ala Trp Met
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthetic Construct

<400> SEQUENCE: 193

Ala Val Tyr Gly Gly Ser Leu Ser Gly Tyr Tyr Trp Ser
1               5                   10

<210> SEQ ID NO 194
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 194

Glu Ile Asn His Ser Gly Ser Thr Asn
1               5

<210> SEQ ID NO 195
<211> LENGTH: 21
<212> TYPE: PRT
<213> ORGANISM: Artificial Sequence
<220> FEATURE:
<223> OTHER INFORMATION: Synthetic Construct

<400> SEQUENCE: 195

Ala Arg Ala Trp Lys Tyr Ser Ser Ser Trp Tyr Ser Gly Gly Ile Tyr
1               5                   10                  15

Tyr Gly Met Asp Val
            20

<210> SEQ ID NO 196
<211> LENGTH: 14
<212> TYPE: PRT
<213> ORGANISM: Artificial Sequence
<220> FEATURE:
<223> OTHER INFORMATION: Synthetic Construct

<400> SEQUENCE: 196

Ser Gly Thr Ser Ser Asp Val Gly Ser Tyr Asn Leu Val Ser
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Synthetic Construct

<400> SEQUENCE: 197

Tyr Glu Gly Thr Lys Arg Pro Ser
1               5

<210> SEQ ID NO 198
<211> LENGTH: 10
<212> TYPE: PRT
<213> ORGANISM: Artificial Sequence
<220> FEATURE:
<223> OTHER INFORMATION: Synthetic Construct

<400> SEQUENCE: 198

Cys Ser Tyr Ala Gly Phe Ser Thr Trp Val
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Synthetic Construct

<400> SEQUENCE: 199

Ala Val Ser Gly Phe Ile Phe Ser Ser His Gly Met His
1               5                   10

<210> SEQ ID NO 200
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 200

Val Ile Ser Tyr Asp Gly Ser Lys Lys His
1               5                   10

<210> SEQ ID NO 201
<211> LENGTH: 22
<212> TYPE: PRT
<213> ORGANISM: Artificial Sequence
<220> FEATURE:
<223> OTHER INFORMATION: Synthetic Construct

<400> SEQUENCE: 201

Ala Lys Asp Ala Thr Tyr Cys Asp Ser Ile Thr Ser Trp Cys Ala Arg
1               5                   10                  15

Tyr Ser His Met Asp Val
            20

<210> SEQ ID NO 202
<211> LENGTH: 14
<212> TYPE: PRT
<213> ORGANISM: Artificial Sequence
<220> FEATURE:
<223> OTHER INFORMATION: Synthetic Construct

<400> SEQUENCE: 202

Ser Gly Ala Ser Ser Asp Leu Gly Ala Tyr Asn Tyr Val Ser
1               5                   10

<210> SEQ ID NO 203
<211> LENGTH: 8
<212> TYPE: PRT
<213> ORGANISM: Artificial Sequence
<220> FEATURE:
<223> OTHER INFORMATION: Synthetic Construct

<400> SEQUENCE: 203

Tyr Asp Val Asn His Arg Pro Ser
1               5

<210> SEQ ID NO 204
<211> LENGTH: 10
<212> TYPE: PRT
<213> ORGANISM: Artificial Sequence
<220> FEATURE:
<223> OTHER INFORMATION: Synthetic Construct

<400> SEQUENCE: 204

Ser Ser Tyr Thr Ser Arg Ser Thr Leu Val
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Synthetic Construct

<400> SEQUENCE: 205

Thr Val Ser Gly Gly Ser Ile Arg Ser Tyr Tyr Trp Ser
1               5                   10
```

-continued

```
<210> SEQ ID NO 206
<211> LENGTH: 9
<212> TYPE: PRT
<213> ORGANISM: Artificial Sequence
<220> FEATURE:
<223> OTHER INFORMATION: Synthetic Construct

<400> SEQUENCE: 206

Tyr Ile Tyr Tyr Ser Gly Ser Thr Asn
1               5

<210> SEQ ID NO 207
<211> LENGTH: 13
<212> TYPE: PRT
<213> ORGANISM: Artificial Sequence
<220> FEATURE:
<223> OTHER INFORMATION: Synthetic Construct

<400> SEQUENCE: 207

Ala Ser Tyr Ser Gly Tyr Asp Trp Gly Gly Phe Asp Tyr
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic Construct

<400> SEQUENCE: 208

Ser Gly Ser Arg Ser Asn Ile Gly Ser Asn Thr Val Asn
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Synthetic Construct

<400> SEQUENCE: 209

Tyr Ser Asp Asn Gln Arg Pro Ser
1               5

<210> SEQ ID NO 210
<211> LENGTH: 11
<212> TYPE: PRT
<213> ORGANISM: Artificial Sequence
<220> FEATURE:
<223> OTHER INFORMATION: Synthetic Construct

<400> SEQUENCE: 210

Ala Ala Trp Asp Asp Ser Leu Asn Gly Pro Val
1               5                   10

<210> SEQ ID NO 211
<211> LENGTH: 15
<212> TYPE: PRT
<213> ORGANISM: Artificial Sequence
<220> FEATURE:
<223> OTHER INFORMATION: Synthetic Construct

<400> SEQUENCE: 211

Thr Val Ser Gly Gly Ser Ile Ser Asn Ser Asn Tyr Tyr Trp Gly
1               5                   10                  15

<210> SEQ ID NO 212
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 212

Ser Leu Tyr Tyr Thr Gly Ser Thr Tyr
1               5

<210> SEQ ID NO 213
<211> LENGTH: 17
<212> TYPE: PRT
<213> ORGANISM: Artificial Sequence
<220> FEATURE:
<223> OTHER INFORMATION: Synthetic Construct

<400> SEQUENCE: 213

Ala Arg Leu Phe Ser Ser Gly Tyr Tyr Ser Pro Leu Tyr Ser Phe Asp
1               5                   10                  15

Tyr

<210> SEQ ID NO 214
<211> LENGTH: 15
<212> TYPE: PRT
<213> ORGANISM: Artificial Sequence
<220> FEATURE:
<223> OTHER INFORMATION: Synthetic Construct

<400> SEQUENCE: 214

Thr Gly Thr Thr Ser Ser Asp Val Gly Gly Tyr Asn Phe Val Ser
1               5                   10                  15

<210> SEQ ID NO 215
<211> LENGTH: 8
<212> TYPE: PRT
<213> ORGANISM: Artificial Sequence
<220> FEATURE:
<223> OTHER INFORMATION: Synthetic Construct

<400> SEQUENCE: 215

Tyr Asp Val Ser Asn Arg Pro Ser
1               5

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Ser Ser Tyr Thr Ser Ser Ser Thr Leu Ile
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Synthetic Construct

<400> SEQUENCE: 217

Trp Glu Ser Asn Gly Asn Glu Leu Ser Asp Phe Lys Thr Thr
1               5                   10
```

```
<210> SEQ ID NO 218
<211> LENGTH: 8
<212> TYPE: PRT
<213> ORGANISM: Artificial Sequence
<220> FEATURE:
<223> OTHER INFORMATION: Synthetic Construct

<400> SEQUENCE: 218

Asn Gly Asn Glu Leu Ser Asp Phe
1               5

<210> SEQ ID NO 219
<211> LENGTH: 14
<212> TYPE: PRT
<213> ORGANISM: Artificial Sequence
<220> FEATURE:
<223> OTHER INFORMATION: Synthetic Construct

<400> SEQUENCE: 219

Trp Glu Ile Asp Gly Ser Glu Arg Gln Asn Gly Lys Thr Thr
1               5                   10

<210> SEQ ID NO 220
<211> LENGTH: 9
<212> TYPE: PRT
<213> ORGANISM: Artificial Sequence
<220> FEATURE:
<223> OTHER INFORMATION: Synthetic Construct

<400> SEQUENCE: 220

Ile Asp Gly Ser Glu Arg Gln Asn Gly
1               5

<210> SEQ ID NO 221
<211> LENGTH: 10
<212> TYPE: PRT
<213> ORGANISM: Artificial Sequence
<220> FEATURE:
<223> OTHER INFORMATION: Synthetic Construct

<400> SEQUENCE: 221

Trp Glu Asp Asn Pro Val Tyr Lys Thr Thr
1               5                   10

<210> SEQ ID NO 222
<211> LENGTH: 5
<212> TYPE: PRT
<213> ORGANISM: Artificial Sequence
<220> FEATURE:
<223> OTHER INFORMATION: Synthetic Construct

<400> SEQUENCE: 222

Asp Asn Pro Val Tyr
1               5

<210> SEQ ID NO 223
<211> LENGTH: 14
<212> TYPE: PRT
<213> ORGANISM: Artificial Sequence
<220> FEATURE:
<223> OTHER INFORMATION: Synthetic Construct

<400> SEQUENCE: 223

Trp Glu Ser Asn Ile Ala Gln Pro Arg Asn Tyr Lys Thr Thr
1               5                   10

<210> SEQ ID NO 224
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Ser Asn Ile Ala Gln Pro Arg Asn Tyr
1               5

<210> SEQ ID NO 225
<211> LENGTH: 18
<212> TYPE: PRT
<213> ORGANISM: Artificial Sequence
<220> FEATURE:
<223> OTHER INFORMATION: Synthetic Construct

<400> SEQUENCE: 225

Trp Glu Ser Asn Gly Gln Pro Glu Lys Arg Asn Glu Asn Asn Tyr Lys
1               5                   10                  15

Thr Thr

<210> SEQ ID NO 226
<211> LENGTH: 13
<212> TYPE: PRT
<213> ORGANISM: Artificial Sequence
<220> FEATURE:
<223> OTHER INFORMATION: Synthetic Construct

<400> SEQUENCE: 226

Ser Asn Gly Gln Pro Glu Lys Arg Asn Glu Asn Asn Tyr
1               5                   10

<210> SEQ ID NO 227
<211> LENGTH: 18
<212> TYPE: PRT
<213> ORGANISM: Artificial Sequence
<220> FEATURE:
<223> OTHER INFORMATION: Synthetic Construct

<400> SEQUENCE: 227

Trp Glu Ser Asn Gly Gln Pro Glu Leu Ala Asn Glu Asn Asn Tyr Lys
1               5                   10                  15

Thr Thr

<210> SEQ ID NO 228
<211> LENGTH: 13
<212> TYPE: PRT
<213> ORGANISM: Artificial Sequence
<220> FEATURE:
<223> OTHER INFORMATION: Synthetic Construct

<400> SEQUENCE: 228

Ser Asn Gly Gln Pro Glu Leu Ala Asn Glu Asn Asn Tyr
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic Construct

<400> SEQUENCE: 229

Trp Glu Ser Asn Gly Gln Pro Asp Arg Arg Tyr Lys Thr Thr
1               5                   10
```

```
<210> SEQ ID NO 230
<211> LENGTH: 9
<212> TYPE: PRT
<213> ORGANISM: Artificial Sequence
<220> FEATURE:
<223> OTHER INFORMATION: Synthetic Construct

<400> SEQUENCE: 230

Ser Asn Gly Gln Pro Asp Arg Arg Tyr
1               5

<210> SEQ ID NO 231
<211> LENGTH: 14
<212> TYPE: PRT
<213> ORGANISM: Artificial Sequence
<220> FEATURE:
<223> OTHER INFORMATION: Synthetic Construct

<400> SEQUENCE: 231

Trp Glu Ser Asn Gly Gln Pro Glu Asp Asn Phe Lys Thr Thr
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Synthetic Construct

<400> SEQUENCE: 232

Ser Asn Gly Gln Pro Glu Asp Asn Phe
1               5

<210> SEQ ID NO 233
<211> LENGTH: 14
<212> TYPE: PRT
<213> ORGANISM: Artificial Sequence
<220> FEATURE:
<223> OTHER INFORMATION: Synthetic Construct

<400> SEQUENCE: 233

Trp Glu Ser Asn Gly Gln Pro Asp Gln Gln Tyr Lys Thr Thr
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Synthetic Construct

<400> SEQUENCE: 234

Ser Asn Gly Gln Pro Asp Gln Gln Tyr
1               5

<210> SEQ ID NO 235
<211> LENGTH: 14
<212> TYPE: PRT
<213> ORGANISM: Artificial Sequence
<220> FEATURE:
<223> OTHER INFORMATION: Synthetic Construct

<400> SEQUENCE: 235

Trp Glu Thr Trp Leu Asn Pro Asp Pro Ser Gln Lys Thr Thr
1               5                   10
```

```
<210> SEQ ID NO 236
<211> LENGTH: 9
<212> TYPE: PRT
<213> ORGANISM: Artificial Sequence
<220> FEATURE:
<223> OTHER INFORMATION: Synthetic Construct

<400> SEQUENCE: 236

Thr Trp Leu Asn Pro Asp Pro Ser Gln
1               5

<210> SEQ ID NO 237
<211> LENGTH: 13
<212> TYPE: PRT
<213> ORGANISM: Artificial Sequence
<220> FEATURE:
<223> OTHER INFORMATION: Synthetic Construct

<400> SEQUENCE: 237

Trp Glu Tyr Met Pro Met Glu Asn Asn Tyr Lys Thr Thr
1               5                   10

<210> SEQ ID NO 238
<211> LENGTH: 8
<212> TYPE: PRT
<213> ORGANISM: Artificial Sequence
<220> FEATURE:
<223> OTHER INFORMATION: Synthetic Construct

<400> SEQUENCE: 238

Tyr Met Pro Met Glu Asn Asn Tyr
1               5

<210> SEQ ID NO 239
<211> LENGTH: 14
<212> TYPE: PRT
<213> ORGANISM: Artificial Sequence
<220> FEATURE:
<223> OTHER INFORMATION: Synthetic Construct

<400> SEQUENCE: 239

Trp Glu Gln Lys Leu Ile Ser Glu Glu Asp Leu Lys Thr Thr
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Synthetic Construct

<400> SEQUENCE: 240

Gln Lys Leu Ile Ser Glu Glu Asp Leu
1               5

<210> SEQ ID NO 241
<211> LENGTH: 12
<212> TYPE: PRT
<213> ORGANISM: Artificial Sequence
<220> FEATURE:
<223> OTHER INFORMATION: Synthetic Construct

<400> SEQUENCE: 241

Trp Glu Asp Tyr Lys Asp Asp Asp Asp Lys Thr Thr
1               5                   10
```

```
<210> SEQ ID NO 242
<211> LENGTH: 7
<212> TYPE: PRT
<213> ORGANISM: Artificial Sequence
<220> FEATURE:
<223> OTHER INFORMATION: Synthetic Construct

<400> SEQUENCE: 242

Asp Tyr Lys Asp Asp Asp Asp
1               5

<210> SEQ ID NO 243
<211> LENGTH: 15
<212> TYPE: PRT
<213> ORGANISM: Artificial Sequence
<220> FEATURE:
<223> OTHER INFORMATION: Synthetic Construct

<400> SEQUENCE: 243

Trp Glu Ser Asn Gly His His His His His His Tyr Lys Thr Thr
1               5                   10                  15

<210> SEQ ID NO 244
<211> LENGTH: 10
<212> TYPE: PRT
<213> ORGANISM: Artificial Sequence
<220> FEATURE:
<223> OTHER INFORMATION: Synthetic Construct

<400> SEQUENCE: 244

Ser Asn Gly His His His His His His Tyr
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Synthetic Construct

<400> SEQUENCE: 245

Asp Leu Thr Arg Trp Asp Val Gly Asn Val
1               5                   10

<210> SEQ ID NO 246
<211> LENGTH: 6
<212> TYPE: PRT
<213> ORGANISM: Artificial Sequence
<220> FEATURE:
<223> OTHER INFORMATION: Synthetic Construct

<400> SEQUENCE: 246

Leu Thr Arg Trp Asp Val
1               5

<210> SEQ ID NO 247
<211> LENGTH: 10
<212> TYPE: PRT
<213> ORGANISM: Artificial Sequence
<220> FEATURE:
<223> OTHER INFORMATION: Synthetic Construct

<400> SEQUENCE: 247

Asp Lys Asp Arg Trp Glu Arg Gly Asn Val
1               5                   10

<210> SEQ ID NO 248
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 248

Lys Asp Arg Trp Glu Arg
1               5

<210> SEQ ID NO 249
<211> LENGTH: 11
<212> TYPE: PRT
<213> ORGANISM: Artificial Sequence
<220> FEATURE:
<223> OTHER INFORMATION: Synthetic Construct

<400> SEQUENCE: 249

Trp Glu Leu Asp Arg Trp Asp Val Lys Thr Thr
1               5                   10

<210> SEQ ID NO 250
<211> LENGTH: 6
<212> TYPE: PRT
<213> ORGANISM: Artificial Sequence
<220> FEATURE:
<223> OTHER INFORMATION: Synthetic Construct

<400> SEQUENCE: 250

Leu Asp Arg Trp Asp Val
1               5

<210> SEQ ID NO 251
<211> LENGTH: 10
<212> TYPE: PRT
<213> ORGANISM: Artificial Sequence
<220> FEATURE:
<223> OTHER INFORMATION: Synthetic Construct

<400> SEQUENCE: 251

Asp Asn Asp Arg Trp Gln Gln Gly Asn Val
1               5                   10

<210> SEQ ID NO 252
<211> LENGTH: 6
<212> TYPE: PRT
<213> ORGANISM: Artificial Sequence
<220> FEATURE:
<223> OTHER INFORMATION: Synthetic Construct

<400> SEQUENCE: 252

Asn Asp Arg Trp Gln Gln
1               5
```